(12) United States Patent
Duhr et al.

(10) Patent No.: US 8,741,570 B2
(45) Date of Patent: Jun. 3, 2014

(54) THERMO-OPTICAL CHARACTERISATION OF NUCLEIC ACID MOLECULES

(75) Inventors: Stefan Duhr, München (DE); Philipp Baaske, München (DE)

(73) Assignee: Ludwig-Maximilians-Universitat Munchen, Munich (DE)

( * ) Notice: Subject to any disclaimer, the term of this patent is extended or adjusted under 35 U.S.C. 154(b) by 0 days.

(21) Appl. No.: 12/865,985

(22) PCT Filed: Feb. 6, 2009

(86) PCT No.: PCT/EP2009/000847
§ 371 (c)(1),
(2), (4) Date: Aug. 3, 2010

(87) PCT Pub. No.: WO2009/098079
PCT Pub. Date: Aug. 13, 2009

(65) Prior Publication Data
US 2010/0330578 A1    Dec. 30, 2010

Related U.S. Application Data

(60) Provisional application No. 61/026,645, filed on Feb. 6, 2008.

(51) Int. Cl.
*C12Q 1/68*    (2006.01)
*C07H 21/02*    (2006.01)
*G01J 1/58*    (2006.01)

(52) U.S. Cl.
USPC .......... 435/6.12; 435/6.1; 536/23.1; 250/362; 250/361 R; 250/458.1; 250/459.1

(58) Field of Classification Search
USPC .......... 435/6.12, 6.1; 536/23.1; 250/362, 361, 250/458.1, 459.1
See application file for complete search history.

(56) References Cited

U.S. PATENT DOCUMENTS 6,850,363 B1    2/2005    Wendenburg et al.
2004/0091911 A1*    5/2004    Morgan et al. .......... 435/6

(Continued)

FOREIGN PATENT DOCUMENTS

WO    WO 2008/061706 A    5/2008

OTHER PUBLICATIONS

Duhr et al. The European Physical Journal. 2004. 15: 277-286.*

(Continued)

*Primary Examiner* — Robert T. Crow
*Assistant Examiner* — Joseph G Dauner
(74) *Attorney, Agent, or Firm* — Foley & Lardner LLP; Richard C. Peet

(57) ABSTRACT

The present invention pertains to a method and a device for the determination of thermo-optical properties, particularly the size or size distribution, of fluorescently labeled biomolecules or biomolecule complexes, particularly nucleic acids, in a reaction solution. The method comprises the steps of: (i) providing a reaction solution with fluorescently labeled biomolecules or biomolecule complexes; (ii) irradiating a laser light beam into the solution to obtain a spatial temperature distribution in the solution around the irradiated laser light beam; (iii) exciting fluorescently said fluorescently labeled biomolecules and detecting the fluorescence at two or more defined regions representing different mean temperatures in said spatial temperature distribution, wherein said detection of fluorescence is performed at least once at a predetermined time after the start of the laser irradiation; and (iv) determining the thermo-optical properties, particularly the size or size distribution, of the fluorescently labeled biomolecules or biomolecule complexes from the detected fluorescence intensity or fluorescence intensity distribution.

24 Claims, 35 Drawing Sheets

(56) References Cited

U.S. PATENT DOCUMENTS

2004/0161767 A1* 8/2004 Baldwin et al. ............... 435/6
2004/0195101 A1* 10/2004 Sharaf et al. ............... 204/452

OTHER PUBLICATIONS

TechTerms.com's definition of "CCD" (retrieved on Feb. 26, 2013 from the internet: <http://www.techterms.com/definition/ccd>).*
Braun. Physical Review Letters. 2003. 91(15): 158103, 1-4.*
NEBuffer 1 (retrieved on Feb. 28, 2013 from the internet <https://www.neb.com/products/b7001-nebuffer-1>).*
The International Search Report received in the corresponding International Patent Application No. PCT/EP2009/000847, dated May 25, 2009.
Baaske, et al., "Melting curve analysis in a snapshot", *Applied Physics Letters*, vol. 91, No. 13, 2007, pp. 133901-133901.
Duhr, et al., "Optothermal molecule trapping by opposing fluid flow with thermophoretic drift", *Physical Review Letters*, vol. 97, No. 3, 2006, pp. 38103/1-4.
Duhr, et al., "Thermophoresis of DNA determined by microfluidic fluorescence", *European Physical Journal E. Soft Matter*, vol. 15, No. 3, 2004, pp. 277-286.
Duhr, of al., "Why molecules move along a temperature gradient", *Proceedings of the National Academy of Sciences of USA*, vol. 103, No. 52, 2006, pp. 19678-19682.
Orlando, et al., "Developments in Quantitative PCR", *Clinical Chemistry and Laboratory Medicine*, vol. 36, No. 5, 1998, pp. 255-269.
Braun and Libchaber, Trapping of DNA by Thermophoretic Depletion and Convection, Physical Review Letters, vol. 89, No. 18, pp. 188103-1 thru 188103-4, Oct. 28, 2002.
Braun and Libchaber, Thermal Force Approach to Molecular Evolution, Physical Biology 1, pp. P1-P8, 2004.
Saiki et al., Enzymatic Amplification of β-Globin Genomic Sequences and Restriction Site Analysis for Diagnosis of Sickle Cell Anemia, Science, vol. 230, pp. 1350-1354, Dec. 20, 1985.
Saiki et al., Primer-Directed Enzymatic Amplification of DNA with a Thermostable DNA Polymerase, Science, vol. 239, pp. 487-491, Jan. 29, 1988.
Rychlik et al., Optimization of the Annealing Temperature for DNA Amplification in vitro, Nucleic Acids Research, vol. 18, No. 21, pp. 6409-6412, 1990.
Wiedmann et al., Ligase Chain Reaction (LCR)—Overview and Applications, Genome Res. 3, pp. S51-S64, 1994.
Piazza and Guarino et al., Soret Effect in Interacting Micellar Solutions, Physical Review Letters, vol. 88, No. 20, pp. 208302-1 thru 208302-4, May 20, 2002.
The Office Action received in the related U.S. Appl. No. 12/515,641, dated Mar. 19, 2012.
Duhr and Braun, "Two-dimensional colloidal crystals formed by thermophoresis and convection," Applied Physics Letters, vol. 86, Iss. 13, published Mar. 24, 2005. Retrieved from internet [Mar. 13, 2012]. Retrieved from uri <http://apl.aip.org/resource/1/applab/v86/i13/p131921_s1>.
Rusconi et al., "Thermal-lensing measurement of particle thermophoresis in aqueous dispersions," Journal of Optical Society of Ameria, vol. 21, Iss. 3, pUblished Mar. 2004; Retrieved from the internet [Mar. 13, 2012]; Retrieved from uri <http://www.opticsinfobase.orgfjosab/abstract.cfm?uri=josab-21-3--605>.

* cited by examiner

.66 Structures of 6-JOE SE (C6171MP), 6-HEX SE (C20091) and 6-TET SE (C20092).

|     | R¹ | R² | R³ |
|-----|----|----|----|
| JOE | Cl | OCH₃ | H |
| HEX | Cl | Cl | Cl |
| TET | I  | Cl | Cl |

QD

OD + Strep    OD + Strep + DNA a b

SEQUENCE LISTING

```
<160> NUMBER OF SEQ ID NOS: 4

<210> SEQ ID NO 1
<211> LENGTH: 17
<212> TYPE: DNA
<213> ORGANISM: artificial sequence
<220> FEATURE:
<221> NAME/KEY: source
<223> OTHER INFORMATION: /note="Description of artificial sequence: DNA
      aptamer"

<400> SEQUENCE: 1
tggttggtgt ggttggt                                                    17

<210> SEQ ID NO 2
<211> LENGTH: 22
<212> TYPE: DNA
<213> ORGANISM: artificial sequence
<220> FEATURE:
<221> NAME/KEY: source
<223> OTHER INFORMATION: /note="Description of artificial sequence:
      artificial probe sequence"

<400> SEQUENCE: 2
attgagatac acattagaac ta                                              22

<210> SEQ ID NO 3
<211> LENGTH: 22
<212> TYPE: DNA
<213> ORGANISM: artificial sequence
<220> FEATURE:
<221> NAME/KEY: source
<223> OTHER INFORMATION: /note="Description of artificial sequence:
      artificial target sequence"

<400> SEQUENCE: 3
tagttctaat gtgtatctca at                                              22

<210> SEQ ID NO 4
<211> LENGTH: 25
<212> TYPE: DNA
<213> ORGANISM: artificial sequence
<220> FEATURE:
<221> NAME/KEY: source
<223> OTHER INFORMATION: /note="Description of artificial sequence:
      Primer"

<400> SEQUENCE: 4
gatgagttcg tgtccgtaca actgg                                           25
```

THERMO-OPTICAL CHARACTERISATION OF NUCLEIC ACID MOLECULES

CROSS-REFERENCE TO RELATED PATENT APPLICATIONS

This application is the U.S. National Phase of PCT/EP2009/000847, filed Feb. 6, 2009, which claims priority to U.S. Provisional application 61/026,645, filed Feb. 6, 2008, which is incorporated herein by reference in entirety.

The present invention relates to a method and an apparatus for the thermo-optical characterisation of nucleic acid molecules. In particular, the present invention relates to a method and a device to measure and/or characterize nucleic acid molecules, in particular during and after (in vitro) amplifications of said nucleic acid molecules, like during and after polymerase chain reactions (PCR), in particular reverse transcription polymerase chain reactions, real-time polymerase chain reactions (RT-PCR), multiplex PCRs or quantitive real-time PCRs. The present invention also provides for means, methods and devices for the determination of e.g. length/size/size distribution of bio molecules, in particular nucleic acid molecules. For example, the present means, methods and devices provide for the determination of and/or size and a quantification of amplification product(s) and/or primer sequence copies in a PCR-solution. The technology provided herein is, however, not limited the measurement/characterization of length/size or quantification of intermediate and or end-products of amplification reactions, i.e. of nucleic acid molecules. Therefore, also other characteristics of nucleic acid molecules can be measured and determined by the means, methods and devices disclosed herein, for example kinetic events and interactions of nucleic acid molecules may be determined and/or measured. Such kinetic events and interactions comprise, inter alia, hybridizations of nucleic acid molecules The present invention provides for a thermo-optical method for the determination or characterization of the size/size distribution/length of nucleic acids in particular during or after (a) PCR reaction(s). For example and in one embodiment, the present invention provides for means, methods and devices for the determination of the length, size or secondary structure of nucleic acid molecules, in particular through the means of determination of the thermo-optical properties during nucleic acid amplification methods like PCR (i.e. in different cycles; once in each cycle). This allows for example for the determination of the threshold cycle or of the efficiency of an amplification method (e.g. PCR) and/or the endpoint of a PCR. A particular gist of the present invention is the fact that such information can be obtained with a single covalently or intercalating fluorescent dye and no special PCR probe(s) is/are necessary.

In one particular embodiment, the present invention provides for a method for the thermo-optical determination of the size of fluorescently labeled nucleic acids in a reaction solution or the size distribution of fluorescently labeled nucleic acids in a reaction solution, comprising the steps of: (a) providing a reaction solution with fluorescently labeled nucleic acids; (b) irradiating a laser light beam into the solution to obtain a spatial temperature distribution in the solution around the irradiated laser light beam; (c) exciting fluorescently said fluorescently labeled nucleic acids and detecting the fluorescence at least at one position or at around one position in the solution or detecting the fluorescence distribution of said fluorescently excited nucleic acids, wherein said detection of fluorescence is performed at least once at a predetermined time after the start of the laser irradiation; and (d) determining the size or size distribution of the fluorescently labeled nucleic acids from the detected fluorescence intensity or fluorescence intensity distribution. Optionally, an additional detection of fluorescence may be performed at least once before the start of the laser irradiation.

Furthermore, devices for carrying out the methods provided herein are disclosed and provided. For example, the present invention provides for a device for thermo-optical determination of the size or size distribution of fluorescently labeled nucleic acids in a reaction solution, in particular according to a method as disclosed herein and, comprising: (a) a receiving means for receiving a reaction solution with fluorescently labeled nucleic acids; (b) a laser for irradiating a laser light beam into the solution to obtain a spatial temperature distribution in the solution around the irradiated laser light beam, (c) means for fluorescently exciting the labeled nucleic acids; and (d) means for detecting fluorescence and/or fluorescence distribution of the fluorescently excited nucleic acids; and wherein said device is adapted to perform at least two fluorescence detections at least two predetermined times. In addition to preferred embodiments of these methods and devices corresponding uses are disclosed, in particular, the use of the method as provided herein or use of the device as provided herein for the detection and/or quantification of fluorescently labeled nucleic acids in real-time PCR; quantitive real-time PCR, nested PCR, reverse transcription PCR or in multiplex PCR or for the determination of the size of fluorescently labeled nucleic acids in real-time PCR; quantitive real-time PCR, nested PCR, reverse transcription PCR or in multiplex PCR.

In conventional methods known in the art for all-optical biomolecule characterisation, samples with biomolecules in solutions are homogeneously heated to a certain temperature at a time followed by further heating to the next temperature point. A common procedure is to start at 20° C. The temperature is then increased for example by 1° C. A waiting time of approx. 2 minutes is then required until the whole system (cuvette and solution) has reached the applied temperature. This is due to the large thermal mass. Only then fluorescence is measured. This procedure is repeated until 90° C. in a stepwise manner. Accordingly, the heating of the whole sample volume takes long and it is necessary to employ heat conducting materials in contact with the liquid.

Separation techniques known in the art such as gel electrophoresis are at core of modern DNA and protein biotechnology. However, electrophoresis is hard to miniaturize due to electrochemical effects at the metal-buffer interface and the tedious preparation of the gel phase. Duhr et. al. in European Phys. J. E 15, 277, 2004 relates to "Thermophoresis of DNA determined by microfluidic fluorescence" and makes use of thermophoretic driving forces in miniaturized biotechnology devices. This article discusses an all-optical approach in thin micro fluids to measure and apply thermophoresis for biomolecules in small volumes. The temperatures are measured with high spatial resolution by the temperature sensitive fluorescence of a fluorescent dye. Typically, one measurement according to Duhr et al. (2004, loc. cit.) takes 300 s or even more. It is further speculated in Duhr et al. (2004, loc. cit.), that the movement of polymers, in particular DNA, in a temperature gradient is independent of the chain length of the molecule, an assumption in line with theoretical considerations, see e.g. Braun and Libchaber, Physical Review Letters 89, 18 (2002). This assumption strongly confines thermo-optical characterization of molecules based on thermophoresis, since the technique would solely be dependent on changes in size of molecules and would exhibit no sensitivity to surface properties, as it is the gist of the present invention. The means, methods and devices of the present invention allow, inter alia, the measurement/determination of the length, size or secondary structure of nucleic acid molecules, in particular of intermediate and end-products during molecular (nucleic acid) amplifications, like the nucleic acid/DNA product during or after a PCR reaction. When the thermo-optical technique as disclosed herein is for example applied multiple times during a PCR reaction (e.g. to the same solution), the characteristics of this biochemical reaction, like threshold cycle, efficiency and endpoint can easily be determined. All these features render analytical techniques normally used after an amplification of nucleic acid molecules, for example gel-electrophoresis, unnecessary.

The above mentioned method has the disadvantage that it is very time consuming. This is also the case for established methods for measuring interactions, size and stability, like Biacore (GE Healthcare), Evotec FCS-plus (Perkin-Elmer) or Lightcycler 480 (Roche Applied Science). The time consumption of these techniques is typically longer than an hour. The present invention relating to the fast thermo-optical characterization of biomolecules, in particular nucleic acid molecules, allows (inter alia) to determine the length/size of said molecules during a PCR reaction. The means, methods and devices disclosed herein avoid to perform secondary read-out measurement, like performing gel analysis after the corresponding amplification techniques. Accordingly, the means, methods and devices of the present invention leads to a considerably less time consuming analysis of nucleic acid amplifications and thus saves time of typically 30 minutes or even more.

Therefore, the present invention provides for an improved method and device for a thermo-optical characterisation of nucleic acid molecules in order to provide a very fast method to measure the characteristics of these nucleic acid molecules, in particular the length/size or size distribution. The present invention also provides for means, methods and devices which allow for the temporal as well as spacial tracing of nucleic acid molecules during reactions, like polymerase chain reactions and most preferably in the detection and or characterization of nucleic acid molecule reactions products (end products as well as intermediate products) in reverse transcription polymerase chain reaction (RT-PCR) or real-time polymerase chain reactions.

These objects are achieved by the features of the independent claims. Further preferred embodiments are characterized in the dependent claims.

Provided herein are means, methods, and devices for measuring the stability of molecules, in particular biomolecules, the interaction of (bio)molecules with other or further (bio) molecules, or with particles (e.g. nanoparticles, microparticles, beads, e.g. microbeads), and/or measuring the length or size of molecules, like biomolecules, particles (e.g. nanoparticles or microparticles, microspheres, beads, e.g. microbeads), In particular the characteristics of nucleic acid molecules, like the size and/or length are determined and measured by the means, methods and devices provided herein. Furthermore, the thermo-optical techniques provided herein may be applied multiple times/repeatedly during a nucleic acid amplification reaction (e.g. a PCR reaction). Such a repetition may be for example a thermo-optical measurement during every cycle of such an amplification method, i.e. such a PCR reaction. This allows for, e.g. the determination of the characteristics of this biochemical reaction, like the threshold cycle, efficiency and intermediates determination as well as endpoint or end product determination. Also combinations of these characteristics may be determined by the means and methods of this invention. The method of the present invention allows contact free, thermo-optical measurements of these parameters/characteristics within a time span of a few milliseconds up to a few seconds, i.e. a very fast analysis is possible. The present invention also comprises the thermo-optical determination of the characteristics of nucleic acid molecules which are bound or linked to matrices, beads or particles In the context of this invention, in particular the claims, it is noted that the terms "particle" or "particles" preferably relates to the nucleic acids (such as DNA, RNA, LNA, PNA) to be analyzed by the means, methods and devices of the present invention. The term "modified particle", "modified bead" or "modified nucleic acid molecule" relates in particular to beads/particles/nucleic acid molecules which comprise or are linked to other molecules, like other bio molecules (like peptides, proteins amino acids etc) or labels, like fluorescent labels. This also comprises coating of such beads or particles with these nucleic acid molecules to be analyzed or measured and determined in accordance with this invention. Again, the major gist of this invention lays in the fact that a fast a convenient method (and corresponding devices) are provided which allow for the characterization and/or determination of nucleic acid molecules, in particular to the characterization and/or determination of amplification products (intermediate products as well as end-products) in polymerase chain reactions.

In accordance with this invention, a method for the thermo-optical determination of the size, length or secondary structure of fluorescently labelled nucleic acids in a reaction solution or the size distribution of fluorescently labeled nucleic acids in a reaction solution is provided, said method comprising the steps of: (a) providing a reaction solution with fluorescently labeled nucleic acids; (b) irradiating a laser light beam into the solution to obtain a spatial temperature distribution in the solution around the irradiated laser light beam; (c) exciting fluorescently said fluorescently labeled nucleic acids and detecting the fluorescence at least at one position or at around one position in the solution or detecting the fluorescence distribution of said fluorescently excited nucleic acids, wherein said detection of fluorescence is performed at least once at a predetermined time after the start of the laser irradiation; and (d) determining the size or size distribution of the fluorescently labeled nucleic acids from the detected fluorescence intensity or fluorescence intensity distribution. Optionally, an additional detection of fluorescence may be performed at least once before the start of the laser irradiation.

The thermo-optical characterization means, methods and devices of this are in particular able to detect/measure/analyze structural changes in biomolecules (e.g. nucleic acid molecules, like DNA or RNA). Since the hydrodynamic radius and the mobility in the temperature gradient are dependent on the structure of a nucleic acid molecule, differences in secondary structure lead to distinct changes in the spatial concentration pattern. Accordingly, the present invention also provides for the means, methods and devices to measure/determine/analyze the secondary structure of biomolecules, in particular also of nucleic acid molecules.

Furthermore, devices for carrying out the methods provided herein are disclosed and provided in this invention. In addition to preferred embodiments of these methods and devices corresponding uses are disclosed, in particular, the use of the method as provided herein or use of the device as provided herein for the detection and/or quantification of fluorescently labeled nucleic acids in real-time PCR; quantitive real-time PCR, nested PCR, reverse transcription PCR or in multiplex PCR or for the determination of the size of fluorescently labeled nucleic acids in real-time PCR; quantitive real-time PCR, nested PCR, reverse transcription PCR or in multiplex PCR.

One method provided herein is based on the absorbance of infrared LASER radiation by aqueous solutions and the subsequent conversion into heat. Thereby it is possible to create broad spatial, i.e., two-dimensional or three-dimensional (2D, 3D), temperature distributions comprising all desired temperatures, e.g. between 0° C. and 100° C. within an area of e.g. about 250 µm in diameter or length, established by local laser heating, whereby desired temperature gradients are created, in particular strong temperature gradients. Both, local temperature distributions and temperature gradients, can be used as described below to measure parameters, in particular biomolecular parameters. In a particular embodiment, the temperature distribution is on the micrometer scale. This may be advantageous since strong temperature gradients shorten the equilibration time of the system needs to equilibrate (i.e. measurement time). In particular embodiments, it is advantageous to increase the temperature on a length scale of less than 100 µm.

Generally, the measurement of the thermo-optically characteristics of particles/molecules in a solution comprise the steps of: providing a sample probe with marked particles/molecules in a solution; exciting (e.g. fluorescently) said marked particles and firstly detecting and/or measuring (e.g. fluorescence of) said excited particles/molecules; irradiating a laser light beam into the solution to obtain a spatial temperature distribution in the solution around the irradiated laser light beam (i.e. in and/or nearby the area of the solution which is directly irradiated by the laser light beam); detecting and/or measuring secondly (e.g. a fluorescence of) the particles/molecules in the solution at a predetermined time after irradiation of the LASER into the solution has been started, and characterizing the particles/molecules based on said two detections.

Without differing from the gist of the invention it is also envisaged that instead of a detection based on fluorescence other detection methods are possible. Depending on the size and properties of the particles to be detected, the step of fluorescently exciting may be omitted, and a detection based on light scattering, (UV) absorption, phase contrast, phosphorescence and/or polarisation are possible. Moreover, for particles larger than 100 nm, the movement of such particles can be detected by single particle tracking.

The thermo-optical characterization in accordance with this invention allows to determine properties of molecules or particles in solutions, in particular in aqueous solutions. In particular, it allows to discriminate between different conformations of molecule species (like nucleic acid molecules) and it also allows to discriminate between different species of particles or different molecules. In a most particular embodiment of the present invention, the characteristic(s) of nucleic acid molecules, like the length and/or size of said nucleic acid molecules and of nucleic acid amplification products can be determined. It is also possible, to, inter alia, determine the concentration of primer(s) and concentration of intermediate and/or end products of amplification methods, like PCR methods. For example, multiple measurements of these nucleic acid characteristics during a PCR reaction (i.e. in different cycles) allow to quantify and/or determine the threshold cycle, the efficiency and the endpoint of said PCR reaction. Such measurements can be readily carried out by the person skilled in the art using the means, methods and devices provided herein. The thermo-optical characterization as provided herein can be used in all cases where the particles, in particular the nucleic acid molecules or beads/particles linked to nucleic acid molecules show a response to changes in the temperature gradient and changes in the absolute temperature. An advantageous feature of the present invention is the presence of a defined spatial temperature distribution. In particular, the temperature distribution is generated locally on microscopic length scales by local heating with a focussed laser. Another advantageous feature is that the response of the particles or molecules is assigned to a certain place of the known, optically generated spatial temperature distribution. Accordingly, temperature, place and response of the particles are directly correlated. With the means, methods and devices provided herein and illustrated in the appended examples and figures, it is in particular feasible and useful to trace and follow fast PCR-reaction products (end as well as intermediate products). The means, methods and devices provided herein are particularly useful in tracing PCR products obtained or obtainable in PCR reaction, in particular but not limiting in RT-PCR reactions. Accordingly, the present invention provides, inter alia, for thermo-optical means for the detection and/or verification of amplification products as obtained during amplification methods for nucleic acid molecules, like during PCR reactions, in particular but nor limiting RT-PCR reactions.

Furthermore, and in contrast to Duhr (2004; loc. cit.) the present invention provides means and methods for the thermo-optical measurements and/or thermo-optical characterization of particles or molecules, in particular nucleic acid molecules, by the measurements and/or the detection of differences in the thermo-optical properties. Their thermo-optical properties mainly originate from differences in thermophoretic mobility DT (i.e. the velocity of particles/molecules in a temperature gradient). In particular, the detected signal is dependent on the thermophoretic mobility $c/c_0=\exp[-(D_T/D)(T-T_0)]$, with the diffusion coefficient D, concentration c and temperature T. A DT independent of the polymer length as expected from Duhr (2004; loc. cit.) and others (e.g. Chan et al., Journal of Solution Chemistry 32, 3 (2003); Schimpf et al., Macromolecules 20, 1561-1563 (1987)) would render the analytics of biopolymers like nucleic acid molecules (in particular DNA) and proteins almost impossible since only changes in the diffusion constant would contribute to the thermo-optical properties, which are minute in most cases.

Thermo-optical characterization in accordance with this invention is based on the creation of strong temperature gradients at microscopic length scales in solution, in particular in aqueous solution. By doing so, the energetic states of the molecules (i.e. in accordance with this invention nucleic acid molecules either per se or nucleic acid molecules linked to matrices, particles or beads) in the solution are changed depending on the temperature and the properties of the molecule, i.e. the molecules experience a spatial potential originating from the spatial differences in temperature. This potential drives a directed motion of molecules along the temperature gradient, an effect called thermophoresis. In other cases the change in temperature leads, beside thermophoresis, to an unfolding of biopolymers, in particular in accordance with this invention nucleic acid molecules, like DNA or RNA. The unfolding effect is observed at high temperatures and is a measure for the stability of molecules (the reason for unfolding is the increased influence of the entropy component of the energy), the effect is separated from thermophoresis by a characteristic time scale. The stability analysis takes place in milliseconds to one second, preferably about 1 ms to 250 ms, 1 ms to 200 ms, 1 ms to 100 ms, 1 ms to 80 ms, 1 ms to 50 ms, more preferably about 40 ms, 80 ms-180 ms, 80 ms-150 ms, most preferably about 50 ms.

Thermophoresis is observed at times in a range from about 0.5 seconds to 250 seconds, preferably 0.5 seconds to 50 seconds, preferably 1 second to 250 seconds, preferably 1 second to 50 seconds, preferably 1 second to 40 seconds, preferably 5 seconds to 20 seconds, preferably 5 seconds to 40 seconds, preferably 5 seconds to 50 seconds, preferably 5 seconds to about 80 seconds, more preferably 5 seconds to 100 seconds. Thermophoresis is a method which is sensible to surface properties of molecules in a solution. It is not necessary to expose molecules to a different matrix (like in chromatography) or to interact with the molecules physically in any way (e.g. by direct contact or by adding substances). Infrared radiation is used for contact free spatial heating.

The gist of thermo-optical characterization of nucleic acid molecules (in particular in context of the PCR reactions, most particular in real-time polymerase chain reactions (RT-PCR), multiplex PCRs or quantitive real-time PCRs as well as reverse transcription polymerase chain reaction) based on thermophoresis as provided herein is that differences in thermophoretic mobility (i.e. the velocity of molecules in a temperature gradient), and hydrodynamic radius can be detected by analyzing the spatial distribution of concentration (i.e. by the spatial distribution of e.g. fluorescence) or the fluctuations of single particles trapped in the spatial temperature profile. This embodiment is of particular relevance for the herein described thermo-optical trap for trapping particles, molecules, beads, cellular components, vesicles, liposomes, cells and the like. While the hydrodynamic radius is only related to the radius of a molecule, the thermophoretic mobility is sensitive to charge, surface properties (e.g. chemical groups on the surface), shape of a molecule (i.e. size of surface), conformation of a protein or interaction between biomolecules or biomolecules and particles/nanocrystals/microbeads. This means that if any of the mentioned properties are changed, the molecules will experience a different thermodynamical potential, resulting in differences in thermophoretic mobility (i.e. change in spatial concentration profile or fluctuation amplitude of trapped particles).

Thus, the present invention relates to thermally induced processes, e.g. temperature gradient induced directed motion or thermal denaturation.

The thermo-optical characterization mentioned above provides the means for fast thermo-optical analysis of particles and/or molecules, in particular for the thermo-optical characterisation of biomolecules, most preferably, in context of this invention, nucleic acid molecules (e.g. DNA, RNA, PNA). This characterisation comprises, inter alia, size determination, length determination, determination of biophysical characteristics, like melting points or melting curves, complex formations, protein-protein interactions, protein or peptide folding/unfolding, of intra-molecular interactions, intermolecular interactions, the determination of interactions between particles or molecules, and the like. In a particular preferred embodiment of the present invention means, methods and devices for the determination of the characteristics of nucleic acid molecules, for example in form of intermediate or end-products of amplification methods, like PCRs, in particular in multiplex PCRs, reverse transcription polymerase chain reactions, real-time polymerase chain reactions (RT-PCR), multiplex PCRs or quantitive real-time PCRs is provided Prior art methods for detection and quantification of molecular interactions and characteristics, in particular biomolecular interactions and characteristics are very time consuming which means that the time needed for an analysis is in the order of 30 minutes up to hours. In accordance with the present invention, one measurement typically takes less than 300 s, less than 200 s, less than 100 s or even less than 50 s, which is clearly faster than the methods described in the prior art. The present invention can detect and quantify molecular interactions and characterisations, in particular biomolecular interactions and/or biochemical/biophysical properties within 1 second to 50 seconds. The term interaction comprises interaction between biomolecules (e.g. protein, DNA, RNA, hyaluronic acids etc.) but also between (modified) (nano)particles/(micro)beads and biomolecules. The term also, relates to interactions between (individual) nucleic acid molecules, like during hybridisation processes or processes as they occur in techniques, like PCR techniques. In this context, modified particles, molecules, biomolecules, nanoparticles, microparticles, beads or microbeads comprise fluorescently labelled particles, molecules, biomolecules, nanoparticles, microparticles, beads or microbeads. Fluorescently labelled particles, molecules, biomolecules, nanoparticles, microparticles, beads or microbeads may be e.g. particles, molecules, biomolecules, nanoparticles, microparticles, beads or microbeads, to which one or more fluorescent dyes have been attached, e.g. covalently attached. For example, the fluorescent dyes may be selected from the group of 6-carboxy-2',4,4',5',7,7'-hexachlorofluorescein (6-HEX SE; C20091, Invitrogen), 6-JOE SE or 6-TET SE (see also appended FIG. 6). In other cases, the intrinsic fluorescence of e.g. particles, molecules, biomolecules may be exploited according to the invention, e.g. the fluorescence properties of tryptophan, tyrosine or phenylalanine in a protein may be exploited. The terms "marked" and "labelled" are used synonymously in the context of this invention. In the context of this invention, "marked particles" refer to fluorescently labelled molecules/particles or other molecules/particles which can be detected by fluorescence means, e.g. molecules/particles comprising an intrinsic fluorophor, molecules/particles comprising intercalating dyes or particles/molecules with fluorophores attached.

A typical experiment in accordance with this invention, but not limiting the scope of the invention, to detect/quantify interactions may be described as follows:

Step 1a, Background Measurement:

A sample buffer without fluorescently labelled sample molecules/particles is filled into a microfluidic chamber and the fluorescence is measured, while the excitation light source is turned on.

Step 1b, Determination of Fluorescence Level Before Laser Heating:

An aqueous solution of a fluorescently labelled sample (e.g. biomolecules, particles, like nanoparticles or microparticles, beads, particularly microbeads, nucleic acid molecules, wherein in particular embodiments all of them have a specific affinity for other biomolecules) at a given concentration is filled in the microfluidic chamber (preferably a capillary) which preferably provides a defined height of the chamber. Fluorescence is excited and recorded with (e.g. CCD-Camera) or without (e.g. Photomultiplier tube, Avalanche Photodiode) spatial resolution for less than 10 seconds e.g. on a CCD device or photomultiplier with exposure times of 25 milliseconds up to 0.5 seconds. Then the fluorescence excitation is turned off.

Step 2, Starting of Infrared Laser Heating:

The infrared heating laser is turned on and the spatial temperature distribution is established within a few milliseconds within the solution. The temperature gradient has been calibrated once and it is not necessary to repeat this calibration every time an experiment is performed. In particular a setup where infrared heating and fluorescence imaging are performed through the same optical element from one side is advantageous for the stability of the optical and infrared foci.

A decrease of fluorescence due to photobleaching lower than 5% is advantageous in the experiment. In particular embodiments of the invention, no correction for photobleaching is necessary.

In some particular embodiments for measuring thermophoretic properties, the maximal temperature is below the temperature which is known to cause damage to the molecules in the solution or disturb their interaction (e.g. temperatures between 1 and 5° C. above ambient temperature).

Depending on the thermophoretic properties of the particles or molecules in the solution (i.e. if they move fast in a thermal gradient or slow) the infrared laser heats the solution for 5 seconds up to 100 seconds, preferably for 5 seconds up to 50 seconds, more preferably for 5 seconds up to 20 seconds.

Step 3, Recording of the Spatial Fluorescence (i.e. Concentration) Profile:

After this period of time, the fluorescence excitation is turned on and images are recorded with the same frame rate and length as described in step 1b. Step 3 is the last acquisition step necessary for evaluation of thermo-optical properties.

For detection and quantification of interactions more measurements following the protocol described previously are necessary. Step 1a is repeated with sample buffer and in step 1b the aqueous solution of a fluorescently labelled sample is mixed with an amount of the biomolecule with which the interaction should be detected or quantified. For example, in the detection of an interaction of particles and/or molecules, the fluorescently labelled sample (comprising one binding partner) is mixed with a sufficient amount of the second binding partner so that a substantial amount of the fluorescently labelled molecule or particle is in the complex with the binding partner. If the strength of the interaction is to be quantified in terms of e.g. a dissociation or association constant (Ka, Kd), than the procedure described previously may be conducted with varying concentrations of binding partner (e.g. 0.1×-10× the concentration of the fluorescently labelled binding partner). This means that a titration of binding partner may be performed.

Processing the Raw Data:

Optionally, a (linear) bleaching correction can be performed for which it is advantageous to wait for the back-diffusion of all molecules following the end of step 3. This increases the time consumption of the analysis dramatically. For precise and fast measurements it is advantageous to determine the strength of bleaching from image to image and correct every individual image with its own bleaching factor. For a precise bleaching correction it is advantageous that the temperature gradient at distance from the heat spot is low (e.g. below 0.001 K/μm). The images taken in step 1b are used to correct all images for inhomogeneous illumination. In case fluorescence is recorded without spatial resolution (e.g. avalanche photodiode or photomultiplier) photobleaching is corrected best by determining once the bleaching characteristic of a certain dye without heating laser in a control experiment.

Data Evaluation:

Qualitative detection of interaction: From the image series the spatial fluorescence distribution of the reference experiment (i.e. fluorescently labelled to molecule/particle without binding partner) and the second experiment (i.e. were the binding partner is present) is extracted. The fluorescence is plotted versus the distance from the heat spot. An averaging is only possible for pixels with the same temperature and same distance. The spatial concentration distribution is obtained by correcting the fluorescence intensities for the respective temperature dependence of the dye. With knowledge of temperature dependence of the fluorescent dye and the spatial temperature distribution, the effect of a decreasing fluorescence due to temperature increase can be corrected. In particular embodiments, a correction for temperature dependency is not necessary for the qualitative detection of interaction as well as their quantification, and the spatial fluorescence distribution is sufficient. Any fluorescent dye on the market may be used, in particular embodiments even without characterization of its temperature dependency. The fluorescent properties of a dye may vary with buffer conditions, such as pH.

The values of the fluorescence profile are integrated up to the distance were the temperature is below e.g. 10% of the maximum temperature (e.g. 70 μm). The integrated values are compared and a change give a precise indication if there is an affinity between the substances at the concentrations used, since the interaction changes the thermo-optic properties (e.g. thermophoretic mobility, surface size and chemical groups on surface). In most cases, the interaction leads to higher fluorescence (concentration) at higher temperatures In case the whole cross-section of a capillary is heated (i.e. using e.g. cylindrical lenses to give the IR laser beam a ellipsoidal shape, which heats a cross section of a capillary homogeneously), the intensity of two or more pixels from the centred heat spot may be averaged. In particular embodiments all pixels at the same distance to the heated line have the same temperature. This is advantageous for high precision measurements. In case fluorescence is recorded without spatial resolution, the fluorescence change in the centre of the heat spot/line is measured. In particular embodiments it may be advantageous to heat the whole cross section. In general if more than a single frame is recorded in step 1b and 3 an integration of multiple frames is possible.

For a quantification of molecular affinities or particle affinities the same procedure is performed for all experiments at various concentrations of non-fluorescent binding partner. The result of the integration for the reference experiment (i.e. without binding partner) is subtracted from the integrated values obtained for the different concentrations of binding partners. From this evaluation, the amount of interacting complexes in arbitrary units may be obtained. By dividing these values by the value where binding is saturated, the relative amount of formed complexes between the interacting molecules, particularly the binding partner, at a certain concentration of binder may be obtained. From these datasets also the concentration of free, e.g. non-fluorescent, binding partner may be determined and the strength of the interaction may be quantified in terms of association or dissociation constant (see also appended examples).

As mentioned previously, it is also possible to detect the binding of molecules to larger inorganic particles or nanocrystals using the procedure described previously and herein below. Inorganic particles, e.g. CdSe particles, may be modified with a varying numbers (e.g. 1, 2, 3, or 3 or more, yet preferably up to 3) of Poly-ethylen-glycol (PEG) of different molecular weight. In particular embodiments, 1 to 3 Poly-ethylen-glycol (PEG) molecules are attached to the particles. The spatial fluorescence profile is measured as described herein for the detection of biomolecular interactions (see appended examples). Also the raw data are processed as described herein. To measure the number or size of PEG molecules bound to the particles or nanocrystals, it may be sufficient to compare the spatial fluorescence profiles obtained with the protocol described previously. However, a correction for the temperature dependent decrease of the fluorescence allows a quantification in terms of the Soret coefficient. It is illustrated in the appended figures and examples, particularly in appended FIG. 26, that the Soret coefficient increases linearly with the number of PEG molecules bound to the nanocrystals. The slope of the increase depends on the molecular weight of the PEG. The binding of single molecules of the size of a protein is detectable as illustrated in e.g. appended FIG. 26.

The terms "interaction" or "affinity" as used herein and in particular in the above outlined, non-limiting illustrative experiment not only relates to the interaction of distinct molecules/particles (e.g. intermolecular interactions), but also to intramolecular interactions, like protein folding events and the like.

It is understood by the person skilled in the art that the term "fluorescence" as employed herein is not limited to "fluorescence" per se but that the herein disclosed means, methods and devices may also be used and employed by usage of other means, in particular, luminescence, like phosphorescence. Accordingly, the term "exciting fluorescently said marked particles and firstly detecting and/or measuring fluorescence of said excited particles" relates to the "excitation step" in the above identified method and may comprise the corresponding excitation of luminescence, i.e. excitation is carried out with a shorter wave length than detection of the following emission. Therefore, the term "detecting and/or measuring secondly a fluorescence of the particles" in context of this invention means a step of detection said emission after excitation. The person skilled in the art is aware in context of this invention that the "excitation"-wave length and the "emission"-wave length have to be separated.

According to a first illustrative embodiment of the present invention, the predetermined time (after which (e.g. a fluorescence of) the particles/molecules in the solution are detected and/or measured secondly) is small enough that concentration changes induced by thermophoresis and artefact related to or due to convection are negligible small. In other words, the predetermined time is short enough to separate the inter- and intra-molecular reaction time scale from slower temperature effects, e.g. thermophoresis, thermal convection. Thus, the predetermined time is preferably within the range of from 1 ms to 250 ms, more preferably between 80 ms and 180 ms, in particular 150 ms. In particular, in cases where the solution is provided in a chamber with good thermal conductivity, e.g. sapphire, diamond, and/or silicon, a shorter predetermined time is already sufficient, e.g. 1 ms, 5 ms, 10 ms or 15 ms. For the measurement it is advantageous that the chamber and the solution are in a thermal equilibrium. In other words, for chambers with a good thermal conductivity, the solution and the chamber are faster in a thermal equilibrium such that shorter predetermined times are sufficient. In case the thermal conductivity is poor, it takes longer until the chamber and the solution are in thermal equilibrium, i.e. the predetermined time is longer, e.g. 100 ms to 250 ms.

In particular embodiments of the invention, the detection or exposure time is in the range of from 1 ms to 50 ms. The time in which the detection signal is recorded must be short enough that the change of position of an individual molecule is negligible for the detection during the detection step. For example, in case the detection is conducted with a CCD camera with a resolution of 320×200 pixel, it is advantageous that during detection time an individual molecule/particle will be detected by only one pixel, since each pixel represents a certain temperature. If the position of a particle changes too much, i.e. more than one pixel, the particle may be exposed to a different temperature which decreases the measurement accuracy. The use of a CCD camera device for detection also comprises the use of a camera with only a single line of pixel (e.g. line camera) for one-dimensional detection.

In a particular embodiment of the invention, the laser beam is defocused such that a temperature gradient within the temperature distribution is in the range of from 0.0 to 2K/μm, preferably from 0.0 to 5K/μm. Thus, small temperature gradients ensure that the thermophoretical particle movement is negligible small during the time from the start of laser irradiation to the end of detection.

At least all temperatures needed to detect the thermal denaturation of a molecule have to be within the field of view of the camera device.

According to a further aspect of the present invention, the laser beam is irradiated through one or a plurality of optical elements into the solution. The focusing of the laser beam is in some embodiments performed in such a way that the temperature gradients lie within the above defined ranges. Focusing of the laser can be achieved e.g. by a single lens, a plurality of lenses or a combination of a optical fibre and a lens or a plurality of lenses or an objective where the divergence of the incident laser beam is adjusted properly. Moreover, further optical elements for controlling the focus and or direction of the laser beam may be arranged between the solution and the laser.

According to yet a further embodiment of the present invention, the temperature distribution around the laser beam is measured by an additional measurement, e.g. the temperature distribution is measured under the same conditions on the basis of the known temperature-dependent fluorescence of a dye, as illustrated in the appended figures, in particular FIGS. 3a, 3b and 15. In particular, a temperature distribution may be determined based on detected fluorescence of the temperature sensitive dye, wherein said temperature sensitive dye is heated (via the solution) by the irradiated laser beam and the fluorescence spatial fluorescence intensity is measured substantially perpendicular around the laser beam.

According to a second illustrative embodiment of the present invention, the predetermined time (after which (e.g. a fluorescence of) the particles/molecules in the solution are detected and/or measured secondly) is sufficiently long so that changes of concentration based on the thermophoretical motion can be detected. Thus, the predetermined time is preferably within the range of from 0.5 to 250 s. In said predetermined time the concentration changes within the spatial temperature distribution in the solution due to thermophoretic effects and such an concentration change may be detected by a change of the distribution of fluorescence.

In particular embodiments of the invention the laser beam is focused such that a temperature gradient within the temperature distribution is achieved in the range of from 0.001 to 10K/μm. The temperature within the field of view (particularly at the edge of the field of view) does not necessarily reach the value of ambient temperature. A temperature increase at distance to the heat centre (i.e. at the edge of the field of view) of 10% or less (in ° C.) in comparison to the maximal temperature (in ° C.) is advantageous.

According to a further embodiment, the fluorescence before and after irradiation the laser is detected with a CCD camera. The use of a CCD camera provides the advantage that the concentration change can be detected at a plurality of positions simultaneously. In particular embodiments, the CCD camera is a 2D (two dimensional) CCD camera, i.e., the CCD array comprises a plurality of sensor pixels (photoelectric light sensors) in a first and a second direction, wherein the first and second directions are preferably perpendicular to each other. According to a further embodiment, the CCD camera is a line or line-scan camera, i.e., the CCD array comprises a plurality of sensor pixels in a first direction (a line of sensor pixels) but merely one pixel in a second direction. Such a camera is also referred to as 1D (one dimensional) CCD camera. In other words, a one-dimensional array, used in line-scan cameras, captures a single slice or line of an image, while a two-dimensional array, captures a whole 2D image. The CCD array of the line camera may also comprise three sensor lines, each for one colour channel (Red, Green, and Blue). However, according to a further aspect of the present invention, it is also possible to measure the characteristics of the particles based on a detected fluorescence change of a single pixel of the CCD. Thus, it is also possible to use a photodiode or a photomultiplier instead of a single pixel of the CCD. In some embodiments the brightness of the fluorescence before and after irradiation the laser is measured with a photodiode or a single pixel with the CCD in the centre of the laser beam.

By imaging on a CCD camera device, a line camera or a PMT/Avalanche Photodiode, the fluorescence may be averaged throughout the height of the used liquid sheet. Accordingly, the three-dimensional solution may be reduced to two dimensions. Therefore, the method described in the embodiments is also applicable to two-dimensional lipid sheets, typically used as models system for membrane processes (e.g. surface supported tethered bilayer lipid membrane (tBLM, as illustrated in the appended figures), or classical Langmuir monolayers). Fluorescently labelled compounds floating in this membrane (e.g. lipids, proteins and alike) move in temperature gradients and rearrange according to their solvation energy. The fluorescence redistribution in these lipid layers or membranes may be employed in the context of the invention, like the redistribution of compounds in solution to detect biochemical or biophysical properties or characteristics, like conformational changes, interactions, hydrodynamic radius and the like. In the membrane system, the local temperature distribution is established by the surrounding aqueous solution, e.g. the aqueous solution above a surface supported membrane. By heat conduction the lipid layer above a aqueous solution also adopts the corresponding temperature.

According to the first and second illustrative embodiments of the invention, the particles can be biomolecules and/or (nano- or micro-)particles and/or beads, particularly microbeads, and combinations of those. With the use of modified nanoparticles/microparticles/microbeads proteins, DNA and/ or RNA can be detected by specific bindings of proteins, DNA and/or RNA to the nanoparticles/microbeads, since the specific binding changes the thermophoretic motion of the nanoparticles/microbeads. The velocity of particles larger than 100 nm can be detected by single particle tracking.

The laser light may be within the range of from 1200 nm to 2000 nm. This range is advantageous for aqueous solutions. The hydroxyl group of water absorbs strongly in said wavelength range. Also other solvents with a hydroxyl group like glycerol can be heated by infrared laser heating). The laser is in some embodiments a high power laser within the range of from 0.1 W to 10 W, preferably from 1 W to 10 W, more preferably from 4 W to 6 W. In some embodiments the particle concentrations of an aqueous solution are within the range of from 1 atto Molar (e.g. single particle microbeads) to 1 Molar, preferably from 1 atto Molar to 100 µMolar.

According to a further embodiment, the solution may be a saline solution with concentrations in the range of from 0 to 1M.

According to still a further embodiment of the invention, the spatial temperature distribution generated by the LASER beam is in a range of 0.1° C. to 100° C. The temperature sensitivity of the material of interest sets the limits to the maximum temperature used in experiments. In particular temperature ranges of 0.1° C. to at least 40° C., preferably to at least 60° C., more preferably to at least 80° C. and even more preferably up to at least 100° C. are generated by the LASER beam to measure the DNA stability for example. The person skilled in the art is aware that corresponding temperatures can be achieved by, e.g., cooling of the experimental system as well as by use of LASER with corresponding power. The person skilled in the art is also aware that by cooling the overall sample a higher amplitude of temperature increase (i.e. by laser heating) is possible without causing damage to temperature sensitive materials. Illustrative, but not limiting, temperature ranges and maximum temperatures for different materials and thermo-optical characterizations is given in table 1. Accordingly, also higher temperatures can be achieved in the centre of the heat gradient (point of maximum laser power in and on the sample to be analyzed/characterized) as, inter alia, illustrated in appended FIG. 3. Such high temperatures may be achieved in high pressure chambers. Moreover, in some embodiments a temperature gradient is created within the range of from 0.1 µm to 500 µm in diameter around the LASER beam.

TABLE 1

Illustrative temperature ranges for thermo-optical analytics

| | | | | thermo-optic char.* | | |
|---|---|---|---|---|---|---|
| Sample Material | Stability analysis | Interaction, kinetic events | Hydrodynamic-Radius, length | conformation, structure, chemical modification | Thermo-optic Trap | PCR, LCR, chemical Reaction |
| nucleic acids (DNA, RNA etc.) | p. 0° C.-100° C. mr. p. 20° C.-95° C. mr. p. 30° C.-80° C. ms. p. 30° C.-85° C. | p. 0° C.-80° C. mr. p. 20° C.-80° C. mr. p. 20° C.-40° C. ms. p. 20° C.-30° C. | p. 0° C.-80° C. mr. p. 20° C.-80° C. mr. p. 20° C.-40° C. ms. p. 20° C.-30° C. | p. 0° C.-100° C. mr. p. 10° C.-90° C. ms. p. 20° C.-90° C. | p. 0° C.-80° C. mr. p. 20° C.-60° C. mr. p. 20° C.-40° C. ms. p. 20° C.-30° C. | p. 0° C.-100° C. mr. p. 10° C.-95° C. mr. p. 20° C.-80° C. ms. p. 50° C.-80° C. |
| proteins | p. 0° C.-100° C. mr. p. 20° C.-95° C. ms. p. 30° C.-85° C. | p. 0° C.-40° C. mr. p. 0° C.-30° C. mr. p. 10° C.-20° C. mr. p. 15° C.-20° C. ms. p. 20° C.-25° C. | p. 0° C.-60° C. mr. p. 0° C.-40° C. mr. p. 10° C.-40° C. ms. p. 20° C.-30° C. | p. 0° C.-80° C. mr. p. 20° C.-60° C. mr. p. 20° C.-40° C. ms. p. 0° C.-60° C. | p. 0° C.-40° C. mr. p. 10° C.-30° C. mr. p. 15° C.-30° C. ms. p. 20° C.-30° C. | p. 0° C.-100° C. mr. p. 10° C.-60° C. mr. p. 15° C.-50° C. ms. p. 20° C.-40° C. |
| vesicles, liposomes | p. 0° C.-100° C. mr. p. 20° C.-95° C. ms. p. 30° C.-85° C. | p. 0° C.-40° C. mr. p. 10° C.-40° C. mr. p. 20° C.-40° C. ms. p. 30° C.-40° C. ms. p. 20° C.-25° C. | p. 0° C.-60° C. mr. p. 0° C.-40° C. mr. p. 10° C.-40° C. ms. p. 20° C.-30° C. | p. 0° C.-80° C. mr. p. 20° C.-60° C. mr. p. 20° C.-40° C. ms. p. 20° C.-30° C. | p. 0° C.-40° C. mr. p. 10° C.-30° C. mr. p. 15° C.-30° C. ms. p. 20° C.-30° C. | p. 0° C.-60° C. mr. p. 0° C.-40° C. mr. p. 10° C.-40° C. ms. p. 20° C.-30° C. |
| (Micro-)particles (e.g. silica, | p. 0° C.-100° C. mr. p. 20° C.-95° C. | p. 0° C.-60° C. mr. p. 10° C.-50° C. | p. 0° C.-80° C. mr. p. 0° C.-60° C. | p. 0° C.-100° C. mr. p. 10° C.-60° C. | p. 0° C.-80° C. mr. p. 20° C.-60° C. | p. 0° C.-100° C. mr. p. 10° C.-95° C. |

TABLE 1-continued

Illustrative temperature ranges for thermo-optical analytics

| Sample Material | Stability analysis | Interaction, kinetic events | Hydrodynamic-Radius, length | thermo-optic char.* conformation, structure, chemical modification | Thermo-optic Trap | PCR, LCR, chemical Reaction |
|---|---|---|---|---|---|---|
| polystyrene, etc) | ms. p. 30° C.-85° C. | mr. p. 20° C.-40° C. ms. p. 20° C.-30° C. | mr. p. 10° C.-50° C. ms. p. 20° C.-30° C. | mr. p. 20° C.-40° C. ms. p. 20° C.-30° C. | mr. p. 20° C.-40° C. ms. p. 20° C.-30° C. | mr. p. 20° C.-80° C. ms. p. 50° C.-80° C. |
| PEG | p. 0° C.-100° C. mr. p. 20° C.-95° C. ms. p. 30° C.-85° C. | p. 0° C.-100° C. mr. p. 10° C.-50° C. mr. p. 20° C.-40° C. ms. p. 20° C.-30° C. | p. 0° C.-80° C. mr. p. 0° C.-60° C. mr. p. 10° C.-50° C. ms. p. 20° C.-30° C. | p. 0° C.-100° C. mr. p. 10° C.-60° C. mr. p. 20° C.-40° C. ms. p. 20° C.-30° C. | p. 0° C.-80° C. mr. p. 20° C.-60° C. mr. p. 20° C.-40° C. ms. p. 20° C.-30° C. | p. 0° C.-100° C. mr. p. 10° C.-95° C. mr. p. 20° C.-80° C. ms. p. 50° C.-80° C. |
| Sugar Polymers (e.g. alginate, hyaluroic acids) | p. 0° C.-100° C. mr.p 20° C.-95° C. ms. p. 30° C.-85° C. | p. 0° C.-100° C. mr. p. 10° C.-50° C. mr. p. 20° C.-40° C. ms. p. 20° C.-30° C. | p. 0° C.-60° C. mr. p. 0° C.-50° C. mr. p. 10° C.-40° C. ms. p. 20° C.-40° C. | p. 0° C.-100° C. mr. p. 10° C.-60° C. mr. p. 20° C.-40° C. ms. p. 20° C.-30° C. | p. 0° C.-80° C. mr. p. 20° C.-60° C. mr. p. 20° C.-40° C. ms. p. 20° C.-30° C. | |
| two-dimensional lipidsheets (e.g. containing proteins) | p. 0° C.-100° C. mr. p. 20° C.-95° C. ms. p. 30° C.-85° C. | p. 0° C.-40° C. mr. p. 10° C.-40° C. mr. p. 20° C.-40° C. mr. p. 30° C.-40° C. ms. p. 20° C.-25° C. | p. 0° C.-60° C. mr. p. 0° C.-40° C. mr. p. 10° C.-40° C. | p. 0° C.-80° C. mr. p. 20° C.-60° C. mr. p. 20° C.-40° C. ms. p. 20° C.-30° C. | p. 0° C.-40° C. mr. p. 10° C.-30° C. mr. p. 15° C.-30° C. ms. p. 0° C.-60° C. | ms. p. 20° C.-30° C. |
| (Nano-)particles | p. 0° C.-100° C. mr. p. 20° C.-95° C. ms. p. 30° C.-85° C. | p. 0° C.-100° C. mr. p. 10° C.-50° C. mr. p. 20° C.-40° C. ms. p. 20° C.-30° C. | p. 0° C.-80° C. mr. p. 0° C.-60° C. mr. p. 10° C.-50° C. ms. p. 20° C.-30° C. | p. 0° C.-100° C. mr. p. 10° C.-60° C. mr. p. 20° C.-40° C. ms. p. 20° C.-30° C. | p. 0° C.-80° C. mr. p. 20° C.-60° C. mr. p. 20° C.-40° C. ms. p. 20° C.-30° C. | |
| Inorganic Carbon compounds (e.g. carbon-nanotubes, Buckyballs etc.) | p. 0° C.-100° C. mr. p. 20° C.-95° C. ms. p. 30° C.-85° C. | p. 0° C.-100° C. mr. p. 10° C.-50° C. mr. p. 20° C.-40° C. ms. p. 20° C.-30° C. | p. 0° C.-80° C. mr. p. 0° C.-60° C. mr. p. 10° C.-50° C. ms. p. 20° C.-30° C. | p. 0° C.-100° C. mr. p. 10° C.-60° C. mr. p. 20° C.-40° C. ms. p. 20° C.-30° C. | p. 0° C.-80° C. mr. p. 20° C.-60° C. mr. p. 20° C.-40° C. ms. p. 20° C.-30° C. | |

* The temperatures denoted here give the preferred temperature ranges of the sample at which thermo-optical properties may be measured. The temperature increase induced by laser heating may comprise only a small portion of the overall temperature, e.g. a thermo-optical characterization of nanoparticles can be carried out at 75° C. overall sample temperature with an increase in temperature by laser heating of 5° C.; a protein characterization may be carried out in a sample cooled to 10° C. and heated with an infrared laser to a maximum temperature of 30° C.
p.: preferably, mr. p.: more preferably, ms. p.: most preferably In context of the invention, the term LASER is equivalent to the term "laser" and vice versa.

The present invention also relates to a device for measuring thermo-optically characteristics of particles in a solution, in particular a device for the measurement/characterization of nucleic acid molecules and/or PCR products, in particular and most preferably intermediate or end-products of real-time PCR; of quantitive real-time PCR, of nested PCR, of reverse transcription PCR or of multiplex PCR or devices for the determination of the size of fluorescently labeled nucleic acids in real-time PCR; quantitive real-time PCR, nested PCR, reverse transcription PCR or in multiplex PCR. Such a device comprises a receiving means for receiving particles/molecules, particularly marked or labelled particles/molecules, within the solution, means for exciting the particles/molecules, particularly the marked or labelled particles/molecules, means for detecting the excitation of the particles/molecules, particularly the marked or labelled particles/molecules, and means for obtaining a spatial temperature distribution in the solution. A further device also referred to as device according to the present invention for measuring thermo-optically the characteristics of particles/molecules in a solution comprises a receiving means for receiving marked or labelled particles/molecules within a solution, means for fluorescently exciting the marked or labelled particles/molecules, means for detecting the excited fluorescence in said solution, and a laser for irradiating a laser light beam into the solution to obtain a spatial temperature distribution in the solution around the irradiated laser light beam. Particularly, the laser light may be focussed locally into the solution and the spatial temperature distribution may be obtained by the conduction of the absorbed energy as heat in the solution. By adjusting the focus width of the electromagnetic IR radiation, the spatial dimensions of the temperature distribution can be adjusted, i.e. a broad or a narrow temperature distribution is achieved. Further adjustments to the geometry of the temperature distribution can be achieved by choosing a material for the microfluidic chamber/capillary which exhibits a certain heat conductivity (e.g. high heat conductivity, narrow temperature distribution and vice versa). According to $c/c_0 = \exp[-(D_T/D)(T-T_0)]$ the steady state amplitude of the thermo-optical signal is exponentially related to the increase in temperature. Using the relation shown above, a spatial temperature distribution can be fitted precisely to the spatial concentration distribution by adjusting the $D_T$ and $D$ coefficients. The time it takes the system to reach the steady state has, beside a dependence on D, also a strong dependency on $D_T$ and the temperature gradient. The product of temperature gradient and the thermophoretic mobility $D_T$ gives the velocity with which particles move along the temperature gradient. As a rule-of-thumb, the stronger the temperature gradient and the higher the thermophoretic mobility the shorter is the time needed to measure the thermo-optical properties. Therefore, it is advantageous that a temperature distribution is established on microscopic length scales (e.g. 250 μm) to obtain a strong temperature gradient.

In a particular embodiment of this invention, a device for thermo-optical determination of the size or size distribution of fluorescently labeled nucleic acids in a reaction solution, in particular according to the methods as provided herein, is disclosed, said device comprising: a receiving means for receiving a reaction solution with fluorescently labeled nucleic acids; a laser for irradiating a laser light beam into the solution to obtain a spatial temperature distribution in the solution around the irradiated laser light beam, means for fluorescently exciting the labeled nucleic acids; and means for detecting fluorescence and/or fluorescence distribution of the fluorescently excited nucleic acids; and wherein the device is adapted to perform at least two fluorescence detections at least two predetermined times.

According to further embodiments of the present invention, the means for exciting, preferably fluorescently exciting the particles/molecules or marked particles/molecules may be any suitable device selected from the group consisting of laser, fibre Laser, diode-laser, LED, Halogen, LED-Array, HBO (HBO Lamps are, e.g., Short Arc Lamps in which the Discharge Arc fires in an atmosphere of mercury vapour under high pressure), HXP (HXP lamps are, e.g., short arc lamps in which the discharge arc burns in an atmosphere of mercury vapour at very high pressure. E.g., in contrast to HBO lamps they are operated at a substantially higher pressure and they employ halogen cycle. HXP lamps generate UV and visible light, including significant portion of red light). Further means for exciting as referred to in the specification are also preferably used.

According to particular embodiments of the present invention, the means for detecting the excited particles, particularly for detecting the fluorescence, in the solution may be any suitable device selected from the group consisting of CCD camera (2D or line-scan CCD), Line-Camera, Photomultiplier Tube (PMT), Avalanche Photodiode (APD), CMOS-Camera. Further means for detecting as referred to in the specification are also used in particular embodiments.

The receiving means for receiving the particles, particularly the nucleic acid molecules to be analyzed/measured in accordance with this invention, within a solution may be a chamber, a thin microfluidic chamber, a cuvette or a device for providing the sample in form of a single droplet. Accordingly, the sample may also be provided in a single drop/droplet. According embodiments are also illustrated in the appended examples and figures, see, e.g. example 11 and FIGS. 40 to 42.

The sample probe may be provided within a chamber which has a thickness in direction of the laser light beam from 1 μm to 500 μm, in particular 1 μm to 250 μm, in particular 1 μm to 100 μm, in particular 3 μm to 50 μm, in particular 5 μm to 30 μm. A person skilled in the art will understand that the term "chamber" also relates to e.g. a capillary, microfluidic chip or multi-well plate. However, as pointed out above, the sample may also be provided in form of drop/droplet. In some embodiments the chamber has the same width as the dimension in direction of the laser light (e.g. a capillary). In combination with a corresponding ellipsoidal laser heating geometry such a system can be reduced from radial symmetry to a single dimension since a CCD camera with only a single line of pixels (line-scan CCD) can be used to integrate the fluorescence of the whole width of the chamber. In a particular embodiment, receiving means for receiving the marked particles within a solution alias specimen holder is attached to an optical element, such as an objective. Such a setup avoids relative movements of the specimen holder with respect to the objective. Further means for receiving as referred to in the specification are also used in some embodiments.

The laser for irradiation the laser light may e.g. be an IR laser, e.g., a laser with a wavelength between 1200 and 2000 nm, preferably of 1455 nm and/or 1480 nm and a radiation power of 0.1 to 10 W. The light of the Laser may be coupled into the device of the present invention by means of optical units like laser fibres (single mode or multimode) with or without collimator. Further means for irradiating as referred to in the specification are also used in some embodiments and are within the normal skill of the artisan.

The device according to the present invention may further comprise a control unit for controlling the means for exciting the particles and/or the means for detecting the excited particles. In particular, the control unit is adapted to enable the device of the present invention to perform the method steps as discussed with regard to the present inventive method.

The control unit may control the type (e.g. wavelength), the intensity, the duration, and/or the time for start and stop of the irradiation of the means for the excitation. For instance, in a particular embodiment in which the means for excitation is a laser, the duration and/or the start and stop time for generating a laser beam may be controlled by the control unit.

The control unit may further or alternatively control the exposition, the sensitivity, the duration, and/or the time for start and stop time for detecting/measuring by means of the means for detecting. For instance, in a particular embodiment in which the means for detecting is a CCD camera, the exposition timing of the CCD camera may be controlled by the control unit.

The control unit may be further adapted to control the means for detecting dependent on functional state of the means for exciting. In particular, it may be advantageous to synchronize the timing of excitation with the timing of the detection. For instance, in a particular embodiment in which the mean for excitation is a laser and the means for detecting is a CCD camera, the exposure timing of the CCD is synchronized with the irradiation of the laser. This may be achieved by controlling the CCD and the laser directly, e.g. by switching on and off the CCD and the laser synchronously.

The control unit may alternatively or additionally control means, in particular optical means, which are arranged between the means for the excitation and the receiving means and/or are arranged between the means for the detecting and the receiving means.

The device according to the present may comprise at least a shutter arranged between the receiving means for receiving the marked particles/molecules and the means for exciting the particles/molecules, in particular the laser. The device according to the present may additionally or alternatively comprise at least a shutter arranged between the receiving means for receiving the marked particles and the means for detecting the particles/molecules, in particular the CCD camera. Such a shutter may be controlled by the control unit in order to adapt the timing of the step of excitation with the timing of the detection.

A single control unit may fulfil the functions of several items, i.e. the control unit may comprise a plurality of sub-units which are adapted for controlling particular means.

The device according to the present may further comprise at least a beam splitter and/or a mirror, e.g. a dichroic filter or dichroic mirror, i.e. a colour filter used to selectively pass light of a small range of colours while reflecting other colours, or a AOFT. The dichroic mirror may reflect short wavelength (reflectance >80%) and transmit long wavelength (transmission >80%). The dichroic mirror may e.g. comprise an IR-transmission larger than 90% and a at least a reflectance for wavelength between 350 to 650 nm. In some embodiments, instead of a dichroic mirror a silver mirror may be used. The (dichroic) mirror may be arranged in a fixed position within the device. However, according to some embodiments, the (dichroic) mirror may be movable, e.g. driven by a driving means (which may be controlled by the control means).

The device according to the present may comprise at least an emission and/or excitation filter (band pass/long pass) for filtering specific wavelength.

In other words, the device according to the present invention may also comprise optical means arranged between the receiving means for receiving the marked particles and the means for detecting the particles and/or between the receiving means for receiving the marked particles and the means for exciting the particles. Such optical means may be adapted for controlling the propagation direction of light by way of transmission or reflection and/or for filtering or separating different wave length by (dichroic) filters. Such optical means may be passive optical means or active optical means which may be controlled by the control unit. For instance, there may be arranged a scanning module (e.g. a Galvano scanning mirror) between the receiving means for receiving the marked particles and the means for exciting the particles. The scanning range and timing of such a scanning module may be controlled by the control unit, preferably in dependency with the control of the means for receiving and/or means for exciting.

Optical means which are advantageous for the device according to the present invention, in particular to perform the method steps of the present invention are exemplified above and below. In particular a plurality of optical means which are useful for a device of the present invention are illustrated in the detailed description of the invention.

According to a further embodiment of the invention, the irradiation of the laser and the detection of the fluorescence is conducted from different directions, e.g. the irradiation is from below and the detection is from above the sample (as illustrated in the appended figures, particularly FIG. 1). However, the means for irradiation and the detection can be arranged on the same side with respect to the sample probe (see e.g. FIG. 2). The device according to the present invention may have any orientation with respect to the direction of gravity, i.e., the device may e.g. be oriented substantially perpendicular, parallel or anti-parallel with respect to the direction of gravity. In context of the thermo-optical measurement/characterization of nucleic acid molecules, in particular in the thermo-optical measurement/characterization of nucleic acid molecules, more preferably in the thermo-optical measurement/characterization of intermediate as well as end-products of polymerase chain reactions, illustrative devices are illustrated in appended example 11 and appended FIGS. 40 to 42

The sample probe may be provided in a chamber as well as in form of small liquid volumes, like drops/droplets. The thickness of the sample probe in the chamber or the drop/droplet in direction of the laser light beam is preferably small, e.g. from 1 µm to 500 µm, in particular 1 µm to 250 µm, in particular 1 µm to 100 µm, in particular 3 µm to 50 µm, in particular 5 µm to 30 µm. A person skilled in the art will understand that the term chamber also relates to e.g. a capillary, microfluidic chip or multi-well plate. In a further embodiment the chamber has the same width as the dimension in direction of the laser light (e.g. a capillary). In combination with the corresponding ellipsoidal laser heating geometry such a system can be reduced from radial symmetry to a single dimension. A CCD camera with only a single line of pixels can be used to integrate the fluorescence of the whole width of the chamber. Furthermore only a single pixel (or a photodiode or photomultiplier) mapped to the centre of the heat spot can be used for detection of interactions, conformation etc. It is illustrated in the appended figures, particularly FIG. 27, how a capillary is used for thermo-optical characterization. A capillary may be placed on a solid support/specimen holder/stage with good heat conducting properties. The solid support/specimen holder/stage may be cooled or heated by a Peltier element. By using a Peltier element the "ambient temperature" of the solution can be adjusted. It is advantageous to measure the protein conformation at different temperatures, to adjust thermophoresis of (bio)molecules/(nano)particles/(micro)beads to a value close to the sign change of thermophoresis (i.e. that a binding event changes the thermophoretic behaviour from accumulation at higher temperatures to depletion from higher temperatures). A cooling of the chamber allows to heat temperature sensitive molecules with a much higher laser power. In further embodiments valves are put at the end of the capillary to exclude any drift of the liquid inside the capillary. Often drift is caused by evaporation at the end of a capillary.

For the detection/measurement of intermediate or end-products of PCRs, in particular in the thermo-optical measurement/characterization of nucleic acid molecules generated during such PCRs (e.g., in context of this invention reverse transcription PCR, real-time PCR; quantitive real-time PCR or in multiplex PCR) it is envisaged that the receiving means for receiving the nucleic acid molecules to be analyzed in accordance with this invention may be a drop/droplet.

The person skilled in the art understands that the terms "drop" or "droplet" relates to an amount of liquid with a volume of a few picoliter up to milliliter. The shape of the liquid is predetermined by the properties of the surface(s) it is in contact with. (i.e. on a hydrophobic surface the liquid has the tendency to have a high contact angle; while it spreads out on a hydrophilic surface). The shape also depends on the substances/molecules dissolved in the liquid. On surfaces which are nonuniform with respect to their hydrophilic/hydrophobic properties (e.g. artificially patterned surfaces) the shape of the liquid may have an arbitrary form e.g tube shaped. Small amounts of liquids for molecular reactions, like amplifications are known in the art and have, inter alia, be employed in WO02/85520. Therefore, it is also possible to provide the sample probe/reaction mixture without a chamber, namely in form of a drop or a droplet, e.g. buffer droplet.

In some embodiments of the invention the fluorescence is detected within a range of from about 50 nm to 500 µm in direction of the laser beam.

In further embodiments the fluorescence is detected substantially perpendicular with respect to the laser light beam with a CCD camera. The second fluorescence detection is in some embodiments a spatial measurement of the fluorescence in dependence of the temperature distribution substantially perpendicular with respect to the laser light beam.

The appended figures show particular, non-limiting setups for devices in accordance with the present invention in accordance with the present invention. These devices are particularly useful in measuring thermophoresis. Common to all of them is that fluorescence imaging and the infrared laser focussing are performed through the same optical unit, e.g. through the same objective. Particularly, an objective with very low refraction of the IR light may be used. This is beneficial because a local spatial temperature profile on the micrometer scale is advantageous and desired in context of the means and methods provided herein. High refraction of IR light by the objective may lead to a broad temperature distribution with a high background temperature elevation. To solve this less advantageous effect, an objective with high transmission in the IR region of the electromagnetic spectrum (preferably at 1200-1600 nm, i.e. corrected for IR radiation) may be used. An objective which comprises only a small number of lenses (i.e. objective with less correction for visible wavelengths) is here preferred. As described herein, if a microfluidic chamber with a high aspect ratio (length/width) is used it may be advantageous to change the IR laser beam profile to an ellipsoidal form, to homogeneously heat the whole cross section of the capillary. This allows, inter alia, high precision measurements with a line camera, photodiode or photomultiplier. A line camera provides merely line resolution along the capillary and averages the spatial fluorescence of a whole cross section (width) of the capillary.

The photodiode or photomultiplier has no spatial resolution, but it is positioned in a way to measure the fluorescence in the central heated region. Such a positioning is within the normal skills of the person skilled in the art. Both, line camera and photodiode combined with an ellipsoidal illumination of the microfluidic chamber (i.e. capillary) are used in some embodiments of the invention for data acquisition.

Appended FIG. 23 illustrates an embodiment, wherein the simultaneous detection of two or more different fluorophores/marked particles is documented. The different emission wavelength of the two or more marked particles/molecules are splitted e.g. via a dichroic mirror or AOTF into two or more different directions. In this embodiment, one detection channel can for example be used to measure the temperature via the temperature dependent fluorescence of a dye, e.g. Cy5 at a wavelength for example 680 nm+/−30 nm. In the other channel the melting curve of a marked particle/molecule can be recorded at a wavelength of for example 560 nm+/−30 nm. It also allows for the parallel detection of particles/molecules, e.g. different particles/molecules, with e.g. different luminescent or fluorescent markers.

An advantage of the present invention, is that, in contrast to the prior art, now particles, in particular and as exemplified, (bio)molecules (in particular nucleic acid molecules) or (nano- or micro-)particles or (micro)beads can be measured/determined/characterized by employing spatial temperature distributions with μm resolution.

Accordingly, with the means, methods and devices provided herein it is, inter alia, possible to measure, detect and/or verify biological, chemical or biophysical processes and/or to investigate, study and/or verify samples, like biological or pharmaceutical samples. Also diagnostic tests are feasible and are embodiments of this invention. It is in particular feasible to measure the length of nucleic acid molecules (like DNA, RNA), to measure the melting features of nucleic acid molecules, like, e.g. of double-stranded DNA or double-stranded RNA (dsDNA/dsRNA) or of hybrid nucleic acid molecules, like DNA/RNA hybrids, to measure and or analyze nucleic acid sequences, like the detection and/or measurement of Single Nucleotide Polymorphisms (SNPs) (see also appended figures, in particular FIG. 4) or to measure the stability of nucleic acid molecules in correspondence and as a function of their relative length; to measure and/or verify PCR end products, e.g. in general medical diagnostic, also in polar-body diagnostic, pre-implantation diagnostic, forensic analysis. Accordingly, it is evident for the skilled artisan that the means and methods provided in this invention are, particularly and non-limiting, useful in measurements and/or verifications wherein the length, size, affinities to other molecules/particles of a given particle/molecule is of interest. For example, the methods provided herein as well as the devices are useful in the detection and measurement of length, temperature stability as well as melting points of nucleic acid molecules, in particular nucleic acid molecules. Therefore, it is within the scope of the present invention that, for example, (DNA-) primers and (DNA- or RNA-) probes are measured and or verified after or during their synthesis. Also the measurement of nucleic acid molecules on templates or matrices, like DNA-chips is envisaged. The term melting in context to this invention refers to the thermal denaturation of biomolecules, like nucleic acids (e.g. RNAs, DNAs) or proteins. In a most preferred embodiment of the present invention, means, methods and devices for the thermo-optical measurement/characterization of nucleic acid molecules during or after PCR reactions is provided. Corresponding illustrative examples and figures are provided herein below in Example 11 and in FIGS. 40 to 42.

Therefore, the present invention is in particular useful in the characterization of intermediate or end-products of PCR reactions, for example reverse transcription PCR, real-time polymerase chain reactions (RT-PCR), multiplex PCRs or quantitive real-time PCRs.

Also envisaged in context of the present invention is the measurement, detection and/or verification of mutations and genetic variations in nucleic acid molecules, for example in form of single-strand conformational polymorphisms (SSCPs) or in form of restriction fragment length polymorphisms (RFLPs) and the like. The present invention also provides for the possibility to analyze heteroduplexes. Heteroduplexes are generated by heat denaturation and reannealing of a mixture of. e.g. wild type and mutant DNA molecules. In particular it is also possible to measure the effect of protein binding to a DNA molecule on the stability of the latter. Furthermore it is possible to measure the thermal stability of proteins and the effect of molecules (e.g. small molecules, drugs, drug candidates) on the thermal denaturation.

Also within the scope of the present invention is, e.g., the measurement of protein-protein interactions, like complex formations of proteinaceous structures or of proteins or of fragments thereof. Such measurements comprise, but are not limited to the measurement of antibody-antigen binding reactions (also in form of single chain antibodies, antibody fragments, chromobodies and the like). Yet, the embodiments of the present invention are also related to the detection and or measurement of dissociation events, like, e.g. the dissociation of protein complexes. Therefore, the invention is also useful in the measurement, determination and/or verification of dissociation events, like in the measurement of the dissociation of proteinaceous complexes, e.g. antibody-antigen complexes and the like. The appended figures also show that the means and methods provided herein are useful, for example, in the measurement of melting curves for nucleic acid molecules, proteins and corresponding analyses.

It is understood by the person skilled in the art that the term "modified microparticle/nanoparticle" as employed herein is not limited to "microparticle/nanoparticle" per se but that the herein disclosed means, particles and materials may also be used and employed by usage of other means, in particular, colloidal means, like foams, emulsions and sols.

As microparticles show a very strong thermophoresis, they can be used as a carrier material for the detection and characterisation of for example biomolecules, like proteins or nucleic acids. By using microparticles, the thermophoresis signal of e.g. the biomolecules may be enhanced. The attraction of a microparticle to an extreme value (e.g. the temperature maximum) of the spatial temperature distribution due to thermophoresis may be strong enough to trap the microparticles there (data not shown).

A microparticle is a particle with a characteristic length of less than 1 mm and more than 100 nm without restriction of the material (e.g. coated or uncoated silica-/glass-/biodegradable particles, polystyrene-/coated-/flow cytometry-/PMMA-/melamine-/NIST particles, agarose particles, magnetic particles, coated or uncoated gold Particles or silver Particles or other metals, transition metals, biological materials, semiconductors, organic and inorganic particles, fluorescent polystyrene microspheres, non-fluorescent polystyrene microspheres, composite materials, liposomes, cells and the like).

A nanoparticle is a particle with a characteristic length of less than 100 nm without restriction of the material (e.g. quantum dots, nanocrystals, nanowires, quantum wells).

Particles or beads according to this invention may be modified in such a way that for example biomolecules, e.g. DNA, RNA or proteins, may be able to bind (in some embodiments specifically and/or covalently) to the particles or beads. Therefore, within the scope of this invention is the thermo-optical analysis of characteristics of beads and/or particles and in particular of molecules attached to or linked to such beads or particles. In particular, such molecules are biomolecules. Accordingly, the term "modified (micro)beads/(nano- or micro)particles", in particular, relates to beads or particles which comprise additional molecules to be analyzed or characterized (data not shown). Modified or non-modified microparticles/(nano- or micro)particles may be able to interact with other particles/molecules such as biomolecules (e.g. DNA, RNA or proteins) in solution. The skilled person understands that the thermophoretic properties of the modified particles will change upon binding of the biomolecules in solution to the biomolecules bound to the particle as modification. Such an interaction may influence the force acting on the (modified) particle/molecule. By adjusting the IR-Laser irradiation, the resulting movement can be influenced in such a way that the particle/bead is trapped. "Trapping" the particle/bead, in particular particles/beads comprising biomolecules, means that the particle/bead stays within a certain position, only showing comparably low fluctuations. These fluctuations are different from fluctuations based on Brownian motions. When a biomolecule from solution binds to the biomolecular-modified particle, the force acting on the particle/bead will change due to a change of the thermophoretic properties, which may result in movement of the particle out of the certain position where the particle/bead was trapped or/and in a change of the fluctuations of the particle/bead. The method described here is termed "Thermooptical Trap" and is particularly useful in certain embodiments described herein. The "Thermooptical Trap" is also illustrated in the appended examples and figures. Other synonyms for "Thermooptical Trap" are "Optothermal Trap", "Thermophoretic Trap" as well as "Optothermal Tweezers" or "Thermophoretic Tweezers".

The invention, accordingly, also relates to an optothermal trap. The terms "thermo-optical", "thermooptical", "opto-thermal" and "opto-thermal" are used synonymously. This particular embodiment of the invention illustrates that given targets, e.g. fluorescently labelled modified beads/particles with a size of 100 nm up to several μm (e.g. polystyrene beads or silica beads) and lipid vesicles and cells are showing a directed movement to the temperature maximum of a spatial temperature distribution generated by applying IR-Laser radiation to an aqueous solution as illustrated in the appended figures.

As shown in the appended example, the devices and the methods of the present invention may also be employed for thermophoretic trapping of molecules or particles, including lipid structures (like vesicles or liposomes) as well as cellular components of even cells. It is also envisaged that the devices and methods of the present invention is used for thermophoretic trapping of cells or cellular components, like cell nuclei, chromosomes, mitochondria, chloroplasts and the like. The thermophoretic trapping as shown herein is particular useful for studying interactions of e.g. proteins (e.g. with other proteins, for example antibody-antigen interactions and the like), for studying transport events across membranes (e.g. vesicles or liposomes), for determination of activity of membrane proteins comprised in biological membranes/vesicles/liposomes, like ion pumps, membrane transporters and the like. Also, the mere presence of molecules, particles, liposomes, vesicles, beads, cells or cellular components in said solution can be detected and/or analyzed by use of the herein disclosed thermophoretic trapping devices and methods. Thermophoretically trapped molecules, particles, vesicles, beads, cells or cellular components and the like can be transported and moved within the analyzing solution (see also appended figures). It is envisaged that thermophoretically trapped molecules, particles, liposomes, vesicles, beads, cells or cellular components be exposed to different buffer solutions for certain applications, i.e. buffer around the trapped molecules, particles, vesicles, beads, cells or cellular components etc. may be exchanged and corresponding measurements can be carried out. Further embodiments in context of the thermophoretic trapping in accordance with this invention are also provided in the appended examples. It is evident for the person skilled in the art that the concepts of thermophoresis as disclosed herein can also be employed for example in sorting of vesicles, cellular components (like e.g. mitochondria, chloroplasts, nuclei, chromosomes) or even whole cells. Accordingly, the present invention also provides for a method to thermo-optically trap molecules, particles, vesicles, beads, liposomes, cells or cellular components etc., said method comprising the steps of providing a sample probe with (preferably marked) molecules, particles, vesicles, beads, liposomes, cells or cellular components; irradiating a laser light beam into the solution to obtain a spatial temperature distribution in the irradiated laser light beam; optionally detecting the (preferably marked) molecules, particles, vesicles, beads, cells or cellular components; and trapping the (preferably marked) molecules, particles, vesicles, liposomes, beads, cells or cellular components in accordance to the thermophoretic mobility of said molecules, particles, vesicles, beads, cells or cellular components. For example, the (preferably marked) molecules, particles, vesicles, beads, cells or cellular components can be trapped in center of the laser-generated heat spot (in particular when thermophoretic mobility of the trapped molecules, particles, vesicles, liposomes, beads, cells or cellular components etc is negative). However, the (preferably marked) molecules, particles, vesicles, beads, cells or cellular components can also be trapped in a (global or local) temperature minimum, in particular, when the thermophoretic mobility of the trapped molecules, particles, vesicles, beads, cells or cellular components etc is positive. The person skilled in the art is aware that the term "thermophoretic mobility", DT refers to a coefficient which relates the velocity (v) of a given molecule/particle/bead etc to the temperature gradient ($\nabla T$), according to $v=-D_T \nabla T$.

The embodiments provided herein above in context of the method for measurement of thermo-optical characteristics of particles/molecules etc. in a solution apply to the method of thermo-optically trapping molecules, particles, vesicles, beads, liposomes, cells or cellular components, etc mutatis mutandis. Also devices for the thermo-optically trapping are provided herein and are also illustrated in the appended figures, for example the device as shown in appended FIG. 19 or 24. A corresponding device comprises, accordingly, an IR laser for irradiating a laser beam into the solution containing the (preferably marked) molecules, particles, vesicles, beads, liposomes, cells or cellular components to be trapped, to obtain a spatial temperature distribution in said solution around the irradiated laser light beam. Said device for thermo-optically trapping (preferably marked) molecules, particles, vesicles, beads, liposomes, cells, cellular components, etc, may therefore comprise: (a) a receiving means for receiving (optionally marked) molecules, particles, vesicles, beads, cells, cellular components, etc within a solution; (b) (optionally) means for fluorescently exciting the marked particles; (c) (optionally) means for detecting the excited fluorescence in said solution; and (d) an IR laser for irradiating a laser light beam into the solution to obtain a spatial temperature distribution in the solution around the irradiated laser light beam.

The movement of molecules, particles, vesicles, liposomes, beads, cells, cellular components, etc. can be described by a thermophoretic force acting on the particle. Presuming thermodynamic equilibrium, this force may be derived from the Gibbs free enthalpy at constant pressure:

$$F = -\tfrac{1}{2} * S_T * k_B * \mathrm{grad}(T^2)$$

Where $S_T$ is the Soret coefficient and $k_B$ the Boltzmann constant.

The temperature T is a function of x and y: $T=T(x,y)$. For example, in a radial symmetric geometry like the spatial temperature distribution generated by a focused IR-laser (as illustrated in the appended figures, particularly in FIG. 3a) it can easily be seen that the force can attract a particle to the maximum of the spatial temperature distribution. If $S_T<0$ this results in a force trapping the given target particle/bead, e.g. a silica microparticle, preferably a coated silica microparticle, at the maximum (local or global) of the temperature distribution.

In contrast to the optical tweezers/optical trapping known from the art, the thermo-optical trap according to the present invention is based on different principles. Instead of using an electromagnetic field gradient as used for optical tweezing, a temperature gradient is used to trap, move and control a particle according to the present invention. Therefore, no sophisticated confocal optic is necessary in some embodiments of the thermo-optical trap. Using temperature gradients also allows for attraction of molecules from distances of 1 μm to several hundred micrometer distance to the laser focus, depending on the width of the temperature gradient (e.g. the width of the IR laser focus). Compared to the thermo-optical trap, the catchment region for optical tweezers is very narrow on the order of a few micrometer.

As shown in the appended Example 1, the Soret coefficient $S_T$ is a function of the surface area A of the target particle, e.g. the bead, the quadratic effective charge $\sigma_{e\!f\!f}$ and particle-area-specific hydration entropy $s_{hyd}$. So the thermophoretic force will also be proportional to this particle properties.

If one of this properties changes (preferably the effective charge or the hydration entropy), the trapping force changes also. If the trapping force/the trapping potential changes, the fluctuations (as also illustrated in the appended FIG. 32) also change By recording the fluctuations of the particle, a change in the thermophoretic properties of the particle can be detected and so the binding of for example biomolecules to this particle/bead can be detected.

In case of a particle/bead, e.g. a silica microparticle, preferably a coated silica microparticle, more preferably a silica microparticle coated with special groups on its surface (e.g. proteins). These groups may be able to specifically bind to proteins, antibodies, small molecules, DNA, RNA etc. If there is a binding of one of this species to the specific group on the bead/particle, the properties (for example the surface A) of the particle, e.g. bead changes, which may result in a different $S_T$ and thus to a different thermophoretic force F (e.g. the sign/direction of the force may change).

A particular embodiment of the invention relates to the measurement of the fluctuations of such a given target particle/molecule in the maximum of the temperature distribution by detecting its position via measurement of fluorescence or the like. When the particle/molecule is trapped in the temperature distribution, the solution around it can be easily exchanged with a solution containing non-labelled or labelled molecules which are envisaged to bind to the "trapped" particle, e.g. when modified in a way that allows the specific binding (e.g. by antibodies). A binding event may be detected by a change in the amplitude of fluctuations (i.e. the potential in which the particle is trapped changes due to the binding of molecules to the particle's surface). By detecting the time dependent characteristics of the variation in amplitude, a binding kinetic can be measured and established.

In a further particular embodiment of the invention, the change in sign of $S_T$ of the target particle may be exploited. If $S_T<0$ a particle, e.g. a bead or a fluorescent silica microparticle, with specific binding groups/sites is trapped at the maximum temperature in the spatial temperature distribution. If $S_T$ of the target particle changes its sign upon e.g. crowding or linking of the binding groups with molecules e.g. small molecules, the target particle is forced away from the maximum of the spatial temperature distribution and the particle, e.g. bead, experiences repulsion instead of attraction, resulting in a detectable qualitative change of the behaviour of the target particle. For example if the force changes from attraction to repulsion, the particle may move away from the maximum of the spatial temperature distribution. Thereby, molecules, e.g. small molecules, binding to said binding groups at the surface of the particle/bead, may be detected. The binding of molecules, e.g. small molecules, can easily be measured just by simple particle tracking methods. The particle can be brought to conditions close to a sign change by changing the buffer conditions (e.g. salt concentration) the temperature of the solution or by specific modifications with e.g. hydrophobic or charged molecules. It is evident that the term "target particle" or "target bead" also relates in this embodiment to correspondingly modified particles and beads, like particles/beads comprising or linked to biomolecules or particles/beads coated with such biomolecules. Therefore, the above recited embodiments for "particles/beads" and in particular modified particles/beads apply here mutatis mutandis.

The force acting on the target particle, e.g. a silica microparticle coated with special groups, can be measured by tracking its position by an appropriate method like fluorescence (if the particle is fluorescently excitable), phase contrast, interference, farfield imaging etc.

It is also possible to apply a second force onto the target particle, e.g. a specifically coated magnetic microparticle, in a way that the resulting force is a superposition of the thermophoretic force and the second force (e.g. a magnetic force). The second force can be for example a magnetic force (for magnetic particles) or an electric force (for charged particles) or a hydrodynamic force or another optical force like it is generated by an optical tweezers.

Then the resulting superposition of forces may then be measured, for example by measuring the fluctuations of the particle (as also illustrated in the appended FIG. 32). This superposition may be used to increase the sensitivity of the method for example by using counteracting forces in such a way that a small change in one of the properties of the target particle/bead, will result in a movement of the target particle/bead, whereas without a change in the properties of the particle/bead, the particle/bead stays at the same place. The increase of sensitivity may be due to the possible minute adjustability of the second force (e.g. a magnetic force).

The "Thermooptical Trap" can also be used to move a target particle/molecule, e.g. a bead/particle, in two dimension perpendicular to the axis of the incident IR-Laser radiation. If the focus of the IR-Laser is moved for example by use of galvanic mirrors or an acoustic optic deflector (AOD) the resulting maximum of the spatial temperature distribution is also moved and so is the target particle/molecule/bead. Or vice versa, the chamber may be moved and the IR-Laser focus is kept fixed (data not shown).

Using a variety of IR-Laser focal spots lots of particles/beads/molecules can be moved simultaneously, giving the opportunity of multiplexing and also of combining different target particles, e.g. specifically coated microparticles, with each other. So if there is one target particle with an antibody and another target particle with the corresponding antigen, the target particles can be moved by two IR-Laser foci until they are in contact and the antibody binds to the antigen. In this way the target particles/molecules bind to each other and a composition of particles may be created.

In accordance with this invention, it is also possible to generate an interference pattern of the IR-Laser radiation, resulting in a spatial grating of temperature maxima. With this spatial grating of spatial temperature distribution target particles/molecules can be trapped and they can also be moved by moving the interference pattern.

As also demonstrated in the appended figures, the present invention is useful in the determination of single or double stranded nucleic acid molecules (see, e.g. appended FIGS. 5a-5b). This allows, inter alia, to determine in a given probe/sample whether it comprises single and/or double stranded nucleic acid molecules. This is in particular relevant in cases when it has to be determined whether a given biological sample comprises, e.g. viral nucleic acids, like single stranded DNA or single stranded RNA. Particularly useful are the means, methods and devices of the present invention in context of the thermo-optical characterization of nucleic acid molecules, for example as intermediate or end-products of PCR reactions and most preferably in context of reverse transcription PCR, real-time polymerase chain reactions (RT-PCR), multiplex PCRs or quantitive real-time PCRs.

The person skilled in the art is aware of the basic principles of PCRs. Polymerase chain reaction (PCR) itself is the process used to amplify specific parts of a nucleic acid molecule, i.e. aDNA molecule, via the temperature-mediated enzyme DNA polymerase. PCR per se is, inter alia, described in U.S. Pat. No. 4,683,202, U.S. Pat. No. 4,683,195, EP-A2 201,184, EP-A2 258,017 (relating to taq polymerase) or WO 92/01814.

Reverse transcription polymerase chain reaction is a method for amplifying a defined piece of a ribonucleic acid (RNA) molecule. The RNA strand is first reverse transcribed into its DNA complement or complementary DNA, followed by amplification of the resulting DNA using polymerase chain reaction. This can either be a 1 or 2 step process. The exponential amplification via reverse transcription polymerase chain reaction provides for a highly sensitive technique, where a very low copy number of RNA molecules can be detected. Reverse transcription polymerase chain reaction is widely used in the diagnosis of genetic diseases and, quantitatively, in the determination of the abundance of specific different RNA molecules within a cell or tissue as a measure of gene expression. Examples of reverse transcriptase PCR are provided, inter alia, in U.S. Pat. No. 5,057,410.

In real-time polymerase chain reaction, also called quantitative real time polymerase chain reaction (QRT-PCR) or kinetic polymerase chain reaction, is a laboratory technique based on polymerase chain reaction, which is used to amplify and simultaneously quantify a targeted DNA molecule. It enables both detection and quantification (as absolute number of copies or relative amount when normalized to DNA input or additional normalizing genes) of a specific sequence in a DNA sample. The procedure follows the general principle of polymerase chain reaction; its key feature is that the amplified DNA is quantified as it accumulates in the reaction in real time after each amplification cycle. Two common methods of quantification are the use of fluorescent dyes that intercalate with double-strand DNA, and modified DNA oligonucleotide probes that fluoresce when hybridized with a complementary DNA.

Real-time polymerase chain reaction (RT-PCR) may be combined with reverse transcription polymerase chain reaction to quantify low abundance messenger RNA (mRNA), enabling a researcher to quantify relative gene expression at a particular time, or in a particular cell or tissue type. The means, method and devices provided herein are particular useful in the thermo-optical characterization of intermediate and/or end-products (nucleic acid molecules) as obtained during such PT-PCRs/quantitative real time polymerase chain reactions (QRT-PCRs). Real-time PCRs have been described, inter alia, in WO97/46708, U.S. Pat. No. 5,314,809 or EP-A1 519,338.

Means, methods and devices as provided herein are also useful in, e.g. multiplex PCRs, which relate to the use of multiple, unique primer sets within a single PCR reaction to produce amplicons of varying sizes specific to different DNA sequences. By targeting multiple genes at once, additional information may be gained from a single test run that otherwise would require several times the reagents and more time to perform.

The person skilled in the art is readily in a position to use the means, methods and devices provided herein in the thermo-optical characterization of nucleic acid molecules during elaborated or modified PCRs, like "nested PCR", "Methylation-specific PCR (MSP)", "Ligation-mediated PCR", "overlap-extension PCR" and the like.

The thermo-optical detection/analysis of PCR products by means, methods and devices of the present invention are particularly useful in both diagnostic and research applications.

As documented herein, one embodiment of the present invention is based on the fact that with the means, methods and devices of this invention it is possible to measure, in very short time intervals, inter- as well as intra-molecular interactions. In the first illustrative embodiment of the invention as described herein, a thermo-optical method is disclosed that allows for the detection of a broad temperature range (in a given probe/sample) at the same time, whereby said "same time" is a time range of about 1 ms to 250 ms, in particular 80 ms to 180 ms and, as exemplified at 150 ms, yet, at the most at 250 ms. This first illustrative embodiment of the invention is not based on or related to thermophoresis. In contrast, thermophoresis is, to a large extend excluded. The first embodiment is, e.g. related to the determination of melting curves, e.g. the determination of DNA and protein melting (point) curve(s). A non-limiting example of this first embodiment is the determination/measurement of single nucleotide polymorphism, based as provided in appended FIG. 4. The "melting point" is defined by 50% dissociated molecules. It is evident herein that the disclosed method as provided in the first embodiment is not limited to the determination of melting points of DNA molecules.

In the second illustrative embodiment of the invention, thermophoresis or thermophoretic effects play a role, inter alia, in a pre-determined time of about 0.5 second to about 250 seconds, preferably about 1 second to about 150 seconds, more preferably about 5 seconds to about 100 seconds, more preferably about 5 seconds to about 80 seconds more preferably about 5 seconds to about 50 seconds and even more preferably in about 5 seconds to about 40 seconds, concentration changes within a spatial temperature distribution are measured and/or detected. Here, concentration changes and not structural changes of the particles/molecules to be characterized in accordance with the inventive methods are measured/detected. Structural changes in this context are related to thermal denaturation mentioned in the first embodiment. The second illustrative embodiment illustrates that conformational changes and changes in surface (like size and chemistry) and interactions may be measured by thermo-optical characterization because the thermophoretic properties are altered. Also, thermo-optical "trapping" devices are illustrative for this embodiment. Corresponding illustrations of the usefulness of this embodiment of the invention are also illustrated in the appended examples, e.g. the determination of hydrodynamic radius and interaction between proteins, the detection of interactions between biomolecules and discrimination of nucleic acids by size, the detection of binding of molecules to particles, the investigation of conformation, structure and surface of (bio)molecules, the detection of conformational changes, like folding/unfolding of biomolecules, the trapping of particles (e.g. the trapping of vesicular structures or lipids) or (bio)molecules, and the detection of covalent and non-covalent modifications of particles.

It is documented and exemplified herein below that, e.g. the thermophoresis of nucleic acids (in particular of DNA) is length/size dependent and the means and methods provided herein allow for the determination and elucidation of single versus double stranded DNA as well as the determination also of small nucleic acids up to e.g. 100, 300, 1000, or 5000 nucleotides or base pairs. A non-limiting example is illustrated in appended FIGS. 5a-5b, wherein mobility in a temperature gradient is measured by the means and methods provided herein. Here it is shown that in particular the second embodiment of this invention allows for the distinguishing verification between length/size (in the particular example 20mer versus 50mer) and/or "strandness" of nucleic acid molecules (in the particular example single stranded DNA versus double-stranded DNA). Again, also this second illustrative embodiment of the present invention is not-limited to the detection of short DNA or the determination of double- or single-stranded nucleic acid molecules. Also interactions between particles/molecules, conformations, hydrodynamic radii, binding kinetics and stabilities of particles/molecules, e.g. proteins, nucleic acids (e.g. DNA, RNA, PNA, LNA), nanoparticles, beads, particularly microbeads, lipids, liposomes, vesicles, cells, biopolymers (hyaluronic acid, alginate and alike), two-dimensional lipid sheets, inorganic substances (e.g. carbon-nanotubes, buckyballs, etc), Poly-ethylenglycol (PEG) may be measured. The molecules mentioned above show e.g. differences in temperature stability. Illustrative molecule specific temperature ranges for the measurement of respective thermo-optical properties are given in table 1. This table 1 also provides illustrative specific temperature ranges for the thermo-optical detection/analysis/measurement of nucleic acid molecules during or after PCR reactions, i.e. the corresponding detection/analysis/measurement of intermediate or end-products of PCR reactions.

The examples for uses of the means, methods and devices disclosed herein are not to be considered to be limiting and illustrate the invention. In particular, the present invention and its corresponding means and methods are not limited to the use of the detection, measurement and/or verification of biomolecules, like nucleic acids or proteins/proteinaceous structures. As is evident from the invention as disclosed herein, also any temperature-sensitive system can be adopted to the methods and devices disclosed herein.

It is, e.g. feasible to measure also chemical reactions, like inorganic or organic reactions.

The person skilled in the art is aware that the invention as disclosed herein is only restricted by the fact that the reaction to be measured, detected, verified and or assessed has to take place in an solution that can be heated, in particular heated optically.

In some embodiments the device according to the present invention is based on a fluorescence microscopy setup with an excitation means, e.g. a Light Emitting Diode (LED) for excitation, an excitation/emission filterset, a specimen holder for a microfluidic chamber and a fast CCD Camera for spatial resolved recording of the fluorescence intensity. Such a fluorescence microscopy setup is well established in life science and other areas. According to the present invention, such a common setup is extended by an infrared (IR) laser whose radiation is focused. The laser may be arranged below the specimen holder such that the radiation is focused from below the specimen holder into the microfluidic chamber by an IR corrected lens (as illustrated in the appended figures, particularly FIG. 1). However, the laser, the detection means and the excitation means may be arranged on one common side of the specimen holder, e.g. below the specimen holder as depicted for example in FIG. 2. In one embodiment, the specimen holder is attached to the objective. Such a setup avoids relative movements of the specimen holder with respect to the objective. According to a further embodiment, it is possible to move the laser freely in the object plane by using two voltage driven infrared mirrors. It is further advantageous to use thin liquid films (approx. 1 μm to 500 μm, preferably 1 μm to 50 μm, more preferably 1 μm to 20 μm, even more preferably 1 μm to 10 μm), e.g. in thin liquid chambers, of biomolecule solutions with local coherent IR radiation. However, the method of the present invention is not limited to thin liquid chambers. An extension to μl-drops or nl-drops of aqueous solutions, capillaries and micro-well plates is possible as illustrated in the appended figures, e.g. FIGS. 2 and 16 to 24. Even very small reaction volumes in the pico liter are envisaged, in particular when amplification products of PCR reactions are to be determined/measured and/or characterized in accordance with the devices, means and methods of this invention. According to a further embodiment, the infrared heating and fluorescence detection are realised through the same objective, which makes the setup much more flexible and compact (see e.g. FIGS. 2 and 16 to 24). The use of one objective to focus both electromagnetic radiation from the infrared and visible part of the spectrum comprises the necessity that the objective does both with high optical quality. In particular the infrared radiation must not exhibit a strong dispersion by the objective. Strong dispersion would lead to a high temperature offset and a comparably strong temperature gradient at distances from the heated centre. This situation is in some embodiments described here avoided. Strong dispersion increases the time of measurement and decreases the precision. Without being limited by theory, this may be due to an increase of the length scale where thermophoresis is strong whereby the system needs more time to reach steady state. The second effect may be due to the fact that the nonlinear bleaching correction is only precise if thermophoresis is negligible at greater distance to the heat spot. This is achieved when diffraction of the infrared radiation is low. Accordingly and in accordance with this invention, only one direction in space may be used for detection and manipulation. The described method and the herein disclosed devices may be integrated into established instruments and high throughput systems.

Water shows a strong absorption of radiation in the infrared regime larger than 1200 nm. The absorbed energy is converted into heat. Coherent IR LASER and IR optics allow the creation of a very high power density of infrared radiation in solution. By controlling the LASER optics the LASER focus can be moved and changed. This includes optics which change the aspect ratio of the radial symmetric laser beam to produce a line shaped focus. This is in particular useful if measurements are conducted in a capillary. Since the whole cross section is heated homogeneously, a spatial temperature profile exist only along the length of the capillary. A temperature gradient in only one direction of space increases the precision of the measurement since the all pixels with same distance from the heated centre can be averaged. In particular this allows the use of a CCD camera with a single line of pixels. In this case the integration of fluorescence is obtained by hardware. By using a photodiode or photomultiplier the fluorescence from a finite volume element (i.e. from the centre of the heat spot/line) is measured, without any spatial resolution. A spatial resolution of fluorescence detection is only necessary in cases were the hydrodynamic radius is the thermo-optic property of interest. The optical heating technique allows the creation of broad temperature distributions and strong temperature gradients on the micron scale. At the position of the LASER focus there is the highest temperature. This upper temperature limit may be adjusted by controlling the power of the LASER and the shape of the laser focus. With increasing distance to the laser focus the temperature of an aqueous solution is decreasing due to thermal conductivity. The lower limit of the temperature may be set by the temperature of the surrounding chamber material. This material can be cooled down, e.g. up to 0° C. In this way it is possible to generate a temperature distribution containing all temperatures between 100° C. (with high laser power) at the laser focus and 0° C. at greater distances to the heat spot.

With the method of the present invention it is possible to heat and analyze solutions, particularly aqueous solutions in a thermo-optical way. There is no need for heat conducting materials like heat transducers from a heating element (copper wire, Peltiers etc.). The solution itself is directly heated by the LASER light. Because the laser focussing is only diffraction limited, temperature distributions spanning all temperatures between 0° C. and 100° C. (the complete liquid phase of water) can be observed simultaneously on a length scale of a few hundred micrometers.

With the method of the present invention, measurements are 3000-10000 times faster than the fastest available measurement systems known in the art. The method of the present invention allows to obtain all temperatures between 0° C. and 100° C. at the same time because a spatial temperature distribution is used. The temperature is not created by contact with a heating element, but within the sample itself. By using the infrared scanning optics, arbitrary two dimensional temperature patterns can be created in solution. This way, any structuring of the surface is obsolete. In addition, all materials transparent for radiation in the infrared can be used to build a microfluidic measurement chamber (glass, sapphire, plastic, silicon, crystals).

In addition, the method of the present invention can also be used to create temperature distributions in the aqueous solution near a surface. Because of the continuity of temperature the surface also adopts a temperature distribution. Therefore it is possible to heat the surface as well as the solution. A possible application is the analysis of DNA-microarrays. Temperature gradients close to a surface may be used to move molecules toward a surface or away from a surface. These local concentration changes can be measured precisely by total internal reflection fluorescence (TIRF) system shown in the appended figures, particularly FIGS. 24 and 36, or any optical system (1) capable of TIRF. This thermophoretic motion in the direction of the incident laser light can be used to direct molecules into a microfluic structure in order to capture and/or concentrate them. Therefore, temperature gradients generated according to the present invention can also be used to capture and/or concentrate molecules/particles. The capture and concentration of molecules/particles is dependent on their thermo-optical properties (e.g. the sign of the thermophoretic effect).

One way to suppress secondary effects related to inhomogeneous temperatures in solution can be suppressed by choosing the right microfluidic chamber geometry. For example convection is dealt with by using only a thin sheet of liquid. This also means that it is advantageous for reproducible and precise measurements that the height of the thin sheet of liquid does not vary from measurement to measurement. The speed of the convective flow, which is accompanied by the spatial temperature distribution depends quadratically on the height of the liquid sheet. This nonlinearity means that slight changes in chamber height lead to comparatively strong changes in the speed of the convective flow which in turn effects the concentration and temperature profile in a very complicated way. Therefore experiments are preferably performed in microfluidic measurement chambers of defined height (e.g. capillaries). Since in accordance with the means and methods of this invention temperature is generated herein by the generation of heat due to the absorption process, the constant height is also advantageous to obtain reproducible temperature distributions. Differences in height would lead to deviations due to differences in the amount of energy absorbed and because of differences in the volume/surface ratio. This ratio determines the rate of heat transfer to the surrounding and therefore also the temperature distribution in solution. The reproducibility of the temperature profile determines the maximal possible measurement precision.

Another way is to measure even faster to avoid disturbances by convection opening the possibility to measure in single droplets or micro-well plates (thicker sheet of liquid). Since the IR laser is absorbed on a length scale of 300 µm (1/e) thin samples, e.g., thin chambers are heated homogeneously in the z-direction (height).

Accordingly, the present invention provides an improved method to measure thermo-optically characteristics of particles/molecules in a solution with the steps of (a) providing a sample probe with marked particles/molecules in a solution; (b) exciting fluorescently said marked particles and firstly detecting fluorescence of said excited particles/molecules; (c) irradiating a laser light beam into the solution to obtain a spatial temperature distribution in the solution around the irradiated laser light beam; (d) detecting secondly a fluorescence of the particles/molecules in the solution at a predetermined time after irradiation of the laser into the solution has been started, and characterizing the particles/molecules based on said two detections.

In one embodiment the predetermined time is within the range of from 1 ms to 250 ms. Preferably the detection time is in the range of from 1 ms to 50 ms. In a particular embodiment, the laser beam is defocused such that a temperature gradient within the temperature distribution is in the range of from 0.0 to 2K/µm, preferably from 0.0 to 5K/µm. Preferably the laser beam is irradiated through an optical element into the solution. In a particularly embodiment the optical element is a single lens. In a particular embodiment of the invention, the method is further comprising the step of measuring the temperature distribution in the solution around the irradiated beam with a temperature sensitive dye. The temperature distribution may be determined based on detected fluorescence of the temperature sensitive dye, wherein the solution comprising said temperature sensitive dye is heated by the irradiated laser beam and the fluorescence spatial fluorescence intensity is measured substantially perpendicular around the laser beam. In a further embodiment the predetermined time is within the range of from 0.5 s to 250 s. Preferably in said predetermined time concentration change(s) within the spatial temperature distribution in the solution due to thermophoretic effects and such (an) concentration change(s) is(are) detected by a change of the distribution of fluorescence. In some embodiments the laser beam is focused such that a temperature gradient within the temperature distribution is achieved in the range of from 0.001 to 10K/µm. In a further embodiment of the invention fluorescence is detected with a CCD camera. In some embodiments, the brightness of said fluorescence is detected with a photodiode or a single pixel with the CCD in the centre of the laser beam. In further embodiments the particles are biomolecules and/or nanoparticles and/or microbeads and/or combinations thereof. In particular embodiments, the laser light is within the range of from 1200 nm to 2000 nm. Preferably the laser is a high power laser within the range of from 0.1 W to 10 W, more preferably of from 0.1 W to 10 W, even more preferably from 4 W to 6 W. In some embodiments, the solution is an aqueous solution with an particle concentration within the range of from 1 atto Molar (single Particle Microbeads) to 1M, preferably from 1 atto Molar to 100 µMolar. Particularly, the solution is a saline solution with concentrations in the range of from 0 to 1M. Preferably, the spatial temperature distribution is between 0.1° C. and 100° C. In preferred embodiments, the temperature gradient is created within 0.1 µm to 500 µm in diameter around the laser beam. The irradiation of the laser and the detection of the fluorescence is in a preferred embodiment of the invention conducted from the same side with respect to the sample probe. Preferably, the solution is provided with a thickness in direction of the laser light beam from 1 µm to 500 µm. In particular embodiments, the fluorescence is detected within a range of from 1 nm to 500 µm, particularly from 50 nm to 500 µm in direction of the laser beam. Preferably, the fluorescence is detected substantially perpendicular with respect to the laser light beam with a CCD camera. More preferably the second fluorescence detection is spatial measurement of the fluorescence in dependence of the temperature distribution substantially perpendicular with respect to the laser light beam. In preferred embodiments, the sample solution is in a capillary.

The present invention also provides a device for measuring thermo-optically characteristics of particles in a solution as described in any of the above embodiments, wherein the device comprises: a receiving means for receiving marked particles within a solution; means for fluorescently exciting the marked particles; means for detecting the excited fluorescence in said solution; a laser for irradiating a laser light beam into the solution to obtain a spatial temperature distribution in the solution around the irradiated laser light beam. In some embodiments, the means for fluorescently exciting the marked particles is a LED. Preferably, the laser is a high power laser within the range of from 0.1 W to 10 W, preferably 1 W to 10 W, more preferably from 4 W to 6 W. In a particular embodiment, the laser and the means for detecting the excited fluorescence are arranged on the same side with respect to the receiving means. In a more preferred embodiment, the device further comprises an optic for magnifying the detected region. In particular embodiments, the device further comprises an optic for focusing or defocusing the laser beam. Preferably the optic is a single lens. In preferred embodiments the detecting means is a CCD camera. In some preferred embodiment, the CCD camera is a line CCD camera. In particular embodiments, the detection is one-dimensional along the length of a capillary. In another particular embodiment, the detecting means is a photo diode.

The present invention also relates to the use of the methods and the devices described in any of the above embodiments for detecting and/or measuring the characteristics of particles and/or molecules in solution. The molecules to be detected, measured or characterized in accordance with this invention may also be drug candidates.

In particular embodiments of the invention, the characteristics to be detected or measured in accordance with this invention are selected from the group of stability, length, size, conformation, charge, interaction, complex formation and chemical modification of particles. In preferred embodiments, the particles to be measured are selected from the group consisting of (a) molecule, biomolecule(s), nanoparticles, beads, microbeads, (an) organic substance(s), (an) inorganic substance(s) and/or combinations of these. Preferably said particle is selected from the group consisting of (a) (bio)molecule(s), nanoparticles, microparticles, microbeads, (an) organic substance(s), (an) inorganic substance(s) and/or combinations of these. More preferably, the (bio)molecule is selected from the group consisting of (a) protein(s), (a) peptide(s), (a) nucleic acid(s) (e.g. RNA (e.g. mRNA, tRNA, rRNA, snRNA, siRNA, miRNA), DNA), (an) RNA aptamer(s), (an) antibody/antibodies (or fragments or derivatives thereof), (a) protein-nucleic acid fusion molecule(s), (a) PNA(s), (a) locked DNA(s) (LNAs) and (a) biopolymer(s) (sugar polymer, hyaluronic acids, alginate, etc.). Also intra- or inter-molecular interactions, e.g. protein folding/unfolding, are within the scope of this embodiment. As pointed out above and herein below, the particular gist of the present invention is the provision of means, methods and devices for the thermo-optical detection/analysis/measurement of PCR products, in particular in RT-PCRs.

A particularly preferred embodiment of the present invention relates to a method to measure thermo-optically the physical, chemical or biological characteristics of particles/molecules in a solution with the steps of (a) providing a sample probe with marked particles/molecules in a solution in a capillary; (b) exciting fluorescently said marked particles/molecules and firstly detecting fluorescence of said excited particles/molecules one-dimensionally along the length of the capillary; (c) irradiating a laser light beam into the solution to obtain a linear temperature distribution in the solution around the irradiated laser light beam along the length of the capillary; and (d) detecting secondly a fluorescence of the particles/molecules in the solution at a predetermined time after irradiation of the laser into the solution has been started, and characterizing the particles based on said two detections.

The present invention also provides a particular device for measuring thermo-optically the physical, chemical or biological characteristics of particles/molecules in a solution as described in any of the above embodiments, wherein the device comprises: a capillary for receiving marked particles/molecules within a solution; means for fluorescently exciting the marked particles/molecules; means for detecting the excited fluorescence in said solution one-dimensionally along the length of said capillary; a laser for irradiating a laser light beam into the solution to obtain a linear temperature distribution in the solution around the irradiated laser light beam.

The device according to the present invention with a fluorescence microscopy and local infrared laser heating may also be used to measure the effect of temperature gradients (i.e. temperature in homogeneities) on dissolved molecules (see second embodiment of the present invention). Almost all dissolved molecules start to move in a temperature gradient, either to hot or cold regions. This effect is called thermophoresis or Soret effect and is known for 150 years. But the mechanism of molecule movement in liquids stayed unclear. A mayor step towards a theoretical understanding of thermophoresis in liquids has been done recently.

With the method and the device according to the invention, the stability, conformation, size and/or length of molecules, in particular biomolecules may be characterized and/or determined. The interaction of (bio)molecules with other molecules or particles, e.g. further (bio)molecules, nanoparticles or beads, e.g. microbeads is characterized in particular embodiments of the invention. The molecules to be analyzed may also be linked (e.g. covalently or non-covalently) to beads or particles, e.g. the beads or particles may be coated with molecules (e.g. biomolecules) to be analyzed, characterized in accordance with this invention.

In the following two illustrative methods according to the present invention which rely on a very similar measurement protocol but analyze very different molecule parameters will be discussed. Only in the method of the second illustrative embodiment of the present invention the thermophoretic motion of particles is used. In the method of the first illustrative embodiment this effect has to be excluded. Furthermore, particular embodiments of the present invention will be explained in detail with reference to the figures and with reference to the appended detailed examples. Said references to the figures and examples are not considered to be limiting.

First Illustrative Embodiment of the Invention

The method according to a first illustrative embodiment is in particular useful in a temperature stability measurement of molecules, in particular biomolecules. However, it is again of note that the means and methods provided herein are not limited to the detection, verification and/or measurement of biomolecules. The method described and illustrated as a non-limiting example, in the following allows, e.g., the measurement of melting temperatures (FIG. 3) (stability, thermodynamic parameters like dS (change in entropy), dH (change in enthalpy) and dG (change in Gibbs free energy)) of biomolecules (proteins, double stranded (ds)RNA, dsDNA were one nucleic acid strand could also be bound to a (nano)particle, microbead, surface etc). With said method measurements of melting curves of dsDNA and DNA hairpins have been conducted. The results are very well comparable to respective literature values. As mentioned herein above, the present invention is in particular useful in the measurement of biomolecules in general. Illustratively, it is shown hereon that e.g. SNPs (single nucleotide polymorphisms) in (short) DNA strands can easily be detected (see also FIG. 4).

A particular embodiment of the first illustrative method will be explained in the following. Nucleic acids with a fluorescence tag are given into a thin microfluidic chamber (i.e. e.g. 40 µm, 20 µm, 10 µm, or 5 µm, preferably 20 µm). The modification of nucleic acids with tags, like fluorescent tags is a well established technique which is broadly used. Before heating starts, the fluorescence is observed to determine the fluorescence level of 100% not melted molecules. It is important that the used fluorescence tag reacts on the melting of the two DNA strands (or RNA strands or protein structure, or the fluorescence of a nanoparticle reacts on whether ssDNA/RNA or dsDNA/RNA are bound to it). This can be realized by using e.g. fluorophore/quencher pair (Donor/Quencher pair particularly Donor/Acceptor pair: Energy Transfer (ET), e.g. Resonance Energy Transfer (RET), particularly Fluorescence Resonance Energy Transfer (FRET)) or by the dissociation of an intercalating nucleic acid stain (e.g. SYBR Green/POPO/YOYO) or a protein stain (e.g. SYPRO Orange (Invitrogen)). In case of e.g. gold-nanoparticles, fluorescence changes by changing of index of diffraction by DNA binding. The laser coupled to the microscope is defocused and adjusted in a way that the temperature gradients are low enough to decrease the thermophoretic particle drift to negligible values. At the same time focusing must be tight enough to reach temperature high enough for melting of the molecules. The measurements is in some particular embodiments performed with high temporal resolution in the microsecond range, since the measurement has to be performed in a time span were thermophoretic motion is still negligible but the heating process of the microfluidic chamber is completed. The measurement is strongly dependent on the experimental conditions. The data necessary for determining the melting temperature are typically obtained within 200 ms, within 150 ms, within 100 ms or within 50 ms, preferably within 150 ms. This is very surprising and supports the gist of this invention. Even shorter time spans are possible. In context of this invention, e.g. for a qualitative discrimination of different species or nucleic acids. A first image is taken before the IR laser is turned on to obtain the fluorescence level of 100% not melted molecules. A second image is taken 100 ms, preferably 50 ms, more preferably 40 ms after the laser is turned on (were the chamber has reached its steady state temperature). These two images contain all necessary information. The first image contains the fluorescence of the not melted molecule. The image taken while the laser is turned on allows the observance of the percentage of melted molecules at all different temperatures simultaneously, ranging from 0% far away from the heat spot (cold) to 100% in the centre of the heat spot (hot). From an independent measurement the temperatures of all pixels in the melting experiment are known. Plotting the percentage of i.e. melted DNA strands vs. temperature allows to determine the stability of the molecule (i.e. the melting temperature) and to derive the thermodynamic parameters.

In summary, the first illustrative embodiment of the present invention connects the measurement of a spatial temperature distribution on the micrometer scale with the measurement of temperature dependent chemical/biochemical reactions and temperature dependent interactions between molecules/biomolecules/nanocrystals/microbeads. For the measurements the absolute temperatures not the temperature gradients are important. One can consider each detection volume (mapped onto a CCD-camera-pixel) as an microreactor. For the measurement it is very important that every molecule stays in this microreactor during the time of measurement. Therefore the measurement has to be as fast as to prevent thermophoresis and convection to move the particle out of the area addressed as microreactor. This requirement is satisfied with measurement time of 150 ms.

With the method and the device according to the first illustrative embodiment one is able to discriminate between dsDNA molecules with a single nucleotide mismatch (SNP, single nucleotide polymorphism), as well as salt dependent and length dependent differences in stability. The differences in stabilities can also be measured for dsRNA, DNA and RNA hairpins (ssDNA/RNA base pairing with themselves) and proteins. Also the influence of different aqueous buffers systems to the stability can be measured (pH, salt concentration, valency of ions). The biomolecules can also be coupled to (nano)particles, (micro)beads. The fluorescence of these modified particles changes depending on whether e.g. ssDNA/RNA or dsDNA/RNA (or other biomolecules) is bound to it. Heating of such solutions leads to the same result without the need of specific fluorescent markers bound to the biomolecule. Beside a qualitative discrimination, also a quantitative thermodynamic analysis is possible. Since the measurement times are in some cases below the relaxation times of intermolecular reactions, it is not in all cases possible to determine the thermodynamic parameters like dS (change of entropy), dH (change of enthalpy) and dG (change of Gibbs free energy) directly. But by using non equilibrium thermodynamics, these can be easily calculated. For the qualitatively discrimination of (i.e.) single nucleotide polymorphisms, working under non equilibrium condition can increase the measured differences in stability of the compared molecules. The measurement of mismatches in nucleotide sequences is of great importance in medical diagnostics. The method allows identifying hereditary diseases. It can also be used in pharmaceutical high throughput screenings for the binding of low molecular weight compounds to nucleic acids. Furthermore the melting of double-stranded (ds) nucleic acids allows to determine their length.

The measured melting curves of the present invention reproduce the results measured by established techniques but up to 3000× faster than Peltier or heating bath based methods, like PCR cycler or fluorimeter methods. The inventive method is much faster since it is not necessary to heat the volume by direct contact, and the reaction of molecules on a specific temperature between 0° C. and 100° C. is observed at the same time. Again, the gist of this embodiment is that temperatures are generated and measured with spatial instead of temporal resolution. There are no delays due to heating and cooling times which makes the method of the present invention very fast. At the same time only thin sheet of liquids are used which decreases the necessary sample volume. In addition the manipulation and analysis of the molecules occurs all optically without the risk of contamination. This is essential if the analysis is combined with PCR reactions where any contamination with i.e. human DNA renders an analysis impossible.

By performing the thermal denaturation within e.g. 100 ms, preferably 50 ms, it is possible to measure the effect of substances on the DNA/protein stability which are sensitive to high temperatures (e.g. DNA binding proteins, substances like cyclic-Adenosin Monophosphate (cAMP)). These substances will be damaged or degraded in an experiment with techniques of the prior art and an effect on the thermal stability is not detectable with such prior art techniques.

Within the spatial temperature distribution there are temperature gradients. If the measurement time is longer than the 150 ms (for the here proposed chamber thickness of e.g. 20 μm) one can measure the thermophoretic movement of the biomolecules (molecules, nanoparticles, microbeads). From this measurements additional information can be gathered.

Second Illustrative Embodiment of the Invention

The method according to a second illustrative embodiment (i.e. the above recited method relating to measurements wherein the pre-determined time in said second detection of the method of the invention is within a range of 0.5 seconds to 250 seconds, preferably within a range of 0.5 s to 50 s, more preferably within a range of 0.5 s to 40 s) is in particular useful for a measure of the mobility of molecules in a temperature gradient and its use for biomolecule characterisation. The method of the first embodiment described above analyzes molecules in a temperature distribution on a short timescale of milliseconds. Dynamics effects like thermophoresis can be neglected in this short time interval. If molecules are observed for a time period in the order of seconds, thermophoresis sets in and molecules start moving in the temperature gradient. This effect drives molecules analogous to electrophoresis along a gradient to lower temperatures (in some cases the opposite is also observed). The velocity of the molecules is directly proportional to the temperature gradient with a molecule specific coefficient $D_T$ (thermophoretic mobility): $v=-D_T \nabla T$.

Unexpectedly the thermophoretic mobilities of biopolymers vary strongly with the chain/molecule length.

The thermophoretic mobility of these molecules varies strongly with molecule parameters which change the entropy of solvation, size, charge, kind of surface, size of surface, hydrodynamic radius etc. This opens the possibility to discriminate biomolecules and detect an interaction between them (also between nanoparticles/micro beads and biomolecules) (as illustrated in the appended figures, particularly FIG. 4).

Since thermophoresis builds up concentration gradients, the effect is counteracted by ordinary diffusion. The interplay between these two effects leads to a steady state concentration profile which is expressed by the following equation $$\frac{c}{c_0} = \exp[-S_T \times \Delta T].$$

The concentration at any given point in a temperature distribution is solely dependent on the difference in temperature and not the temperature gradient any more. The quotient of thermophoretic mobility $D_T$ and ordinary diffusion constant D is called Soret coefficient $S_T$ and describes the magnitude of thermophoresis in steady state. It is exponentially dependent on the temperature difference. Thus the precision of the measurement is strongly dependent on the reproducibility of the temperature profile.

A typical measurement procedure according to the second embodiment will be described in the following. In the very beginning an image is taken without IR LASER heating to determine the fluorescence intensity of the 100% relative concentration level. Then the LASER is turned on. In this experimental setup it is possible to focus the laser tightly with a half width below 6 μm to create strong temperature gradients or to use it defocused (as described above with a temperature profile half width of e.g. 200 μm). This influences the velocity of the molecules and how fast the steady state is reached. The necessary temperature increase varies between 0.1° C. and 80° C. above ambient temperature (20° C.). If the chamber is e.g. cooled to 0° C., a temperature range between 0.1° C. and 100° C. temperature increase can be realized, dependent on the thermal stability of the sample and the magnitude of the thermophoretic effect. In general no high temporal resolution of the image recording is necessary to determine the thermophoretic effect of the (bio)molecules, (nano)particles, or (micro)beads. The measured signal is the steady state or close to steady state concentration which is in most cases reached after a few seconds. The signals of most molecules differ strong enough from each other before steady state is reached to identify them without any doubt. For the data analysis beside the initial concentration the concentration at a certain time after LASER heating is turned on is needed (also time courses can be taken). It is sufficient to determine the concentration of a single pixel (i.e. point of maximum temperature).

Before the laser is turned on there is a homogenous distribution of the biomolecules. Therefore the fluorescence intensity (or whatever the measurement signal is), which is direct proportional to the concentration, has the same magnitude at each point. When the LASER is turned on the concentration distribution changes. The molecules are moving away from the hot laser focus. Therefore the magnitude of the fluorescence intensity is decreasing until the steady state is reached. This decrease can be measured and thus the characteristics of the molecules can be derived by the theory of thermophoresis and different molecules can be discriminated by comparison.

With the methods as disclosed herein, in particular in relation to the second embodiment, for means and methods are provided to detect, measure and/or verify a large variety of interactions. For example DNA/DNA, RNA/RNA, protein/protein, protein/DNA, protein/RNA interactions, but also protein, DNA, RNA interaction with other materials like nanoparticle/microbeads can be measured. The only requirement is a label, in particular a fluorescent label, bound to one of the molecules. An exception is, e.g. the case of large microbeads, where light scattering can be used (directly) for detection. If one uses modified microbeads in a manner that for example DNA single strands can bind to this modifications, the mobility of this bead is changed due to the binding. Hence, the method of the second embodiment allows to detect this binding. Because this modified beads are used in sequencing setups the method of the present invention can be applied there. With the present method it is possible to detect everything that changes the size, charge or surface of a molecule. It has been shown that the method of the present invention is also able to measure specific DNA binding to nanoparticles and polystyrene microbeads via Streptavidin/Biotin (see FIG. 35). Also interactions between antibody and an epitope are detectable. Also the binding of a protein to a DNA strand, for example of a polymerase, is detectable.

Since no high temporal and spatial resolution is needed the method of the second embodiment is cost-efficient and easy to realize. For example instead of a CCD camera an avalanche photodiode can be used (only information of a single Pixel is needed). If the microfluidic chamber is a capillary (i.e. a microfluidic chamber with high aspect ratio (Length/Width)), no spatial resolution in direction of the width is needed and for the detection of fluorescence distribution only a line-CCD-camera is needed. This alternative in between CCD-Camera and avalanche photodiode/photomultiplier is very cost efficient and safes time for data evaluation since the integration of fluorescence is performed by the hardware. The measured systems can exhibit concentration down to nanomolar without any restriction at higher concentrations. Also a comparable high degree of contamination is tolerated by the methods of the present invention. Measurements are also possible in crude extract of cells or in blood. Beside tolerance to contaminations the method also sustains strong variations in the viscosity of the solution. Measurement can for example be performed in water or glycerol or in aqueous solution with a gel like consistence. Since measurements are performed in microfluidic chambers the volume needed for an experiment is e.g. only 0.5 µl, 1 µl, 2 µl, 5 µl, 10 µl, preferably 2 µl, and can be further reduced. Because of its easy calibration the method has a big advantage compared to FCS (Fluorescence Correlation Spectroscopy) and can be easily automated. The method is distinguishable faster than any other method on the market to determine interactions between biomolecules/nanoparticles/microbeads (i.e. Biacore). The length of short DNA molecules is determined within seconds compared to an hour which is needed by gel electrophoresis, an established method in this field. A further advantage is that the measurements are performed in aqueous solution. It is not necessary to change the phase in which the molecule is dissolved (gel in gel electrophoresis or C18, HIC-columns in HPLC). The possibility to differentiate between single and double stranded DNA that fast opens up new possibilities in diagnosis as well as scientific research. One example is, e.g. the diagnosis of infectious diseases, like viral diseases or bacterial infections.

In summary, the inventive method of the second embodiment manipulates concentrations of biomolecules/nanoparticles/microbeads in aqueous solutions by temperature gradients (up to 10K/µm, in some embodiments up to 5K/µm, particularly up to 2K/µm) established with an IR LASER. In the enclosed example a general theory for thermophoresis in liquids is described.

The most important features and advantages of the present invention will be summarized in the following. The method and the device of the present invention works all optical, i.e. manipulation and detection is made by optical means. With the present invention, it is possible to optically manipulate molecules down to the size of a single fluorescent dye which is not possible by optical traps which are limited to spherical particles of 500 nm. The method is free of contaminations and easy to miniaturize and to parallelize. That makes it possible to integrate the system in established instruments like pipetting robots etc. Heating of aqueous solutions on the micron scale allows to create temperature distributions which renders long heating and cooling periods unnecessary. The criterions for materials which can be used to build measurement chambers are very unspecific. Another advantage is that IR LASER are getting more and more common in the telecommunication industry and are produced in big quantities. Furthermore the technique of fluorescent dye coupling to biomolecules has become a cost-efficient standard technology. Thus, with the present invention, it is possible to measure stability of molecules as well as any kind of interaction (with each other, the buffer system, other solutes, etc.). Therefore, the invention is not limited for use in the measurement, detection and/or verification of biomolecules or biological, biomedical, biophysical and/or pharmacological (in vitro) processes.

With the means and methods of the first embodiment of the present invention, melting curves over a large range of temperatures can be measured and determined. According to this embodiment, thermophoresis should be avoided. The temperature achieves a change in the structure, which is detectable via the fluorescence behaviour. The characteristics can be detected and/or measured over a wide temperate range at one time. None of the known prior art documents discloses an inter- and/or intramolecular reaction induced via temperature. According to the first embodiment, the laser can be irradiated into the solution via optical fibres. The light may exit the optical fibres divergent. According to a preferred embodiment of the present invention, the optical system for focussing the laser can be a single lens.

The means and methods of the second illustrative embodiment of the present invention provides the advantages that the effect of thermophoresis is used in a controlled manner. In particular, concentration changes, induced by thermophoresis effect(s) are measured via a change in fluorescence behaviour. Thus, the fluorescence signal recorded in the second embodiment is primary based on changes of concentration and not on changes in the structure of the tested particles or biomolecules. The second illustrative embodiment includes that changes in concentration are sensitive to changes in the structure of a particle or molecule. In the known prior art only a maximum temperature difference of only 2.5K is disclosed. Moreover, only measurements with a low power laser (320 mW) are described in the prior art. Particularly, a CCD camera can be used for detecting or measuring the fluorescence of the sample. According to another embodiment, only one pixel of the CCD camera has to be used for the measurement or the detection of the fluorescence light, e.g. only a central 1×1 µm pixel has to be used. This has the advantage, that further spatial information may be neglected according to certain embodiments of the present invention.

According to a further aspect of the present invention, temperature distributions around the irradiated laser light beam are measured with independent measurements. These measurements are typically based on known temperature-dependent fluorescence behaviour of dyes.

In a most preferred embodiment of the present invention, means, methods and devices are provided which relate to the thermo-optical detection/analysis/measurement of nucleic acid molecules as provided or obtained during PCR reactions, preferably specific PCR reactions, like real time PCR (RT-PCR), quantitive RT-PCR, multiplex PCR and the like.

In general, the devices. means and methods of the present invention can be employed for the thermo-optical determination of the length, size or secondary structure of fluorescently labeled nucleic acids in a reaction solution or the length, size, size distribution or secondary structure of fluorescently labelled nucleic acids in a reaction solution or for the quantification of such nucleic acids. This may, for example, be in the context of PCR, real-time PCR, and particularly quantitative real-time PCR, nested PCR, reverse transcription PCR, multiplex PCR and combinations thereof and also in the context of nucleic acid restriction and ligation (e.g. ligase chain reaction (LCR)) reactions. In such embodiments, the length (i.e. the size) of fluorescently labeled nucleic acids, such as fluorescently labeled primers, fluorescently labeled primer extension products, fluorescently labeled nucleic acid probes and fluorescently labeled PCR products, in PCR reaction solutions can be determined before, after or during PCR reactions. The ratio of the concentrations of the fluorescently labeled nucleic acids at two different temperatures in the temperature gradient encodes their length and the intensity of the detected fluorescence at a given position is indicative for the concentration and quantity of fluorescently labeled nucleic acid at that position. Also the ratio of the concentration of the fluorescently labeled nucleic acids at a position in the temperature gradient to the concentration of the fluorescently labeled nucleic acids in the case where no temperature gradient is applied encodes their length. The intensity of the detected fluorescence at a given position is indicative for the concentration and quantity of fluorescently labeled nucleic acid at that position. Also the lengths and quantities of two or more nucleic acids can be determined simultaneously. The term "length" in the context of nucleic acids is used here synonymously with the term "size" and relates to the molecular weight or the number of bases or base pairs.

A "size distribution" (or "length distribution") relates to the distribution of nucleic acids of different size (length) in the sample (i.e. the reaction solution) or part of the sample. The distribution can be spatial or a distribution in the area detected. The "fluorescence distribution" or "fluorescence intensity distribution" relate to the distribution of detected fluorescence intensities in the sample or in the detected area of the sample. I.e. the "fluorescence distribution" or "fluorescence intensity distribution" is the fluorescence intensity dependent on the position in the sample or in the detected area.

The present invention also relates to the combination of the devices and methods according to the present invention with conventional PCR devices (e.g. a thermocycler) and methods (e.g. real-time PCR, quantitative real-time PCR and multiplex PCR, reverse transcriptase PCR; endpoint PCR, diagnostic PCR, nested PCR, genomic PCR, colony PCR, single cell PCR, quantitative fluorescence PCR). The use of different fluorescence labels for different nucleic acids is possible, e.g. in the context of a multiplex PCR.

In some embodiments, the length/size and or quantity of the fluorescently labeled nucleic acids is determined for normalization and comparison purposes before the first cycle of the PCR reaction. Depending on the purpose of a particular PCR reaction, the length and/or quantity of the fluorescently labeled nucleic acids may be determined after every PCR cycle or at the end of the PCR reaction or after or during every second, fifth, tenth, etc. PCR cycle and the like. Also the determination of a fluorescence threshold as a reference measurement may be performed. In addition, the measurement of samples with nucleic acids of known concentration/quantity and length may be performed as a reference or for comparison.

A typical PCR experiment comprises repetitive cycles of a denaturation step (at high temperature), a primer annealing step and a primer extension step. In real-time PCR, fluorescent dyes are present, either covalently attached to nucleic acids, e.g. primers or probes, or are intercalating or binding to nucleic acids. The increase in PCR products or the decrease of labeled primers can for example be used to monitor a PCR reaction in real-time.

The PCR products can with the devices and methods according to the present invention be distinguished by their length. This may be, for example, used for the analysis of single nucleotide polymorphisms (SNPs). Also the combination of length and attached dye may be used in some embodiments for the discrimination and/or identification of different nucleic acids.

A "reaction solution", and a "PCR reaction solution" in particular, may comprise nucleic acids, nucleic acid processing enzymes, such as ligases, polymerases and nucleases, buffering agents, salts, nucleotides and auxiliary proteins, such as BSA, lipids and detergents. Such reaction solutions are routinely used in molecular biology and their composition for various applications is well known to a skilled person.

As outlined above, in preferred embodiments of the present invention the thermo-optical properties of molecules can be determined while a biochemical process modifies the fluorescently labeled nucleic acids, e.g. PCR reactions, modifications of DNA/RNA by restriction enzymes, HCR (hybridization chain reaction) and LCR (Ligase chain reaction). Common to these is that the size of one or more species of nucleic acid molecules (e.g. RNA or DNA) in the solution changes over time (typical on a time scale of more than 20 minutes, more than 30 minutes, more than 40 minutes) due to the polymerization or restriction of DNA molecules. During this time multiple thermo-optical characterizations to measure the size distribution of the biomolecules (e.g. DNA) can be performed. The time span needed for a characterization is 1 second to 250 seconds, more preferably 1 second to 50 seconds, even more preferably 5 seconds to 40 seconds. The repetitive characterization allows to monitor the progress of the reaction and to detect the endpoint of the respective biochemical process. In a PCR reaction this information can be used to determine the threshold cycle, a measure for the initial number of template DNA molecules present in the solution. Also the time course and endpoint of the reaction and properties like size distribution (but also properties like surface modifications or charge) of molecules may be quantified in each thermo-optical characterization step.

The quantification of product and primer sequence copies in a solution works as follows: The thermo-optical properties of the covalently marked PCR primer in the solution are measured before the first polymerization cycle is completed. The thermo-optical properties of the product DNA are known from reference experiments. The initial primer concentration is known as well. If primer DNA molecules are elongated in a PCR reaction, the size distribution will change from PCR primer to elongated products. As the size distribution is shifted the thermo-optical properties change as well. If all primer molecules are converted to product, the thermo-optical characteristics of the pure product are measured and the product concentration is equal to the concentration of primer initially used for the PCR reaction. If not all primer molecules in the solution are elongated the thermo-optic properties are an intermediate between the pure primer and the pure product characteristics and the concentration of the product and the not elongated primer can be calculated.

In case that the primer are not covalently labeled, but an intercalating dye, binding to double stranded DNA, is used instead, the fluorescence will increase if (double stranded) DNA is amplified. In this case the total length can be determined from thermo-optical properties without any knowledge of the expected product. Since the fluorescence of the intercalating dye is related to the concentration of DNA, the amount of product DNA can be obtained from the fluorescence intensity.

The thermo-optical method also allows for the detection of the hybridization of nucleic acids. For example the hybridization of primer molecules to a target sequence can be detected. If temperatures are chosen high enough that two DNA strands are separated by thermal denaturation (as described herein above) the re-annealing can be measured after the IR-laser is turned off. More preferably the re-annealing can be measured immediately after the denaturation step of the PCR reaction.

In comparison to other techniques monitoring the progress of a reaction by measuring fluorescence, the measuring it thermo-optically does not necessarily involve an increase or decrease in the measured fluorescence signal from cycle to cycle or from time to time. In contrast, it is advantageous that the fluorescence of the marked molecules does not change during the biochemical reaction. The measured signal is the relative change of concentration induced by the local temperature distribution created by infrared laser heating in the solution.

Other known techniques monitoring the progress of a reaction by measuring fluorescence involve fluorescence quenchers or chemical modifications influencing the fluorescence of the labeled nucleic acids or the like to ensure that the fluorescence intensity is influenced by the PCR reaction. In contrast, the devices and methods according to the present invention do not necessarily need changes in the overall fluorescence intensities from cycle to cycle to monitor the PCR reaction and to quantify and characterize the PCR products. Therefore, no fluorescence quenchers and chemical modifications influencing the fluorescence of the labeled nucleic acids are necessary for the devices and methods according to the present invention.

In the present invention, repetitive thermo-optical measurements can be performed to obtain information about a biochemical process (i.e. in case of a PCR: threshold cycle, efficiency and endpoint cycle). Time resolved thermo-optical measurements on non-homogeneous mixtures of nucleic acids (e.g. mixture of primer and elongated primer molecules) are not known in the literature. For example, measurement according to Duhr et al. (2004, loc. cit.) are performed in highly monodisperse solution and the molecule properties are not altered over time (e.g. in a biochemical process).

The present invention allows for the measurement of the DNA length (i.e. the DNA size) during a PCR reaction, without a substantial increase in the time needed for the PCR reaction.

The solution may be provided in a measurement chamber, a capillary, a multi-well plate or a droplet. To measure the time course of a PCR reaction, in some embodiments a device to analyze the sample solution is provided with a means to cycle the whole solution through the different temperatures needed to amplify the DNA (i.e. the overall solution temperature during PCR and not the temperature distribution). It is advantageous to measure the thermo-optical properties in each cycle of the PCR reaction. It is advantageous that the global temperature of the solution is constant during the measurement. It is also of great advantage that the thermo-optical properties are analyzed at low temperature. The methods of the present invention can be performed at a temperature range of from 0° C. to 100° C., preferably of from 15° C. to 75° C. The method according to some embodiments is performed at around 80° C., at around 70° C., at around 60° C., at around 50° C., at around 40° C., at around 35° C., at around 30° C., at around 25° C., preferably at around 20° C., more preferably at around room temperature. It is also advantageous to perform the thermo-optical measurement in temperature step of a PCR cycle specifically introduced and/or programmed for this purpose. In particular in nucleic acid amplification methods (PCR and the like), the methods of the present invention can be performed at a temperature range of from 0° C. to 100° C., more preferably 10° C. to 95° C., even more preferably 20° C. to 80° C., most preferably 50° C. to 80° C.; see also Table 1 herein above.

The thermo-optical characterization method of the present invention allows quantification of the length distribution of labeled/marked primers (or double stranded DNA molecules marked by intercalating dye) in each step/cycle of PCR reactions. Since the primers are elongated by the polymerase, the measurement of the length distribution of the primers provides information about efficiency, quality and progress of the PCR reaction. The length/size distribution of primers/elongated primers/PCR products in PCR reaction solutions is from less than 5 bases/base pairs up to several million bases/base pairs. Nucleic acids differing in size by more than 1000 bases/base pairs, 1000 bases/base pairs, 500 bases/base pairs, 100 bases/base pairs, 10 bases/base pairs, 5 bases/base pairs, 2 bases/base pairs or 1 base/base pair can be distinguished according to the present invention. The PCR reaction may be carried out in a microfluidic chamber, a capillary or a liquid droplet. It is advantageous to cover the droplet with oil to prevent its evaporation.

Minimizing (i.e. slowing down) convection is advantageous and in case of a droplet realized by using moderate laser power (i.e. a laser power of from around 50 mW to 1 W, preferably from around 100 mW to 300 mW) and/or a not tightly focused laser beam. Changes in the thermo-optically created spatial concentration pattern due to the convective flow are not important, since the thermo-optical signal (e.g. the measured concentration change as derived from the detected fluorescence intensity) is dependant convection and on molecule parameters, i.e. size, charge, kind of surface and the like.

Another way is to measure even faster to reduce the disturbances by convection even more. This opens the possibility to measure in single droplets or micro-well plates (thicker sheet of liquid).

Since the IR laser is absorbed on a length scale of around 300 μm (1/e) thin samples, e.g. thin chambers are heated homogeneously in the z-direction (height).

In contrast to thin measurement chambers, the solution in multi-well plates or liquid droplets (thicker than 100 µm) are not heated homogeneously in z-direction (direction of incident IR-Laser light), as they often exhibit an extension in z-direction larger than the absorption length of the laser (e.g. in aqueous solutions around 300 µm at 1480 nm Laser wavelength). It is preferred to measure the fluorescence from molecules substantially influenced by the temperature gradient. Therefore it is advantageous to measure the fluorescence locally with an optical element with small depth of focus (e.g. 100 µm) and to place the focus close to the point of maximum temperature. The optical element averages out the differences of temperature in the z-direction, so that the system is treated as if the spatial temperature distribution is two dimensional.

In the following, preferred embodiments of the invention are described:

The present invention relates to a method for the thermo-optical determination of the size of fluorescently labeled nucleic acids in a reaction solution or the size distribution of fluorescently labeled nucleic acids in a reaction solution, comprising the steps of: (i) providing a reaction solution with fluorescently labeled nucleic acids; (ii) irradiating a laser light beam into the solution to obtain a spatial temperature distribution in the solution around the irradiated laser light beam; (iii) exciting fluorescently said fluorescently labeled nucleic acids and detecting the fluorescence at least at one position or at around one position in the solution or detecting the fluorescence distribution of said fluorescently excited nucleic acids, wherein the detection is performed least once at a predetermined time after the start of the laser irradiation; and (iv) determining the size or size distribution of the fluorescently labeled nucleic acids from the detected fluorescence intensity or fluorescence intensity distribution. Optionally/additionally the detection of said fluorescence may also be performed at least once before the start of the laser irradiation The term "before the start of the laser irradiation" herein relates to the time before the laser irradiation is turned on.

It is particularly preferred that the fluorescence is detected at least at two positions or at around two positions in the solution.

Therefore, the present invention relates to a method for the determination of thermo-optical properties, particularly the size or size distribution of fluorescently labeled nucleic acids in a reaction solution comprising the steps of:
i. providing a reaction solution with fluorescently labeled nucleic acids;
ii. irradiating a laser light beam into the solution to obtain a spatial temperature distribution in the solution around the irradiated laser light beam;
iii. exciting fluorescently said fluorescently labeled nucleic acids and detecting the fluorescence at two or more defined regions representing different mean temperatures in said spatial temperature distribution, wherein said detection of fluorescence is performed at least once at a predetermined time after the start of the laser irradiation; and
determining the thermo-optical properties, particularly the size or size distribution, of the fluorescently labeled nucleic acids from the detected fluorescence intensity or fluorescence intensity distribution.

A region herein refers to a defined area in the temperature distribution in the reaction solution. Preferably, one of the regions in the reaction solution where fluorescence is detected is in the center of the irradiating laser light beam, i.e. preferably fluorescence is measured at the highest temperature in the temperature distribution. The two or more regions have preferably a difference in mean temperature of between 0.1 and 50 K, more preferably between 0.1 and 20 K, more preferably between 0.1 and 5 K, even more preferably between 0.1 and 2 K, most preferably between 0.1 and 1 K. Particularly preferred temperature differences between the two regions where fluorescence measurement is performed are 0.1 K, 0.2 K, 0.5 K, 1 K, 1.2 K, 1.5 K, 2 K and 5 K. The temperature difference between each of the regions is at least 0.1 K. The two or more regions may be of different size or even overlap. The regions have preferably sizes (areas) in the range of from 1 µm$^2$ to 40000 µm$^2$, e.g. 1 µm×1 µm, 5 µm×5 µm, 10 µm×10 µm, 15 µm×15 µm, 20 µm×20 µm, 50 µm×50 µm, 100 µm×100 µm. The size of the regions may also be expressed in terms of pixels on the CCD chip of the detector. CCD chips of different resolution and pixel numbers are available, e.g. CCD chips with 512×512 pixels, 640×480 pixels, 1344×1024 pixels, 4000×2624 pixels etc. The chips may e.g. be quadratic or rectangular. The size of the regions in the temperature distribution may than be expressed in terms of a section represented on the CCD chip, e.g. 1 pixel, 1% of the pixels (first dimension)×1% of the pixels (second dimension), 5%×5%, 10%×10%, 25%×25%, 50%×50% or 100%×100% for quadratic regions, or e.g. 1%×10%, 50%×10%, 10%×50%, 100%×20% for rectangular regions.

As stated above, fluorescent excitation and detection may be repeated at one or more predetermined times after the start of the laser light beam. Preferably, fluorescent excitation and detection is performed during laser excitation, i.e. before the laser is switched off. Fluorescence excitation and detection may in addition also be performed at least once before laser irradiation.

Preferably, a fluorescence detection is additionally performed at least once before the start of the laser irradiation. In this context, fluorescence detection includes fluorescence excitation.

Therefore, the fluorescence detection before laser irradiation may in some embodiments be performed or may in other embodiments not be performed.

The second fluorescence detection may be performed during laser irradiation or after the laser irradiation has been terminated.

Particularly, the reaction solution is selected from the group of PCR reaction solution, nucleic acid restriction reaction solution and ligase chain reaction solution.

In some preferred embodiments of the invention the fluorescently labeled nucleic acids are selected from the group of fluorescently labeled primers, fluorescently labeled primer extension products, fluorescently labeled nucleic acid probes and fluorescently labeled PCR products.

The length of the fluorescently labeled nucleic acids may in particular embodiments of the invention be determined during or between PCR cycles or after PCR has been terminated.

Preferably, the size of the fluorescently labeled nucleic acids is determined after or during the primer annealing phase, after or during the primer extension phase or after or during the denaturation phase.

In a particular embodiment, the reaction solution is cooled for laser irradiation and fluorescence detection to a temperature of in the range of from about 0° C. to 50° C., preferably of from about 4° C. to 25° C., more preferably of from about 4° C. to room temperature, most preferably to about 4° C. This can for example be achieved by incorporating an additional phase of cooling in a PCR cycle.

Preferably, the fluorescence distribution is a spatial fluorescence intensity distribution.

More preferably, a spatial concentration distribution of said fluorescently labeled nucleic acids is determined from said spatial fluorescence intensity distribution.

The nucleic acids may be fluorescently labeled by covalently attached dyes or are fluorescently labeled by non-covalently bound dyes, e.g. intercalating dyes.

In a preferred embodiment, said PCR reaction solution is a drop or droplet and/or is in a container selected from the group of capillary, multi-well plate, chamber, microfluidic chip and glass capillary chip. The drop or droplet may preferably have a volume of from 1 pico liter (pl) to 20 µl, or 1 pl to 10 µl, or 1 nano liter (nl) to 10 µl.

Preferably, said predetermined time after irradiation is from 5 s to 40 s.

The laser beam may in some embodiments be focused such that a temperature gradient within the temperature distribution is achieved in the range of from 0.001 to 10K/µm.

Fluorescence is preferably detected with a detector with spatial resolution or a detector without spatial resolution. It is also preferred that the fluorescence is detected with a detector with spatial resolution or with at least two detectors without spatial resolution. Said detector with spatial resolution may for example be selected from the group of CCD camera, CMOS camera or line camera and said detector without spatial resolution may for example be selected from the group of avalanche photodiode, photomultiplier tube and photodiode.

Preferably, the laser light is within the range of from 1200 nm to 2000 nm.

Also preferred is that said laser is a high power laser within the range of from 0.1 W to 10 W, preferably from 4 W to 6 W.

Preferably, the method according to the present invention is performed within a temperature range of from about 0° C. to 100° C., more preferably of from about 4° C. to 100° C. In other embodiments it may also be performed at a temperature range of from about 15° C. to 75° C.

The present invention relates in preferred embodiments also to a device for thermo-optical determination of the size of fluorescently labeled nucleic acids in a reaction solution according to the methods described herein above.

Furthermore, the invention relates to a device for thermo-optical determination of the size or size distribution of fluorescently labeled nucleic acids in a reaction solution, in particular according to the methods described herein above, comprising: (i) a receiving means for receiving a reaction solution with fluorescently labeled nucleic acids; (ii) a laser for irradiating a laser light beam into the solution to obtain a spatial temperature distribution in the solution around the irradiated laser light beam, (iii) means for fluorescently exciting the labeled nucleic acids; and (iv) means for detecting fluorescence and/or fluorescence distribution of the fluorescently excited nucleic acids; and wherein the device is adapted to perform at least two fluorescence detections at least two predetermined times.

Thus, the invention also relates to a device for thermo-optical determination of thermo-optical properties, particularly the size or size distribution of fluorescently labeled nucleic acids in a reaction solution, in particular according to any of the methods of the invention, comprising:
  a receiving means for receiving a reaction solution with fluorescently labeled nucleic acids;
  a laser for irradiating a laser light beam into the solution to obtain a spatial temperature distribution in the solution around the irradiated laser light beam,
  means for fluorescently exciting the labeled nucleic acids; and
  means for detecting fluorescence and/or fluorescence distribution of the fluorescently excited nucleic acids; wherein the device is adapted to perform at least one fluorescence detection at least two regions within the spatial temperature distribution.

The device may further comprise a determination unit for determining the change in size of said nucleic acids based on the at least two fluorescence and/or fluorescence distribution detections.

Preferably, the device is further adapted to fluorescently excite the fluorescently labeled nucleic acids and to detect a fluorescence and/or a fluorescence distribution of said fluorescently excited nucleic acids at least once before start of the laser irradiation and/or at least once at a predetermined point of time after start of the laser irradiation, preferably when the laser is still irradiating.

The device may further be adapted to fluorescently excite the fluorescently labeled nucleic acids and to detect a fluorescence and/or a fluorescence distribution of said fluorescently excited nucleic acids continuously or intermittently at one or more predetermined or predeterminable points of time.

As stated above the reaction solution may be selected from the group of PCR reaction solution, nucleic acid restriction reaction solution and ligase chain reaction solution.

In preferred embodiments, the device further comprises a temperature control element for heating and/or cooling the reaction solution to a desired, preferably constant, temperature and/or for performing a reaction such as a PCR reaction, preferably within a range of about 0° C. to 100° C., more preferably within a range of about 4° C. to 100° C.

The receiving means is preferably be adapted for receiving or is a container, a chamber, a capillary, a multi-well plate, a microfluidic chip, a glass capillary chip and/or or a means adapted for receiving a drop, a droplet, or a sealed droplet (e.g. oil sealed droplet). In particular embodiments, the receiving means is adapted to receive a drop or droplet having a volume of from about 1 pl to 10 µl, preferably of from 0.001 µl to 1 µl.

More in particular, the device is adapted to cycle the whole PCR reaction solution through different temperatures needed to amplify DNA. Preferably, the device is adapted to measure thermo-optical properties in each cycle of a PCR reaction.

The means for fluorescently exciting the labeled nucleic acids is a Laser, Fibre Laser, Diode-Laser, LED, HXP, Halogen, LED-Array and/or HBO.

In a preferred embodiment, the laser beam is focused such that a temperature gradient within the temperature distribution is achieved in the range of from 0.001 to 10K/µm. The laser light of the laser of the device is preferably within a wavelength of in the range of from 1200 nm to 2000 nm. Preferably, the laser and the means for detecting the excited fluorescence are arranged on the same side with respect to the receiving means.

The device may further comprise an optic for magnifying the detected region. The device may further comprises an optic for focusing or defocusing the laser beam. The optic of the device is preferably a single lens.

Preferably, the detecting means comprises a detector with spatial resolution such as a CCD camera, a CMOS camera, and/or a line camera and/or a detector without spatial resolution such as an avalanche photodiode, a photomultiplier tube and/or a photodiode.

The present invention also relates to the use of the method according to any one of the described methods or use of any one of the described devices for the detection and/or quantification of fluorescently labeled nucleic acids in real-time PCR; quantitive real-time PCR, nested PCR, reverse transcription PCR or in multiplex PCR or for the determination of the size of fluorescently labeled nucleic acids in real-time PCR; quantitive real-time PCR, nested PCR, reverse transcription PCR or in multiplex PCR.

Preferably the nucleic acid elongation in PCR is detected and/or monitored in such a use. Also preferred is the use for simultaneously detecting, quantifying and/or identifying two or more fluorescently labeled nucleic acids of different size.

The novel and inventive methods and devices for the analysis of nucleic acids that are described herein in detail can equally be adapted for other relevant molecules, particularly biomolecules and interactions of biomolecules such as proteins, protein-protein interactions, e.g. antibody-antigen binding. This is exemplified in the appended examples, particularly in example 15, where fluorescence is excited and detected in two regions within the temperature distribution.

Therefore, the present invention also relates to a method for the determination of thermo-optical properties, particularly the size or size distribution of fluorescently labeled biomolecules or biomolecule complexes in a reaction solution comprising the steps of:
 i. providing a reaction solution with fluorescently labeled biomolecules or biomolecule complexes;
 ii. irradiating a laser light beam into the solution to obtain a spatial temperature distribution in the solution around the irradiated laser light beam;
 iii. exciting fluorescently said fluorescently labeled biomolecules and detecting the fluorescence at two or more defined regions representing different mean temperatures in said spatial temperature distribution, wherein said detection of fluorescence is performed at least once at a predetermined time after the start of the laser irradiation; and
determining the thermo-optical properties, particularly the size or size distribution, of the fluorescently labeled biomolecules or biomolecule complexes from the detected fluorescence intensity or fluorescence intensity distribution.

The apparent size of the detected (bio)molecules in the temperature distribution is dependent on the binding to other (bio)molecules, i.e. an antibody-antigen complex or a nucleic acid hybridized to another nucleic acid will have a different apparent size than the single molecules.

In the following a particular protocol for data collection and evaluation is described for an embodiment where hybridization or binding between two or more molecules is to be determined, e.g. in order to detect a certain nucleic acid sequence in a solution (i.e. binding between a "probe" molecule and a "target" molecule):
Data Acquisition:
Step 1. A solution of fluorescently labelled probe molecule is present in a microfluidic chamber, multiwell plate or droplet in the presence of a target molecule. The thermo-optical properties (i.e. concentration change) of the free probe molecule may be known from an independent experiment. Alternatively the thermo-optical properties of a molecule similar (i.e. of same length and GC content but not complementary to the target sequence) to the probe molecule is measured simultaneously in a multiplex approach as an internal reference.

Step 2. The infrared laser heating is turned on. The immediately established local spatial temperature distribution causes the labelled probe molecules (as well as internal reference standards) to drift to lower or higher temperatures, depending on the particular molecule to be analyzed and conditions like pH, salt concentration etc. The laser is focused in a way that temperature gradients are between 0.0001 and 10 K/μm in the field of view. The temperature gradient has to be calibrated only once and it is not necessary to repeat this calibration every time an experiment is performed. The maximum temperature elevation is set below values which would harm the molecules to be analyzed or hinder their hybridization/binding. For particular applications the temperature may be increased above the melting temperature and the separation of both strands is observed. Temperature increase can mean the laser induced temperature or the whole sample temperature (e.g. maintained by a Peltier element). Typically the infrared laser heats the solution for less than 30 seconds, typically 10 seconds or less.

Step 3. During the laser heating an image of the fluorescence distribution is recorded (or multiple frames which may be averaged to a single image). Afterwards the infrared laser and the fluorescence excitation light source are turned off.
Data Processing/Evaluation:
Two "regions of interest" (ROI-1 and ROI-2) are defined in the images recorded in step 3. Both ROIs have a particular size (area) within the limits described e.g. 15×15 μm and the fluorescence intensity is averaged over each ROI. ROI-1 is positioned at the center of the infrared laser spot, while ROI-2 is positioned in a distance of e.g. 100 μm. Alternatively also two detectors without spatial resolution may be positioned in a way, that the intensities from these positions can be compared. The ROIs may vary in size or even overlap. The ROI represent different average temperatures. For an analysis of the signal the quotient of both averaged intensities is calculated according to ROI-1/ROI-2. The quotient is analyzed for all samples. Changes in the quotient reflect the change in binding or hybridization (i.e. change in the ratio of hybridized/bound to free probes).

The relative amount of a molecule complex (e.g. hybridized nucleic acids) can be determined, by (1) subtracting the signal of the free probe molecule from all other signals followed by (2) a division of the subtracted signals by the saturation value (i.e. concentration change determined in saturation) determined at an excess of target.

In case the target molecule concentration is not known, the target concentration may be calculated the following way: The thermo-optical signal strength (i.e. concentration change) is known for the free sample and for the target molecule. The measured concentration change averages the signal of free and hybridized/bound probe molecule. Thus, by knowing the thermo-optical properties of target and probe, the target concentration can be calculated, in case the hybridization of the probe to the target is about 100%. Alternatively the probe molecule may be used in different concentration to define the concentration at which saturation occurs. In cases where the thermo-optical properties of the free probe are known, a single measurement is sufficient to detect hybridization.

Another typical measurement protocol in a particular embodiment comprises:
Step 1: The IR-Laser is switched on;
Step 2: A few seconds (e.g. 5, 10, 15 s) after the IR-Laser is switched on, the CCD-camera and the LED are switched on and the CCD-camera records one or more images;
Step 3: another few seconds later (e.g. 2, 3, 4, 5, 10, 15 s) the IR-Laser, the LED and the CCD-camera recording are switched off and the recorded image or movie of fluorescence images is saved. The data may be recorded, preferably with all setting parameters, in a digital or electronical way. Such an embodiment is further illustrated in example 15.

A particularly preferred data analysis protocol, particularly for a binding assay, is described in the following:
Two regions ("regions of interest", ROI-1 and ROI-2) are defined in the images. The ROI's have a size (area) as described above, for example 15 μm×15 μm or 10 pixel×10 pixel of the image, and the fluorescence intensity is averaged over these ROI's. ROI-1 is positioned at the center of the infrared laser (IR-Laser), while ROI-2 is positioned in a distance of e.g. 100 µm to the spot of the IR-Laser. Alternatively also two detectors without spatial resolution may be positioned in a way, that the intensities from these positions can be compared. The ROI's may be of different size or even overlap. The ROI represent different average temperatures. For an analysis of the signal the ratio of both averaged intensities is calculated according to ROI-1/ROI-2. The ratios may be averaged over the two or more recorded images, e.g. 10, to reduce noise.

The ratio ROI-1/ROI-2 of each measurement of mixed sample can be plotted versus the final concentration of one of the biomolecules in the sample. In this way a titration curve is obtained from which the dissociation constant KD or the association constant or the IC50 or EC50 can be calculated and a binding event can be determined. This is further illustrated in appended example 15. The normalized data may be fitted according to the following relation: $f(c)=(A+c+K_D-\sqrt{(A+c+KD)^2-4*A*c})/(2*A)$. Where A is the concentration of the probe, c is the concentration of the titrated binding partner and $K_D$ is the dissociation constant.

As illustrated in the appended examples, particular embodiments of the present invention relate to the detection of thermodiffusion or thermophoresis of (bio)molecules or particles, the determination of hydrodynamic radii (bio)molecules or particles, the detection of binding of or between (bio)molecules or particles, the detection of interactions of or between (bio)molecules or particles, the detection of conformational changes in (bio)molecules, the detection of denaturation of proteins or melting of nucleic acids and to optothermal trapping of (bio)molecules or particles.

BRIEF DESCRIPTION OF THE DRAWINGS

The invention is described with reference to the figures in which.

DETAILED DESCRIPTION OF DRAWINGS

Figure 1A:
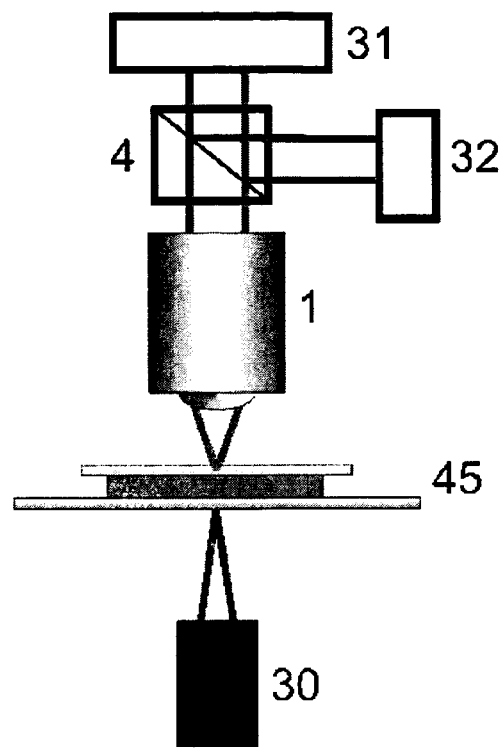
FIG. 1a, 1b show an fluorescence IR scanning microscope according to the present invention.

In the following description of examples of preferred embodiments of the invention, elements having the comparable technical or physical effect have the same reference numerals.

FIG. 1a shows an fluorescence IR scanning microscope according to the present invention. The IR scanning microscope is based on a standard fluorescence microscopy setup (e.g. Zeiss AxioTech, Vario). Said device comprises: one or more light sources 32, preferably high power LED (e.g. V-Star, Luxeon) to excite the particles. The signal from the particles may be collected with an optical system 1, preferably a 40× oil objective and is separated from the light of the light source by one or more light separation elements 4, preferably a dichroic mirror. The said signal is recorded with one or more detectors 31, preferably CCD Camera (e.g. SensiCam QE, PCO). The beam of an IR LASER 30 (e.g. IPG, Raman fibre RLD-5-1455) is coupled into microfluidic chamber 45 (e.g. a multiwell plate). The system may comprise other components as would ordinarily be found in fluorescence and wide field microscopes. Examples for means of excitation and detection of fluorescence may be found in: Lakowicz, J. R. Principles of Fluorescence Spectroscopy, Kluwer Academic/Plenum Publishers (1999).

Figure 1B:
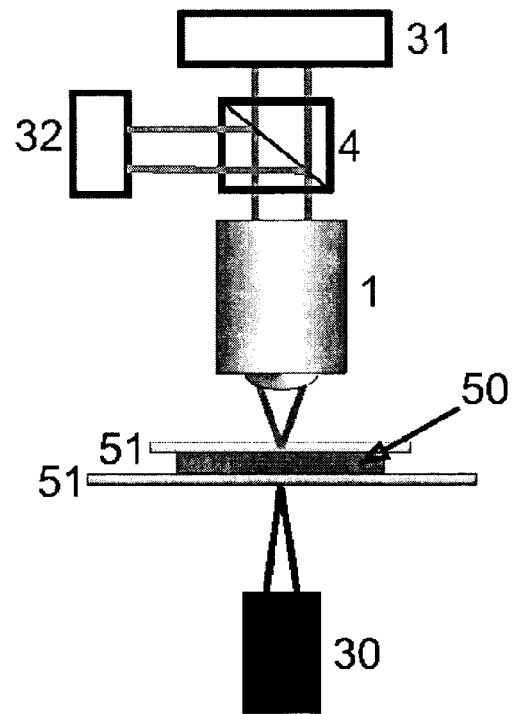

FIG. 1b shows a further embodiment of an fluorescence IR scanning microscope according to the present invention similar to the embodiments shown in FIG. 1a. However, the light source 32 is oriented in a different way with respect to the dichroic mirror 4. The testing sample 50 is sandwiched between two pieces of glass 51, preferably coverslips.

Figure 2:
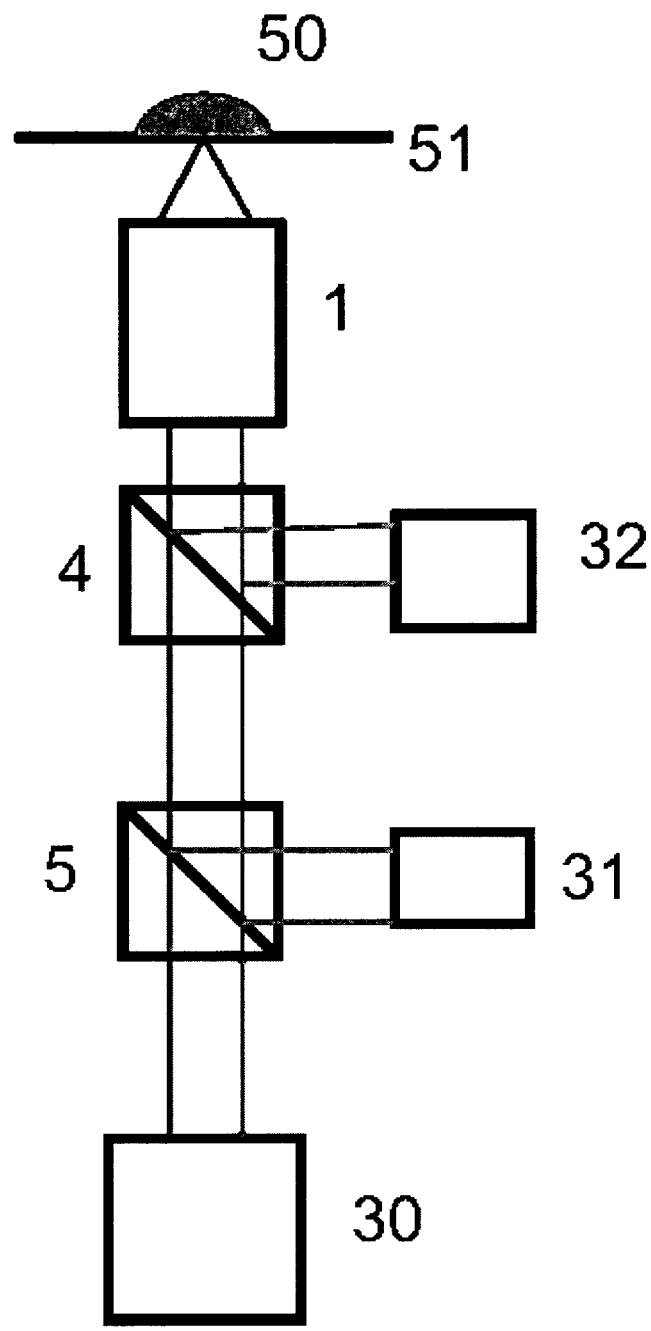
FIG. 2 shows another embodiment of an IR scanning microscope according to the invention.
Figure 3:
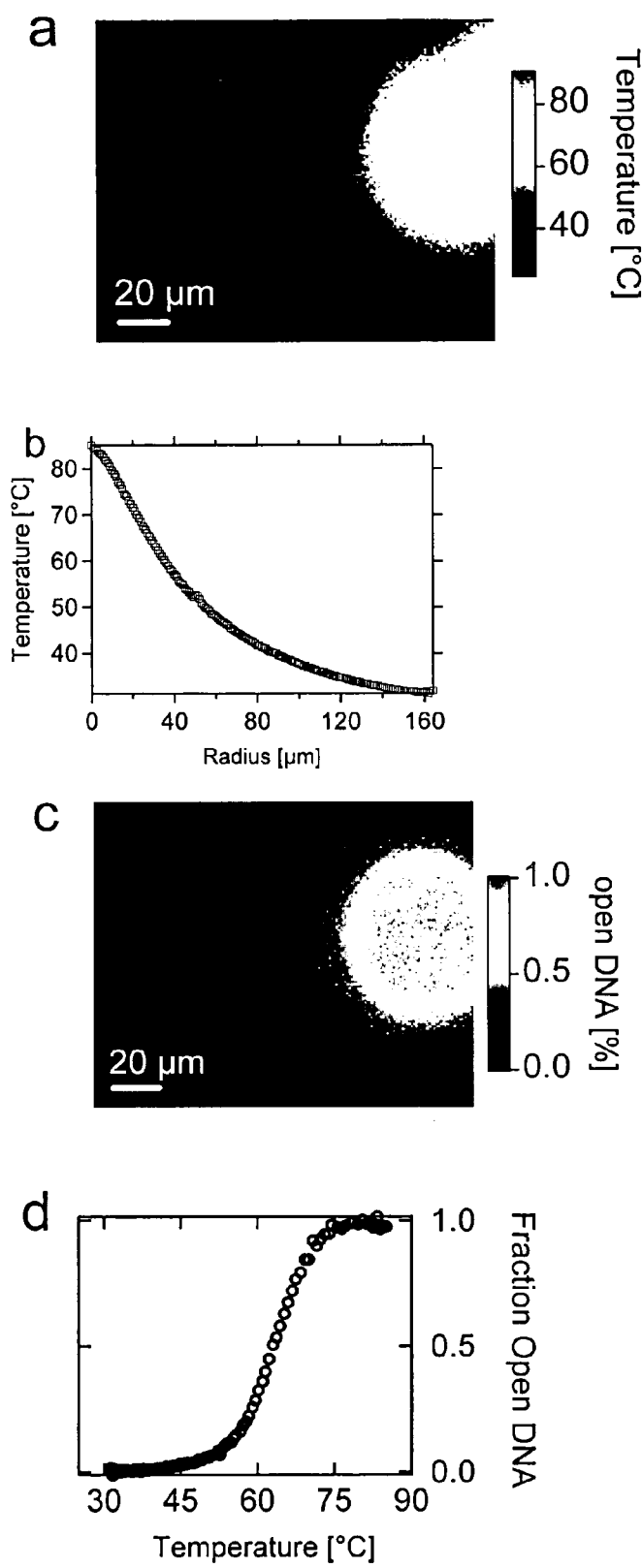
FIG. 3a-3d show how melting curves with an radiation of 150 ms can be taken.

FIG. 2 shows another embodiment of an IR scanning microscope according to the invention. According to this embodiment of the present invention, the testing sample 50 is provided in form of a single droplet with the marked particles. The volume (preferably some nanoliter up to some microliter) of such a droplet can be easily adjusted such that also the dimensions, i.e. the thickness of the droplet which is irradiated with the laser beam, is predictable. In this embodiment, the laserbeam, the fluorescently exciting light from the light source 32, preferably a LED as well as the measured fluorescent light are all focussed by a common optical system 1, preferably a microscope objective with high numerical aperture and more preferably a objective with high numerical aperture and high IR transmission. Therefore, the LED, the LASER 30 and the detector 31, preferably a CCD can be arranged at a common side with respect to the sample. The exciting light is separated from the fluorescent light by a light separation element 5, preferably a dichroic mirror, which preferably separates different parts of the light spectrum than the light separation element 4.

FIG. 3*a*-*d* show how melting curves with an radiation of 150 ms can be taken. (a) By measuring the fluorescence of a temperature sensitive dye, the temperature distribution in the microfluidic chamber can be measured. (b) shows the radial average of the temperatures measured by fluorescence. (c) Aprox. 150 ms after the IR LASER is turned on an image of the fluorescently labelled DNA is taken. The high intensity shows melted ds DNA. From (a) and (c) the melting curve can be determined very fast (d).

Figure 4:
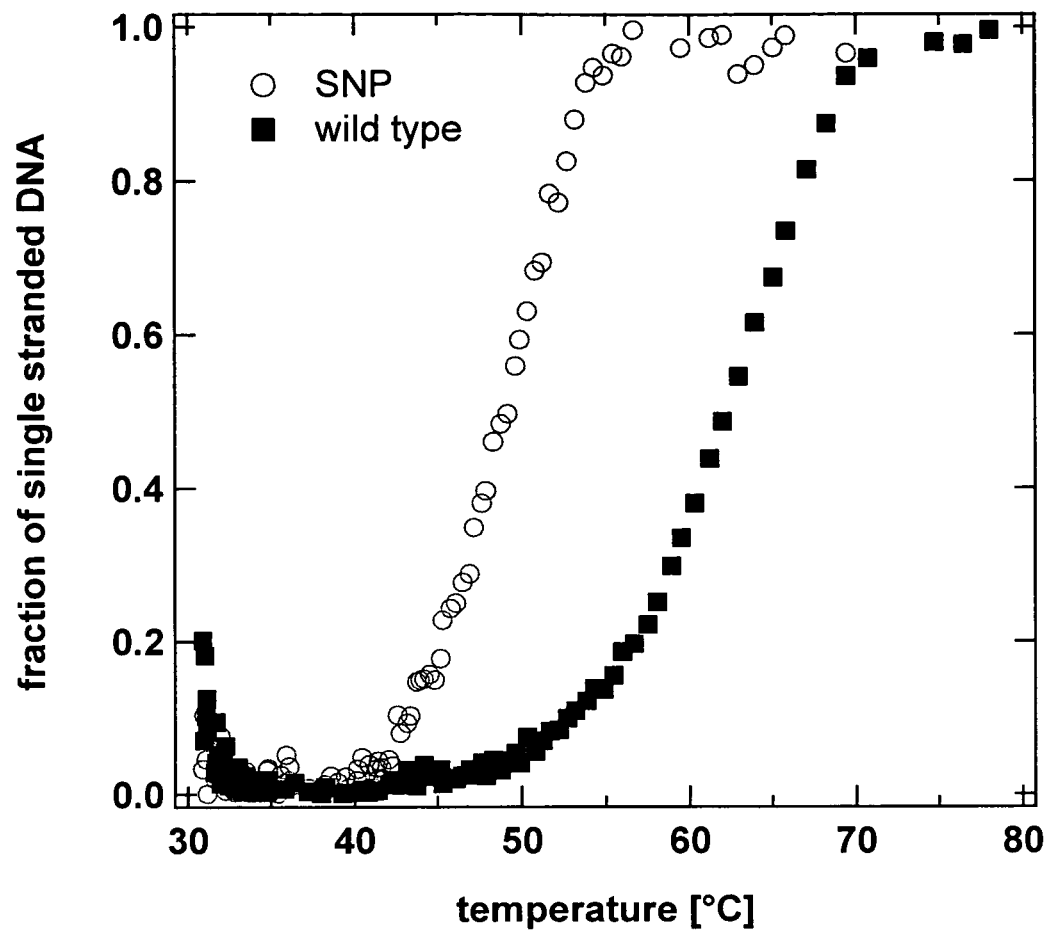
FIG. 4 shows a fast SNP detection.

FIG. 4 shows a fast SNP detection. A 16mer of dsDNA with a single nucleotide mismatch in the center (blue) is compared with the wild type (black). Within 150 ms both species can be clearly discriminated. The ordinate describes the fraction of dissociated dsDNA. The melting point is defined by 50% dissociated molecules. It is shifted by 15° C. by a single mismatch.

Figure 5A:
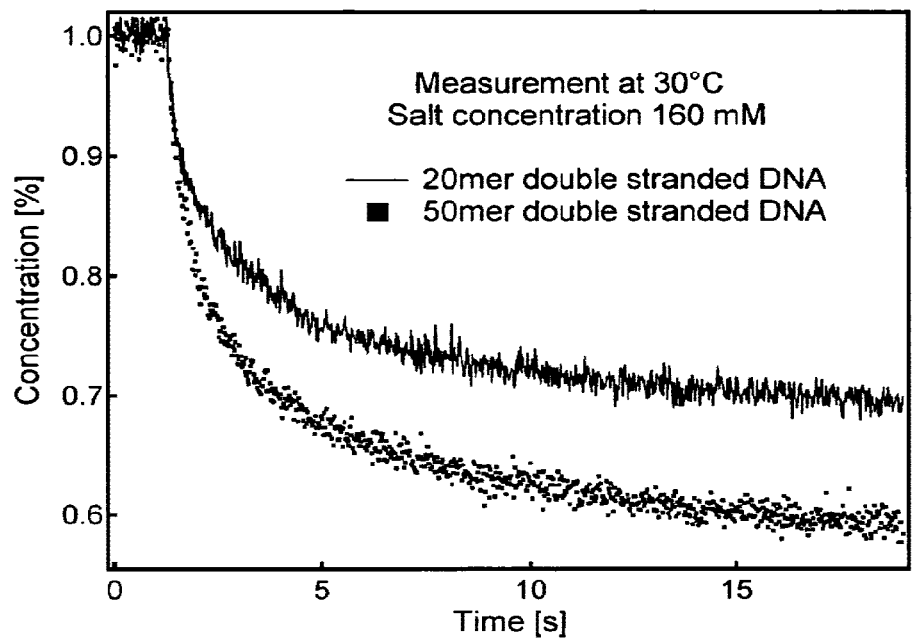
FIG. 5a-5b show the mobility in a temperature gradient.
Figure 5B:
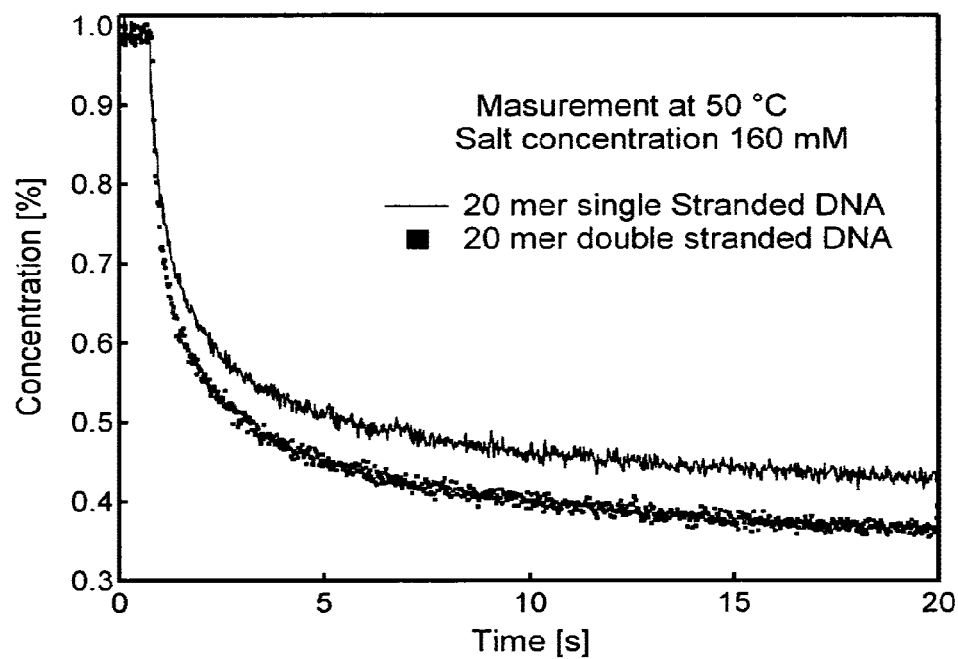

FIG. 5*a*-5*b* show the mobility in a temperature gradient. The figures show the change of concentration in the central pixel of a heat spot over time. A few seconds after the start of the measurement the laser is turned on and the concentration decreases until a steady state is reached. The signal allows to distinguish between a 20mer and 50mer dsDNA (a) as well as between 20 bases ssDNA and 20 basepair dsDNA (b).

Figure 6:
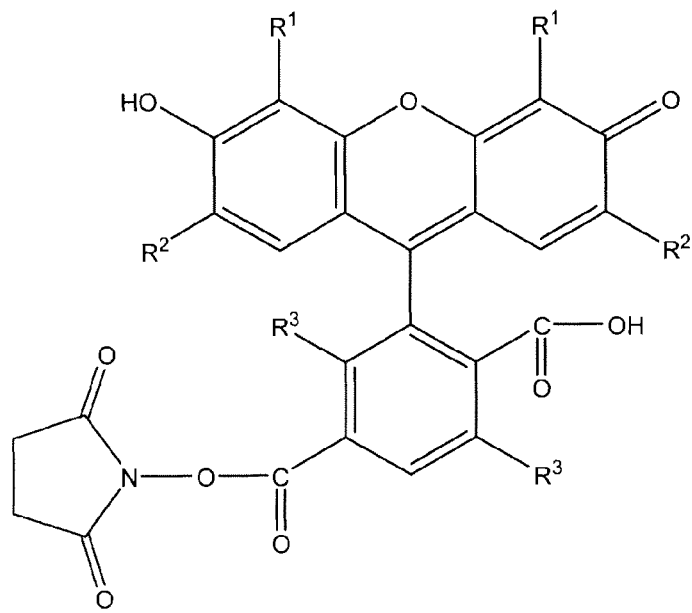
FIG. 6 is an example for a fluorescence dye to be used in the methods of the present invention

FIG. 6 is an example for a fluorescence dye to be used in the methods of the present invention (6-carboxy-2',4,4',5',7,7'-hexachlorofluorescein (HEX, SE; C20091) from Invitrogen).

Figure 7:
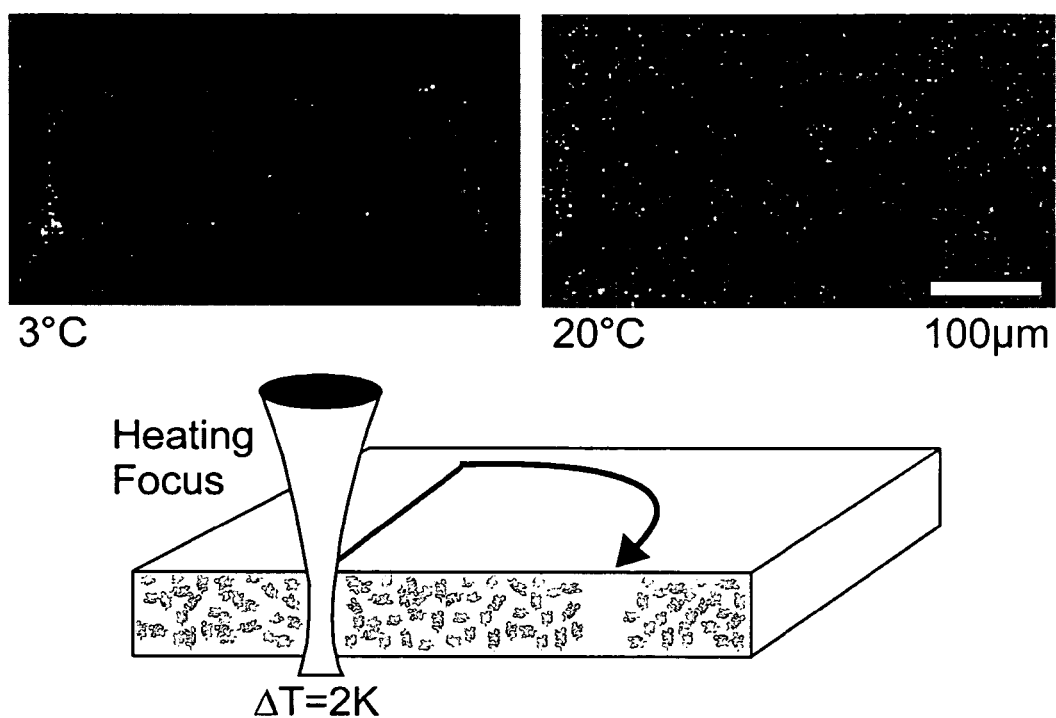
FIGS. 7-14 show further information with regard to a detailed example according to the present invention.

FIGS. 7-14 show further information with regard to a detailed example according to the present invention. These figures show in particular:

FIG. 7: illustrates how thermodiffusion manipulates the DNA concentration by small temperature differences within the bulk solution. A thin water film is heated by 2 K along the letters "DNA" with an infrared laser. For a cooled chamber at 3° C., fluorescently tagged DNA accumulates to the warm letters. However at room temperature DNA moves into the cold, showing reduced fluorescence. The chamber is 60 μm thin, containing 50 nM DNA in 1 mM TRIS buffer. Every 50th base pair is labelled with TOTO-1.

Figure 8:
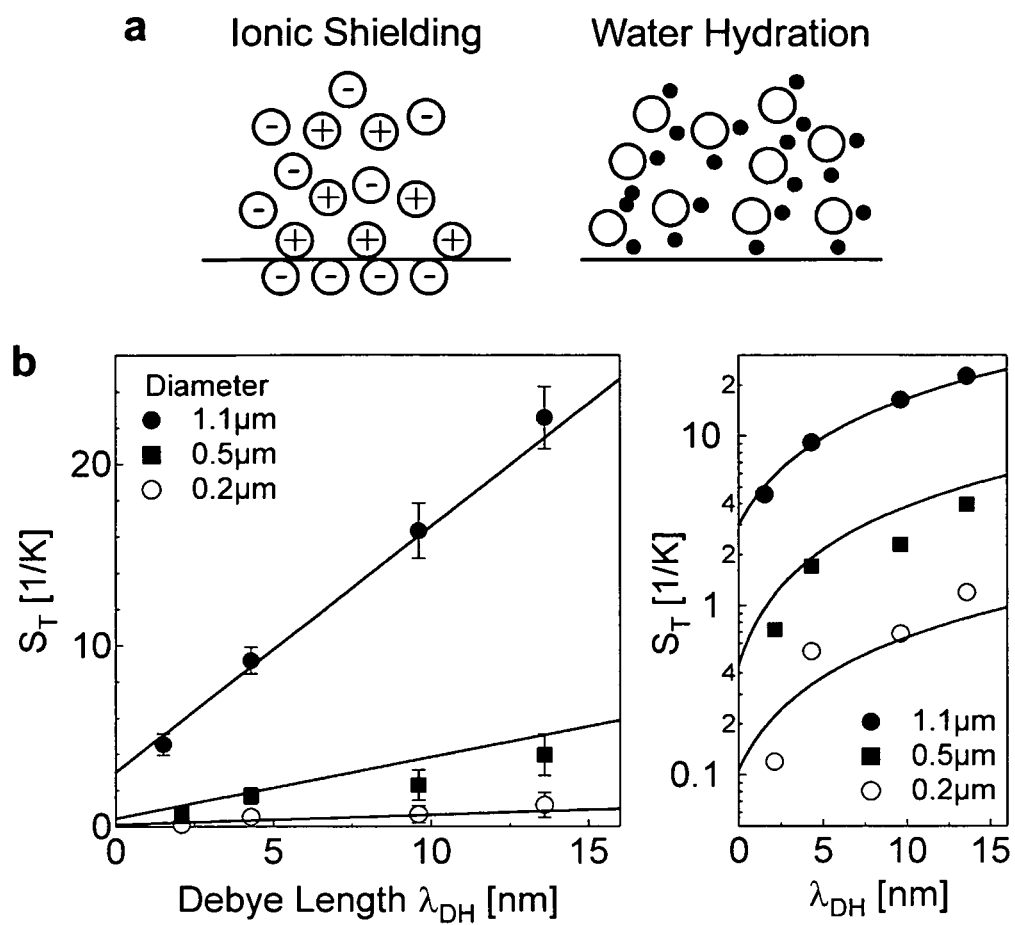

FIG. 8 illustrates the salt dependency. (a) Thermodiffusion in water is dominated by ionic shielding and water hydration. (b) Soret coefficient ST versus Debye length for carboxyl modified polystyrene beads of diameter 1.1, 0.5 and 0.2 μm. Linear plot (left) and logarithmic plot (right). The Soret coefficients are described by equation (2) with an effective surface charge of σeff=4500 e/μm2 known from electrophoresis. The intercept $S_T(\lambda_{DH}=0)$ is fitted with an hydration entropy per particle surface of Shyd=−1400 J/(molKμm2).

Figure 9:
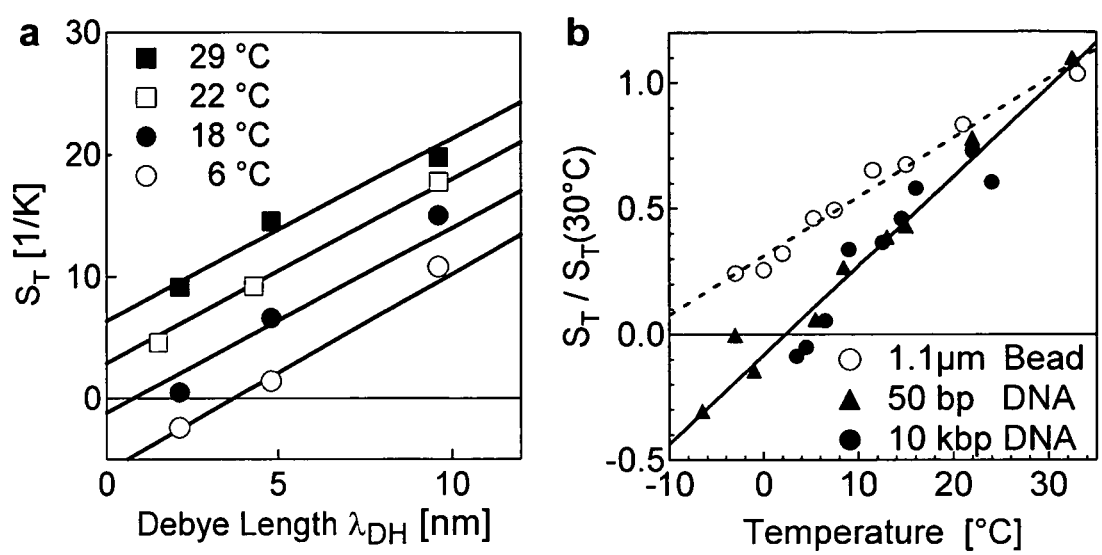

FIG. 9 shows a temperature dependency. (a) The temperature dependence is dominated by the linear change in the hydration entropy Shyd. It shifts the salt dependent thermodiffusion ST(λDH) to lower values. The particle size is 1.1 μm. (b) The Soret coefficient ST increases linearly with the temperature as expected for a hydration entropy Shyd(T). It depends on the molecule species, not its size, as seen from the rescaled Soret coefficients for DNA with different lengths.

Figure 10:
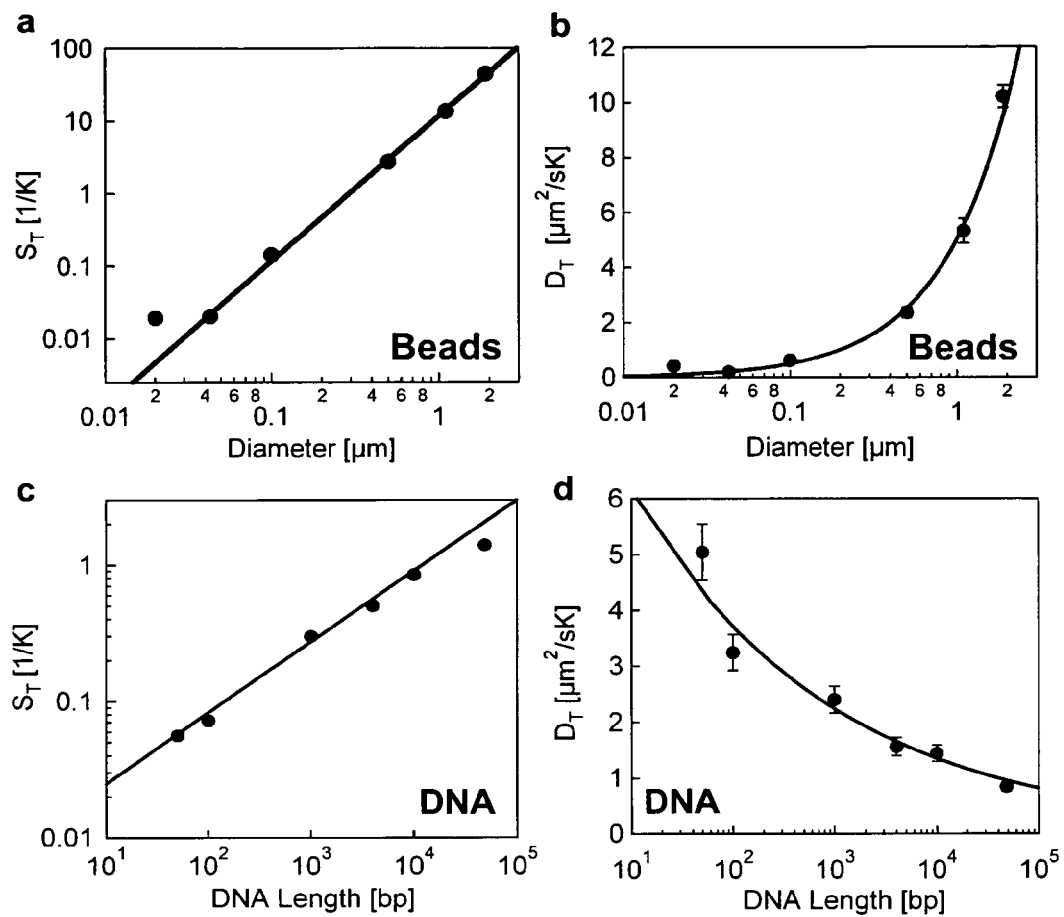

FIG. 10 shows a size dependency. (a) For polystyrene beads, the Soret coefficient scales with the particle surface over four orders of magnitude. Measurements are described by equation (2) with an effective surface charge density of σeff=4500 e/μm2 and negligible hydration entropy. The deviation for the bead with 20 nm diameter can be understood from an increased effective charge due to the onset of charge normalization for a≤λ_{DH}. (b) Accordingly, the thermodiffusion coefficient DT scales linearly with bead diameter. (c) The Soret coefficient of DNA scales according to $S_T \propto \sqrt{L}$ with the length L of the DNA based on equation (2) with an effective charge per base pair of 0.12 e. (d) Thermodiffusion coefficient DT decreases over DNA length with $D_T \propto L^{-0.25}$, caused by the scaling of diffusion coefficient $D \propto L^{-0.75}$.

Figure 11:
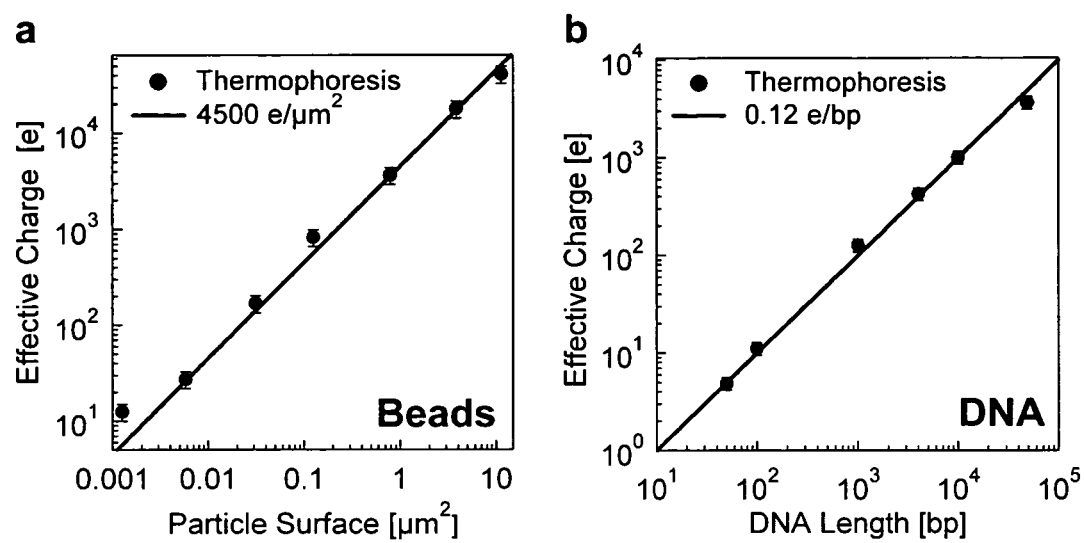

FIG. 11: shows an effective Charge from Thermodiffusion. Effective charge is inferred from thermodiffusion using equation (3). Polystyrene beads (20 . . . 2000 nm) (a) and DNA (50-50,000 bp) (b) are measured over a large size range, impossible with electrophoresis. As expected, the effective charge of the beads scales with particle surface and linearly with length of DNA.

Figure 12:
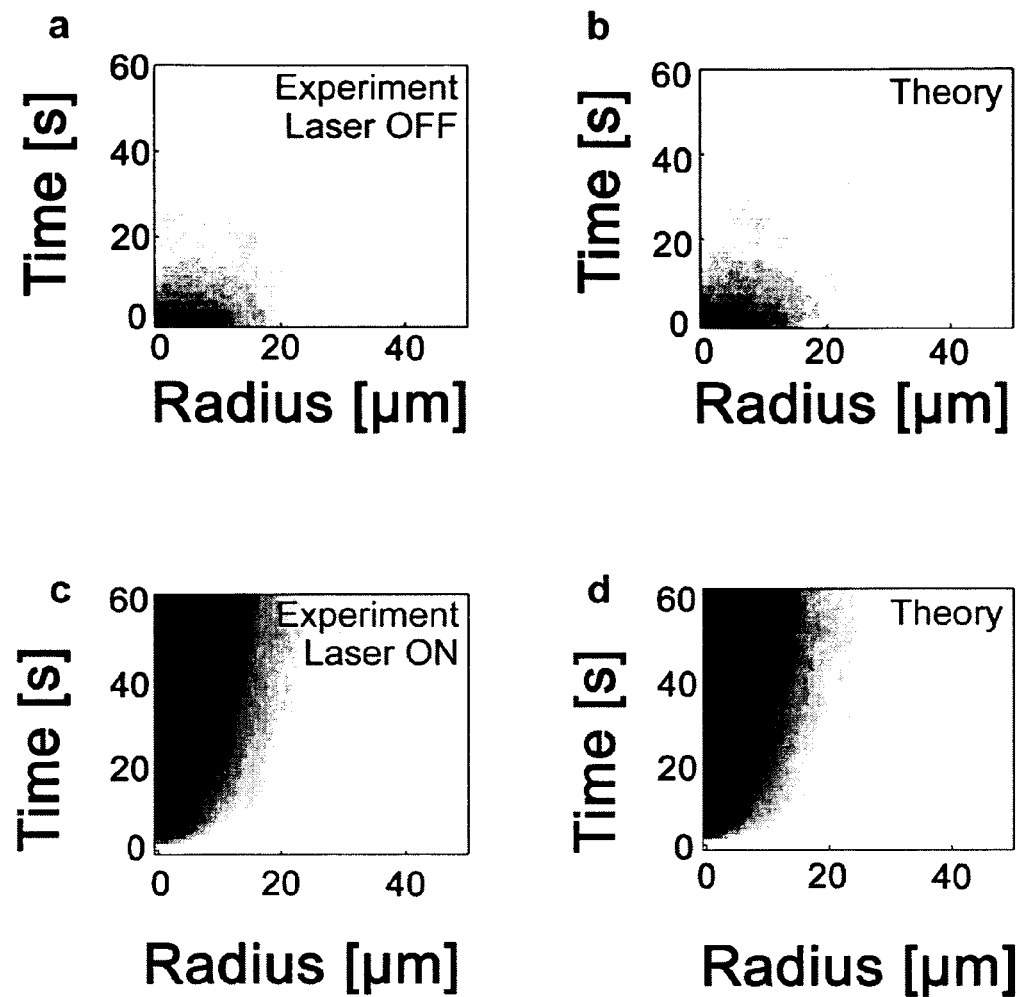

FIG. 12: shows the dependency of thermodiffusion from concentration over time. (a) Diffusion coefficient D was obtained from back diffusion after switching off the heat source. (b) D is varied until the finite element simulation matches the experiment. (c) Radial depletion of DNA from a focussed 2K heat spot is monitored over time. (d) Comparison with simulation with known D yields DT and ST.

Figure 13:
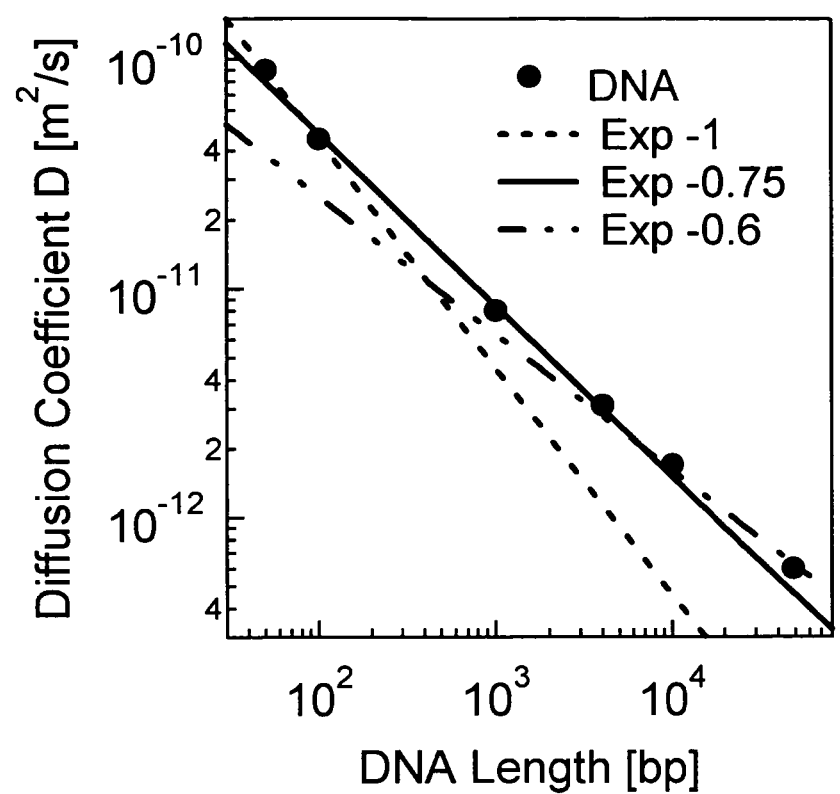

FIG. 13 shows a scaling of DNA diffusion coefficients. The diffusion coefficients as measured in this study at room temperature. The scaling over DNA length matches literature values with two scaling regimes with exponent −1 for short and −0.6 for long DNA. As approximation, diffusion across the two scaling regimes is well described with an overall exponent of −0.75.

Figure 14:
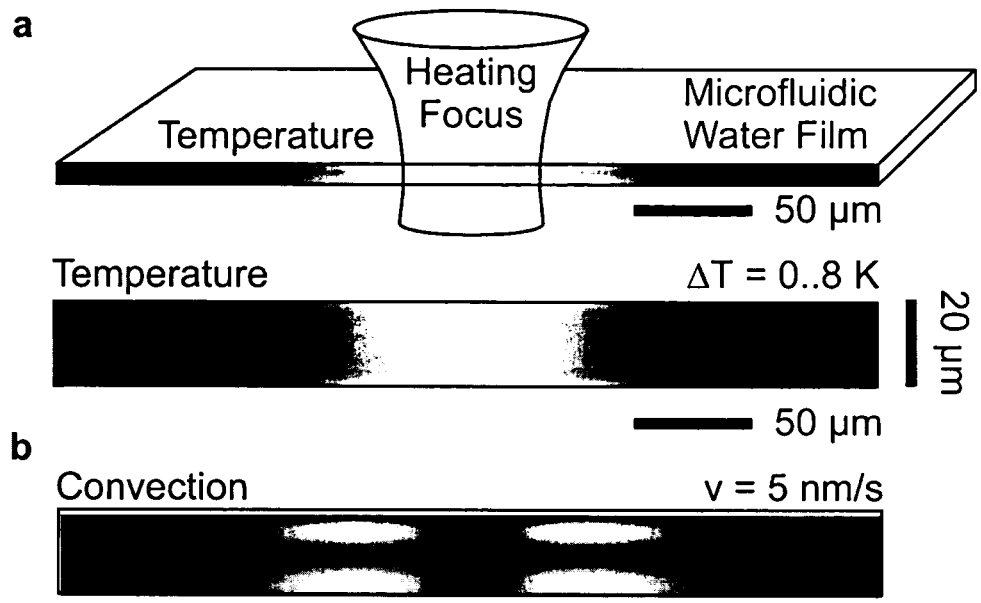

FIG. 14: shows a simulation of Microfluidic Heating. (a) A 10 μm thin water film is enclosed between PS walls. Low thermal conduction of the chamber walls allow a thickness independent temperature profile, confirmed by the shown finite element calculation. (b) Convection is slow at maximal velocities of 5 nm/s due to thin chamber and comparable broad heating focus.

Figure 15:
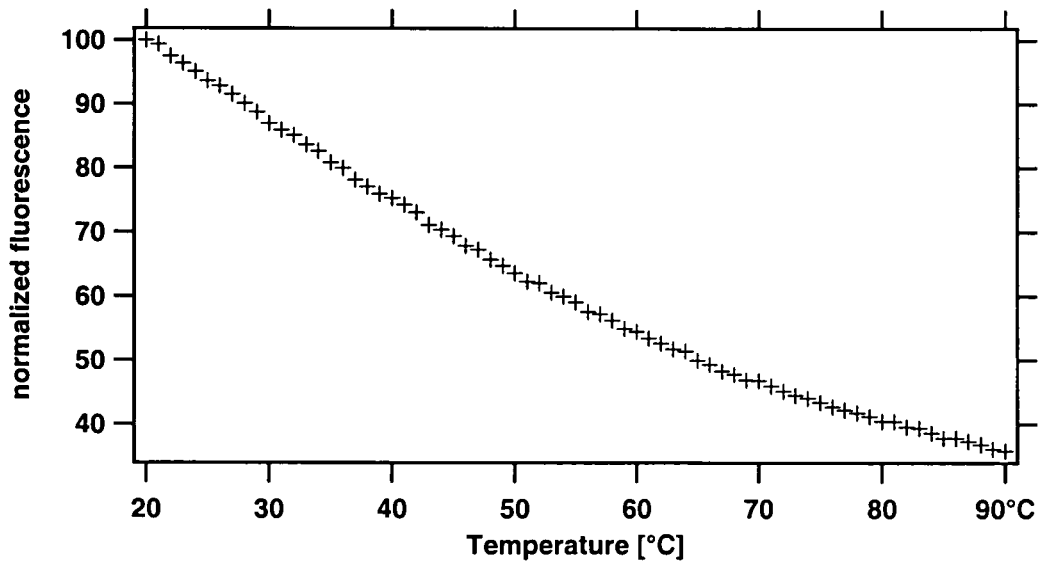
FIG. 15: shows the temperature dependence of a fluorescent dye measured by a fluorimeter with temperature control (Peltier element).

FIG. 15 shows the temperature dependence of a fluorescent dye measured by a fluorimeter with temperature control (Peltier element).

Figure 16:
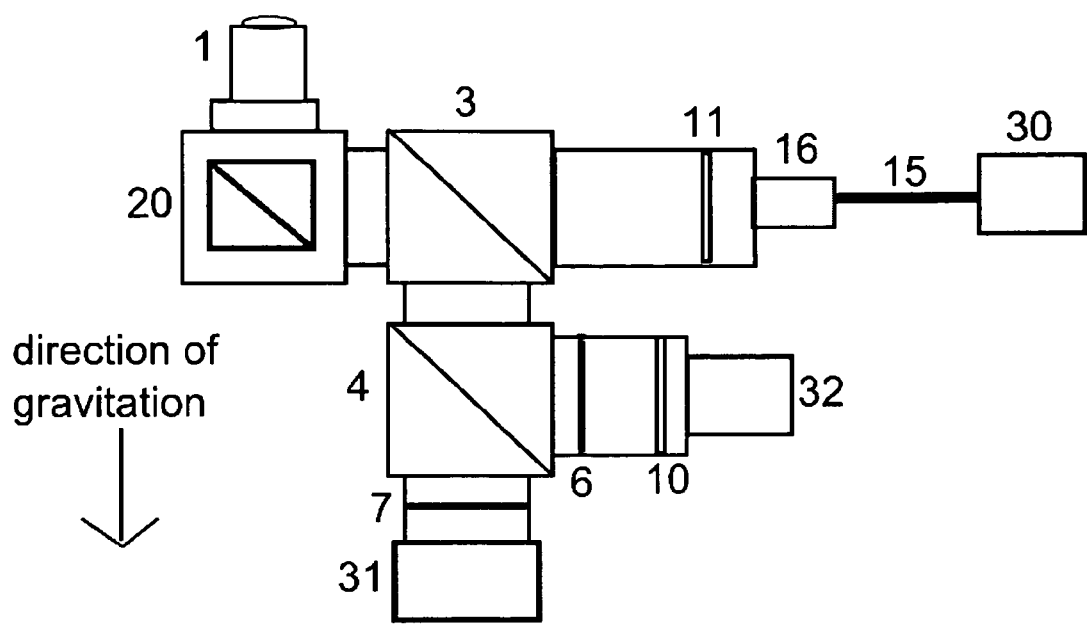
FIGS. 16-24 show particular embodiment of the device according to the present invention.

FIG. 16 illustrates a particular embodiment of a device accordingly to the present invention. The device may have an substantially arbitrary orientation with respect to the direction of gravitation, preferably the device is oriented perpendicular with respect to the direction of gravitation, more preferably the device is oriented substantially parallel or anti-parallel with respect to the direction of gravitation. Preferably the orientation of the device with respect to the testing sample or chamber may be adjusted as shown in FIG. 1*a*, FIG. 1*b* and FIG. 2. The device comprises: 1: Objective (e.g. 40×, NA 1.3, oil immersion, ZEISS "Fluar"); 20: Scanning module, may be Galvano scanning mirror or may be acoustic optic deflector (AOD); 3: cold mirror, preferably high IR-transmission and preferably >90% reflection 350 nm-650 nm; 11: beam shaping module to determine laser beam diameter and focusing, may be a lens system which may comprise one, two or more lenses; 16: Laser fibre coupler w/o collimator; 15: Laser fibre (single mode or multimode); 30: IR-Laser (e.g. 1455 nm, 1480 nm, 0.1 W-10 W); 4: Dichroic mirror/beam splitter reflecting short wavelength (R>80%), transmitting long wavelength (T>80%); 7: Emission Filter (band pass/long pass); 31: detector, may be a CCD-Camera, Line-Camera, Photomultiplier Tube (PMT), Avalanche Photodiode (APD), CMOS-Camera; 6: Excitation Filter (e.g. band pass/long pass); 10: lens system to determine the beam properties of the excitation light source, may comprise one, two or more lenses; 32: Excitation light source, may be Laser, Fibre Laser, Diode-Laser, LED, HXP, Halogen, LED-Array, HBO. Preferably the listed parts are enclosed in a housing; a cold mirror is a specialized dielectric mirror, a dichromatic interference filter that operates over a very wide temperature range to reflect the entire visible light spectrum while very efficiently transmitting infrared wavelengths.

Figure 17:
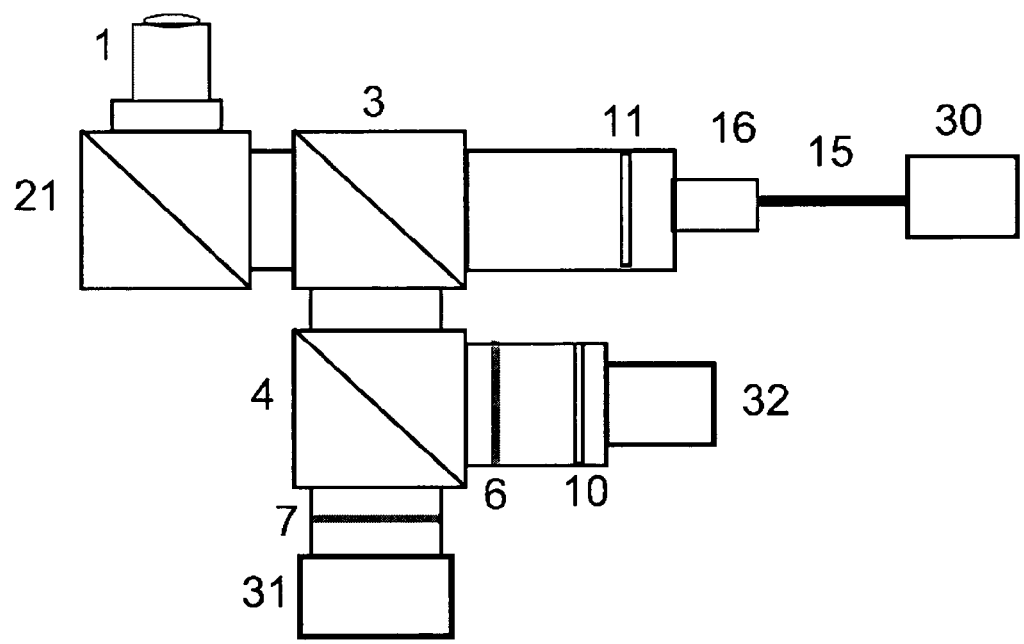

FIG. 17 shows an embodiment of the invention according to FIG. 16, wherein the scanning module 20 is replaced by a fix mirror 21, preferably a silver mirror.

Figure 18:
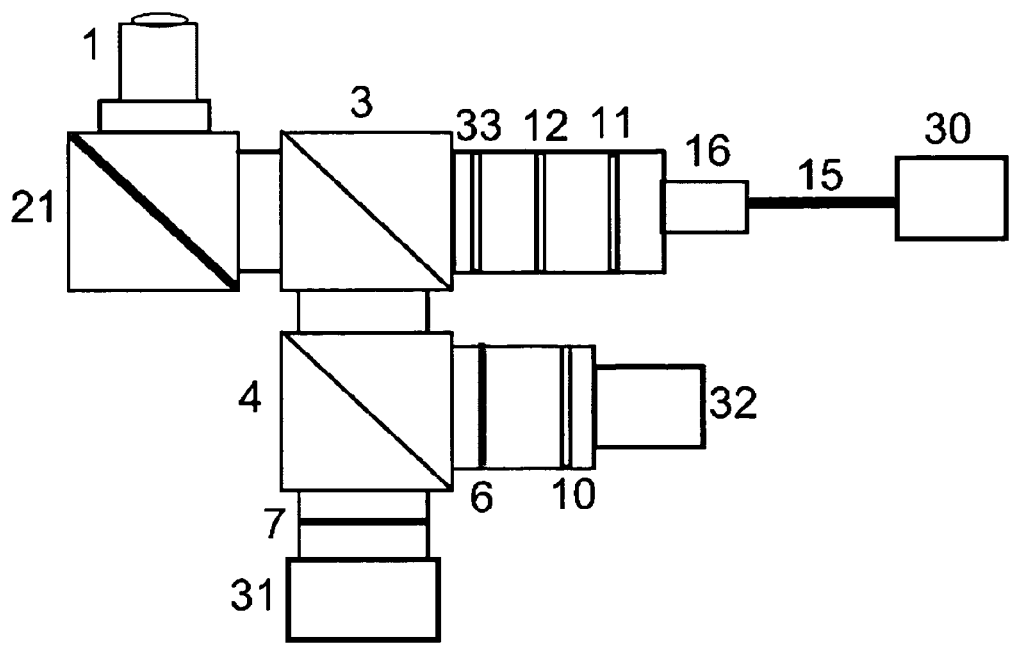

FIG. 18 shows an embodiment of the invention according to FIG. 16, wherein the scanning module 20 is replaced by a fix mirror 21, preferably a silver mirror, and wherein a shutter 33 for controlling the IR LASER radiation is added and wherein a line forming module 12, may be a cylinder lens system or preferably a Powell lens, are added.

Figure 19:
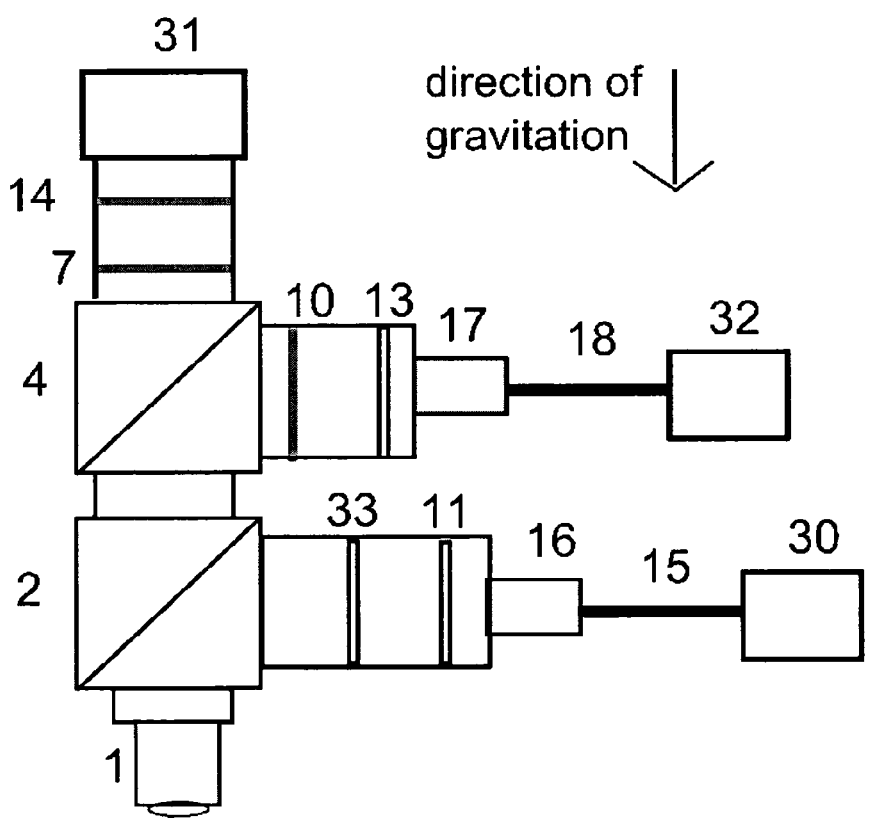

FIG. 19 shows a further embodiment of the device according to the present invention, in particular a confocal setup. The device may have an arbitrary orientation with respect to the direction of gravitation, preferably the device is oriented substantially perpendicular with respect to the direction of gravitation, more preferably the device is oriented substantially parallel or anti-parallel with respect to the direction of gravitation. Preferably the orientation of the device with respect to the testing sample or chamber may be adjusted as shown in FIG. 1a, FIG. 1b and FIG. 2. The device comprises: 1: Objective (e.g. 40×, NA 1.3, oil immersion, ZEISS "Fluar"); 2: hot mirror, high IR-reflection, visible light transmission >80%; 4: Dichroic mirror reflecting short wavelength (R>80%), transmitting long wavelength (T>80%); 7: Emission Filter (band pass/long pass); 31: Detector, may be Photomultiplier Tube (PMT), Avalanche Photodiode (APD); 13: Pinhole aperture; 10: lens system to determine the beam properties of the excitation light source, may comprise one, two or more lenses; 32: excitation light source preferably a laser, more preferably a fibre coupled laser 11: beam shaping module to determine laser beam diameter and focusing, preferably lens system which may comprise one, two or more lenses; 16: Laser fibre coupler w/o collimator; 15: Laser fibre (single mode or multimode); 30: IR-Laser (e.g. 1455 nm, 1480 nm, 0.1 W-10 W); 33: Shutter; 14: pinhole aperture in confocale position to laser pinhole 13 or to laser fibre coupler 17 whereas the pinhole 13 may not be needed, preferably if a fibre coupled laser is used as excitation light source 32; 18 Laser fibre may be single mode or may be multi mode.

Figure 20:
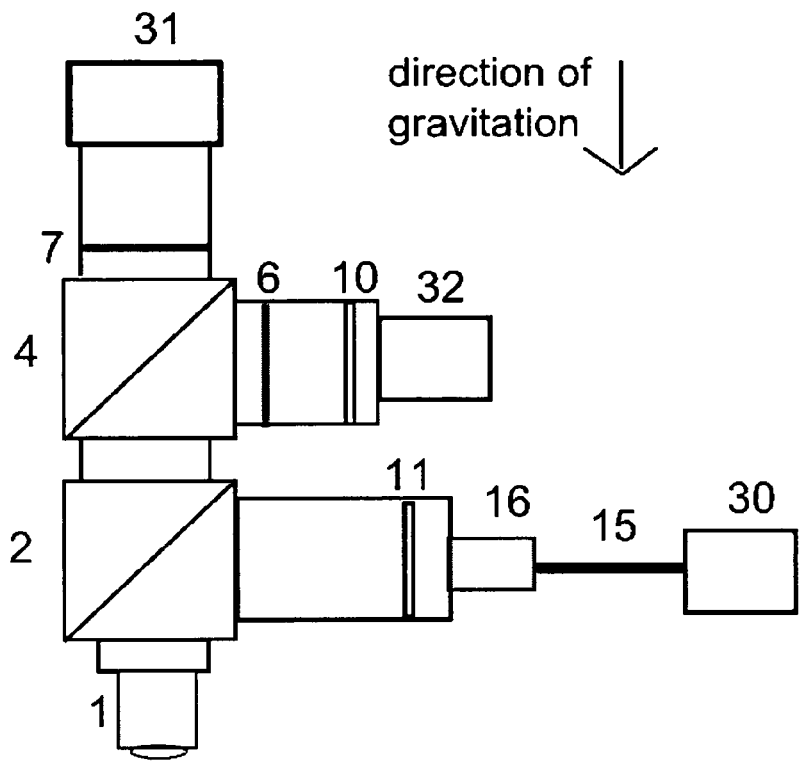

FIG. 20 shows a further embodiment of the device according to the present invention. The device may have an arbitrary orientation with respect to the direction of gravitation, preferably the device is oriented substantially perpendicular with respect to the direction of gravitation, more preferably the device is oriented substantially parallel or anti-parallel with respect to the direction of gravitation. Preferably the orientation of the device with respect to the testing sample or chamber may be adjusted as shown in FIG. 1a, FIG. 1b and FIG. 2. The device comprises: 1: Objective (e.g. 40×, NA 1.3, oil immersion, ZEISS "Fluar"); 2: hot mirror, high IR-reflection, visible light transmission >80%; 4: Dichroic mirror reflecting short wavelength (R>80%), transmitting long wavelength (T>80%); 6: Excitation Filter (e.g. band pass/long pass); 7: Emission Filter (band pass/long pass); 10: lens system to determine the beam properties of the excitation light source; 31: Detector, may be Photomultiplier Tube (PMT), Avalanche Photodiode (APD); 32: excitation light source 16: Laser fibre coupler w/o collimator; 15: Laser fibre (single mode or multimode); 30: IR-Laser (e.g. 1455 nm, 1480 nm, 0.1 W-10 W); a hot mirror is a specialized dielectric mirror, a dichromatic interference filter often employed to protect optical systems by reflecting heat back into the light source. Hot mirrors can be designed to be inserted into the optical system at an incidence angle varying between zero and 45 degrees, and are useful in a variety of applications where heat build-up can damage components or adversely affect spectral characteristics of the illumination source. By transmitting visible light wavelengths while reflecting infrared, hot mirrors can also serve as dichromatic beam splitters for specialized applications in fluorescence microscopy.

Figure 21:
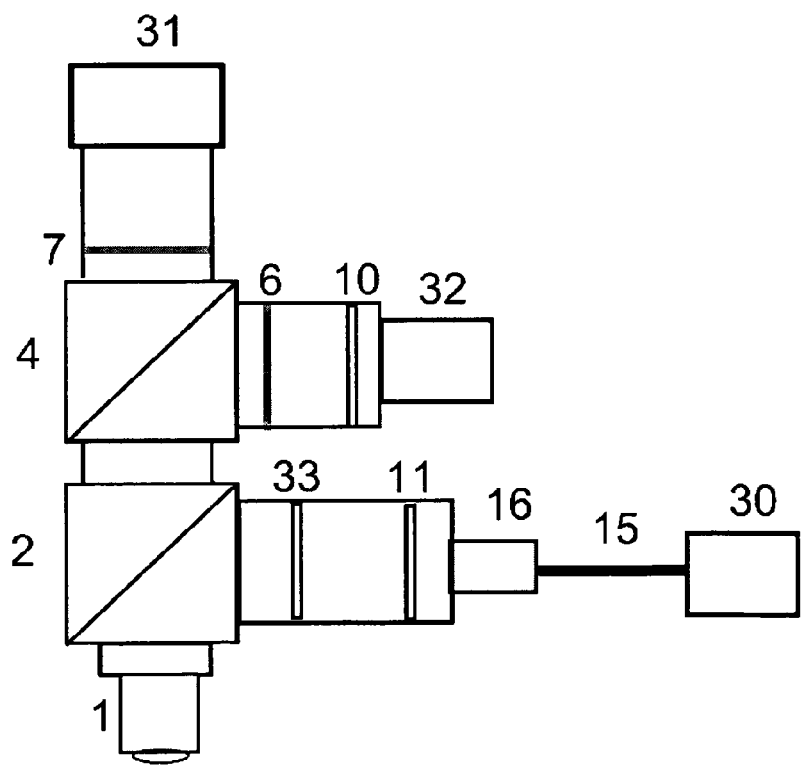

FIG. 21 shows an embodiment of the invention according to FIG. 20, wherein a shutter 33 is added to control the IR laser radiation.

Figure 22:
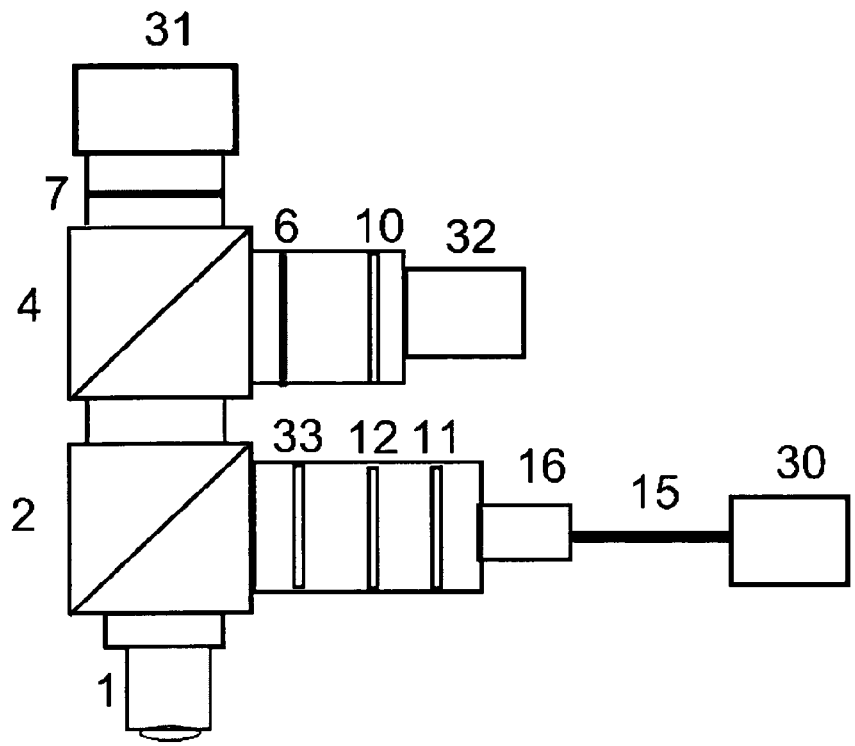

FIG. 22 shows an embodiment of the invention according to FIG. 20, wherein a shutter 33 and a line forming module 12, preferably a lens system comprising one, two or more lenses or more preferably a Powell lens are added to control the IR laser radiation.

Figure 23:
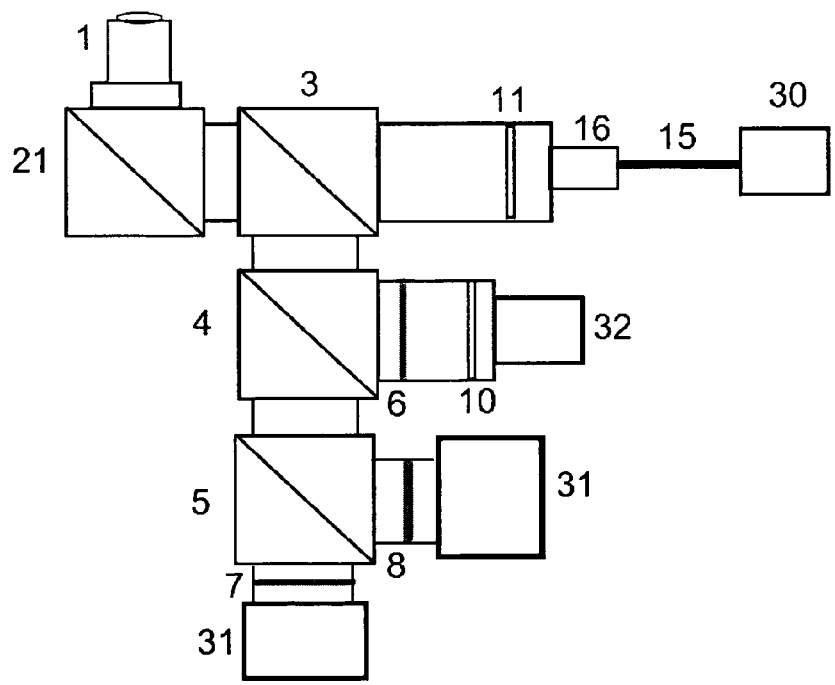

FIG. 23 shows an embodiment of the invention according to FIG. 16, wherein the scanning module 20 is replaced by a fix mirror 21, preferably a silver mirror and wherein an additional light separation element 5, preferably a dichroic mirror, which preferably separates different parts of the light spectrum than the light separation element 4 is added and wherein an emission filter 8 is added, preferably transmitting another range of wavelength than the emission filter 7 and wherein a second detector 31 is added which detects the signal passing through the filter 8.

Figure 24:
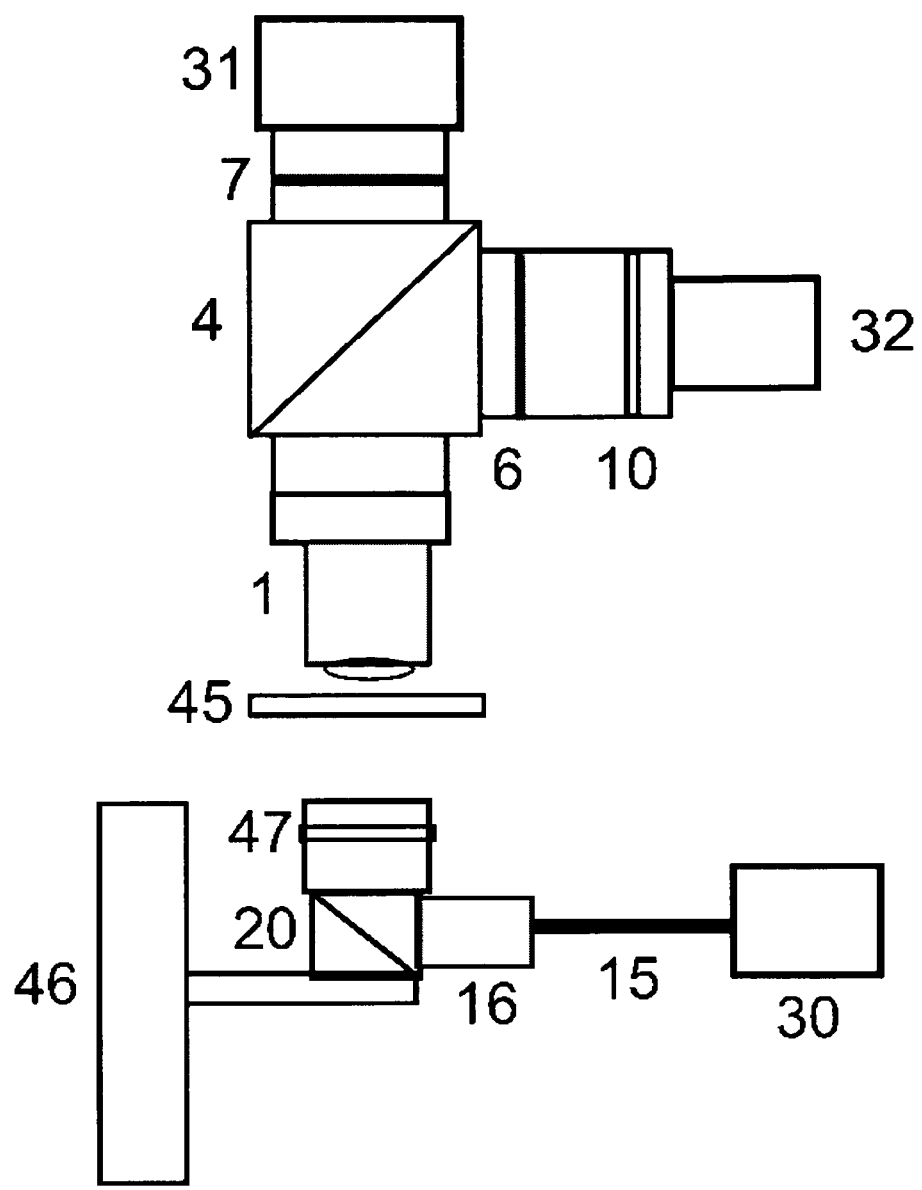

FIG. 24 shows a further embodiment of the device; 31: CCD camera; 7: Emission filter (e.g. bandpass or longpass); 4: light separation element, preferably a dichroic mirror for splitting excitation light pathway and emission light pathway; 1: Objective; 45: Chamber; 10: Lens system for focusing IR-Laser onto sample; 20: scanning module, may be galvanometric mirrors or an acoustic optical deflector; 16: Laser fibre coupler with collimating optics; 15: Laser fibre; 30: IR-Laser; 6: Excitation Filter; 10: optical system for excitation, may be a lens system comprising one, two or more lenses; 32: Light source (HXP,LED); 46: xyz-Translation stage for laser positioning, may be automated, preferably may be automated for scanning the chamber. 47: optical system for beam shaping of the IR Laser, may be a lens system comprising one, two or more lenses or may be a objective, preferably with high IR transmission.

Figure 25:
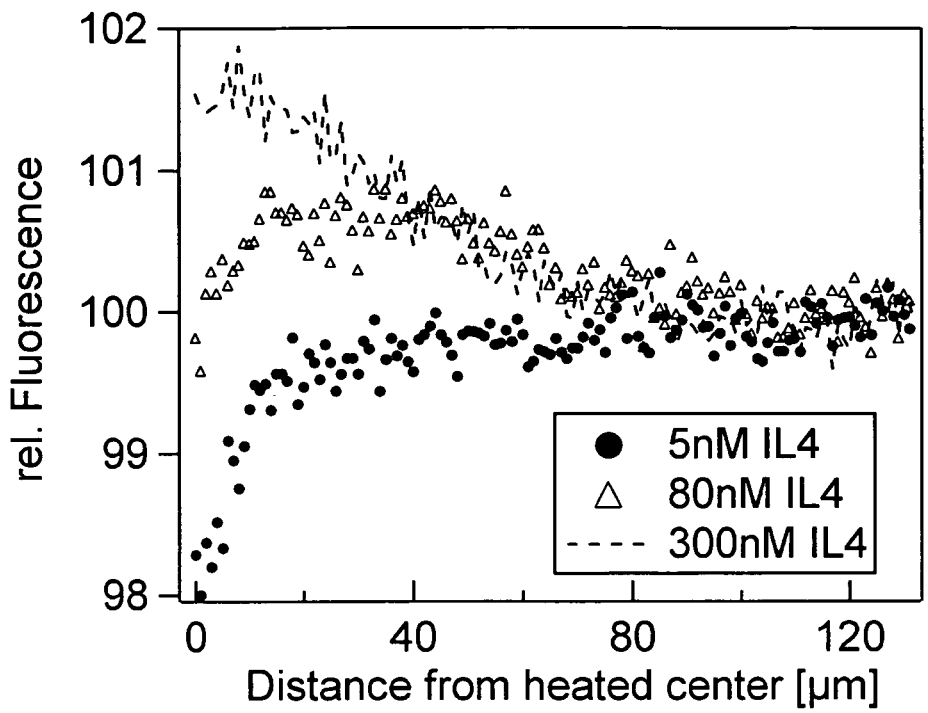
FIG. 25: shows quantification of interaction between biomolecules.
Figure 25:
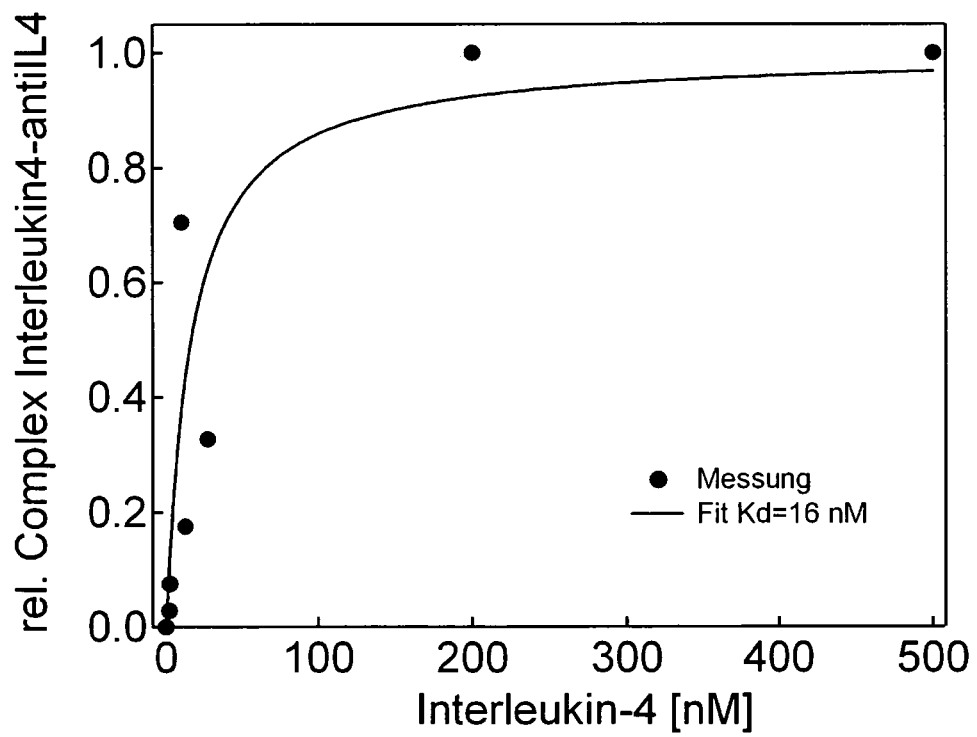

FIG. 25 shows a quantification of interaction between biomolecules. 100 nM of a fluorescently labelled antibody (anti-Interleukin 4) are titrated with various amounts interleukin. (left) The spatial fluorescence distribution in steady state is measured. Three curves with 5 nM, 80 nM and 300 nM are shown exemplarily. The signal changes dramatically from fluorescence decrease to a fluorescence increase. Integration of the fluorescence profile up to 80 µm (distance from the heated centre) allows to determine the number of complexes in solution. (right) The concentration of free Interleukin 4 can be calculated plotted versus the concentration formed complex. These data can be fitted to determine the $K_D$.

Figure 26:
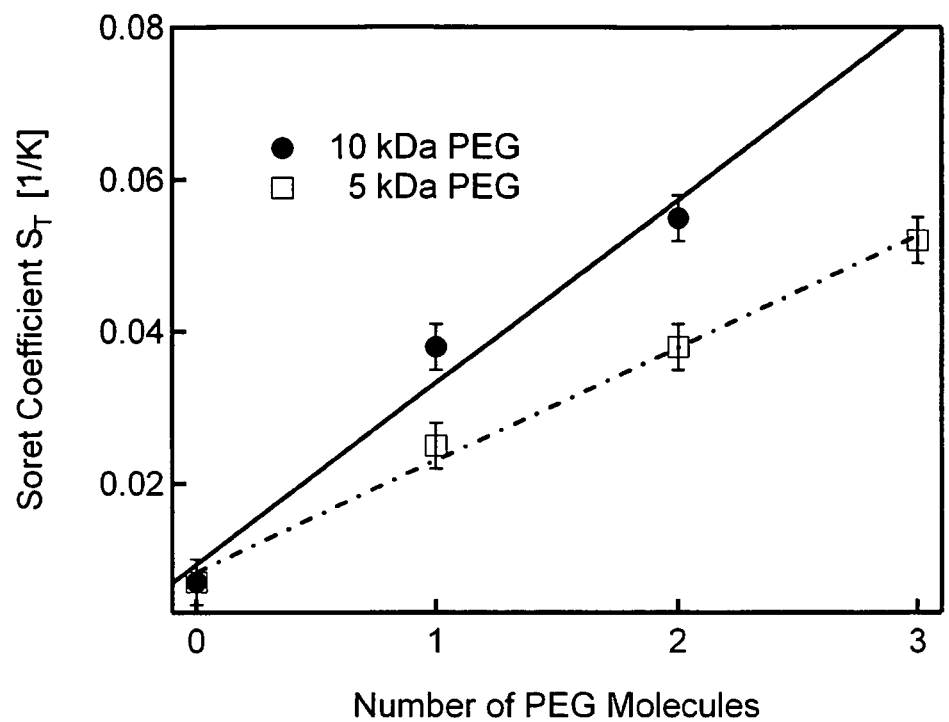
FIG. 26: shows single molecule binding to nanoparticles.

FIG. 26 shows a single molecule binding to nanoparticles. The Soret coefficient of nanocrystals in complex with PEG molecules is measured by evaluating the concentration profile in steady state. The Soret coefficient increases linearly with the number of PEG molecules covalently bound to the particle. PEG molecules with a higher molecular weight show a steeper increase in the Soret coefficient. The PEG molecules shown here are comparable in size to proteins or short DNA molecules, which can be detected in the same manner.

Figure 27:
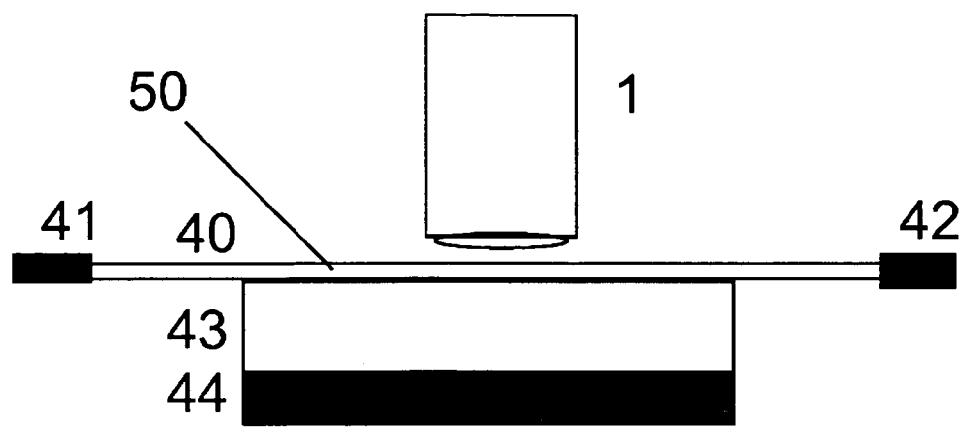
FIG. 27: shows a particular embodiment of the device according to the present invention.

FIG. 27 shows a further embodiment of a device according to the present invention. The receiving means for receiving the sample probe 50 is a capillary 40 with inner diameter 5 µm to 500 µm such that the thickness of the sample probe is small in the direction perpendicular to the laser beam. The first valve 41 and the second valve 42 are provided for the controlled input/output of the sample probe 50 in/from the capillary 40. The capillary is mounted on a solid support 43, preferably a material with good thermal conductivity, e.g. aluminium, copper. The Peltier-element 44 is mounted on the solid support 43 such that the capillary 40 can be cooled.

Figure 28:
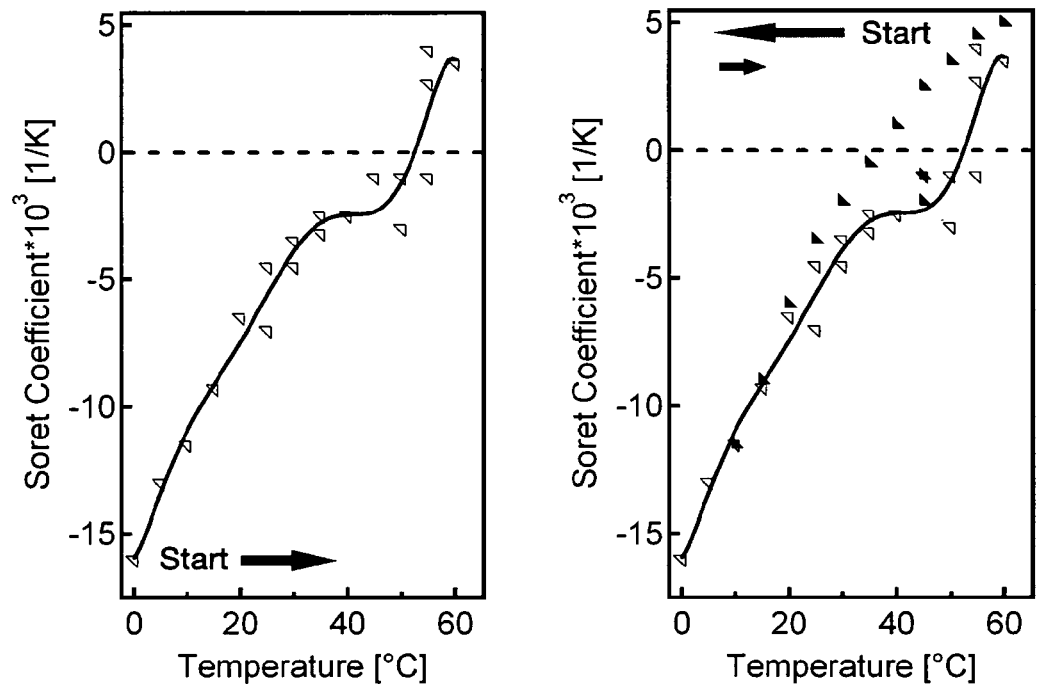
FIG. 28: shows the characterization of protein conformation

FIG. 28 shows the characterization of protein conformation. Thermo-optical characterization provides the means to characterize the conformation of a protein in solution. The temperature of a solution containing Bovine Serum Albumin (BSA) is cooled down to 0° C. Starting from this temperature the Soret coefficient is measured at different temperatures which are increased in a stepwise manner up to 60° C. The Soret coefficient is negative, up to values close to thermal denaturation, where a sudden jump to positive Soret coefficients is observed. At physiological temperatures (30-40° C.) the Soret coefficient does not change much. In this temperature range the protein has to have similar properties to perform its tasks. Because of the tight relation between structure and function, the conformation is preserved in this temperature range. The results are confirmed by the experiment shown on the right, which starts at high temperatures. The Soret Coefficients are still positive below 50° C. since the measurements are faster than the time the protein needs for refolding. After a certain time span (i.e. 20 minutes) the values reach the negative Soret coefficients obtained in the measurements started at low temperatures. A following temperature increase reproduces the negative Soret coefficient measured in the experiment starting at low temperatures.

Figure 29:
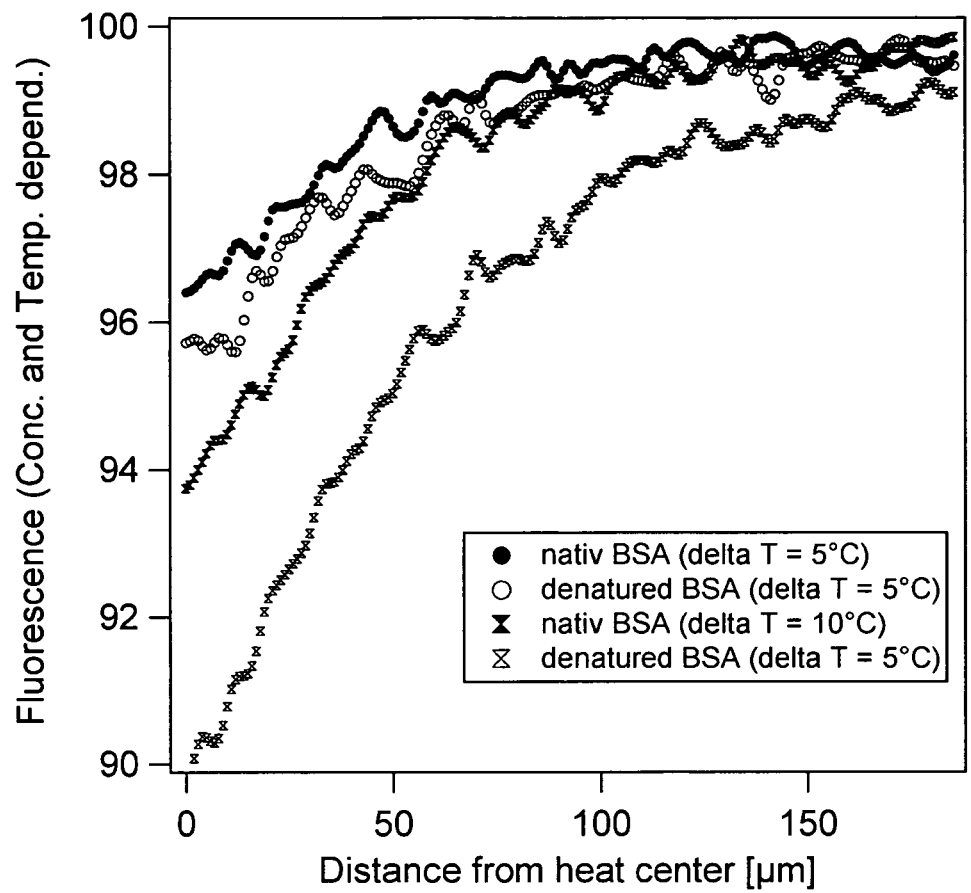
FIGS. 29-30: show measurements with a sample of fluorescently labelled bovine serum albumin (BSA).

FIG. 29 shows measurements with a sample of fluorescently labelled bovine serum albumin (BSA). A sample of fluorescently labelled bovine serum albumin (BSA) has been split in two parts. One is only exposed to ambient temperatures, while the other half is heated up to 100° C. for several minutes. The thermo-optical properties of both samples (native and denatured) are measured at different power of the infrared laser (i.e. maximal temperature increase of 5° or 10° C.). As can be seen from the figure, the fluorescence of the denatured protein is lower than the fluorescence of the native protein. This is explained as follows. The fluorescence dye of both samples shows the same decrease in fluorescence due to the increase in temperature (i.e. temperature sensitivity of the fluorescence). But the denatured protein shows a positive thermophoretic mobility (i.e. moves to the cold), while the native protein has a negative thermophoretic mobility (i.e. moves to the hot). The accumulation at elevated temperatures is the reason, why the decrease in fluorescence is lower for the native protein, while the denatured protein is, in addition to temperature dependency, depleted from the region of elevated temperature. The differences between both samples is further increases by raising the temperature (i.e. maximum temperature of 10° C.), since positive and negative thermophoresis is enhanced.

Figure 30:
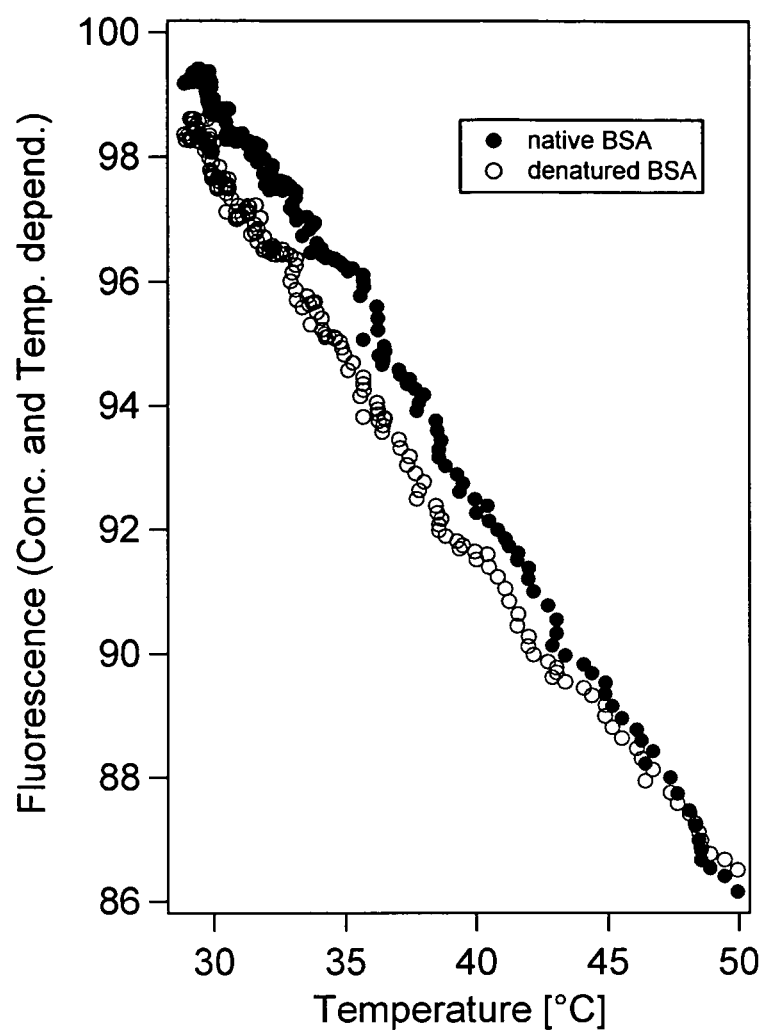

FIG. 30 measurements with a sample of fluorescently labelled bovine serum albumin (BSA). A sample of fluorescently labelled bovine serum albumin (BSA) has been split in two parts. One is only exposed to ambient temperatures, while the other half is heated up to 100° C. for several minutes (i.e. irreversibly denatured). The thermo-optical properties of both samples (native and denatured) are measured at 800 mA power of the infrared laser (i.e. maximal temperature increase of 20° C.). As can be seen from the figure, the fluorescence of the denatured protein is lower than the fluorescence of the native protein. This is explained as follows. The fluorescence dye of both samples shows the same decrease in fluorescence due to the increase in temperature (i.e. temperature sensitivity of the fluorescence). But the denatured protein shows a positive thermophoretic mobility (i.e. moves to the cold), while the native protein has a negative thermophoretic mobility (i.e. moves to the hot). The accumulation at elevated temperatures is the reason, why the decrease in fluorescence is lower for the native protein, while the denatured protein is, in addition to temperature dependency, depleted from the region of elevated temperature. Interestingly, by approaching the denaturing temperature (i.e. 50° C.) of the protein the amplitudes of the native and denatured protein approach each other an are essentially the same. This means that by measuring the amplitude of the fluorescence change an comparison to the reference sample allows to detect the melting temperature of a protein and to discriminate between native and denatured form of a protein. And to detect a shift in melting temperature due to interactions of the protein with other biomolecules or small molecules (e.g. drug candidates).

Figure 31:
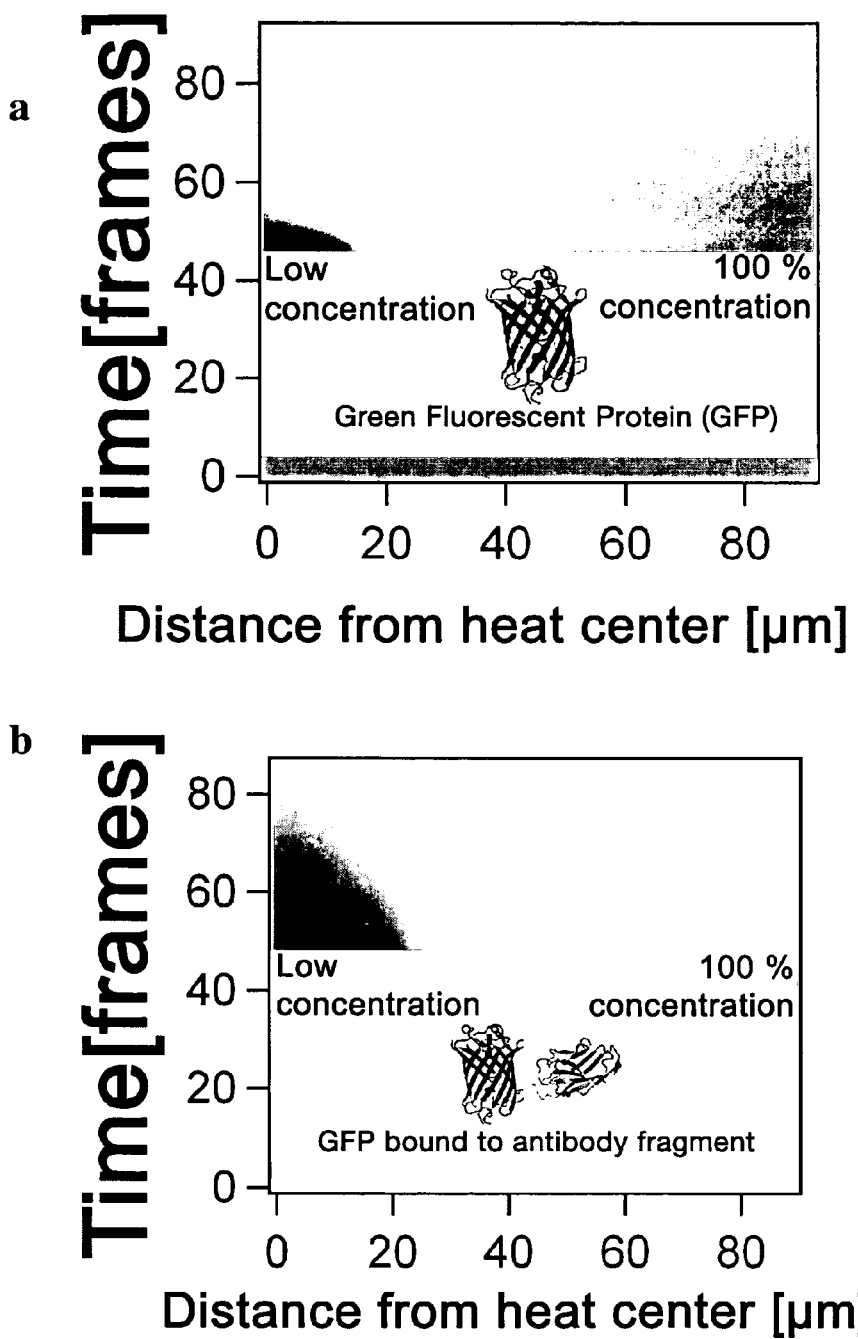
FIG. 31: shows the measurement of the thermo-optical properties of two samples with/of Green Fluorescent protein (GFP).

FIG. 31 shows the measurement of the thermo-optical properties of two samples with/of Green Fluorescent protein (GFP). The thermo-optical properties of two samples of Green Fluorescent protein (GFP) are measured. In the first sample only GFP is present, while in the second sample the GFP is mixed with a 2 fold excess of an antibody fragment, specifically binding to GFP. In both cases, first the fluorescence is recorded without laser heating. Then the fluorescence excitation is turned off and the IR-laser radiation is turned on. The laser is turned off after a few seconds of heating and the fluorescence excitation is turned on at the same time. The relaxation of the spatial fluorescence distribution (i.e. concentration distribution) to a homogeneous state is recorded for a few seconds. As can be observed from the figure, in the sample with the two interacting species (i.e. GFP and the antibody fragment) the fluorescence profile needs more time to relax. This is explained by slower diffusion of the larger complex. The time evolution of the fluorescence profile is analyzed via a software tool to determine the diffusion constant. By using the Stokes-Einstein relation, an hydrodynamic radius is attributed to the diffusion constant. In case of the free GFP this is 5 nm and the complex has an radius of 10 nm.

Figure 32:
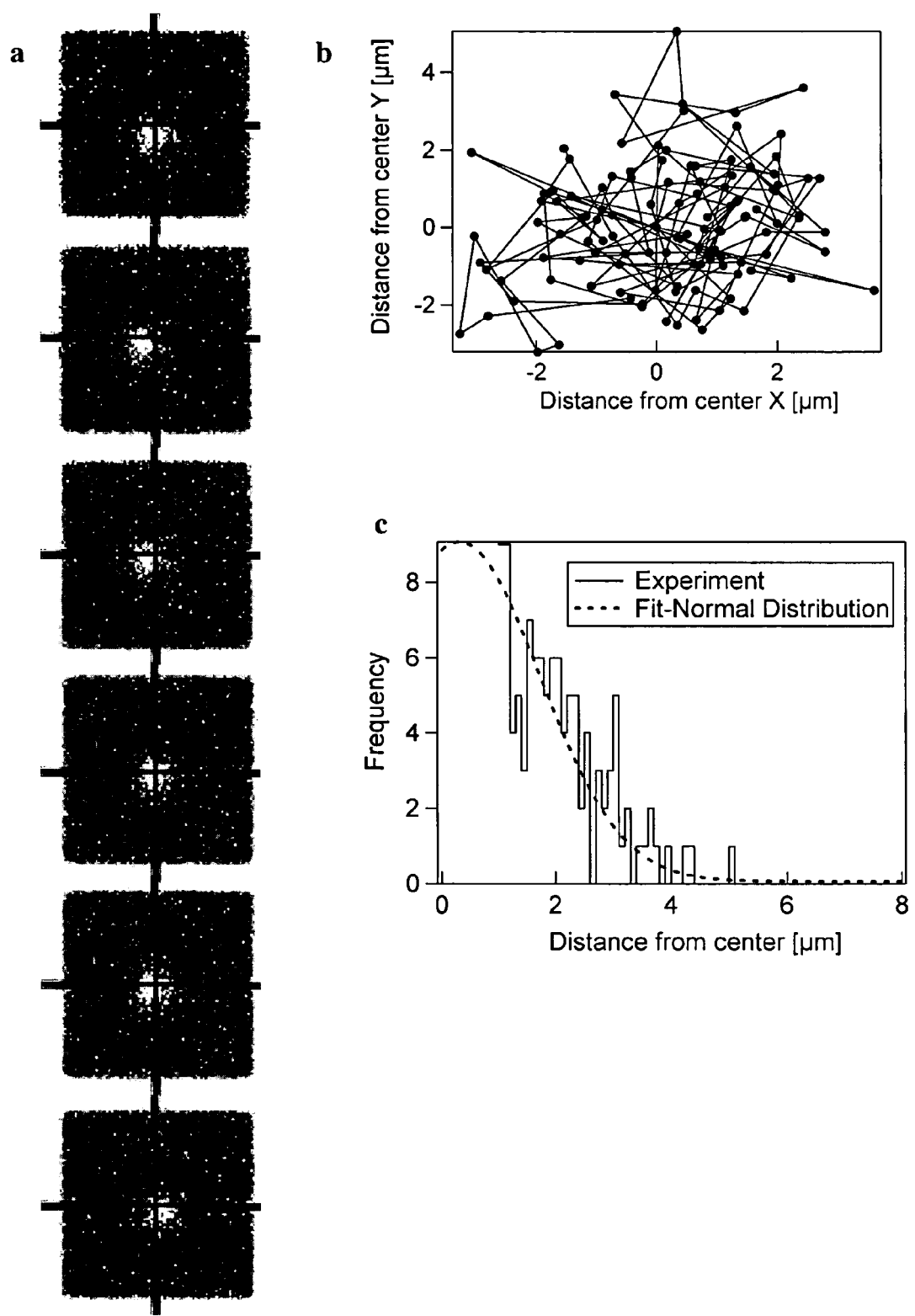
FIG. 32: shows a measurement of a particle which is trapped in a potential well created by a spatial temperature distribution

FIG. 32 shows a measurement of a particle which is trapped in a potential well created by a spatial temperature distribution. (a) A particle is trapped in a potential well created by a spatial temperature distribution. For silica particles the well is deepest at high temperatures. The fluctuations are recorded via a CCD camera (at t=1 s, 2 s, 3 s, 4 s, 5 s, 6 s, 7 s) and (b) the positions are tracked by Software with nanometer resolution. (c) A histogram is calculated from the positional information. The width of the distribution is very sensitive to the thermo-optical properties of the particle. If molecules bind to the surface of the particle, the effective potential for the bead changes and the amplitude of the fluctuations increases or decreases. By observing the amplitude change over time, a kinetic binding curve can be measured.

Figure 33:
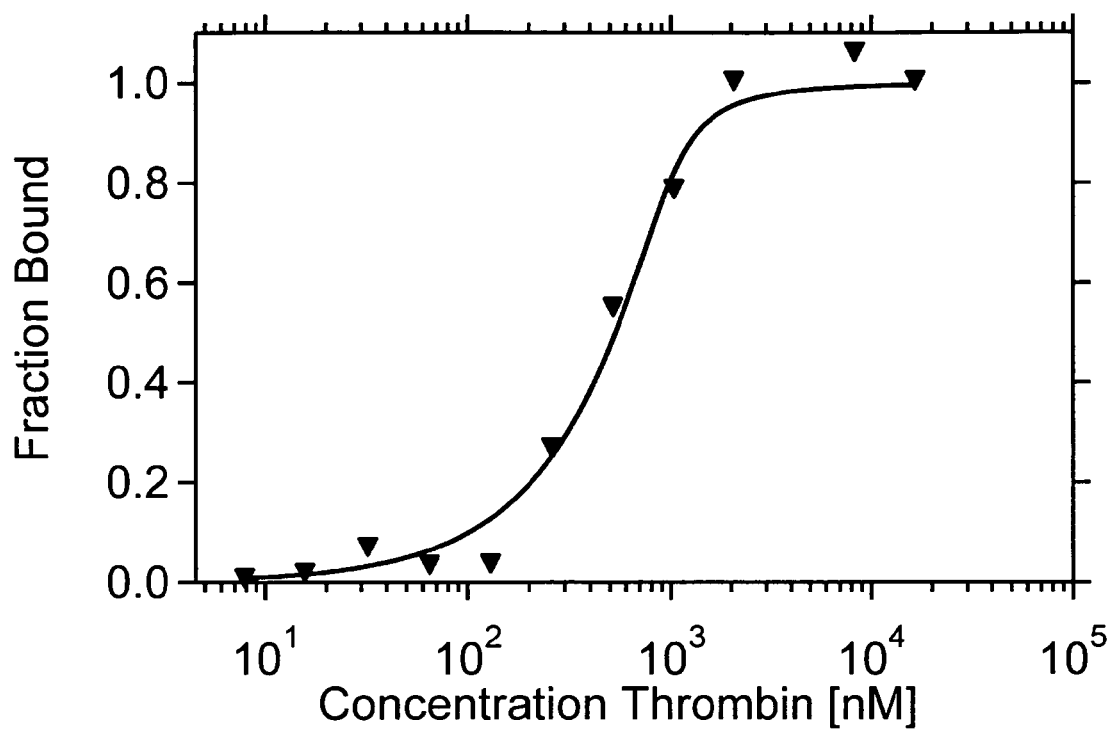
FIG. 33: shows the specific binding of a DNA aptamer to the protein thrombin.

FIG. 33 shows a quantification of the binding of a DNA-aptamer to human alpha thrombin. 100 nM of a fluorescently labelled DNA (Cy5-5'-tggttggtgtggttggt-3') are titrated with various amounts of thrombin. The measurements of the thermo-optical properties of the different concentrations of thrombin are normalized to the difference between the thermo-optical properties of the aptamer alone and the thermo-optical properties at 16580 nM where the binding of the aptamers to thrombin is in saturation. These normalized values correspond to the fraction of aptamer bound to thrombin. The fraction of aptamer bound to thrombin is plotted versus the different thrombin concentrations (triangles). The solid line shows a nonlinear fit to the titration curve from which $K_D$ can be determined.

Figure 34:
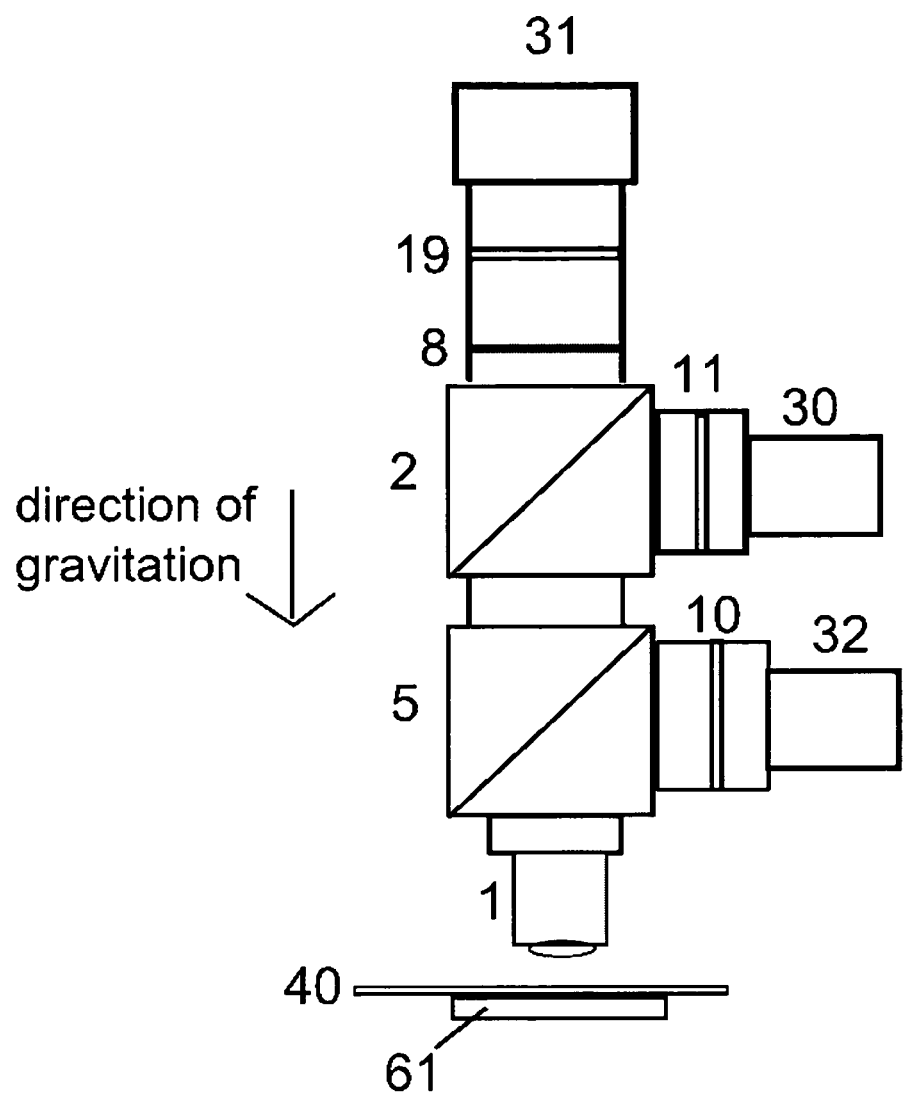
FIG. 34: shows a particularly preferred device capable of thermo-optical analysis
Figure 35:
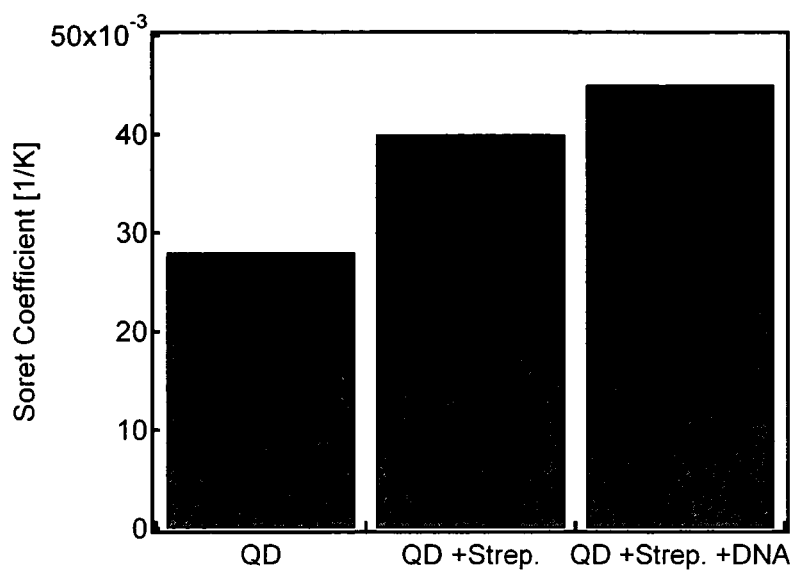
FIG. 35: shows the determination of the Soret Coefficient of complexes of nanocrystals (=quantum dot QD) and biomolecules.
Figure 35:
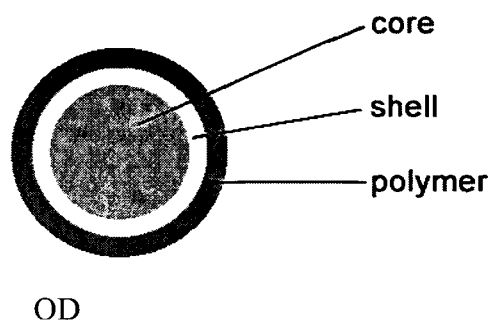
Figure 35:
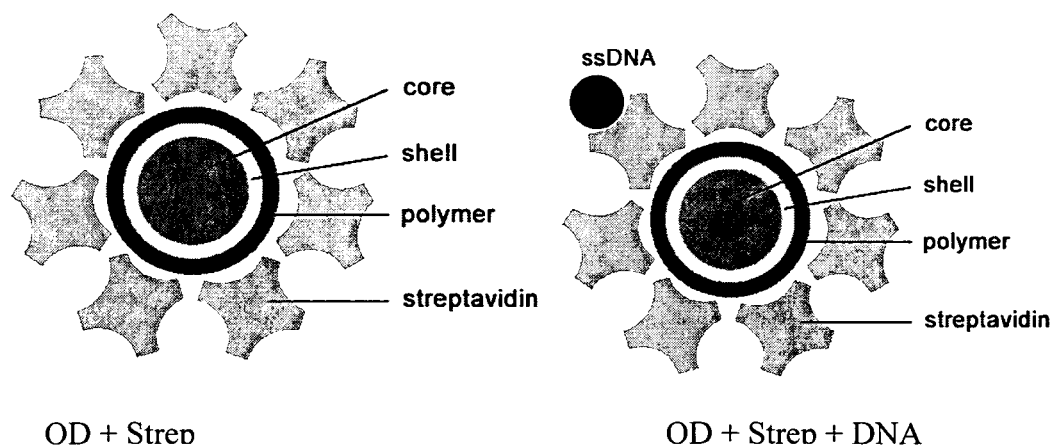

FIG. 34 shows a further embodiment of the device according to the present invention. The device may have an arbitrary orientation with respect to the direction of gravitation, preferably the device is oriented substantially perpendicular with respect to the direction of gravitation, more preferably the device is oriented substantially parallel or anti-parallel with respect to the direction of gravitation, more preferably the device is oriented parallel to the direction of gravitation. Preferably the orientation of the device with respect to the testing sample or chamber may be adjusted as shown in FIG. 1a, FIG. 1b and FIG. 2. The device comprises: 1: Objective (e.g. 40×, NA 0.8, infinity corrected air objective); 2: hot mirror, high IR-reflection, visible light transmission >50%, may also be a 50/50 beamsplitter; 5: Dichroic mirror reflecting short wavelength (R>50%), transmitting long wavelength (T>50%), may also be a 50/50 beamsplitter; 8: Emission Filter (band pass/long pass), preferably comprises one or more filter; 31: Detector, may be charge coupled device camera (CCD-camera), complementary metal oxide semiconductor camera (CMOS-camera); 10: lens system to determine illumination properties, preferably Köhler illumination, preferably lens system which may comprise one, two or more lenses and apertures; 32: excitation light source preferably a LED, more preferably a high power or point source LED, superluminescent LED or a Laser, preferably driven in constant power mode; 11: lens system to determine beam properties of the IR radiation, preferably lens system which may comprise one, two or more lenses and apertures; 30: IR-Laser (e.g. 1455 nm, 1480 nm, 0.1 W-10 W); 19: optical system for e.g. magnification or diminution and projection of real or virtual images to the detector, may contain more than one lens (e.g. tube lens) and more than one aperture; 40: capillary, preferably transparent capillary (e.g. glass, borosilicate, PDMS, PMMA) with an inner diameter of preferably 20 μm to 2 mm, more preferably 100 μm to 1 mm; 61: receiving means, adapted for receiving or being a container, a chamber, a capillary, a multi-well plate, a slide, a microfluidic chip, a glass capillary chip and/or or a means adapted for receiving a drop, a droplet or a sealed, e.g. oil sealed, droplet;

FIG. 35 shows the determination of the Soret Coefficient of complexes of nanocrytals (=quantum dot QD) and biomolecules. The Soret Coefficient of complexes of nanocrytals (=quantum dot QD) and biomolecules is determined by relating the spatial concentration distribution to a spatial temperature distribution. Three different samples have been analyzed. First a nanocrystal without protein modification is measured (QD), followed by a sample nanocrystals modified with the protein streptavidin (QD+Strep.)(approximately 5 proteins per nanocrystal). By binding the protein to the nanocrystal, the Soret-Coefficient is strongly increased. By adding a single stranded DNA to the sample (one DNA per Particle), the Soret coefficient is increased further (QD+Strep.+DNA).

Figure 36:
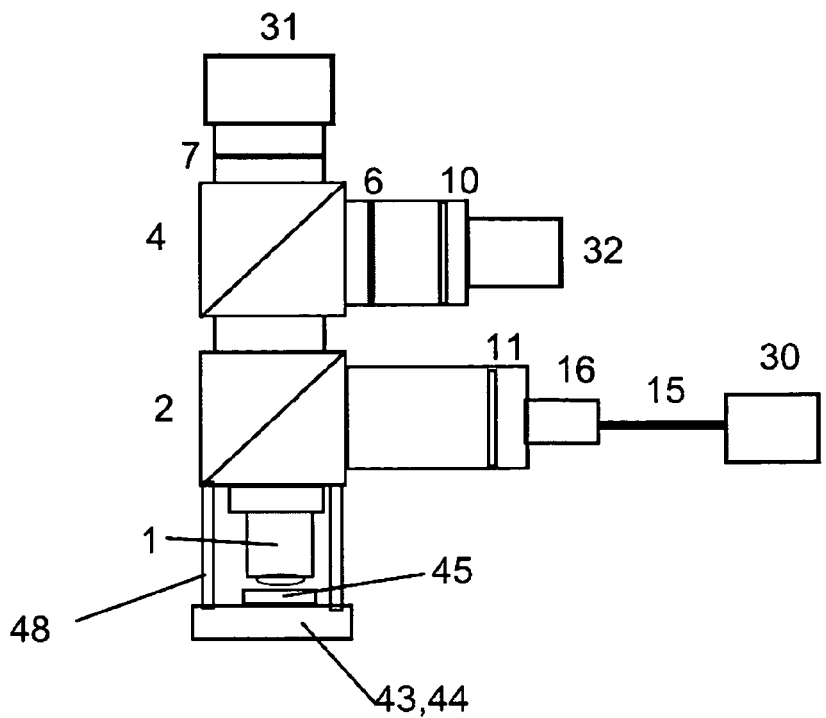
FIGS. 36-37: show particular embodiments of the device according to the present invention.

FIG. 36 shows a further embodiment of the invention according to FIG. 20, wherein a stage 43 carrying a temperature control element 44 and the chamber 45 is connected to the optical system via connectors 48. The optical system 1 may also be also comprise a TIRF (total internal reflection fluorescence) objective so that Thermophoresis can be measured in direction of the Laser beam.

Figure 37:
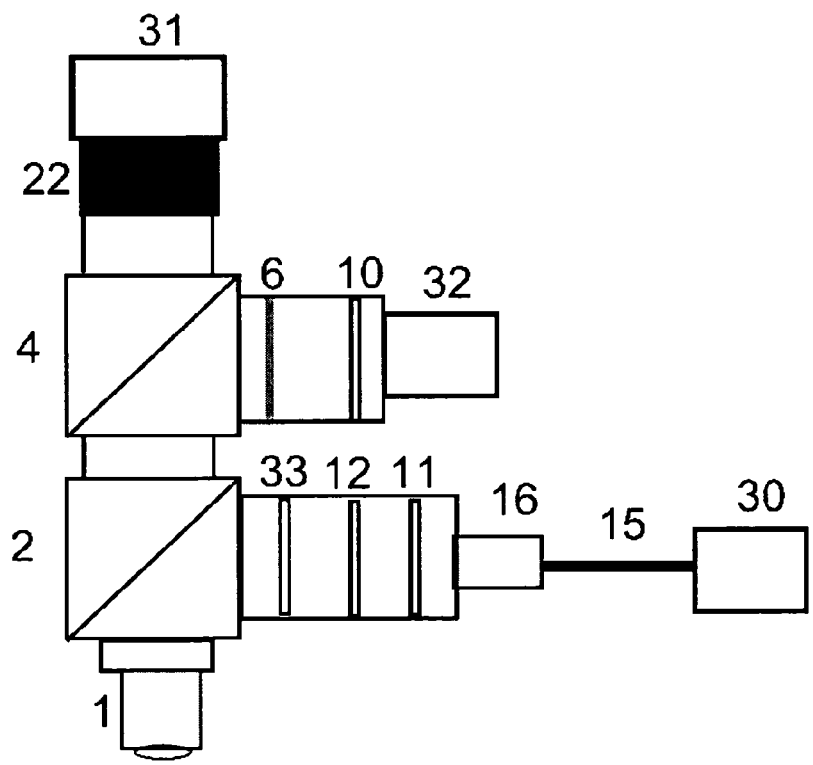

FIG. 37 shows a further embodiment of the invention according to FIG. 20, wherein a shutter 33 and a line forming module 12, preferably a lens system comprising one, two or more lenses or more preferably a Powell lens are added to control the IR laser radiation and wherein the emission filter 7 is replaced by an optical instrument 22 which may be a spectrograph, polychromator or monochromator or combinations of one or more of these, e.g. an optical instrument which transforms different intervals of wavelength/frequency of light into different intervals of angles/distances or different places for example on a CCD.

Figure 38:
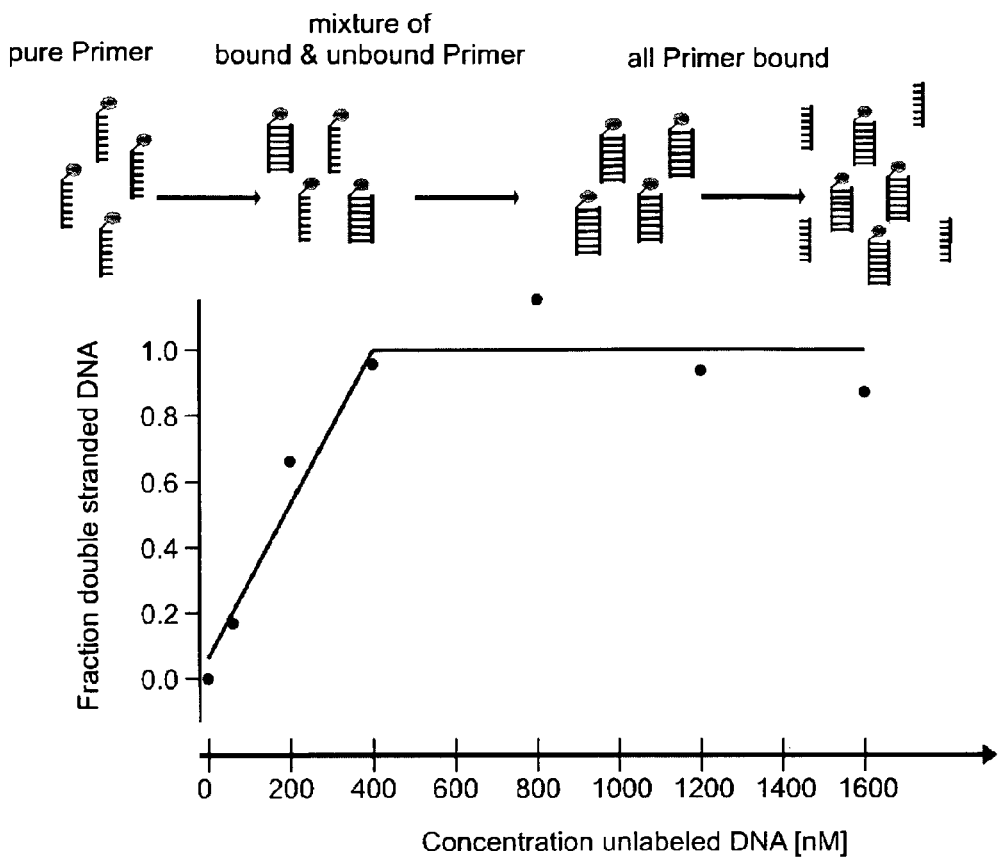
FIG. 38: shows an example for the measurement of DNA hybridization and the specific detection of a DNA molecule.
Figure 38:
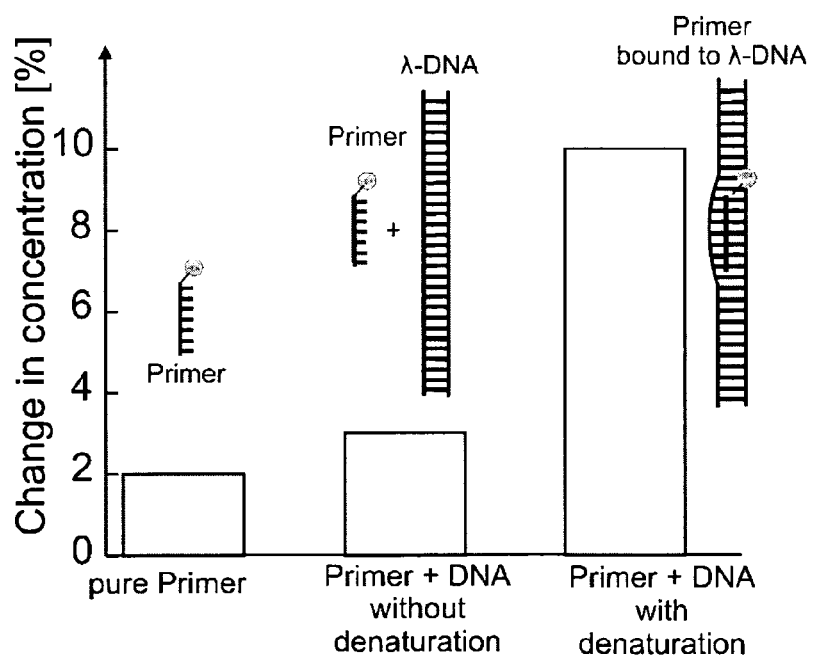

FIG. 38 shows two DNA hybridization experiments. a) The hybridization of a short labelled ssDNA 20mer with its corresponding strand is shown. As soon as the concentration of unlabeled DNA reaches the concentration of the labelled Primer the signal does not change significantly anymore. This allows a exact quantification of the concentration of the primer. b) Thermophoresis is feasible to recognize DNA sequences in large genomes. When the primer can hybridize to its complementary sequence it shows a strong signal, since it adapts the thermophoretical properties of its target strand. Without denaturation prior to hybridization, it is not possible for the primer to bind to the sequence and nearly no change in the signal is measurable.

Figure 39:
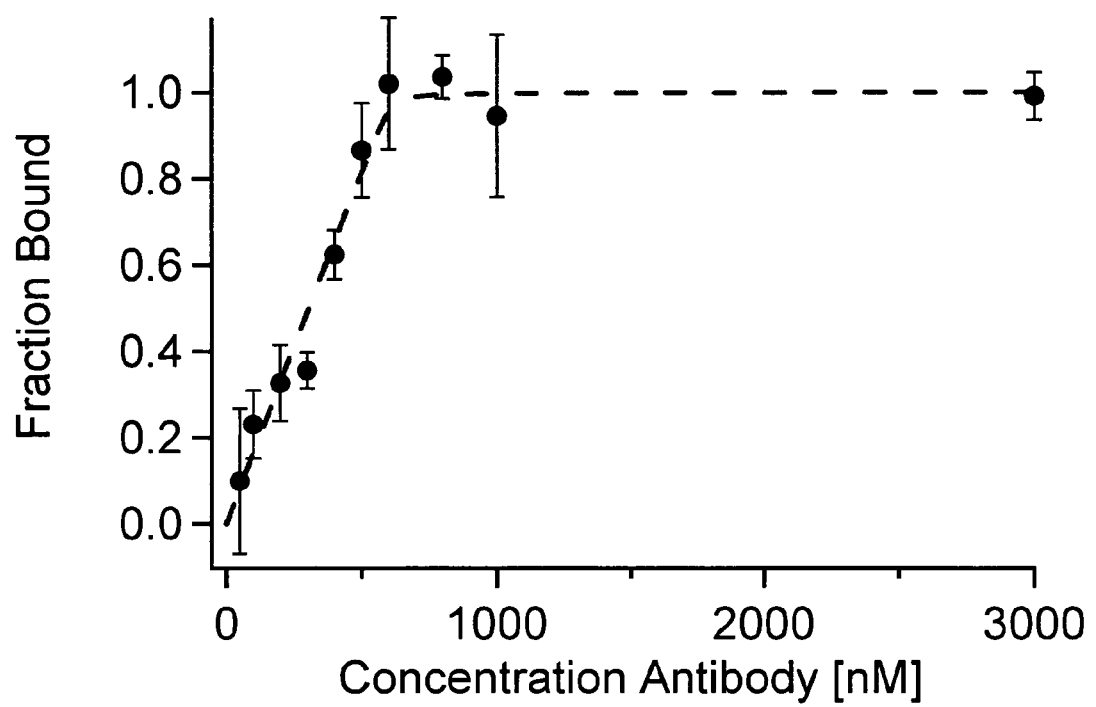
FIG. 39: shows the quantification of the interaction between an antibody fragment and the protein GFP.

FIG. 39 shows a titration series with Anti-GFP Antibody at constant GFP concentration. The association degree is calculated from the measured concentration change. From the data a Dissociation coefficient of 1 nM is calculated.

Figure 40:
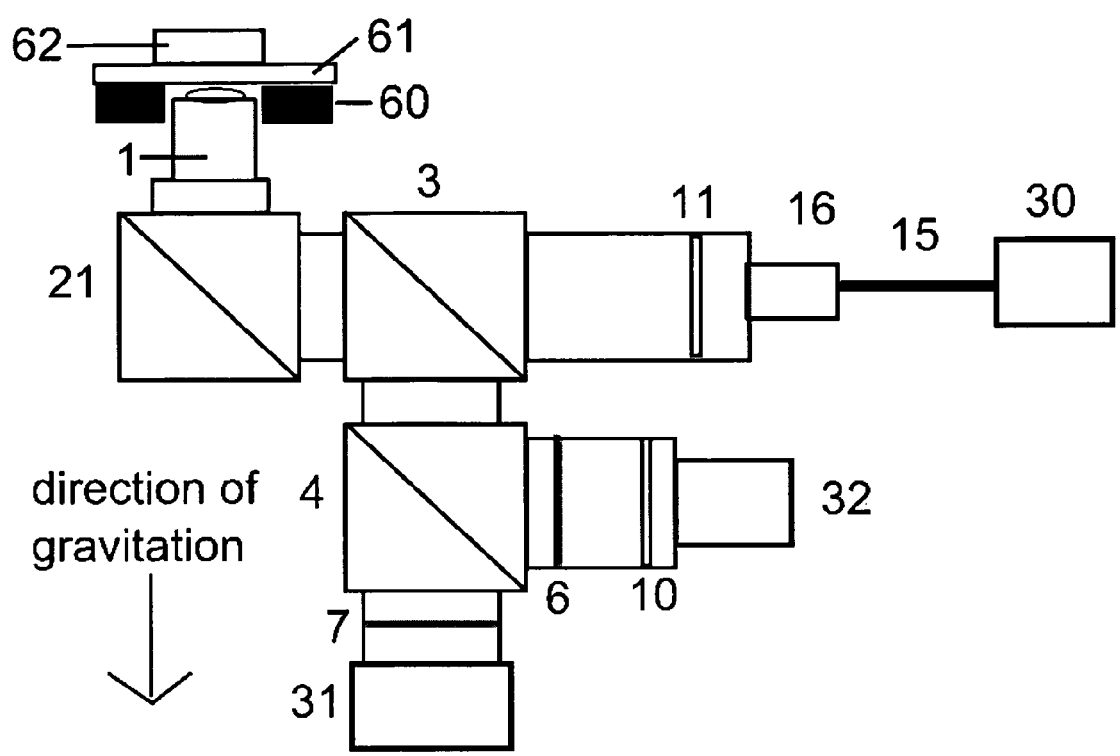
FIGS. 40-41 show particular embodiments of the device according to the present invention.

FIG. 40 illustrates a particular embodiment of a device accordingly to the present invention, in particular a setup for running and measuring PCR reactions. The embodiment according to FIG. 40 substantially corresponds to that discussed with regard to FIG. 17. The device may have a substantially arbitrary orientation with respect to the direction of gravitation, preferably the device is oriented perpendicular with respect to the direction of gravitation, more preferably the device is oriented substantially parallel or anti-parallel with respect to the direction of gravitation. Preferably the orientation of the device with respect to the testing sample or chamber may be adjusted as shown in FIG. 1a, FIG. 1b and FIG. 2. The device comprises: 1: Objective (e.g. 40×, NA 1.3, oil immersion, ZEISS "Fluar"); 21: fix mirror, preferably a silver mirror; 3: cold mirror, preferably high IR-transmission and preferably >80% reflection 350 nm-900 nm; 11: beam shaping module to determine laser beam diameter and focusing, may be a lens system which may comprise one, two or more lenses; 16: Laser fibre coupler w/o collimator; 15: Laser fibre (single mode or multimode); 30: IR-Laser (e.g. 1455 nm, 1480 nm, 0.1 W-10 W); 4: Dichroic mirror/beam splitter reflecting short wavelength (R>80%), transmitting long wavelength (T>80%); 7: Emission Filter (band pass/long pass); 31: detector, may be a CCD-Camera, Line-Camera, Photomultiplier Tube (PMT), Avalanche Photodiode (APD), CMOS-Camera; 6: Excitation Filter (e.g. band pass/long pass); 10: lens system to determine the beam properties of the excitation light source, may comprise one, two or more lenses; 32: Excitation light source, may be Laser, Fibre Laser, Diode-Laser, LED, HXP, Halogen, LED-Array, HBO. Preferably the listed parts are enclosed in a housing; a cold mirror is a specialized dielectric mirror, a dichromatic interference filter that operates over a very wide temperature range to reflect the entire visible light spectrum while very efficiently transmitting infrared wavelengths; 60: temperature control element, preferably a temperature control element for heating and/or cooling and for controlling the temperature of a sample. Preferably, temperature control element 60 is adapted to apply a temperature cycle used in PCR to the sample holder and/or a sample; the temperature control element is preferably adapted for heating and/or cooling the reaction solution, preferably within a range of about 4° C. to 100° C., to a desired, preferably constant, temperature and/or for performing a reaction such as a PCR reaction; 61: receiving means, adapted for receiving or being a container, a chamber, a capillary, a multi-well plate, a slide, a microfluidic chip, a glass capillary chip and/or or a means adapted for receiving a drop, a droplet or a sealed, e.g. oil sealed, droplet; 62: sample, for example PCR reaction solution with marked molecules, in/on e.g. a multi-well plate, capillary, microfluidic chip contained in or supported on a receiving means 61.

Figure 41:
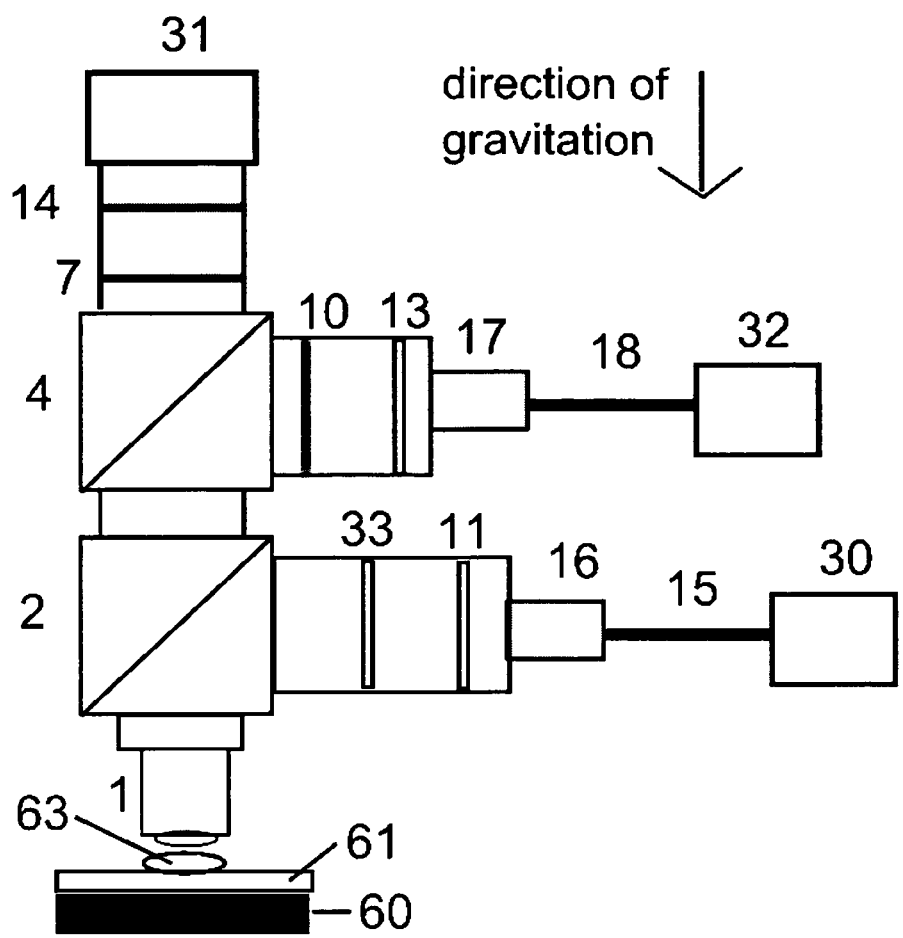

FIG. 41 shows a further embodiment of the device according to the present invention, in particular a confocal setup for running and measuring PCR reactions. The embodiment according to FIG. 41 substantially corresponds to that discussed with regard to FIG. 19. The device may have an arbitrary orientation with respect to the direction of gravitation, preferably the device is oriented substantially perpendicular with respect to the direction of gravitation, more preferably the device is oriented substantially parallel or anti-parallel with respect to the direction of gravitation. Preferably the orientation of the device with respect to the testing sample or chamber may be adjusted as shown in FIG. 1*a*, FIG. 1*b* and FIG. 2. The device comprises: 1: Objective (e.g. 40×, NA 1.3, oil immersion, ZEISS "Fluar"); 2: hot mirror, high IR-reflection, visible light transmission >80%; 4: Dichroic mirror reflecting short wavelength (R>80%), transmitting long wavelength (T>180%); 7: Emission Filter (band pass/long pass); 31: Detector, may be Photomultiplier Tube (PMT), Avalanche Photodiode (APD), Photodiode, CCD-Camera; 13: Pinhole aperture; 10: lens system to determine the beam properties of the excitation light source, may comprise one, two or more lenses; 32: excitation light source preferably a laser, more preferably a fibre coupled laser 11: beam shaping module to determine laser beam diameter and focusing, preferably lens system which may comprise one, two or more lenses; 16: Laser fibre coupler w/o collimator; 15: Laser fibre (single mode or multimode); 30: IR-Laser (e.g. 1455 nm, 1480 nm, 0.1 W-10 W); 33: Shutter; 14: pinhole aperture in confocal position to laser pinhole 13 or to laser fibre coupler 17 whereas the pinhole 13 may not be needed, preferably if a fibre coupled laser is used as excitation light source 32; 18 Laser fibre may be single mode or may be multi mode; 60: temperature control element, preferably a temperature control element for heating and/or cooling and for controlling the temperature of a sample. Preferably, temperature control element 60 is adapted to apply a temperature cycle used in PCR to the sample holder and/or a sample; the temperature control element is preferably adapted for heating and/or cooling the reaction solution, preferably within a range of about 4° C. to 100° C., to a desired, preferably constant, temperature and/or for performing a reaction such as a per reaction; 61: receiving means, adapted for receiving or being a container, a chamber, a capillary, a multi-well plate, a slide, a microfluidic chip, a glass capillary chip and/or a means adapted for receiving a drop, a droplet or a sealed, e.g. oil sealed, droplet; 63: sample, for example PCR reaction solution with marked molecules, preferably a droplet and more preferred a sealed droplet, contained in or supported on receiving means 61.

The devices discussed above with regard to FIGS. 40 and 41 may be adapted in line with the disclosure of the present application and particularly the further devices discussed therein, such as the devices discussed above with regard to FIGS. 1*a*, 1*b*, 2, 16 to 24, 36 and 37 and vice-versa, wherein components may be exchanged or replaced.

The devices according to the present invention, particularly those shown in and discussed with regard to FIGS. 40 and 41 are particularly suitable for thermo-optical determination of the size or size distribution of fluorescently labeled nucleic acids in a reaction solution, in particular according to a method discussed in the present application. In particular, the devices comprise a receiving means 61 for receiving a reaction solution with fluorescently labeled nucleic acids; a laser 30 for irradiating a laser light beam into the solution to obtain a temperature at and/or around (in the vicinity of) a certain point and/or a spatial temperature distribution in the solution around the irradiated laser light beam; means for fluorescently exciting 32 the labeled nucleic acids; and means 31 for detecting fluorescence and/or fluorescence distribution of the fluorescently excited nucleic acids. The devices are further adapted to perform at least two fluorescence detections at at least two predetermined times, preferably by means of a control unit as discussed in this application. The device is preferably further adapted to fluorescently excite the fluorescently labeled nucleic acids and to detect a fluorescence and/or a fluorescence distribution of said fluorescently excited nucleic acids at least once before start of the laser irradiation and/or at least once at a predetermined point of time after start of the laser irradiation, preferably when the laser is still irradiating. Alternatively or additionally, the device is preferably adapted to perform said detection at two different points of time after start of the laser irradiation.

The devices according to the present invention and particularly those discussed above with regard to FIGS. 40 and 41 are adapted to fluorescently excite the fluorescently labeled nucleic acids and to detect a fluorescence and/or a fluorescence distribution of said fluorescently excited nucleic acids at least once before start of the laser irradiation and at least once at a predetermined point of time after start of the laser irradiation, preferably when the laser is still irradiating. This means on excitation and/or detection before the laser is turned on, i.e. before start of the laser irradiation. From such start of laser irradiation the laser preferably continuously and/or intermittently irradiates, i.e. is turned on. After a predetermined time, i.e. during or after laser irradiation, a second excitation and/or detection is performed. The devices according to the present invention are particularly adapted and controlled to perform such irradiation, excitation and/or detection.

Moreover, the devices according to the present invention are adapted such that irradiation, excitation and/or detection is preferably performed at or at about the same place within the solution. The devices are preferably adapted or comprise means to, particularly if the places of irradiation, excitation and/or detection differ from one another, adjust or calibrate the respective irradiation, excitation and/or detection means, or to compensate for the difference in place by e.g. adjusting parameters such as the laser power accordingly or by means of calculation.

The devices described herein can be used for the detection and characterization of fluorescently labeled nucleic acids in solutions, e.g. reaction solutions of PCR reactions. The described devices can be used in the methods described herein for the detection and characterization of nucleic acids. Particularly, the determination of the size of fluorescently labeled nucleic acids can be performed with the present devices. The devices may thus be used to monitor the progress of reactions involving nucleic acids, such as the elongation, hybridization, ligation and/or restriction of nucleic acids, e.g. the primer elongation by DNA polymerases during PCR. Particularly, monitoring PCR reactions, e.g. in multiplex and/or real-time PCR, can be performed with the devices described herein, preferably the devices of FIGS. 40 and 41. A change in size of fluorescently labeled nucleic acids e.g. in the cycles of a PCR reaction, can be detected by the herein described devices by changes in fluorescence intensity at a given position or by changes of the fluorescence distribution in the sample/reaction solution.

Figure 42:
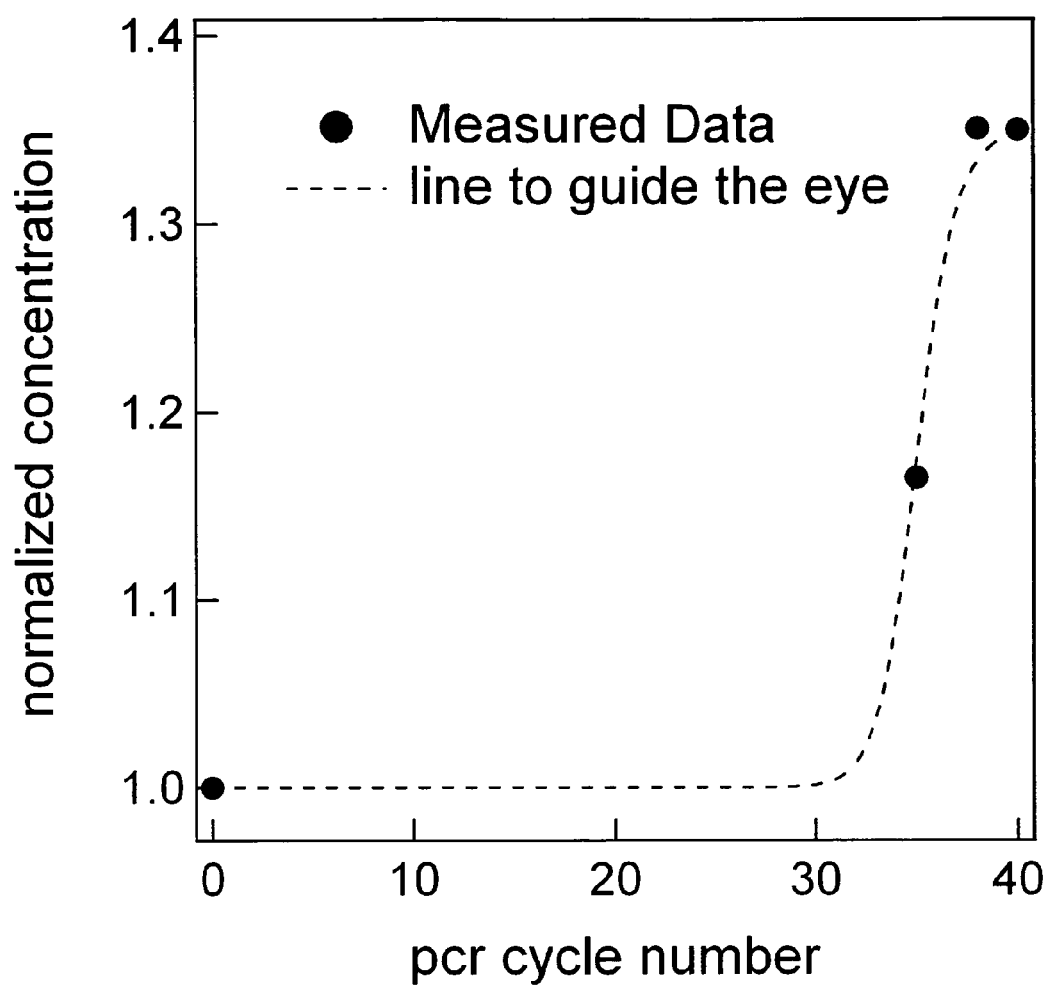
FIG. 42: shows the normalized concentration of fluorescently labeled primers determined during a PCR reaction

FIG. 42 illustrates the results of the thermo-optical detection and length determination of fluorescently labeled primers during primer extension in a PCR reaction. The figure shows the normalized concentration of fluorescently labeled primers determined during a PCR reaction The progress, threshold, efficiency and endpoint of a PCR reaction can be measured by performing thermo-optical analysis during a PCR reaction. The thermo-optical analysis is performed in some cycles of a PCR reaction. Data points are taken while the temperature of the whole sample volume is adjusted to 20° C. The values are normalized to the value measured before the first PCR cycle (error bars are smaller than the marker). The relative increase of concentration is dependent on the length of DNA molecules. As the content of primer DNA decreases and the concentration of longer product/elongated primer DNA increases, a change in thermo-optical properties compared to the pure primer DNA is observed. In cycle 38 the PCR reaction reaches its endpoint. No further increase in product/elongated primer is observed. Also threshold cycle and PCR efficiency can be obtained from these datasets.

EXAMPLES

The following detailed example illustrates the invention without being limiting.

Example 1

Thermodiffusion

Molecules drift along temperature gradients, an effect called thermophoresis, Soret-effect or thermodiffusion. In liquids, its theoretical foundation is subject of a long standing debate. Using a new all-optical microfluidic fluorescence method, we present experimental results for DNA and polystyrene beads over a large range of particle size, salt concentration and temperature. The data supports a unifying theory based on the solvation entropy. Stated in simple terms, the Soret coefficient is given by the negative solvation entropy, divided by kT. The theory predicts the thermodiffusion of polystyrene beads and DNA without any free parameters. We assume a local thermodynamic equilibrium of the solvent molecules around the molecule. This assumption is fulfilled for moderate temperature gradients below the fluctuation criterion. Above this criterion, thermodiffusion becomes nonlinear. For both DNA and polystyrene beads, thermophoretic motion changes sign at lower temperatures. This thermophilicity towards lower temperatures is attributed to an increasing positive entropy of hydration, whereas the generally dominating thermophobicity is explained by the negative entropy of ionic shielding. The understanding of thermodiffusion sets the stage for detailed probing of solvation properties of colloids and biomolecules. For example, we successfully determine the effective charge of DNA and beads over a size range which is not accessible with electrophoresis.

Introduction.

Thermodiffusion has been known for a long time, but its theoretical explanation for molecules in liquids is still under debate. The search for the theoretical understanding is motivated by the fact that thermodiffusion in water might lead to powerful all-optical screening methods for biomolecules and colloids. Equally well, thermodiffusion handles and moves molecules all-optically and therefore can complement well established methods as for example electrophoresis or optical-tweezers. For the latter, forces of optical tweezers scale with particle volume and limit this method to particles only larger than 500 nm. Electrophoresis does not suffer from force limitations, but is difficult to miniaturize due to electrochemical reactions at the electrodes.

On the other hand, thermodiffusion allows the microscale manipulation of even small particles and molecules. For example, 1000 bp DNA can be patterned arbitrarily in bulk water (FIG. 7). The temperature pattern "DNA", heated by 2 K, was written into a water film with an infrared laser scanning microscope. The concentration of 1000 bp DNA was imaged using a fluorescent DNA tag. In an overall cooled chamber at 3° C., DNA accumulates towards the heated letters "DNA" (negative Soret effect) whereas at room temperature DNA is thermophobic (positive Soret effect) as seen by the dark letters.

In the past, the apparent complexity of thermodiffusion prevented a full theoretical description. As seen for DNA in FIG. 13, molecules characteristically deplete from regions with an increased temperature, but they can also show the inverted effect and accumulate[3]. Moreover, the size scaling of thermodiffusion recorded by thermal field flow fractionation (ThFFF) showed fractional power laws with a variety of exponents which are hard to interpret[4]. The latter effect was resolved recently by revealing nonlinear thermophoretic drift for the strong thermal gradients used in ThFFF.

A variety of methods were used to measure thermodiffusion, mostly in the nonaqueous regime. They range from beam deflection[3,7], holographic scattering[8,9], electrical heating to thermal lensing. Recently we have developed a fluorescence microfluidic imaging technique[13,14] which allows the measurement of thermodiffusion over a wide molecule size range without artifacts induced by thermal convection. Highly diluted suspensions can be measured and therefore particle-particle interactions do not have an influence. We only apply moderate temperature gradients. In the following we used this method to confirm a straightforward theoretical explanation of thermodiffusion.

Theoretical Approach.

For diluted concentrations, it is generally assumed that the thermodiffusive drift velocity $\vec{v}$ depends linearly on the temperature gradient $\nabla T$ with a proportionality constant which equals the thermodiffusion coefficient $D_T$: $\vec{v}=-D_T\nabla T$. In steady state, thermodiffusion is balanced by ordinary diffusion. Constant diffusion and thermodiffusion coefficients both lead to an exponential depletion law[16] $c/c_0=\exp[-(D_T/D)(T-T_0)]$, with the concentration c depending on the temperature difference $T-T_0$ only. The concentration c is normalized by the boundary condition of the concentration $c_0$ with temperature $T_0$. The Soret coefficient is defined as ratio $S_T=D_T/D$ which determines the magnitude of thermodiffusion in the steady state. While the above exponential distribution could motivate an approach based on Boltzmann equilibrium statistics, it is commonly argued that thermodiffusion without exception is a local non-equilibrium effect that requires fluid dynamics, force fields or particle-solvent potentials[17-20]. However, in two previous papers[16] we demonstrated that for moderate temperature gradients, the thermal fluctuations of the particle are the basis for a local equilibrium. This allows the description of the thermodiffusive steady state by a succession of local Boltzmann laws, yielding $c/c_0=\exp[(G(T_0)-G(T))/kT]$ with G the Gibbs-free enthalpy of the single particle-solvent system. Such an approach is only valid if the temperature gradient $\nabla T$ is below a threshold $\nabla T<(aS_T)^{-1}$ which is given by the particle fluctuations with the hydrodynamic radius a and Soret coefficient $S_T$, as shown recently. For larger temperature gradients, thermodiffusive drift is nonlinearly dependent on the temperature gradient. In the present study, temperature gradients below this limit were used so that thermodiffusion is measured at local thermodynamic equilibrium conditions.

Local thermodynamic equilibrium allows the derivation of a thermodynamic foundation of the Soret coefficient. The local Boltzmann distribution relates small concentration changes $\delta c$ with small Gibbs-Free Energy differences: $\delta c/c = -\delta G/kT$. We equate this relation with a locally, linearized thermodiffusion steady state given by $\delta c/c = -S_T \delta T$ and thus find the Soret coefficient by the temperature derivative of G $$S_T = D_T/D = (kT)^{-1} \times \partial G/\partial T \quad (1)$$

Whereas above relation is sufficient for the following derivation, it can be generalized by locally applying the thermodynamic relation $dG = -SdT + Vdp + \mu dN$. For single particles at a constant pressure we find that the Soret coefficient equals the negative entropy of the particle-solvent system S according to $S_T = -\Delta S/kT$. This relation is not surprising since the entropy is by definition related with the temperature derivative of the free enthalpy.

The above general energetic treatment is inherent in previously described approaches based on local equilibrium[22], including the successful interpretation of thermoelectric voltages of diluted electrolytes[24,25] which are described by energies of transfer. Recently, the non-equilibrium approach by Ruckenstein was applied to colloids[27] with the characteristic length l assigned to the Debye length $\lambda_{DH}$. If instead it would assigned the characteristic length according to $l=2a/3$ with the particle radius a, the Ruckenstein approach would actually confirm the above local equilibrium relation (1) for the Soret coefficient. Measurements on SDS micelles[27] appeared to confirm this non-equilibrium approach, but for the chosen particles the competing parameter choices $l=2a/3$ and $l=\lambda_{DH}$ yielded comparable values. Thus the experiments could not distinguish between the competing theories.

Here, we will use the above local equilibrium relations to derive the Soret coefficient for particles larger than the Debye length in aqueous solutions and put the results to rigorous experimental tests. Two contributions dominate the particle entropy S in water (FIG. 8a): the entropy of ionic shielding and the temperature sensitive entropy of water hydration. The contribution from the entropy of ionic shielding is calculated with the temperature derivative of the Gibbs-free enthalpy[27,28] $G_{ionic} = Q_{eff}^2 \lambda_{DH}/[2A\varepsilon\varepsilon_0]$ with the effective charge $Q_{eff}$ and particle surface A. Alternatively, this enthalpy can be interpreted as an electrical field energy $G_{ionic} = Q_{eff}^2/[2C]$ in the ionic shielding capacitor C. We neglect the particle-particle interactions since the fluorescence approach allows the measurement of highly diluted systems. To obtain the Soret coefficient, temperature derivatives consider the Debye length $\lambda_{DH}(T) = \sqrt{\varepsilon(T)\varepsilon_0 kT/(2e^2 c_S)}$ and the dielectric constant $\varepsilon(T)$. Both temperature derivatives give rise to a factor $\beta = 1 - (T/\varepsilon)\partial\varepsilon/\partial T$. The effective charge $Q_{eff}$ is largely temperature insensitive which was confirmed by electrophoresis independently[29]. Such a dependence would be unexpected as the strongly adsorbed ions dominate the value of the effective charge. Experimentally, we deal with colloids exhibiting flat surfaces, i.e. the particle radius is larger than $\lambda_{DH}$. In this case charge renormalization does not play a role and we can introduce an effective surface charge density $\sigma_{eff} = Q_{eff}/A$ per molecule area A. From the temperature derivation according to equation (1), the ionic contribution to the Soret coefficient is $S_T^{(ionic)} = (A\beta\sigma_{eff}^2 \lambda_{DH})/(4\varepsilon\varepsilon_0 kT^2)$. A similar relation was derived for charged micelles recently[23], however without considering the temperature dependence of the dielectric coefficient $\varepsilon$. Next, the contribution to the Soret coefficient from the hydration entropy of water can be directly inferred from the particle area specific hydration entropy $s_{hyd} = S_{hyd}/A$, namely $S_T^{(hyd)} = -As_{hyd}(T)/kT$. Finally, the contribution from the Brownian motion is derived as $S_T = 1/T$ by inserting the kinetic energy of the particle $G = kT$ into equation (1). However this contribution is very small ($S_T = 0.0034/K$) and can be neglected for the molecules under consideration. The contributions from ionic shielding and hydration entropy add up to:

$$S_T = \frac{A}{kT}\left(-s_{hyd} + \frac{\beta\sigma_{eff}^2}{4\varepsilon\varepsilon_0 T} \times \lambda_{DH}\right) \quad (2)$$

The Soret coefficient $S_T$ scales linearly with particle surface A and Debye length $\lambda_{DH}$. We test equation (2) by measuring $S_T$ versus the salt concentration, temperature and molecule size. In all cases thermodiffusion is quantitatively predicted without any free parameters. We used fluorescence single particle tracking to follow carboxyl modified polystyrene (PS) beads (Molecular Probes F-8888) of 1.1 µm and 0.5 µm diameter at 25 attomolar concentration, dialyzed into 0.5 mM Tris-HCl at pH 7.6. Thermodiffusion of particles ≤0.2 µm is measured by the fluorescence decrease that reflects the bulk depletion of the particles[13]. The chamber thickness of 20 µm damped the thermal convection to negligible speeds[16]. The experimental design also excludes thermal lensing and optical trapping[16]. Debye lengths $\lambda_{DH}$ were titrated with KCl (see supplementary materials).

Salt Dependence.

FIG. 8b shows the Soret coefficients of polystyrene beads with different sizes versus $\lambda_{DH}$. The Soret coefficients scale linearly with a small intercept at $\lambda_{DH} = 0$ and confirm the $\lambda_{DH}$-dependence of equation (2). For smaller diameters of the beads the Soret coefficients scale with the particle surface area A (FIG. 8) as expected from equation (2). To check whether equation (2) also quantitatively explains the measured Soret coefficients, we inferred the effective charge of the beads by electrophoresis (see supplementary material). Using 40 nm beads with identical carboxyl surface modifications at $\lambda_{DH} = 9.6$ nm, we fluorescently observed free-flow electrophoresis and corrected for electroosmosis, finding an effective surface charge density of $\sigma_{eff} = 4500 \pm 2000 e/\mu m^2$. This value is virtually independent from the used salt concentrations[29]. Using this inferred effective charge, equation (2) fits the Soret coefficient for various bead sizes and salt concentrations well (FIG. 8b, solid lines).

The intercept $S_T(\lambda_{DH} = 0)$, where ionic contributions are zero, also scales with particle surface and is described by a hydration entropy per particle surface of $s_{hyd} = -1400$ J/(molK$\mu m^2$). The value matches the literature values for similar surfaces reasonably well[30,31]. For example, Dansyl-Alanine, a molecule with surface groups comparable with polystyrene beads, was measured to have a hydration entropy[30] of $-0.13$ J/(molK) at a comparable temperature. Linear scaling with its surface area by using a radius of $a=2$ nm results in a value of $s_{hyd} = -2500$ J/(molK$\mu m^2$), in qualitative agreement with our result. The hydration entropy is a highly informative molecule parameter which is notoriously difficult to measure, yielding an interesting application for thermodiffusion.

Temperature Dependence.

Hydration entropies $S_{hyd}$ in water are known to increase linearly with decreasing temperatures[30-32]. Since the slope of the ionic contribution of $S_T$ versus $\lambda_{DH}$ is with high precision temperature insensitive for water ($\beta(T)/(\varepsilon T^2) \cong $ const), only the intercept is expected to decrease as the overall temperature of the chamber is reduced. This is indeed the case, as seen from the temperature dependence of beads with 1.1 µm diameter (FIG. 9a, T=6 ... 29° C.). We infer from the intercept $S_T$ ($\lambda_{DH} = 0$) that the hydration entropy changes sign at about 20°

C. As seen for DNA in FIG. 7, hydration entropy can dominate thermodiffusion at low temperatures and move molecules to the hot ($D_T<0$).

The properties of hydration entropy lead to a linear increase of $S_T$ over temperatures at fixed salt concentration as measured for 1.1 μm beads and DNA (FIG. 9b). We normalize $S_T$ by dividing with $S_T$ (30° C.) to compensate for molecule surface area. The slopes of $S_T$ over temperature differ between beads and DNA. However the slope does not differ between DNA of different size (50 base pairs versus 10000 base pairs). Based on equation (2), this is to be expected since the temperature dependence of the hydration entropy only depends on the type of surface of the molecule, not its size. We measured the diffusion coefficients of the DNA species at the respective temperature independently. Within experimental error, changes in the diffusion coefficient D match with the change of the water viscosity without the need to assume conformational changes of DNA over the temperature range. Please note that the change of the sign of the DNA Soret coefficient is situated near the point of maximal water density only by chance. There, the two entropic contributions balance. For polystyrene beads at $\lambda_{DH}=2$ nm for example, the sign change is observed at 15° C. (FIG. 9a). An increased Soret coefficient over temperature was reported for aqueous solutions before[3], however with a distinct nonlinearity which we attribute to remnant particle-particle interactions.

Size Dependence of the Beads.

The Soret coefficient was measured for carboxyl modified polystyrene beads in diameter ranging from 20 nm to 2 μm (Molecular Probes, F-8888, F-8795, F-8823, F-8827). Beads of diameter 0.2 μm, 0.1 μm, 0.04 μm and 0.02 μm were diluted to concentrations of 10 pM, 15 pM, 250 pM and 2 nM, and its bulk fluorescence was imaged over time to derive $D_T$ and $D^{13,16}$ from the depletion and subsequent back-diffusion. Larger beads with a diameter of 1.9 μm, 1.1 μm and 0.5 μm were diluted to concentrations of 3.3 aM, 25 aM and 0.2 pM, and measured with single particle tracking[6]. The solutions were buffered in 1 mM Tris pH 7.6 with $\lambda_{DH}=9.6$ nm. In all cases interactions between particles can be excluded. Care was taken to keep the temperature gradient in the local equilibrium regime.

We find that the Soret coefficient scales with particle surface over four orders of magnitude (FIG. 10a). The data is described well with equation (2) with an effective surface charge density of $\sigma_{eff}=4500$ e/μm$^2$ and neglected hydration entropy contribution. The 5-fold too low prediction for the smallest particle (20 nm diameter) can be explained by charge renormalization since its radius is smaller than $\lambda_{DH}$.

The diffusion coefficient D for spheres is given by the Einstein relation and scales inversely with radius $D \propto 1/a$. Inserting equation (2) into $S_T=D_T/D$, the thermodiffusion coefficient $D_T$ is expected to scale with particle radius a. This is experimentally confirmed over two orders of magnitude (FIG. 10b). These findings of ours contradict several theoretical studies claiming that $D_T$ should be independent of particle size[17-20,27], based on ambiguous experimental results from thermal field flow fractionation (ThFFF)[4] which were probably biased by nonlinear thermodiffusion in large thermal gradients.

Size Dependence of DNA.

Whereas polystyrene beads share a very narrow size distribution as a common feature with DNA molecules, beads are a much less complicated model system. Beads are rigid spheres which interact with the solvent only at its surface. In addition, the charges reside on the surface where the screening takes place. Thus the finding that thermodiffusion of flexible and homogeneously charged DNA is described equally well with equation (2) is not readily expected and quite interesting (FIG. 10c,d).

We measured DNA sizes with 50 base pairs to 48502 base pairs in 1 mM TRIS buffer ($\lambda_{DH}=9.6$ nm) at low molecule concentrations between 1 μM (50 bp) and 1 nM (48502 bp). Only every 50th base pair was stained with the TOTO-1 fluorescent dye. The diffusion coefficient was measured by back-diffusion after the laser was turned off and depends on the length L of the DNA in a non-trivial way. The data is well fitted with a hydrodynamic radius scaling a $\propto L^{0.75}$. This scaling represents an effective average over two DNA length regimes. For DNA molecules longer than approximately 1000 bp, a scaling of 0.6 is found[33] whereas shorter DNA scales with an exponent of ≈1 (see supplementary material).

We can describe the measured Soret coefficient over three orders of magnitude of DNA lengths with equation (2) if we assume that effective charge of the DNA is shielded at the surface of a sphere with the hydrodynamic radius a. Due to the low salt concentration ($\lambda_{DH}=9.6$ nm), such globular shielding is reasonable. Not only is the experimentally observed scaling of the Soret coefficient with the square root of its length correctly predicted based on equation (2) ($S_T \propto Q_{eff}^2/a^2 \propto L^2/L^{1.5} \propto L^{0.5}$), also the Soret coefficient is fully described in a quantitative manner (FIG. 10c, solid line), with an effective charge of 0.12 e per base, matching well with literature values[34] ranging from 0.05 e/bp to 0.3 e/bp.

As shown in FIG. 10d, the thermodiffusion coefficient for DNA drops with DNA length according to $D_T=DS_T \propto Q_{eff}^2/a^3 \propto L^2/L^{2.25} \propto L^{-0.25}$. Thus, shorter DNA actually drifts faster in a temperature gradient than longer DNA. It is important to point out that this finding is in no contradiction to experimental findings of a constant $D_T$ over polymer length in non-aqueous settings[9]. According to equation (1), the thermodynamic relevant parameter is the Soret coefficient, determined by the solvation energetics. The argument[20] that polymers have to decouple into monomers to show a constant $D_T$ merely becomes the special case where the solvation energetics determine both $S_T$ and D with equal but inverted size scaling. In accordance with our local energetic equilibrium argument, $S_T$ and not $D_T$ dominates thermodiffusion also for non-aqueous polymers near a glass transition[35]. Here, $S_T$ is constant whereas $D_T$ and D scale according to an increased friction. However for a system of DNA in solution, where long ranging shielding couples the monomers, a constant $D_T$ over polymer length cannot be assumed a priori (FIG. 10d).

Effective Charge.

The effective charge $Q_{eff}$ is a highly relevant parameter for colloid science, biology and biotechnology. So far it only could be inferred from electrophoresis, restricted to particles smaller than the Debye length ($a \leq 3\lambda_{DH}$)[36]. Unfortunately, many colloids are outside this regime. As shown before, a similar size restriction does not hold for thermodiffusion. In many cases, the hydration entropy $S_{hyd}$ contributes less than 15% (FIG. 8) and can be neglected at moderate salt levels. Thus we can invert equation (2) to obtain the effective charge $Q_{eff}$ for spherical molecules from $$Q_{eff} = \frac{2T^2}{3\eta D} \sqrt{\frac{\varepsilon \varepsilon_0 k^3 S_T}{\beta \pi \lambda_{DH}}} \quad (3)$$

The effective charge derived from thermodiffusion measurements of polystyrene beads and DNA is plotted in FIG. 11 over several orders of magnitude in size. The effective charge of beads scales linearly with particle surface with a slope confirming the effective surface charge density of $\sigma_{eff}=4500$ e/μm² which was inferred from electrophoresis only for small particles. Average deviations from linear scaling are below 8% (FIG. 11a). The effective charge inferred from thermodiffusion measurements of DNA using equation (3) scales linearly with DNA length with an effective charge of 0.12 e per base pair. The length scaling is confirmed over four orders of magnitude with an average error of 12% (FIG. 11b). Thus thermodiffusion can be used to infer the effective charge with low errors for a wide range of particle sizes. This is even more interesting for biomolecule characterization since measurements of thermodiffusion can be performed all-optically in picoliter volumes.

Conclusion.

We describe thermodiffusion, the molecule drift along temperature gradients, in liquids with a general, microscopic theory. Applied to aqueous solutions, this theory predicts thermodiffusion of DNA and polystyrene beads with an average accuracy of 20%. We experimentally validate major parameter dependencies of the theory: linearity against screening length $\lambda_{DH}$ and molecule hydrodynamic area A, quadratic dependence on effective charge and linearity against temperature. Measurements of thermodiffusion can be miniaturized to micron scale with the used all-optical fluorescence technique and permits microscopic temperature differences to manipulate molecules based on their surface properties (FIG. 7). The theoretical description allows to extract the solvation entropy and the effective charge of molecules and particles over a wide size range.

Infrared Temperature Control.

The temperature gradients used to induce thermodiffusive motions were created by aqueous absorption of an infrared laser at 1480 nm wavelength and 25 mW power (Furukawa). Water strongly absorbs at this wavelength with an attenuation length of κ=320 μm. The laser beam was moderately focussed with a lens of 8 mm focal distance. Typically, the temperature in the solution was raised by 1-2 K in the beam center with a 1/e² diameter of 25 μm, measured with the temperature dependent fluorescence signal of the dye BCECF[13]. Thin chamber heights of 10 μm to 20 μm and moderate focussing removed possible artifacts from optical trapping, thermal lensing and thermal convection[13]. For temperature dependent measurements both the objective and the microfluidic chip were tempered with a thermal bath. Imaging was provided from an AxioTech Vario fluorescence microscope (Zeiss), illuminated with a high power LED (Luxeon) and recorded with the CCD Camera SensiCam QE (PCO).

Molecules.

Highly monodisperse and protein-free DNA of 50 bp, 100 bp, 1000 bp, 4000 bp, 10000 bp and 48502 bp (Fast Ruler, fragments and λ-DNA, Fermentas) were diluted to 50 μM base pair concentration, i.e. the molecule concentration was between 1 μM (50 bp) and 1 nM (48502 bp). DNA was fluorescently labeled by the intercalating TOTO-1 fluorescent dye (Molecular Probes, Oregon) with a low dye/base-pair ratio of 1/50. Carboxyl modified polystyrene beads of diameter 2 μm, 1 μm, 0.5 μm, 0.2 μm, 0.1 μm, 0.04 μm and 0.02 μm (F-8888, F-8823, F-8827, F-8888, F-8795, F-8823, F-8827, Molecular Probes) were dialyzed (Eluta Tube mini, Fermentas) in aq. dest. and diluted in 1 mM Tris pH 7.6 to concentrations between 3.3 aM (2 μm) and 2 nM (0.02 μm).

Concentration Imaging Over Time.

Either the method of concentration imaging[13] or single particle tracking were used to measure thermodiffusion at low concentrations, namely below 0.03 g/l for DNA and $10^{-5}$ g/l for beads. At higher concentrations, we found profound changes of thermodiffusion coefficients. DNA and polystyrene beads smaller than 0.5 μm diameter concentration were imaged over time[13] by bright field fluorescence with a 40× oil immersion objective. Concentrations inferred after correcting for bleaching, inhomogeneous illumination and temperature dependent fluorescence[13] were fitted with a finite element theory. The model captures all details of both thermodiffusive depletion and backdiffusion to measure $D_T$ and D independently (see supplementary material). Measurements were performed in microfluidic chips 10 μm in height with PDMS on both sides[13].

Single Particle Tracking.

Polystyrene particles larger than 0.5 μm in diameter were measured by single particle tracking due to the slow equilibration time and risk that steady state depletion is disturbed by thermal convection. The thermodiffusive drift was imaged with a 32× air objective at 4 Hz at an initial stage of depletion in a 20 μm thick chamber. Averaging over the z-position of the particles removed effects from thermal convection. The drift velocity versus temperature gradient of 400 tracks were linearly fitted by $v=-D_T\nabla T$ to infer $D_T$. The diffusion coefficients D of the particles were evaluated based on their squared displacement, matching within 10% the Einstein relationship.

The present invention is not limited by what has been particularly shown and described hereinabove. Rather the scope of the present invention includes both combinations and sub-combinations of the features described hereinabove as well as modifications and variations thereof which would occur to a person skilled in the art upon reading the foregoing description and which are not in the prior art.

Infrared Heating.

The temperature gradients used to induce thermophoretic motions are created by aqueous absorption of a fiber coupled infrared solid state laser (Furukawa FOL1405-RTV-317), with a wavelength of 1480 nm and a maximum power of 320 mW typically used at 25 mW. Water strongly absorbs at this wavelength with an attenuation length of κ=320 μm. The infrared light is coupled out of the fiber to form a parallel beam with an 1/e² diameter of 1 mm. The beam position in the x/y plane can be adjusted by two galvanoometrically controlled infrared mirrors (Cambridge Technology 6200-XY Scanner with Driver 67120). The laser beam is focussed from below the object stage by an infrared corrected aspheric lens with 8 mm focal distance (Thorlabs, C240TM-C). Typically, temperature was increased by only 2 K in the heated focus.

Temperature Measurement.

The temperature gradient was measured via the temperature dependent fluorescence signal of the dye BCECF, diluted to 50 μM in 10 mM TRIS buffer. Details of bleaching correction and temperature extraction were described previously[13]. From the total temperature dependence of BCECF of −2.8%/K, only −1.3%/K stems from pH drift of the used TRIS buffer. The remaining −1.5%/K are the result of thermodiffusion of the dye itself, measured to be $S_T$=0.015/K with the concentration over time method described below.

"DNA" Image.

Measurement of the "DNA" profile in FIG. 7 was performed in a 60 μm thick chamber between glass slides, imaged with a 10× objective and heated to 2 K along the letters "DNA" with laser scanning. The chamber was filled with a 50 nM solution of 1000 bp DNA stained with the intercalating fluorescent dye TOTO-1 (Molecular Probes) To switch from depletion to accumulation, the experiment was performed at room temperature or with the chamber cooled to 3° C., respectively.

Fluorescence Approaches.

Historically, methods used to measure thermodiffusion in liquids are based on changes in refractive index upon change in solute concentration[27]. Inherently, this signal is small for low solute concentrations near the limit of non-interacting molecules, even for intricate detection methods like thermal lensing or holographic interference[38]. Although operating at much smaller volume, the used fluorescent microfluidic approach[13] allows concentrations of 0.03 g/l for DNA and reaches $10^{-5}$ g/l for single particle tracking. This is necessary, since for example in thermodiffusion of DNA, we see profound changes at higher concentrations.

Thermodiffusion from Concentration Over Time.

Both DNA and polystyrene beads smaller than 0.5 μm in diameter were measured by imaging molecule concentration over time by bright field fluorescence. A more basic steady state method was described previously[13]. Here, we refined it with a numerics theory to infer diffusion coefficient D and Soret coefficient $S_T$ independently.

Highly monodisperse and protein-free DNA of 50 bp, 100 bp, 1000 bp, 4000 bp, 10000 bp and 48502 bp (Fast Ruler, fragments and λ-DNA, Fermentas) were used for the length dependent measurements. The DNA was fluorescently labeled by the intercalating TOTO-1 fluorescent dye (Molecular Probes, Oregon) which shows 1000× fluorescence increase when bound to DNA. The dye/base-pair ratio was low (1/50) to avoid structural or charge artifacts from the bound dye. The fluorescence was observed with an 40× oil objective. DNA stock solutions were diluted to 50 μM base pair concentration, which corresponds to molecule concentrations between 1 μM (50 bp) and 1 nM (48502 bp), respectively. Polystyrene beads of diameter 0.2 μm, 0.1 μm, 0.04 μm and 0.02 μm (Molecular Probes, Oregon, F-8888, F-8795, F-8823, F-8827) were dialyzed (Fermentas, Eluta Tube mini) in aq. dest., and diluted in 1 mM Tris pH 7.6 to concentrations of 10 pM, 15 pM, 250 pM and 2 nM, respectively. DNA thermodiffusion measurements were performed in microfluidic chips 10 μm in height with PDMS on both sides[13]. They allow the measurement of small volumes in thin defined geometries. Polystyrene beads were sandwiched between a 1.25 mm thick polystyrene slide (Petri Dish, Roth) on the bottom and a plastic slide (170 μm thick, 1 cm×1 cm, Ibidi, Munich) on the top and sealed with nail polish. For temperature dependent measurements, both 40× oil objective and microfluidic chip were tempered from below with a thermal bath. Note that temperatures well below 0° C. can be achieved as the microfluidic geometry reduces the probability of water to freeze.

Concentration of DNA was inferred from fluorescence images, that were measured with a 40× oil objective (NA=1.3) on an AxioTech Vario fluorescence microscope (Zeiss), illuminated with a high power LED (Luxeon) and imaged with the CCD Camera SensiCam QE (PCO). The time series allows to correct for inhomogeneous illumination and bleaching[13]. A time series dependent photobleaching means that an individual bleaching factor is determined for every image. This correction is of advantage for high precision measurements for protein thermophoresis. If single molecules were visible in fluorescence, time averaging was used to average over particle positions.

Radial profiles were taken over time and combined to a space-time image of both the thermophoretic depletion and back diffusion (FIG. 12a,c). Fluorescence was adjusted for the temperature dependence of the TOTO-1 dye determined independently with a fluorescence spectrometer as −0.5%/K. Typically, temperature in the solution was raised by 1-2 K in the beam center with a $1/e^2$ diameter of 25 μm.

The Soret coefficient $S_T$ can be obtained from the steady state profile. Given the temperature at radius r obtained from temperature dependent fluorescence, the concentration c(r) can be fitted with the steady state thermophoretic profile[13] given by $$c(r) = c_0 e^{-S_T(T(r)-T_0)} \quad (4)$$

with chamber temperature $T_0$ and bulk concentration $c_0$.

We can also obtain D and $D_T$ independently by analyzing the build up and flattening of concentration profile over time after turning the infrared laser beam on or off, respectively. Theory was provided from finite element model in radial coordinates (FEMLab, Comsol) over time with boundary conditions of concentration obtained from the experiment. Comparison with experiment of the time course of thermophoretic depletion reveals $D_T$ (FIG. 12c,d) and from the time course after switching off the heating source the diffusion coefficient D is obtained (FIG. 12a,b). Results for diffusion coefficients obtained for DNA molecules are shown in FIG. 13. Scaling of D for DNA larger than 1000 bp agree well with literature values and theoretical expectations[33]. However for DNA molecules in the order of the persistence length (about 150 bp) the power law exponent of −0.6 does not precisely fit the measured values and a different scaling with an exponent of −1 is necessary. A good description of DNA diffusion coefficients in the size range analyzed throughout this work is achieved with an intermediate exponent of −0.75.

Screening Length.

Debye-Hückel length was titrated by adding $c_S$=0 mM, 2 mM and 20 mM of KCl to $c_T$=1 mM of TRIS buffer at pH 7.6 and calculated from $$\lambda_{DH} = \sqrt{\frac{\varepsilon \varepsilon_0 kT}{2e^2(c_S + c_T)}} \quad (5)$$

Changes in the effective charge of the molecules can be excluded at these monovalent salt concentrations. For largest values $\lambda_{DH}$=13.6 nm, solely 0.5 mM Tris-HCl pH 7.6 buffer was used.

Thermodiffusion Using Single Particle Tracking.

For fluorescent polystyrene particles of large size (2 μm, 1 μm, 0.5 μm, Molecular probes, Oregon, F-8888, F-8823 and F-8827) a different method had to be used due to the increasing visibility of single particles, slow equilibration time and the risk that steady state depletion is disturbed by thermal convection. Beads were dialyzed (Fermentas, Eluta Tube mini) in aq. dest., and diluted in 1 mM Tris pH 7.6 to concentrations of 3.3 aM, 25 aM and 0.2 pM, respectively. Thermodiffusion was measured in 20 μm thin chambers. A 1.25 mm thick polystyrene slide (Petri Dish, Roth, Karlsruhe) was chosen as for the bottom of the chamber, while a plastic slide (170 μm thick, 1 cm×1 cm, Ibidi, Munich) was taken as cover slip. The low thermal conductivity ensures constant temperature across the chamber. Chamber walls were made hydrophilic in a plasma cleaner (Harrick) for 10 min at 10 W electrical power. As a result, adsorption of polystyrene particles to the plastic is low even at high salt concentrations. Addition of 2 μl bead solution between the plastic sheets, followed by sealing the chamber with fast drying nail polish leads to reproducible chamber heights of 20 μm.

Imaging was provided with an AxioTech Vario fluorescence microscope (Zeiss), illuminated with a high power LED (Luxeon) and imaged with the CCD Camera SensiCamQE (PCO). The center of the plain of view was heated 8 K above room temperature with maximal temperature gradient of 0.2 K/μm and $1/e^2$ spot radius of 50 μm Temperature was imaged with BCECF as described before in a separate chamber. In FIG. 14a finite element simulation of the experimental situation is shown using the commercial available Femlab software (Comsol). A 20 μm chamber is heated to 8 K in the center. Due to low heat conductivity of the PS walls the temperature profile is homogeneous throughout the chamber height (FIG. 14a). Due to the thin chamber the convection speed is suppressed to negligible speeds of 5 nm/s at maximum (FIG. 14b). The thermophoretic movement of the particles was imaged with a 32× air objective and recorded at 4 Hz. Particles all over the 20 μm chamber could be equally tracked with a custom-written LabView program. Artefacts from toroidal thermal convection are averaged out to a high degree as convective attraction near the lower chamber wall cancelled with opposite convective repulsion near the top of the chamber. Typically the velocity of 400 tracks was plotted against radius and fitted with the drift velocity expected from thermodiffusion according to thermophoretic drift $v=-D_T\nabla T$ to find the thermophoretic mobility $D_T$. Thermal fluctuations of the tracks were evaluated based on their squared displacement to obtain the diffusion coefficient D of the particles, which matched within 10% the Einstein relationship $D=kT/(6\pi\eta a)$. This is expected since even for the worst case, the chamber is 20-fold thicker than the diameter of the measured particles.

Electrophoresis.

The effective surface charge density was measured for 40 nm diameter beads by electrophoretic drift in 400 μm thin and 5 cm long chambers (Ibidi, Germany). The velocity profile throughout the chamber height at 5 V was taken from single particle tracking of 2 μm beads. At 80 μm height the electroosmotic flow in a tightly sealed chamber is zero[39]. As expected the velocity of particles in this plane saturates for particles larger than 100 nm and is not related to effective charge[36]. A high numerical aperture oil objective has been used to analyze the velocity of 40 nm particles at the chamber surface at the same conditions. The constant velocity difference between chamber surface and plane of zero electroosmotic flow measured before has been used to calculate the purely electrophoretic velocity.

Additional References referred to herein above in Example 1:

3. S. J. Jeon, M. E. Schimpf and A. Nyborg, Anal. Chem. 69, 3442-3450 (1997)
4. P. M. Shiundu, G. Liu, and J. C. Giddings, Anal. Chem. 67, 2705-2713 (1995) 6
7. B.-J. de Gans, R. Kita, B. Müllner and S. Wiegand, J. Chem. Phys. 118, 8073 (2003).
8. J. Rauch and W. Köhler, Phys. Rev. Lett. 88, 185901 (2002)
9. S. Wiegand and W. Köhler, in *Thermal Nonequilibrium Phenomena in Fluid Mixtures*, Springer, Berlin, 189 (2002)
13. D. Braun and A. Libchaber, Physical Review Letters 89, 188103 (2002)
14. S. R. de Groot, P. Mazur, *Non Equilibrium Thermodynamics* (North-Holland, Amsterdam, 1969)
16. A. H. Jr. Emery and H. G. Drickhammer, J. Chem. Phys. 23, 2252 (1955)
17. J. S. Ham, J. Applied Physics, 31, 1853 (1960)
18. K. I. Morozov, J. Experim. and Theor. Phys. 88, 944 (1999)
19. M. E. Schimpf and S. N. Semenov, J. Phys. Chem. B 104, 9935 (2000)
20. A. Voit, A. Krekhov, W. Enge, L. Kramer, and W. Köhler, Phys. Rev. Lett. 92, 214501 (2005)
22. S. Fayolle, T. Bickel, S. Le Boiteux and A. Würger, Phys. Rev. Lett. 95, 208301 (2005)
24. P. N. Snowdon, J. C. R. Turner, Trans. Faraday Soc. 56, 1409 (1960)
25. E. Ruckenstein, J. Colloid Interface Sci. 83, 77 (1981)
27. J. Israelachvili, Intermolecular & Surface Forces, 2nd edition, Academic Press, 1992
28. W. Lin, P. Galletto and M. Borkovec, Langmuir 20, 7465-7473 (2004)
29. D. Haidacher, A. Vailaya and C. Horváth, Proc. Natl. Acad. Sci. 93, 2290-2295 (1996)
30. N. T. Southall, K. A. Dill and A. D. J. Haymet, J. Phys. Chem. B 106, 521-533 (2002)
31. B. Kronberg, M. Costas and R. Silveston, Pure & Applied Chemistry 67, 897-902 (1995)

Example 2

Determination of Hydrodynamic Radius and Interaction Between Proteins

The thermo-optical characterization method of the present invention allows also to quantify the hydrodynamic radius of proteins and even more important of complexes of biomolecules which are not connected covalently to each other. Thermophoresis provides a comparably robust and precise way to measure the hydrodynamic radius of molecules from less than a nanometer up to a few microns. In comparison to the other thermo-optical characterization methods the precision of this method is not too sensitive on the geometry of measurement (e.g. height of the liquid layer) as it is the case for molecular interactions.

Data Acquisition:

A typical measurement can be described as follows:

Step 1:

A solution of fluorescently labeled molecules is brought into a microfluidic measurement chamber (e.g. capillary, microfluidic chip). Fluorescence is excited and recorded with spatial resolution for less than 5 seconds on a CCD device with a frame rate between 40 Hz down to 0.2 Hz (i.e. for fast diffusing molecules, a high frame rate is chosen). These image(s) provides the necessary information about the fluorescence level at 100% concentration. Then fluorescence excitation is turned off.

Step 2:

The Infrared laser heating is turned on. The immediately established local spatial temperature distribution causes the molecule drift to lower or higher temperatures, depending on the particular molecule to be analyzed. The laser is focused in a way that temperature gradients between 0.0 and 5 K/μm are achieved. The temperature gradient has been calibrated once and it is not necessary to repeat this calibration every time an experiment is performed. The maximal temperature elevation is below the temperature which is known to cause damage to the molecules or disintegrate their interaction. Depending on the thermophoretic properties of the molecules in the solution (i.e. if they move fast in a thermal gradient or slow) the infrared laser heats the solution for 5 seconds up to 100 seconds. After this period of time the infrared laser is turned off Step 3:

After the spatial temperature distribution has vanished (typically 2-50 ms) the fluorescence excitation is turned on and fluorescence is recorded with the same frame rate used in the first step of fluorescence imaging. This time the redistribution of the molecules is imaged for 5 seconds up to 50 seconds. The exact time depends on the velocity with which the molecules diffuse (i.e. the time it takes them to equalize 90% of the concentration gradient established by thermophoresis).

Data Processing—Photobleaching:

The fluorescence images have to be corrected for photobleaching. Since there is no spatial temperature profile in the solution while fluorescence images are taken, the bleaching correction is possible with high precision (i.e. high precision is possible since the rate of photobleaching is temperature dependent).

Therefore, the fluorescence at a edge of the measurement chamber (i.e. a spot as far away from the heated center as possible), were thermophoresis during step 3 was negligible (i.e. for a person skilled in the art, this is where the temperature gradient during laser heating was lower than 0.001 K/µm), is evaluated to determine the photobleaching from the image series taken in step 3. If photobleaching is present, the fluorescence will decrease from image to image. The individual factor for each image is used to correct all images for bleaching. Another possibility is to calculate the bleaching for every single pixel from the images taken in Step 1. The bleaching rate per pixel can be used to correct every pixel from step 3 images for the photobleaching effect.

Data Processing—Inhomogeneous Illumination Correction and Normalization to 100% Concentration:

All images taken in step 4 are divided by a single or all images taken in step 2 and multiplied by 100. This way a correction for inhomogeneous illumination is achieved and the fluorescence is normalized to 100% concentration.

Data Processing—Determining the Hydrodynamic Radius:

From the first images of the step 4 image series the concentration distribution is extracted. A software tool evaluates the Diffusion coefficient (or multiple Diffusion coefficients in case of a mixture) which describes the experimentally measured relaxation of the concentration gradient. Using the Stokes-Einstein relation the hydrodynamic radius is inferred from the diffusion coefficient.

In Particular, the Above Described Experiment was Conducted for a Sample of GFP as Follows:

The thermo-optical properties of two samples of Green Fluorescent protein (GFP) are measured with the devices of the present invention. 2 µl of GFP (5 µM, 1×PBS buffer) is pipetted on an object slide. The sample is sandwiched by pitting an cover slip (round 12 mm diameter) on top. The liquid spreads uniformly in between the glass surfaces an the chamber is sealed off by using nail polish. This prevents the liquid from rapid evaporation, which would in turn lead to a comparably strong flow of liquid in the chamber. This sample is placed on a device shown in FIG. 1a. The measurement steps and data processing steps are performed as described above. The same experiment is performed with a second sample containing 5 µM GFP and 10 µM of a GFP binding antibody fragment, specifically binding to GFP. In both cases, first the fluorescence is recorded without laser heating. Then the fluorescence excitation is turned off and the IR-laser radiation is turned on (the maximum temperature is kept below 35° C. (i.e. about 15° C. above ambient temperature (about 20° C.) to avoid denaturation or damage to the protein). The laser is turned off after a few seconds of heating and the fluorescence excitation is turned on at the same time. The relaxation of the spatial fluorescence distribution (i.e. concentration distribution) to a homogeneous state is recorded for a few seconds. As can be observed from FIG. 31, in the sample with the two interacting species (i.e. GFP and the antibody fragment) the fluorescence profile needs more time to relax. This is explained by slower diffusion of the larger complex. The time evolution of the fluorescence profile is analyzed via a software tool (selfmade Software, Labview, National Instruments) to determine the diffusion constant. By using the Stokes-Einstein relation, a hydrodynamic radius is attributed to the diffusion constant. In case of the free GFP this is 5 nm and the complex has an radius of 10 nm.

Example 3

Detection of Interactions Between Biomolecules and Discrimination of Nucleic Acids by Size The thermo-optical characterization of the present invention provides the means for fast all optical biomolecule analysis. Present methods for detection and quantification of biomolecular interactions are very time consuming which means that the time needed for an analysis is on the order of 30 minutes up to hours. The present invention can detect and quantify biomolecular interactions within 1 second up to 50 seconds. The term interaction comprises interaction between biomolecules (e.g. protein, DNA, RNA, hyaluronic acids etc) but also between modified nanoparticles/micro beads and biomolecules. A typical experiment to detect/quantify, interactions can be described as follows:

Step 1a, Background Measurement:

The sample buffer without fluorescently labelled sample molecules/particles is filled in the microfluidic chamber and the fluorescence is measured, while the excitation light source is turned on.

Step 1b, Determination of Fluorescence Level Before Laser Heating:

An aqueous solution of a fluorescently labelled sample (e.g. biomolecules, nanoparticles, microbeads whereas all of them have a specific affinity for other biomolecules) at a given concentration is filled in a microfluidic chamber (preferably a capillary) which preferably guarantees a defined height of the chamber. Fluorescence is excited and recorded with (CCD-Camera) or without (Photomultiplier tube, Avalanche Photodiode) spatial resolution for less than 10 seconds on a CCD device or photomultiplier with exposure times of 25 milliseconds up to 0.5 seconds. Then the fluorescence excitation is turned off.

Step 2, Starting of Infrared Laser Heating:

In the following the infrared heating laser is turned on and the spatial temperature distribution is established within a few milliseconds within the solution. The temperature gradient has been calibrated once and it is not necessary to repeat this calibration every time an experiment is performed. In particular a setup were infrared heating and fluorescence imaging are performed through the same optical element from one side is advantageous for the stability of the optical and infrared foci.

It is of advantage that in the experiment the decrease of fluorescence due to photobleaching is lower than 5%.

The maximal temperature elevation is below the temperature which is known to cause damage to the molecules in the solution or disturb their interaction (e.g. temperatures between 1 and 5° C. above ambient temperature).

Depending on the thermophoretic properties of the molecules in the solution (i.e. if they move fast in a thermal gradient or slow) the infrared laser heats the solution for 5 seconds up to 100 seconds.

Step 3, Recording of the Spatial Fluorescence (i.e. Concentration) Profile:

After this period of time the fluorescence excitation is turned on and images are recorded with the same frame rate and length as described in step 1b. Step 3 is the last acquisition step necessary for evaluation of thermo-optical properties.

For detection and quantification of interactions more measurements following the protocol described previously are necessary. Step 1a is repeated with sample buffer and in step 1b the aqueous solution of a fluorescently labelled sample is mixed with an amount of the biomolecule with which the interaction should be detected or quantified. For the detection of an interaction it is necessary to mix the fluorescently labelled sample with a sufficient amount of binding partner so that a substantial amount of the fluorescently labelled molecule is in the complex with the binding partner. If the strength of the interaction should be quantified in terms of a dissociation or association constant (Ka, Kd), than the procedure described previously has to be conducted with varying concentrations of binding partner (e.g. 0.1×-10× the concentration of the fluorescently labelled binding partner). This means that a titration of binding partner should be performed.

Processing the Raw Data:

For a linear bleaching correction it is necessary to wait for the back-diffusion of all molecules following the end of step 3. This increases the time consumption of the analysis dramatically. For precise and fast measurements it is of advantage to determine the strength of bleaching from image to image and correct every individual image with its own bleaching factor. For a precise bleaching correction it is important that the temperature gradient at distance from the heat spot is low (e.g. below 0.001 K/μm). The images taken in step 1b are used to correct all images for inhomogeneous illumination. In case fluorescence is recorded without spatial resolution (e.g. avalanche photodiode or photomultiplier) photobleaching is corrected best by determining once the bleaching characteristic of a certain dye without heating laser in a control experiment.

Data Evaluation:

Qualitative detection of interaction: From the image series the spatial fluorescence distribution of the reference experiment (i.e. fluorescently labelled molecule/particle without binding partner) and the second experiment (i.e. were the binding partner is present) is extracted. The fluorescence is plotted versus the distance from the heat spot. An averaging is only possible for pixels with the same temperature and same distance. The spatial concentration distribution is obtained by correcting the fluorescence intensities for the respective temperature dependence of the dye. With knowledge of temperature dependence of the fluorescent dye and the spatial temperature distribution, the effect of a decreasing fluorescence due to temperature increase can be corrected. For the qualitative detection of interaction as well as their quantification a correction for temperature dependency is not necessary, and the spatial fluorescence distribution is sufficient. This enables us to use any fluorescent dye on the market without characterization of its temperature dependency.

The values of the fluorescence profile are integrated up to the distance were the temperature is below 10% of the maximum temperature (e.g. 70 μm). The integrated values are compared and a change give a precise indication if there is an affinity between the substances at the concentrations used, since the interaction changes the thermo-optic properties (e.g. thermophoretic mobility, surface size and chemical groups on surface). In most cases the interaction leads to higher fluorescence (concentration) at higher temperatures.

In case the whole cross-section of a capillary is heated (i.e. using cylindrical lenses to give the IR laser beam a ellipsoidal shape, which heats a cross section of a capillary homogeneously), the intensity of a lot more pixels from the centred heat spot can be averaged since all pixels at same distance to the heated line have the same temperature. This is advantageous for high precision measurements. In case fluorescence is recorded without spatial resolution the fluorescence change in the centre of the heat spot/line is measured, whereas it is again advantageous to heat the whole cross section. In general if more than a single frame is recorded in step 1b and 3 an integration of multiple frames is possible.

For a quantification of affinities the same procedure is performed for all experiments at various concentrations of non fluorescent binding partner. The result of the integration for the reference experiment (i.e. without binding partner) is subtracted from the integrated values obtained for the different concentrations of binding partners. From this evaluation on gets the amount of interacting complexes in arbitrary units. By dividing the values by the value were binding is saturated the relative amount of complexes at a certain concentration of binder is obtained. From these dataset also the concentration of free non fluorescent binding partner can be determined and the strength of the interaction can be quantified in terms of association or dissociation constant (see FIG. 25).

Example 3a

Interaction of Proteins

FIG. 25 shows a quantification of interaction between biomolecules. 100 nM of a fluorescently labelled antibody in 1×PBS buffer (anti-Interleukin 4, Sigma-Aldrich) are titrated with various amounts interleukin 4 1×PBS buffer (0-300 nM IL4 Sigma-Aldrich). (left). Approximately 200 nl of the sample mix are soaked into a capillary of 40 nm inner diameter (World Precision Instruments). The capillary is situated on a device as shown in FIG. 27. Fluid drift is prevented by closing the valves on both sides of the capillary. The measurement is performed with the device shown in FIG. 20. The spatial fluorescence distribution in steady state is measured using the previously described protocol. Three results for 5 nM, 80 nM and 300 nM are shown exemplarily. After each measurement the capillary is flushed with approximately 5 μl of 1×PBS buffer. The binding of IL 4 to the antibody changes the signal dramatically from fluorescence decrease to a fluorescence increase. Integration of the fluorescence profile up to 80 μm (distance from the heated centre, see procedure described in this example herein above) allows to determine the number of complexes in solution. (right) The concentration of free Interleukin 4 can be calculated plotted versus the concentration formed complex. These data can be fitted to determine the $K_D$.

Example 3b

Discrimination of DNA by Size and Interaction of DNA Strands

Qualitative detection of interaction, using a modified protocol according to this example 3, is shown in FIGS. 5a-5b. Here the concentration profiles of 20 base pair DNA has been compared to 50 base pair DNA at a maximum temperature increase of 10° C. (at ambient temperature of 20° C.). In a second experiment 20 bases single stranded DNA is compared with 20 base pair double stranded DNA. All four experiments were performed in 1×SSC buffer the following way: 2 μl of sample are pipetted on an object slide (Roth, 1 mm thick) an sandwiched between an cover slip of 12 mm diameter. The aqueous solution spreads uniformly in between the two glass surfaces yielding a thin sheet of water with a height of approximately 20 μm. The liquid sheet is sealed by using nail polish. This avoids rapid evaporation of the sample. The microfluidic chamber is placed on the object stage of the thermo-optical setup (e.g. FIG. 1a) and imaged via a 40× oil objective (NA 1.3, Zeiss). The laser focus is positioned so that it is approximately in the center of the field of view and has a half width of about 20 µl. Only a single pixel of a CCD camera used for detection of the fluorescence. This pixel measures the fluorescence in the center of the heat spot. The fluorescence is recorded for approx. 1 seconds without laser heating, then the IR Laser is turned on while fluorescence is still recorded. After 20 seconds of laser heating the measurement stopped. As can be seen from FIGS. 5a-5b single stranded DNA can be discriminated from double stranded DNA and DNA of different length can be discriminated within a time span of a few seconds. Bleach correction is not performed in this measurement strong change in concentration is observed.

Example 4

Detection of Binding of PEG Molecules to Nanoparticles

As mentioned previously it is also possible to detect the binding of molecules to larger inorganic particles or nanocrystals using the procedure described previously. Inorganic CdSe particles (core diameter about 12 nm) have been modified with a varying numbers (1 up to 3) of Poly-ethylen-glycol (PEG) of different molecular weight. 2 µl of sample are pipetted on an object slide (Roth, 1 mm thick) and sandwiched between a cover slip of 12 mm diameter. The aqueous solution spreads uniformly in between the two glass surfaces yielding a thin sheet of water with a height of approximately 20 µm. The liquid sheet is sealed by using nail polish. This avoids rapid evaporation of the sample. The microfluidic chamber is placed on the object stage of the thermo-optical setup (e.g. FIG. 1a) and imaged via a 40× oil objective (NA 1.3, Zeiss). The laser focus is positioned so that it is approximately in the center of the field of view and has a half width of about 100 µm. The maximum temperature increase was determined to 5° C. above ambient temperature. The spatial fluorescence profile is recorded as described previously for the detection of biomolecular interactions. Also the raw data are processed as described previously. To measure the number or size of PEG molecules bound to the nanocrystals it is sufficient to compare the spatial fluorescence profiles obtained with the protocol described previously. However, a correction for the temperature dependent decrease of the fluorescence allows a quantification in terms of the Soret coefficient. FIG. 26 shows that the Soret coefficient increases linearly with the number of PEG molecules bound to the nanocrystals. The slope of the increase depends on the molecular weight of the PEG. FIG. 26 shows that the binding of single molecules of the size of a protein is detectable.

Example 5

Thermophoresis of Proteins

An example how the conformation, structure and surface of a molecule effect the thermo-optical characteristic of said molecules and how these characteristics may be measured, detected or characterized is given in the following:

A sample of fluorescently labelled BSA (Bovine Serum Albumin, Fermentas) is transferred in a microfluidic chamber (e.g. capillary). The temperature of the whole sample volume is adjusted by a Peltier element in thermal contact to the solution (the microfluidic chamber is placed on a device shown in FIG. 27). The Peltier element is used to regulate the "ambient temperature" of the solution. It does not create a spatial temperature distribution. The adjustment of temperature is important because the thermo-optic properties (e.g. surface properties, conformation) at varying ambient temperatures (i.e. protein conformations) should be measured. The thermo-optic properties are measured following the protocol described previously for biomolecule interactions (step 1 to step 3, without addition of binding partners since only intramolecular properties are measured). Also the processing of the raw data follows the procedure described for the detection of molecule interactions. The thermo-optical properties are evaluated by determining the concentration profile in steady state. The thermo-optic properties are plotted as Soret coefficient ST as shown in FIG. 28. The Soret Coefficient is obtained by correlating the concentration profile in an exponential fashion ($c=c_0 e^{-S_T(T-T_0)}$) to the temperature distribution. The Soret-Coefficient is sensitive to changes in the interplay between the amino acids of the protein and the water molecules. At low temperatures the molecules are accumulated in a region of elevated temperature, which corresponds to a negative Soret coefficient. At increasing temperatures the accumulation of the molecules changes (i.e. the Soret coefficient increases). This can be readily explained by changes in the conformation of the molecule (e.g. hydrophobic groups or loops rearrange). As can be seen from FIG. 28 the sign of thermophoresis changes from negative values at lower temperatures to positive values (i.e. depletion) at higher temperatures. The sudden jump to positive Soret coefficients correlates very well with the temperature were thermal denaturation occurs (i.e. 50° C.). In the range of body temperature (i.e. 30° C.-40° C.) the thermo-optical signal does not significantly change. An explanation for this unexpected behaviour is that the protein is evolutionary designed to be functional within this temperature range. Since there is a tight structure-function relationship in nature, the structure is preserved in this temperature range. The values shown in FIG. 28 are corrected for the temperature dependence of the fluorescence dye.

The local temperature increase in the system causes a change in fluorescence which is not purely caused by changes in concentration due to thermophoresis. Since the temperature of transition from negative to positive values is important for measurements of absolute protein stability, a correction for the temperature dependence of fluorescence is advantageous. In application were differences in stability should be detected (e.g. small molecule binding to a protein) the correction for temperature dependence of the fluorescence is not necessary. The argument that protein structure/conformation is measured is supported by FIG. 28b where the experiment is started at high temperatures. Even at temperatures below the thermal denaturation temperature the Soret coefficient is positive. This is based on the slow refolding time compared to the speed of measurement, which is faster than 50 seconds. After a certain time span the thermo-optical ST values shown in FIG. 28a are also obtained again in the measurement shown in FIG. 28b. As a control the temperature of the system is increased again and the negative ST values are obtained as expected at temperatures of about 40° C.

Example 6

Detection of Conformational Changes, Like Denaturation of Proteins a) An example where the denatured form of a protein is distinguished from the native form without any correction for the temperature dependence of the fluorescence dye, given in FIG. 15. An aliquot of a fluorescently labelled Bovine Serum Albumin is heated up to 90° C. for 10 minutes, which is well above the temperature of denaturation and the protein cannot refold. Also the thermo-optic characteristics of a native aliquot (i.e. not heated to 90° C.) is measured. Starting with the native sample, approximately 200 nl of the sample are soaked into a capillary of 40 nm inner diameter (World Precision Instruments). The capillary is situated on a device as shown in FIG. 27. Fluid drift is prevented by closing the valves on both sides of the capillary. The measurement is performed with the device shown in FIG. 20. The spatial fluorescence distribution in steady state is measured using the previously described protocol. After each sample the capillary is flushed with approximately 5 µl of 1×PBS buffer. The experiment is performed as described for the measurement of biomolecular interactions (Step 1-Step 4). The experiment is performed twice with different infrared laser powers (i.e. maximal temperatures of 5° C. and 10° C. above ambient temperature are employed). Afterwards the sample with the denatured protein is measured. Again three experiments with different laser powers are used. In FIG. 29 the fluorescence is plotted as a function of the distance to the heat source (i.e. laser focus) is shown for the native and denatured form at two different laser powers (i.e. maximum temperatures of 5° C. and 10° C.). In both cases there are two contributions to the fluorescence change. First there is an increase or decrease in concentration (for the native or denatured form, respectively) and secondly there is a decrease in fluorescence due to the temperature dependence of the fluorescence dye. For a qualitative comparison (i.e. to distinguish between a native and denatured form.) a correction for the temperature dependence of the dye is not necessary. In all cases shown in FIG. 29 the fluorescence decreases. But as expected the decrease in fluorescence for the native protein is not as strong decrease observed for the denatured form. This is readily explained by the negative Soret coefficient of the native protein at 20° C. ambient temperature (see also FIG. 28), which leads to an accumulation of molecules at higher temperatures. This counteracts the decrease in fluorescence caused by the temperature dependence of the fluorescence. At higher laser powers (i.e. a maximum temperature increase of 10° C.) the difference between native and denatured form is even stronger because the thermophoretic accumulation and thermophoretic depletion, for the respective form, get stronger. Also smaller conformational changes can be detected on the basis of different strength of thermophoresis. A different direction of thermophoretic movement is advantageous but not necessary.

b) A sample of fluorescently labelled bovine serum albumin (BSA) has been split in two parts. One is only exposed to ambient temperatures, while the other half is heated up to 100° C. for several minutes (i.e. irreversibly denatured). The thermo-optical properties of both samples (native and denatured) are measured at 800 mA power of the infrared laser (i.e. maximal temperature increase of 20° C.). As can be seen from FIG. 30, the fluorescence of the denatured protein is lower than the fluorescence of the native protein. This is explained as follows. The fluorescence dye of both samples shows the same decrease in fluorescence due to the increase in temperature (i.e. temperature sensitivity of the fluorescence). But the denatured protein shows a positive thermophoretic mobility (i.e. moves to the cold), while the native protein has a negative thermophoretic mobility (i.e. moves to the hot). The accumulation at elevated temperatures is the reason, why the decrease in fluorescence is lower for the native protein, while the denatured protein is, in addition to temperature dependency, depleted from the region of elevated temperature. Interestingly, by approaching the denaturing temperature (i.e. 50° C.) of the protein the amplitudes of the native and denatured protein approach each other an are essentially the same. This means that by measuring the amplitude of the fluorescence change an comparison to the reference sample allows to detect the melting temperature of a protein and to discriminate between native and denatured form of a protein. And to detect a shift in melting temperature due to interactions of the protein with other biomolecules or small molecules (e.g. drug candidates).

Example 7

Optothermal Trap/Thermooptical Trap

In the following, silica particles are employed as illustrative particles/beads to be thermo-optically trapped by the method of the present invention. It is understood that the described method can also be employed for the thermo-optical trapping of other molecules, like biomolecules or lipid vesicles (as also illustrated in a further example).

Silica particles (1 µm diameter, plain, Kisker Biotech) are diluted 1/100 in distilled water. 2 µl are pipetted on an object slide (Roth, 1 mm thick) an sandwiched between an cover slip of 12 mm diameter. In the following the term bead is used as a synonyme for particle. The aqueous bead-containing solution spreads uniformly in between the two glass surfaces, yielding a thin sheet of water with a height of approximately 20 µm. The liquid sheet is sealed by using nail polish. This avoids rapid evaporation of the sample. The microfluidic chamber is placed on the object stage of the thermo-optical setup (as e.g. illustrated in the appended FIG. 1a) and imaged via a 40× oil objective (NA 1.3, Zeiss). The laser focus is positioned so that it is approximately in the center of the field of view and has a half width of about 100 µm. Then the IR Laser is turned on and heats the solution to 10° C. above ambient temperature (20° C.) at the maximum of the spatial temperature distribution in the center of the IR laser focus. In the beginning, without laser heating, the beads are almost equally distributed. The particles show a directed movement to the region of elevated temperature at the laser focus, which can be also referred to as negative Soret effect or negative thermophoresis. Surprisingly, silica particle show negative thermophoresis at room temperature. The particles are trapped in the center of the temperature distribution at the laser focus (data not shown). The particle experiences a potential well created by the spatial temperature distribution. The directed motion to the region of highest temperature is explained by the particle's tendency to minimize its energy of solvation. The position of the particle is not exactly in the center of the heat spot, since the thermal fluctuations push the particle out of its position. By using the thermo-optical trap, particle can be moved arbitrarily and can also be concentrated. After confining antibody modified beads to the heat spot, an interaction between the particles due to a binding of a single antigen in the solution to more than one bead can be detected.

Another approach of a thermo-optical characterization in accordance with this invention is shown in FIG. 32. Silica particles (1 µm diameter, plain, Kisker Biotech) are diluted 1/1000 in distilled water. The dilution factor is empirical. The dilution is such that only a single particle is observed in a region of approximately 400 µm times 400 µm. 2 µl are pipetted on an object slide (Roth, 1 mm thick) an sandwiched between an cover slip of 12 mm diameter. The aqueous bead-containing solution spreads uniformly in between the two glass surfaces yielding a thin sheet of water with a height of approximately 20 µm. The liquid sheet is sealed by using nail polish. This avoids rapid evaporation of the sample. The microfluidic chamber is placed on the object stage of the thermo-optical setup (e.g. FIG. 1a). The laser focus is positioned so that it is approximately in the center of the field of view and has a half width of about 100 µm. Then the IR Laser is turned on and heats the solution to 10° C. above ambient temperature (20° C.) at the maximum in the center of the IR laser focus. Due to the high dilution, a single particle is trapped in a potential well created by a spatial temperature distribution (s. FIG. 32a). As silica particles show a negative thermophoresis the well is deepest at high temperatures (i.e the particles minimize their energy of solvation at high temperatures). The single silica particle fluctuates in the potential well since the thermal fluctuations push the particle out of its position. The fluctuations are recorded via a CCD camera (at t=1 s, 2 s, 3 s, 4 s, 5 s, 6 s, 7 s) and the positions are tracked by Software (selfmade Software, Labview National Instruments, detecting the pixel with highest intensity) with nanometer resolution (see FIG. 32b). A histogram is calculated from the positional information (see FIG. 32c). The width of the distribution is very sensitive to the thermo-optical properties of the particle. If molecules bind to the surface of the particle, the effective potential for the bead changes and the amplitude of the fluctuations increases or decreases. By observing the amplitude change over time, a kinetic binding curve can be measured. In a microfluidic system such an experiment is performed as follows: a solution containing a 1/1000 dilution (distilled water) is flushed or soaked into a capillary (see FIG. 27). The valves at the end of the capillary are closed. A single particle (modified (e.g. coated) with an antibody specific to a certain antigen, e.g. Interleukin 4) is trapped and the fluctuations of the particle are detected for 10 seconds to 100 seconds. The beads is surrounded by pure buffer solution. In a next step the buffer is exchanged with a buffer containing the respective antigen. While the buffer is exchanged the bead is still trapped. After exchange of buffer the fluctuation of the same bead as before are recorded. The change in fluctuation amplitude is used to detect interactions between antibody and antigen. Its change over time is used to measure binding kinetics.

By using a device as illustrated in the appended FIG. 24, a temperature gradient can be generated in solution, by scanning lines (e.g. 10) perpendicular to each other in the solution. Where these lines cross, a temperature maximum is observed. Points on the scanned line have an intermediate temperature, while spaces in between the lines represent temperature minima (e.g. ambient temperature if spaces in between the lines are sufficiently wide). The silica particle described above will move to equilibrium positions on the crossing points of the heated lines. By moving the temperature grating all particles will move simultaneously. In addition the fluctuation of all beads may be measured simultaneously.

Example 8

DNA Melting Curves

Standard protocol for the measurement of melting curves (using the device shown in e.g. FIG. 1a, 1b, 16 to 18, 20 to 24 or 37):
  Raman-Laser 1455 nm; coupled to galvanometric mirrors via fibre
  No collimator after fibre, Laser-beam hits mirrors divergently; mirrors are reflecting the laser-beam onto a lens; laser beam is focused to the chamber via the lens.
  Laser on/off is controlled via moving the laser in an out of the field of view via the mirrors.
  Preparations:
    Coverslips (170 µm) thick, one with a diameter of 12 mm the other quadratic 24×24 mm rinsed with deionized water, rinsed with ethanol, then again rinsed with deionized water.
    Dilution of solutions:
      10 µM Tamra in 1×SSC
      Hairpin from 100 µM in MilliQ-water diluted to 10 µM, 1 µM, 100 nM, or less in SSC-Buffer (1×, 0.5×, 0.1× or less).
      add the detergent TWEEN20 to an end volume of 0.01% (only if there is unspecific adsorption).
  Adjustment:
    Check if everything is ok with the microscope (apertures, filters)
    10 µM Tamra (tetramethylrhodamine) in 1×SSC (150 mM NaCl, 15 mM Na3-citrate, pH 8.1), with 0.01% TWEEN 20; volume of 41 into chamber built with 2 Coverslips (170 µm thick), sealed with nail polish
    Wait until nail polish is dry
    Add immersion oil onto the upper coverslip
    Put chamber onto the measurement stage
    Focussing fluorescence image by nearly closing the aperture
    Find laser spot
    Focus laser
    Defocus laser by increasing the distance between lens and chamber
    Adjust laser focus in a way that a broad and appropriate temperature distribution is established
    Move laser spot with galvanometric mirrors out of the field of view in such a way that the influence of the laser to the fluorescence image is minimal→save this settings to the measurement program (avoid to cross the zero point on the voltage scale of the galvanometric mirrors)
    Measure the room temperature
  Measurement:
  Use the following steps for the measurement of temperature as well as for the measurement of melting curves:
  Conduct the measurement with the trigger-programme.
  Settings: 40× oil immersion-objective, 8×8 Binning, 10 ms exposure time (→28 Hz readout rate)
  To do manually:
  1. Laser on
  2. Light source on (open shutter in case of HXP), write down the settings of the light source
  3. Start the trigger program
  4. Laser off
  Light source on
  The measurement is based on the detection of fluorescence and therefore may be conducted in a device according to appended FIGS. 16-18 and/or 20-24. As the exact timing of measurements is preferable, the used devices like CCD, IR-Laser and light source are synchronised by the use of an electronic trigger signal. As the used CCD-camera (Andor Luca) has a trigger output port, the IR-Laser control element and the light source control element are synchronised with the trigger signal of the CDD-camera. In particular the second high level of the CCD trigger output signal is taken as the zero point of time of the measurement. In the following the exposure time of the CCD-camera is 10 ms and the minimal time span between two images is determined by the frame rate of the CCD-camera. As chamber a 2 µl solution of the fluorescently labelled sample molecules (e.g. 10 µM tetramethyl-rhodamine (TAMRA) in 75 mM NaCl, 7.5 mM Na3-citrate, 0.01% TWEEN 20, pH 8.1) is sandwiched between two 170 µm thick glass coverslips with diameter of 12 mm and sealed with nail polish. This results in a thickness of the chamber of about 20 µm. Then the chamber is moved to the measurement device and the optics are focussed to the chamber.

Brief Description of the Sequence of the Measurement:

Before the measurement starts, the fluorescence background of the measurement device is recorded in "Step 0". As this background is characteristic for the used device and may not change during a long time period this step is preferably done only once to characterize the used device.

Time t=0: Step 1: a first fluorescence image of the spatial fluorescence distribution in the chamber is recorded.

Time t=20 ms Step 2: the IR-Laser is switched on

Time t=60 ms Step 3: a second fluorescence image of the spatial fluorescence distribution in the chamber is recorded.

After these steps the measurement is finished and the raw data processing and the data evaluation is conducted.

Detailed Description of the Sequence of the Measurement:

Step 0, Background Measurement:

A sample buffer without fluorescently labelled sample molecules/particles is filled into a microfluidic chamber and the spatial fluorescence distribution in the chamber is measured with the CCD-camera, while the excitation light source is turned on.

Step 1, Determination of Fluorescence Level at Ambient Temperature Before Laser Heating:

An aqueous solution of a temperature sensitive dye (e.g. TAMRA) at a given concentration (e.g. 10 µM) is filled in the chamber which preferably provides a defined height of the chamber. Fluorescence is excited with the light source (LED) and recorded with spatial resolution with the CCD-camera at ambient temperature.

First the CCD-camera is started and the first high level of the camera trigger output signal is used to synchronise the IR-Laser control element and LED control element with the CCD-camera. For the synchronising a measurement card from e.g. National Instruments can be used.

For good illumination the LED is turned on with the use of the camera trigger signal a short time before the CCD-camera records a first fluorescence image $I_0(x,y)$. Therefore during the exposure time of the CCD-camera of 10 ms the fluorescence excitation light source has reached its steady state level of light output. When the camera starts its recording the output trigger signal of the camera is the second time at the high level state. This second high level state of the output signal determines the zero point of time t=0.

Step 2, Starting of Infrared Laser Heating:

The infrared heating laser is turned on at time t=20 ms and the spatial temperature distribution is established within a few milliseconds within the solution. The temperature distribution has been calibrated once in a way that for example all temperatures between 30° C. and 90° C. are present in the recorded image and it is not necessary to repeat this calibration every time an experiment is performed.

Step 3, Recording of the Spatial Fluorescence Profile with Infrared Laser Heating:

At t=60 ms, 40 ms after IR-Laser irridation was started, a second fluorescence image $I_1(x,y)$ is recorded with the CCD-camera with an exposure time of 10 ms.

After the CCD-camera has taken the second picture, the first and the second picture are saved to the hard disk of a PC for processing the raw data and for data evaluation. Then the measurement process is finished.

Processing the Raw Data and Data Evaluation:

Because of the short time of measurement no correction for bleaching may be necessary. The images $I_0$ and $I_1$ are corrected against camera background. Then calculating the ratio $K(x,y)=I_1(x,y)/I_0(x,y)$ for each pixel of the fluorescence images (second image divided by the first image, both background corrected) ensures the removal of artefacts from an inhomogeneous illumination. As the temperature dependence F(T) (FIG. 15) of the dye TAMRA is known from a calibration experiment in a fluorimeter, the spatial temperature distribution T(x,y) (FIG. 3c) can be derived from to the ratio K(x,y).

As the timing of measurement is the same for the temperature measurement and for the measurement of the melting curve, both measurements can be conducted at one time in one chamber if the emission spectrum of the dye for the temperature measurement (e.g. TAMRA) can be well separated from the emission spectrum of the fluorescent label of for example the molecular beacon (e.g. HEX as fluorophore (see appended FIG. 6) and Dabcyl as a quencher).

Example 9

Detection of Covalent and Non-Covalent Modifications of Nanoparticles

An example for the detection of covalent and non-covalent modification is shown in FIG. 35. Nanoparticles (i.e. nanocrystals or quantum dots) have been obtained from Invitrogen. Particles were purchased which have charged polymere coating to be stable in aqueous solution (diameter 12 nm). In addition particles with covalently coupled strepavidin were purchased (diameter 21 nm), as well as a biotinylated 40 bases single stranded DNA. The following samples have been prepared: First unmodified nanoparticles diluted to 1 µM concentration in 1×SSC (Saline-Sodium Citrate) buffer. Secondly, streptavidin coated nanoparticles diluted in 1×SSC buffer to 1 µM concentration. Thirdly, streptavidin coated nanoparticles diluted in 1×SSC buffer to 2 µM concentration were mixed with 2 µM 40 bases biotinylated single stranded DNA (IBA GmbH, Göttingen) in 1×SSC buffer in a 1/1 ratio. All three experiments were prepared in 1×SSC buffer in accordance with the following protocol: 2 µl of sample are pipetted on an object slide (Roth, 1 mm thick) an sandwiched between an cover slip of 12 mm diameter. The aqueous solution spreads uniformly in between the two glass surfaces leading to a thin sheet of water with a height of approximately 20 µm. The liquid sheet is sealed with nail polish to avoid rapid evaporation of the sample. The microfluidic chamber is placed on the object stage of the thermo-optical setup (e.g. FIG. 1a) and imaged via a 40× oil objective (NA 1.3, Zeiss). The laser focus is positioned so that it is approximately in the center of the field of view and has a half width of about 20 µm. The experiments were conducted as described herein above for the detection of interactions, with a maximum temperature increase of 5° C. above room temperature. A correction for temperature dependent fluorescence has been performed for precise measurement of the Soret Coefficient from the spatial concentration distribution. (i.e. the temperature dependency of the fluorescence of the nanocrystal has been determined in an independent fluorimeter experiment). As can be seen from FIG. 35, the Soret coefficient is positive and larger for the streptavidin coated nanoparticle than for the nanoparticle without protein. Furthermore the binding of a single single-stranded DNA molecule to the particle is detected as a change in Soret coefficient. This is interesting, since the short flexible DNA molecule does not contribute substantially to the size of the nanoparticle (as the streptavidin does). Since thermophoresis is sensible to changes of the surface properties upon binding of the DNA molecule, the binding of the comparatively small DNA molecule to the particle can be detected.

Example 10

Thermophoresis and Thermophoretic Trapping of Lipid Vesicles

Texas-Red DHPE (1,2-dihexadecanoyl-sn-glycero-3-phosphoethanolamine, triethylammonium salt), a fluorescently labelled phospholipid, is used for staining the vesicles. The lipid is added to the process of vesicle formation with approximately 1 mol percent with respect to the main constituting phospholipids. The following stock solutions were used for preparation of the vesicles by electro swelling:
Lipid Stock Solution:
  2.5 mg/ml DPhPC (1,2 Diphytanoyl-sn-Glycero-3-Phosphocholine) in Chloroform ($CHCl_3$)
  1-2% stearylamine
  1% fluorescent lipid (1,2-dihexadecanoyl-sn-glycero-3-phosphoethanolamine, triethylammonium salt (Mol. Probes)
Sucrose Stock Solution:
  300 mM Sucrose in distilled water
Buffer Solution:
  150 mM KCl, 20 mM MES, pH 5

The final vesicle solution is diluted 1/100 in distilled water. 5 µl of the dilution were pipetted on an object slide. The droplet was sandwiched in between the object slide and a round 12 mm diameter coverslip and placed on the measurement apparatus. Fluorescence was observed through an oil objective using the setup from 1a, and alternatively the setup from FIG. 19. In the latter case, IR-Laser heating is performed through the same objective. The maximum temperature increase was about 15° C. The temperature profile had a half width of 20 µm. Images before and after infrared laser heating were taken. The vesicles are attracted by heat spot due to negative thermophoresis. They are accumulating in the centre of the heat spot. The catchment area is dependent on the width of the temperature profile (i.e. a sufficient strong temperature gradient is necessary to drive directed particle motion toward the heated centre within a finite time). The trapping of vesicles has several, important applications, e.g. vesicles (as well as cells) can be transported and moved within a solution. Also, the fluctuation of single vesicles in the potential well (i.e. created by temperature increase) can be observed. Since the amplitude of fluctuations is dependent on the properties of the vesicle, any changes, like protein binding to vesicles or the activity of a membrane protein, e.g. an ion-pumping membrane protein can be detected as a change in fluctuation amplitude. The sign of the thermophoretic motion (e.g. attracted to the heat centre or repelled by the heated centre) is dependent on the properties (e.g. charge, size, surface modification, protein binding). When a vesicle which is normally attracted by the region of highest temperature is repelled from the heated centre, this is indicative for a change in the properties of this vesicle. This behaviour may be observed after changing the buffer around the vesicle to a solution containing, e.g. a binding partner. Also the behaviour of two samples containing vesicles in buffer and vesicles in buffer with binding partner (or membrane protein activating substance, e.g. ATP) may be compared or observed. Finally, the differences in the thermophoretic properties can be used to sort vesicles or cells.

Example 11

Determination of Primer Size Distribution

The thermo-optical characterization method of the present invention also allows to quantify the size/length distribution of primers in each step/cycle of PCR reactions. As the primers are elongated by the polymerase throughout the PCR reaction the measurement of the size/length distribution of the primers provides information about efficiency and quality of the PCR reaction. Thermophoresis provides a comparably robust and precise way to measure the size distribution of primers/elongated primers in PCR reaction solutions from less than 5 bases/base pairs up to 1000000 bases/base pairs or even more. The precision of this thermo-optical characterization methods is not too sensitive on the geometry of measurement (e.g. height of the liquid layer) and it can, accordingly, be conducted in for example standard multi-well plates, capillaries, microfluidic chips or single droplets of the solution.

In contrast to thin measurement chambers, the solution in multi-well plates or liquid droplets is not heated homogeneously in z-direction (direction of incident IR-Laser light), as they often exhibit an extension in z-direction larger than the absorption length of the laser (e.g. in aqueous solutions 300 µm at 1480 nm Laser wavelength). It is preferred to measure the fluorescence from molecules substantially influenced by the temperature gradient. Therefore it is advantageous to measure the fluorescence locally with an optical element with small depth of focus (e.g 100 µm) and to place the focus close to the point of maximum temperature. The optical element averages out the differences of temperature in the z-direction, so that the system is treated as if the spatial temperature distribution is two dimensional.

In the following a typical measurement for the characterization and quantification of a PCR-reaction and the PCR products is described without limiting the scope of the invention:

Data Acquisition:

A typical measurement of the thermo-optical properties:

For this measurement a device as illustrated in the appended figures, e.g. in FIG. 40 and FIG. 41, is used.

Step 1:

The solution of dye labeled primer molecules are fluorescently excited and recorded with spatial resolution in the capillary. The center of the field of view of the objective (e.g. 40× oil immersion objective) corresponds to the center of the IR-laser spot, which is turned on in Step 2. The fluorescence of the marked molecules is measured for less than 10 seconds on a CCD camera with a frame rate between 40 Hz down to 0.2 Hz. These image(s) provides the necessary information about the fluorescence intensity level at 100% concentration. Then fluorescence excitation is turned off.

Step 2:

The Infrared laser heating is turned on. The immediately established local spatial temperature distribution causes the labeled primers and elongated primers drift to lower or higher temperatures, depending on the particular molecule to be analyzed. The laser is focused in a way that temperature gradients between 0.001 and 10 K/µm can be achieved. The temperature gradient has been calibrated once and it is not necessary to repeat this calibration every time an experiment is performed. The maximal temperature elevation is below the temperature which is known to cause damage to the molecules or disintegrate their interaction. Depending on the thermophoretic properties of the primers in the solution (i.e. if they move fast in a thermal gradient or slow) the infrared laser heats the solution for less than 10 seconds. After this period of time the infrared laser is turned off.

Step 3:

During the period where the Infrared laser heating is turned on the fluorescence is excited and recorded preferably with the same parameters described in step 1 and preferably at the same position described in step 1.

Data Processing—Inhomogeneous Illumination Correction and Normalization to 100% Concentration:

All images taken in step 3 are divided by a single or all images taken in step 1 and multiplied by 100. This way a correction for inhomogeneous illumination is achieved and the fluorescence is normalized to 100% concentration. Changes in the concentration of the molecules due to their thermo-optical properties result in a deviation from the 100% and can thus be determined. The area with the biggest deviation from 100% due to the thermo-optical properties is taken (typically a segment of 8×8 pixel) and denominated "dataX". Where the parameter "X" denominates the cycle number of the PCR.

Preparation:

PCR Reaction Solution:

A PCR reaction solution with the volume 50 µl is prepared containing for example 5 µl of 10× standard Taq reaction buffer (100 mM Tris HCl pH 8.8, 500 mM KCl, 15 mM $MgCl_2$), 5 µl of 8 mM total dNTP mix (all four types of nucleotides), 5 µl of 10 µM forward Primer labeled with the dye HEX at the 5'-end, 5 µl of 10 µM reverse Primer, 0.5 µl of 2 units/µl Taq polymerase, 0.5 µl of 10 nM template DNA and 29 µl PCR grade water.

The buffer may also contain PCR enhancers for example BSA, glycerol, Tween 80, betaine, dextran 50 or $(NH_4)_2SO_4$.

The concentrations of buffer components can also be different, for example the $MgCl_2$ concentration in the reaction solution may vary and can be in the range from 1.5 mM to 5 mM or even higher.

Filling of the Chamber:

The above described PCR reaction solution is filled into a capillary (inner diameter for example 100 µm). After the capillary is filled the ends of the capillary are sealed with vacuum grease to prevent evaporation. The capillary is placed and fixed to a temperature controlled which can do the temperature protocol for PCR cycling. The capillary is in good thermal contact with this stage, for example by fixing it with thermal conductive glue (e.g. Arctic Silver Thermal Adhesive).

Instead of the capillary also for example a multi-well plate or a sealed droplet (for example sealed oil) of the PCR reaction solution can be used as chamber.

Determination of the Thermo-Optical Properties of the HEX-Labeled Primers During the PCR:

Cycle 0:

Immediately after the capillary was filled and fixed to the temperature controlled stage and before the PCR reaction is started the thermo-optical properties of the labeled primers are measured at 20° C. The measurement is described herein above in the sections "Data acquisition" and "Data Processing". The measurement data collect at this cycle 0 is named "data0".

PCR-Reaction:

After step 0 the PCR reaction in the capillary is initiated with the following protocol: Initial denaturing for 10 minutes at 95° C.

The temperature cycling contains four different temperature steps and is performed 40 times:

1. Denaturing for 30 seconds at 95° C.
2. Annealing for 60 seconds at 64° C.
3. Elongation for 60 seconds at 72° C.
4. Measurement of thermo-optical properties for 10 seconds at 20° C.

The data collected (i.e. the normalized fluorescence intensity images) in each temperature cycle is denominated with the number of the cycle. For example the data of the thermo-optical measurement in PCR cycle 2 is denominated "data2", the data of the thermo-optical measurement in PCR cycle 15 is denominated "data15".

Characterization of the PCR-Reaction and the PCR Products:

As it is characteristic for PCR the primers are elongated by the polymerase throughout the PCR. The fluorescently labeled forward primer molecules are elongated throughout the PCR. After each cycle the number of elongated labeled primer molecules is increasing.

As the thermo-optical properties of DNA are dependent on the length of the DNA the elongation of the labeled primer molecules due to the PCR changes the thermo-optical properties and thus can be measured thermo-optically.

For the characterization of the PCR-reaction and the PCR-product the data of each PCR cycle is compared with the "data0" described above in cycle 0. For example "data1" of cycle 1 and "data15" of cycle 15 is divided by "data0" giving the values "data1"/"data0" and "data15"/"data0". This data processing is done for the data acquired in each cycle.

If the ratio "dataX"/"data0" deviates from the value 1 this means that the size distribution of the primers in cycle X deviates from the size distribution of the primers in Step 0. In the case of PCR this deviation is due to the elongation of a detectable amount of primers.

The first cycle X where a deviation of the ratio "dataX"/"data0" from 1 is detected is called "threshold" cycle.

The first cycle X of the PCR reaction, where no further deviation of the ratio "dataX"/"data0" from the ratio of the previous cycle "data X-1"/data0 is detected, is called "endpoint" cycle From the threshold cycle to the endpoint cycle an increase in the deviation of the ratio "dataX"/"data0" is measured. If the PCR reaction is complete at the endpoint all labeled primers may be elongated to the length determined by the template and the primer binding sites.

From DNA-standards the thermo-optical properties of for example 10 bp, 50 bp, 100 bp, 500 bp, 1000 bp, 2000 bp, 5000 bp up to more than 1000000 bp and combinations of these are known. By comparing the measured data with the thermo-optical properties of standards the length or length distribution of the PCR products can be determined.

For characterization of the PCR reaction the ratio "dataX"/"data0" is plotted as ordinate against the cycle number X.

From the cycle number of the threshold cycle one can compare the concentration of different templates. For example in the case of 1 nM template the threshold cycle may be at cycle 15 and in the case of 8 nM the threshold cycle may be at cycle 13.

From the increase in the deviation of the ratio "dataX"/"data0" from cycle to cycle the efficiency of the PCR can be calculated by assuming an exponential dependence.

The results of this experiment are illustrated in appended FIG. 42. The progress, threshold, efficiency and endpoint of a PCR reaction can be measured by performing thermo-optical analysis during a PCR reaction. In FIG. 42 thermo-optical analysis is performed in some cycles of a PCR reaction. Data points are taken while the temperature of the whole sample volume is adjusted to 20° C. The values are normalized to the value measured before the first PCR cycle (error bars are smaller than the marker). The relative increase of concentration is dependent on the length of DNA molecules. As the content of primer DNA decreases and the concentration of longer product/elongated primer DNA increases, an increase in concentration compared to the pure primer DNA is observed. In cycle 38 the PCR reaction reaches its endpoint. No further increase in product/elongated primer is observed. Also threshold cycle and PCR efficiency can be obtained from these datasets.

Example 12

Measurement of Primer Elongation During a PCR and PCR Product Length Alternative Scheme for Data Acquisition with Spatial Resolution and Spatial Data PCR Reaction Solution:

A PCR reaction solution with the volume 50 µl is prepared containing for example 5 µl of 10× standard Taq reaction buffer (100 mM Tris HCl pH 8.8, 500 mM KCl, 15 mM $MgCl_2$), 5 µl of 8 mM total dNTP mix (all four types of nucleotides), 5 µl of 10 µM forward Primer labeled with the dye HEX at the 5'-end, 5 µl of 10 µM reverse Primer, 0.5 µl of 2 units/µl Taq polymerase, 0.5 µl of 10 nM template DNA and 29 µl PCR grade water.

The buffer may also contain PCR enhancers for example BSA, glycerol, Tween 80, betaine, dextran 50 or $(NH_4)_2SO_4$.

The concentrations of buffer components can also be different, for example the $MgCl_2$ concentration in the reaction solution may vary and can be in the range from 1.5 mM to 5 mM or even higher.

Data Processing/Evaluation:

The measurements described in the following may be carried out in each cycle of a PCR, to yield real time information about the PCR or after a PCR reaction was carried out (End point measurements of final PCR products).

The following example describes an endpoint DNA characterization by using only one single image (i.e. single timepoint) with spatial resolution (e.g. CCD Camera).

Filling of the Chamber:

The above described PCR reaction solution is filled into a capillary (inner diameter for example 100 µm). After the capillary is filled the ends of the capillary are sealed with vacuum grease to prevent evaporation. The capillary is placed and fixed to a temperature controlled support/controller/cycler which can do the temperature protocol for PCR cycling. The capillary is in good thermal contact with this stage, for example by fixing it with thermal conductive glue (e.g. Arctic Silver Thermal Adhesive).

Instead of the capillary also for example a multi-well plate or a sealed droplet (for example sealed oil) of the PCR reaction solution can be used as chamber.

Data Acquisition:

Step 1. A solution of dye labeled primers/extended primers/final PCR products is present in a microfluidic chamber, multiwell plate or droplet. Optionally an internal reference DNA molecule (used as a length standard) not involved in the PCR reaction and labeled with a different fluorescent dye is measured simultaneously in a multiplexing approach.

Step 2. The infrared laser heating is turned on. The immediately established local spatial temperature distribution causes the labeled primers and elongated primers (as well as internal reference standards) to drift to lower or higher temperatures, depending on the particular molecule to be analyzed. The laser is focused in a way that temperature gradients are between 0.00001 and 10 K/µm in the field of view. The temperature gradient has to be calibrated only once and it is not necessary to repeat this calibration every time an experiment is performed. The maximum temperature elevation is set below values which would harm the molecules to be analyzed. Typically the infrared laser heats the solution for less than 30 seconds, typically 10 seconds or less.

Step 3. During the laser heating an image or a frameset of images of the spatial fluorescence distribution is recorded (or multiple frames which are averaged to a single image). Afterwards the infrared laser and the fluorescence excitation light source are turned off.

Data Processing/Evaluation:

Two "regions of interest" (ROI-1 and ROI-2) are defined in the images recorded in step 3. Both ROI's have a size of 15×15 µm and the fluorescence intensity is averaged over these ROI's. ROI-1 is positioned at the center of the infrared laser, while ROI-2 is positioned in a distance of 100 µm (Alternatively also two detectors without spatial resolution may be positioned in a way, that the intensities from these positions can be compared). The ROI's may be of different size or even overlap. The ROI represent different average temperatures. For an analysis of the signal the quotient of both averaged intensities is calculated according to ROI-1/ROI-2. In case of a Real-Time PCR this quotient is calculated for each PCR-Cycle. Changes in the quotient reflect the change in primer elongation (i.e. change in the ratio of elongated to non-elongated primer). In case an endpoint analysis is performed, the length of the product DNA is determined relative to a reference standard. The reference(s) may have been established once in an independent experiment or may be measured in the same experiment in case a multiplexing experiment is performed. This is accomplished by one or more DNA molecules (not part of the PCR reaction) labeled with a fluorescent dye with good spectral separation to the dye of the Primer DNA which is measured simultaneously at a different wavelength (e.g. one half of the CCD Chip is used for each dye by using a dual view device). By comparing the reference(s) and the elongated PCR Primer signal, the length of the PCR product can be determined.

Example 13

Detection and Quantification of Specific Aptamer Binding to Thrombin

Detection of a Binding of a DNA-Aptamer to a Protein and Determination of the Reaction's Dissociation Constant Preparation of the Samples To determine the binding properties of a DNA-aptamer to a protein, a fixed concentration of the aptamer is mixed with different concentrations of the protein and the thermo-optical properties of each different mix of concentrations are determined. Preferably the aptamer or the protein is labelled with a fluorescent dye or an intercalator like SYBR Gold is used.

For higher accuracy in the results a higher number of diluting steps may be performed. To obtain just a detection of a binding event it is enough to measure two points: one with the aptamer alone and one with aptamer and protein together, where the protein is present in excess concentration compared to the aptamer to assure a complete binding. In case of the binding of a Cy5 labelled DNA-Aptamer (e.g. Cy5-5' tggttggtgtggttggt-3' (SEQ ID NO: 1)) to human alpha-Thrombin the final concentration of the DNA-aptamer in the measurement solution is kept constant at 100 nM in all samples. In each sample is a different final concentration of Thrombin, in detail the concentrations are 16580 nM, 8425 nM, 4213 nM, 2106 nM, 1053 nM, 527 nM, 263 nM, 132 nM, 66 nM, 33 nM, 16 nM, 8 nM, 4 nM, 2 nM, 1 nM, 0 nM. As buffer system for the measurement each sample contains a buffer which consists of: 10% human serum (HSA), 1×SSC-buffer (150 mM NaCl, 15 mM Na3-citrate, pH 7.2), 5 mM KCl, 1 mM $CaCl_2$, 1 mM $MgCl_2$. The samples with different concentrations of thrombin are filled in different glass-capillaries of preferably 100 μm to 0.8 mm inner diameter, each different concentration in a separate capillary. So finally there are 16 different capillaries, representing the 16 different final concentrations of thrombin. In each of these capillaries the concentration of DNA-aptamer, labelled with Cy5, is 100 nM. All capillaries are sealed preferably with biology grade mineral oil to prevent evaporation and drift. The local temperature increase induced by the IR-Laser is preferably 10K or less.

To reduce photobleaching of the samples and to preserve the sample material, the sealed capillaries may be stored in the dark in a refrigerator until the thermo-optical characterization is started.

Performing the Measurement

After an equilibration time of preferably 10 seconds a first capillary can be measured. Therefore, the capillary is placed under the objective, is fixed, immersion oil is put at the objective and the optics are focussed on the sample to provide an image of the samples inside the capillary. The position of the capillary is adjusted in such a way that the focus of the IR-laser is in the middle of the capillary.

For the measurement with an 40× objective, 1.3 numerical aperture, Zeiss Fluar, the following settings are used: LED (Luxeon V Star, red): 50 mA; IR-Laser (PSL-480 (Princeton Lightwave) max. power: 320 mW CW lt. Spec PLW): 50 mW; CCD-Camera (PCO sensicam qe): 100 ms Exposure, 8×8 binning, low light mode;

Every device is controlled and triggered with a national instruments measurement card (NI-6229). Software control for this is written in Labview.

The measurement protocol is:

Step 1: The CCD-camera and the LED are switched on, the camera is recording a continuous movie of frames/images of the spatial fluorescence distribution in the capillary with at least 5 Hz;

Step 2: 5 seconds after the CCD-camera recording was started, the IR-Laser is switched on;

Step 3: 10 seconds after the IR-Laser was switched on, the IR-Laser, the LED and the CCD-camera recording is switched off and the recorded movie of fluorescence images is saved;

All the data is saved, preferably with all setting parameters, in a digital or electronical way and the data is directly correlated with the concentrations of the aptamer and the protein measured. For example the measurement with the mixed sample containing 100 nM of aptamer and 0 nM of thrombin is saved as "Thrombin0nM_Aptamer300nM" and the sample containing 100 nM of aptamer and 16850 nM of thrombin is saved as "Thrombin16850nM_Aptamer100nM".

This is repeated for all prepared samples using the same laser power and LED illumination and camera settings and the same focussing of the optics.

Analyzing the Data

For example one image of the movie which is taken 3 seconds after the IR-Laser was switched on, two "regions of interest" (ROI-1 and ROI-2) are defined. Both ROI's have a size of for example 15×15 μm and the fluorescence intensity is averaged over these ROI's. ROI-1 is positioned at the center of the infrared laser, while ROI-2 is positioned in a distance of 100 μm (Alternatively also two detectors without spatial resolution may be positioned in a way, that the intensities from these positions can be compared). The ROI's may be of different size or even overlap. The ROI represent different average temperatures. For an analysis of the signal the quotient of both averaged intensities is calculated according to ROI-1/ROI-2.

The ratio ROI-1/ROI-2 of each measurement is plotted versus the final concentration of the thrombin included in the sample. In this way a titration curve is obtained from which the dissociation constant KD can be calculated and a binding event can be determined.

Alternatively ROI-1 of one image, IMG1, taken for example 3 seconds after the LED was switched on in step 1 and the ROI-1 of one image, IMG2, taken 3 seconds after the IR-Laser was switched on, in step 2 are divided by each other, giving the ration (ROI-1 of IMG2)/(ROI-1 of IMG1). Plotting this ratios for different concentration of the thrombin versus the concentration of thrombin results in a binding curve from which the dissociation or affinity constant can be determined. The results of the titration experiment described above are shown in FIG. 33.

Example 14

Detection of DNA Molecules and Measurement of DNA Hybridization

Nucleic Acid Hybridization

The measurement of thermo-optical properties can be applied for detection of a specific DNA sequence by hybridization to a complementary strand.

In state-of-the-art techniques the sequence of a DNA molecule is identified by sequencing, melting curve analysis, or allele-specific PCR reactions. Here, an assay is shown where a short fluorescently labeled DNA probe hybridizes with a complementary DNA strand. Upon hybridization the probe adopts the thermo-optical properties of the target molecule. We measure the hybridization of a fluorescently labeled 22 bases DNA to an unlabeled complementary DNA molecule of the same length. A physiological buffer with high ionic strength (1×SSC) is used, in order to stabilize the probe-target interaction by suppressing electrostatic repulsion of the phosphate backbone. We measure the average concentration change of samples containing a constant concentration of the fluorescently labeled probe molecules ("probe", 400 nM) and a varying amount of the complementary strand ("target", 0 nM to 1600 nM). The results are shown in FIG. 38 (a). In case no target molecule is present in the solution, the measured concentration change (or average Soret coefficient) corresponds to that of the free probe molecule. The average concentration change increases as the concentration of unlabeled target molecule approaches the probe's concentration. This is readily understood by the increase in charge and persistence length of the probe upon hybridization. When all probe molecules are hybridized to the target strand (i.e. molecule ratio: sample/probe≈1), no further increase of the signal (i.e. concentration change) upon addition of sample molecules was observed. In FIG. 38 (a) the signal measured by thermo-optical properties is normalized to obtain the relative amount of hybridized strands. Thus, a short target DNA is detected and its abundance can be determined by the saturation value.

Typical target molecules are longer than 20 bases and double stranded. For target molecules longer than 20 bases and double stranded, one has to expect a competing reaction between the labeled probe and the target DNA strands containing the same "probe-sequence". The experiment in this case is comparable to the procedure described before: A fluorescently labeled DNA probe of 24 bases ("probe", 40 nM) is used to detect a small amount of bacteriophage lambda DNA ("target", 10 nM, approximately 50.000 bp). The concentration change is determined in samples containing the pure DNA probe and in solutions containing the probe mixed with lambda DNA. We checked twice for the hybridization of probe DNA and lambda DNA. First after simply mixing of the molecules and second after an additional annealing procedure (94° C., 5 min and 72° C., 5 min) was carried out.

FIG. 38 (b) shows that the concentration change of the free probe is comparatively small (−2%). Without an annealing procedure this behavior is only changed slightly (−3%), indicating that only a small extend of the probe is hybridized to the target molecule. The two strands of the target DNA form a very stable complex at room temperature. When a denaturing (94° C., 5 min) and annealing (72° C., 5 min) procedure is performed on the sample, the hybridization is detected as the expected strong change in molecule concentration (−10%). This amplitude is readily explained by the molar ratio of probe and target molecule.

The concentration change of pure lambda DNA in absence of the probe was determined to 32% in an independent experiment by using an intercalating fluorescent dye. To enhance hybridization by giving the probe a kinetic advance compared to the competing strand, the probe is used in a four times molar excess (i.e. 40 nM). Thus, even at 100% hybridization only one third of the effect observed for pure lambda DNA, is expected.

Thus, the method detects double stranded DNA, even at an excess of probe molecules. That the technique tolerates a substantial amount of non-hybridized probe molecules is preferable since analytical assays can be carried out without any washing procedures. By using multiple fluorescence labels it is possible to detect several sequences simultaneously. The thermo-optical method overcomes limitations of in-situ techniques like FISH (fluorescence in-situ hybridization) and surface supported southern-blot techniques and allows measurements in free solution. Relevant applications for DNA hybridization thermophoresis are wide-spread and can be found in many diagnostic PCR assays, where the technology can be used for the detection of single nucleotide polymorphisms. The measurement conditions (i.e. temperature, salt, etc) may be adjusted to stringent conditions, so that the complex of probe and mismatch-sequence is unstable in solution.

Preparation of the Samples

For the experiment shown in FIG. 38 (a) samples with a constant amount of labelled probe DNA (400 nM) were mixed with varying amount of unlabeled target DNA. In this case target concentrations of 0 nM, 100 nM, 200 nM, 400 nM, 800 nM, 1200 Nm and 1600 nM were measured. It is of advantage to dissolve target and probe in the same buffer (here: 1×SSC (150 mM NaCl, 15 mM Na3-citrate, pH 7.2) buffer), to avoid any change in buffer composition, due to preparation dilution series.

The samples with different concentrations of target are filled in different glass-capillaries of preferably 100 μm to 1 mm inner diameter, each different concentration in a separate capillary. So finally there are 7 different capillaries, representing the 7 different final concentrations of target DNA. In each of these capillaries the concentration of the probe DNA, labelled with HEX, is 200 nM. All capillaries are sealed preferably with biology grade mineral oil to prevent evaporation and drift. The local temperature increase induced by the IR-Laser is preferably 10K or less.

For the detection of the complex formation between the Hex-labeled 22mer and the complementary 22mer target DNA the following substances were used: probe: HEX-5'-AT TGA GAT ACA CAT TAG AAC TA-3' (SEQ ID NO: 2), target: TA GTT CTA ATG TGT ATC TCA AT (SEQ ID NO: 3). Both were purchased from IBA BioTAGnology, Goettingen, Germany.

The experiment shown in FIG. 38 (b) is performed at a constant concentration of 40 nM probe DNA and 10 nM target DNA. All samples are preferably measured in a 100 μm-1 mm Capillary. The thermo-optical properties of the probe DNA have been determined in an independent experiment, followed by a mix of probe and target. Finally the mix of probe and target DNA were subject to a defined melting and annealing procedure, performed in a standard PCR cycler (94° C., 5 min followed by 72° C., 5 min). The melting and annealing took place in an eppendorf cup, prior to transfer of the sample in a capillary.

For the lambda DNA-Hybridization experiment 48502 bp λ-DNA was used bought from Fermentas GmbH, St. Leon-Rot, Germany. For measuring the Soret coefficient of pure λ-DNA it was labeled with the intercalating fluorescent dye TOTO-3 (ex: 640 nm, em: 660 nm) from Invitrogen, Carlsbad, Calif. The corresponding DNA-primer with its sequence 5'-GATGAGTTCGTGTCCGTACAACTGG-3' (SEQ ID NO: 4) was bought from IBA BioTAGnology, Goettingen, Germany containing an Alexa Fluor 700 (ex: 695 nm, em: 720 nm) fluorescent dye at its 5'-end.

For an internal reference experiment using a multiplex approach, a DNA coupled to the dye Alexa Fluor 700 may be used in combination with a DNA coupled to the dye HEX.

Performing the Measurement

After an equilibration time of preferably 10 seconds a first capillary can be measured. Therefore, the capillary is placed under an air objective. The air objective is focussed on the sample to provide an image of the samples inside the capillary. The position of the capillary is adjusted in such a way that the focus of the IR-laser is preferably in the middle of the capillary.

For the measurement with an 20× air objective, 0.5 numerical aperture, Zeiss EC-Plan-Neofluar, the following settings are used: LED (Luxeon V Star, red): 50 mA; IR-Laser (PSL-480 (Princeton Lightwave) max. power: 320 mW CW lt. Spec PLW): 50 mW; CCD-Camera (PCO sensicam qe): 100 ms Exposure, 8×8 binning, low light mode;

All devices are controlled and triggered with a national instruments measurement card (NI-6229). Software control for this is written in Labview.

The data are collected and evaluated as described in the following:

Data Acquisition:

Step 1. A solution of dye labeled probe is present in a microfluidic chamber, multiwell plate or droplet. (The thermo-optical properties (i.e. concentration change) of the free probe molecule is known from an independent experiment. Alternatively the thermo-optical behavior of a DNA molecule similar to the probe, but not complementary to a target molecule, is measured simultaneously in a multiplex approach (internal reference)).

Step 2. The infrared laser heating is turned on. The immediately established local spatial temperature distribution causes the labeled primers and elongated primers (as well as internal reference standards) to drift to lower or higher temperatures, depending on the particular molecule to be analyzed and conditions like pH, salt concentration etc. The laser is focused in a way that temperature gradients are between 0.0001 and 10 K/μm in the field of view. The temperature gradient has to be calibrated only once and it is not necessary to repeat this calibration every time an experiment is performed. The maximum temperature elevation is set below values which would harm the molecules to be analyzed or hinder their hybridization. Typically the infrared laser heats the solution for less than 30 seconds, typically 10 seconds or less.

Step 3. During the laser heating an image of the fluorescence distribution is recorded (or multiple frames which may be averaged to a single image). Afterwards the infrared laser and the fluorescence excitation light source are turned off.

Data Processing/Evaluation:

Two "regions of interest" (ROI-1 and ROI-2) are defined in the images recorded in step 3. Both ROI's have a size of 15×15 µm and the fluorescence intensity is averaged over this ROI's. ROI-1 is positioned at the center of the infrared laser spot, while ROI-2 is positioned in a distance of 100 µm (Alternatively also two detectors without spatial resolution may be positioned in a way, that the intensities from these positions can be compared). The ROI's may vary in size or even overlap. The ROI represent different average temperatures. For an analysis of the signal the quotient of both averaged intensities is calculated according to ROI-1/ROI-2. The quotient is analyzed for all samples. Changes in the quotient reflect the change in hybridization (i.e. change in the ratio of hybridized to free probes). The thermo-optical properties of double stranded is very different to that of a single stranded DNA, even more the longer the target molecule gets.

The relative amount of hybridized strands (as shown in FIG. 38 (a)) can be determined, by (1) subtracting the signal of the free probe molecule from all other signals followed by (2) a division of the subtracted signals by the saturation value (i.e. concentration change determined in saturation) determined at an excess of target.

In case the target molecule concentration is not known, the target concentration may be calculated the following way: The thermo-optical signal strength (i.e. concentration change) is known for the free probe and for the target molecule. The measured concentration change averages the signal of free and hybridized probe. Thus, by knowing the thermo-optical properties of target and probe, the target concentration can be calculated, in case the hybridization of the probe to the target is about 100%. Alternatively the probe DNA may be used in different concentration to define the concentration at which saturation occurs.

Example 15

Detection and Quantification of Antibody Binding to GFP

Detection of a Binding of Proteins to Target Proteins and Determination of the Reaction's Dissociation Constant Preparation of the Samples For the determination of protein binding, a protein A needs to be mixed with known amounts of a protein B and the fraction of protein complexes AB in solution has to be determined. To observe the binding reaction at least one binding partner has to be excited fluorescently directly or may be marked fluorescently, for example protein A. The other protein, for example protein B, is diluted stepwise from high concentrations to lower concentrations. The concentration of protein A is preferably kept constant. For higher accuracy in the results a higher number of diluting steps may be performed. To obtain just a detection of a binding event it is enough to measure two points: one with protein A alone and one with protein A and B where the protein B is present in excess concentration compared to protein A to assure a complete binding. In case of the binding of Green Fluorescent Protein (GFP) (MW 27.51 (Da) to a GFP-antibody (MW 13.7 kDa), concentrations of 0 nM, 2 nM, 20 nM, 100 nM, 200 nM, 400 nM, 600 nM, 800 nM, 1000 nM 1600 nM, 2000 nM, 4000 nM and 6000 nM of the GFP-antibody are prepared, where the GFP-antibody corresponds to protein B and the GFP to protein A, respectively. The samples of different concentration of protein B are then mixed in a given ratio with the protein A. In the GFP experiment, the above concentrations of GFP and GFP-antibody are mixed in a ratio 1:1 which results in a final concentration of 300 nM GFP and final concentrations of GFP-antibody of 0 nM, 1 nM, 10 nM, 50 nM, 100 nM, 200 nM, 300 nM, 400 nM, 500 nM, 800 nM, 1000 nM, 2000 nM and 3000 nM. As buffer a 1×PBS buffer is used. Then preferably 5 to 15 µl of the mixed samples are filled into a preferably 0.8 mm inner diameter glass capillaries and the thermo-optical properties of these mixed samples are determined. Additionally one capillary may be filled with pure buffer to measure the background in the measurement. The tips of the capillaries are sealed by locally heating the tips for example with a lighter until the glass melts and closes the capillary. To reduce photobleaching of the samples, the sealed capillaries are stored in the dark in a refrigerator until the thermo-optical characterization is started. In this example 13 capillaries are used, preferably one for each different concentration of protein B.

Performing the Measurement

After an equilibration time of preferably 15 seconds the first capillary can be measured. Therefore, the capillary is placed under the objective, fixed and the optics are focussed on the sample to provide a spatial fluorescence image of the proteins inside the capillary. The position of the capillary is adjusted in such a way that the focus of the IR-laser is in the middle of the capillary.

For the measurement with an 40× air objective, 0.8 numerical aperture, the following settings are used: LED (Luxeon V Star, blue): 100 mA; IR-Laser (PSL-480 (Princeton Lightwave) max. power: 320 mW CW lt. Spec PLW): 50 mW; CCD-Camera (PCO sensicam qe): 100 ms Exposure, 8×8 binning, low light mode;

Every device is controlled and triggered with a national instruments measurement card (NI-PCI-6229). Software control for this is written in Labview.

The measurement protocol is:

Step 1: The IR-Laser is switched on;

Step 2: 10 seconds after the IR-Laser was switched on, the CCD-camera and the LED are switched on and the CCD-camera records 10 images with at least 5 frames per second;

Step 3: 15 seconds after the IR-Laser was switched on, the IR-Laser, the LED and the CCD-camera recording is switched off and the recorded movie of fluorescence images is saved;

The data is recorded, preferably with all setting parameters, in a digital or electronical way and the data is directly correlated with the concentrations of protein A and protein B measured. For example the measurement with the mixed sample containing 300 nM of protein A and 0 nM of protein B is saved as "B0nM_A300nM" and the sample containing 300 nM of protein A and 3000 nM of protein B is saved as "B3000nM_A300nM".

This is repeated for all prepared samples using the same laser power and LED illumination and camera settings.

Analyzing the Data

Two "regions of interest" (ROI-1 and ROI-2) are defined in the images. Both ROI's have a size of for example 15 µm×15 µm or 10 pixel×10 pixel of the image and the fluorescence intensity is averaged over these ROI's. ROI-1 is positioned at the center of the infrared laser (IR-Laser), while ROI-2 is positioned in a distance of 100 µm to the spot of the IR-Laser. (Alternatively also two detectors without spatial resolution may be positioned in a way, that the intensities from these positions can be compared). The ROI's may be of different size or even overlap. The ROI represent different average temperatures. For an analysis of the signal the ratio of both averaged intensities is calculated according to ROI-1/ROI-2. The ratios may be averaged over the 10 recorded images to reduce noise.

The ratio ROI-1/ROI-2 of each measurement of mixed sample is plotted versus the final concentration of the protein B included in the sample. In this way a titration curve is obtained from which the dissociation constant KD or the association constant or the IC50 or EC50 can be calculated and a binding event can be determined. The result of the experiment described above is shown in FIG. 39.

The invention claimed is:

1. A method for the thermo-optical determination of the size of fluorescently labeled nucleic acids in a reaction solution, comprising the steps of:
   (i) providing a reaction solution comprising fluorescently labeled nucleic acids;
   (ii) irradiating a laser light beam into the solution to obtain a spatial temperature distribution in the solution around the irradiated laser light beam;
   (iii) exciting fluorescently the fluorescently labeled nucleic acids and detecting the fluorescence at least at one position or at around one position in the solution of the fluorescently excited nucleic acids, wherein the detection of fluorescence is performed at a predetermined time of 1 to 250 s after the start of the laser irradiation; and
   (iv) determining the size of the fluorescently labeled nucleic acids from the detected fluorescence intensity;
   wherein the reaction solution is a nucleic acid amplification solution or is a nucleic acid restriction solution.

2. The method according to claim 1, wherein the fluorescence is detected at least at two positions or at around two positions in the solution.

3. The method according to claim 1 wherein additionally the detection of fluorescence is performed at least once before the start of the laser irradiation.

4. The method according to claim 1, wherein a second fluorescence detection is performed during laser irradiation or after the laser irradiation has been terminated.

5. The method according to claim 1, wherein said nucleic acid reaction solution is selected from the group of PCR reaction solution and ligase chain reaction solution.

6. The method according to claim 5, wherein said PCR reaction solution is a drop or droplet and/or is in a container selected from the group consisting of capillary, multi-well plate, chamber, microfluidic chip, and glass capillary chip.

7. The method according to claim 6, wherein the drop or droplet has a volume of from 1 pl to 10 μl.

8. The method according to claim 1, wherein the fluorescently labeled nucleic acids are selected from the group of fluorescently labeled primers, fluorescently labeled primer extension products, fluorescently labeled nucleic acid probes and fluorescently labeled PCR products.

9. The method according to claim 1, wherein the size of the fluorescently labeled nucleic acids is determined during or between PCR cycles or after PCR has been terminated.

10. The method according to claim 9, wherein the size of the fluorescently labeled nucleic acids is determined after or during the primer annealing phase, after or during the primer extension phase or after or during the denaturation phase.

11. The method according to claim 10, wherein for laser irradiation and fluorescence detection the reaction solution is cooled to a temperature of in the range of from about 0° C. to 50° C.

12. The method according to claim 1, wherein the nucleic acids are fluorescently labeled by covalently attached dyes or are fluorescently labeled by non-covalently bound dyes.

13. The method according to claim 1, wherein said predetermined time after the start of irradiation is from 5 s to 40 s.

14. The method according to claim 1, wherein the laser beam is focused such that a temperature gradient within the temperature distribution is achieved in the range of from 0.001 to 10K/μm.

15. The method according to claim 1, wherein said fluorescence is detected with a detector with spatial resolution.

16. The method according to claim 15, wherein said detector with spatial resolution is selected from the group consisting of a CCD camera, a CMOS camera and a line camera.

17. The method according to claim 1, wherein said fluorescence is detected with at least two detectors without spatial resolution.

18. The method according to claim 17, wherein said detector without spatial resolution is selected from the group consisting of an avalanche photodiode, a photomultiplier tube and a photodiode.

19. The method according to claim 1, wherein the laser light is within the range of from 1200 nm to 2000 nm.

20. The method according to claim 1, wherein the laser is a high power laser within the range of from 0.1 W to 10 W.

21. The method according to claim 20, wherein the laser is a high power laser within the range of 4 W to 6 W.

22. The method according to claim 1, wherein the method is performed within a temperature range of from about 4° C. to 100° C.

23. The method of claim 1, wherein said detector is a CCD chip.

24. A method for nucleic acid amplification of a template and thermo-optical determination of the size of a resulting amplified nucleic acid, comprising the steps of:
   (i) providing a nucleic acid amplification solution comprising fluorescently labeled nucleic acids;
   (ii) amplifying the template such that fluorescently labeled nucleic acids are incorporated into the amplified nucleic acid;
   (iii) irradiating a laser light beam into the solution to obtain a spatial temperature distribution in the solution around the irradiated laser light beam;
   (iv) exciting fluorescently the fluorescently labeled amplified nucleic acid;
   (v) detecting the fluorescence at least at one position or at around one position in the solution of the fluorescently excited amplified nucleic acid, wherein the detection of fluorescence is performed at a predetermined time of 1 s to 250 s after the start of the laser irradiation; and
   (vi) determining the size of the fluorescently labeled amplified nucleic acid from the detected fluorescence intensity;
   wherein said amplification and said thermo-optical determination of the size of the amplified nucleic acid occurs in the same reaction chamber.

* * * * *